United States Patent [19]
Washburn et al.

[11] Patent Number: 5,776,983
[45] Date of Patent: Jul. 7, 1998

[54] CATECHOLAMINE SURROGATES USEFUL AS $\beta_3$ AGONISTS

[75] Inventors: William N. Washburn, Titusville; Ravindar N. Girotra, Lawrenceville; Philip M. Sher, Plainsboro, all of N.J.; Amarendra B. Mikkilineni, Easton, Pa.; Kathleen M. Poss, Lawrenceville, N.J.; Arvind Mathur, Basking Ridge, N.J.; Gregory S. Bisacchi, Ringoes, N.J.; Ashvinikumar V. Gavai, Plainsboro, N.J.

[73] Assignee: Bristol-Myers Squibb Company, Princeton, N.J.

[21] Appl. No.: 346,543

[22] Filed: Dec. 2, 1994

Related U.S. Application Data

[63] Continuation-in-part of Ser. No. 171,285, Dec. 21, 1993, abandoned.

[51] Int. Cl.[6] .......... A61K 31/18; A61K 31/22; A61K 31/275; A61K 31/38
[52] U.S. Cl. .......... 514/605; 546/226; 549/58; 549/443; 560/13; 562/430; 564/91; 564/92; 564/99; 514/330; 514/404; 514/406; 514/408; 514/443; 514/466; 514/522; 514/524; 514/539; 514/566; 514/604; 514/866; 514/909; 514/910
[58] Field of Search .......... 564/99, 92, 91; 514/605, 866, 909, 910, 330, 404, 406, 408, 443, 466, 522, 524, 539, 566, 604; 546/226; 549/58, 443; 560/13; 562/430

[56] References Cited

U.S. PATENT DOCUMENTS

| | | | |
|---|---|---|---|
| 3,341,584 | 9/1967 | Larsen et al. | 260/556 |
| 3,574,741 | 4/1971 | Gould et al. | 260/556 |
| 3,660,487 | 5/1972 | Larsen et al. | 260/556 |
| 3,689,524 | 9/1972 | Jack et al. | 260/471 |
| 3,705,233 | 12/1972 | Lunts et al. | 424/45 |
| 3,732,300 | 5/1973 | Lunts et al. | 260/559 |
| 3,803,230 | 4/1974 | Jack et al. | 260/559 |
| 3,804,899 | 4/1974 | Ebnother et al. | 260/570 |
| 3,906,110 | 9/1975 | Francis | 424/330 |
| 3,954,871 | 5/1976 | Buu-Hoi et al. | 260/570.6 |
| 4,012,444 | 3/1977 | Lunts et al. | 260/559 |
| 4,035,512 | 7/1977 | Sugihara et al. | 424/330 |
| 4,066,755 | 1/1978 | Lunts et al. | 424/230 |
| 4,338,333 | 7/1982 | Ainsworth et al. | 424/309 |
| 4,638,070 | 1/1987 | Lambelin et al. | 549/23 |
| 4,707,497 | 11/1987 | Cecchi et al. | 514/647 |
| 4,772,631 | 9/1988 | Holloway et al. | 514/539 |
| 5,061,727 | 10/1991 | Bloom et al. | 514/465 |

FOREIGN PATENT DOCUMENTS

| | | |
|---|---|---|
| A-19241/83 | 9/1983 | Australia. |
| 1204445 | 5/1986 | Canada. |
| 0 023 385 | 2/1981 | European Pat. Off.. |
| 556880 | 8/1993 | European Pat. Off.. |
| 2048555 | 4/1971 | Germany. |
| 2310142 | 9/1974 | Germany. |
| 122967 | 7/1975 | Germany. |
| 0122967 | 11/1976 | Germany. |
| 51125291 | 12/1974 | Japan. |
| 51143678 | 6/1975 | Japan. |
| 51149282 | 6/1975 | Japan. |
| 53002443 | 6/1976 | Japan. |
| 837012 | 9/1983 | South Africa. |
| 1005025 | 9/1965 | United Kingdom. |
| 1367678 | 9/1974 | United Kingdom. |

OTHER PUBLICATIONS

Larsen et al. "Sulfonanilides II, etc." *J. Med. Chem.* 10(3) 462–72 (1967).

*Primary Examiner*—Peter O'Sullivan
*Attorney, Agent, or Firm*—Burton Rodney

[57] ABSTRACT

Compounds of the formula

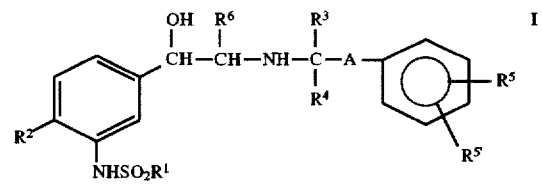

or pharmaceutically acceptable salts thereof wherein:

A is a bond, —(CH$_2$)$_n$— or —CH(B)—, where n is an integer of 1 to 3 and B is —CN, —CON(R$^9$)R$^{9'}$ or —CO$_2$R$^7$;

R$^1$ is lower alkyl, aryl or arylalkyl;

R$^2$ is hydrogen, hydroxy, alkoxy, —CH$_2$OH, cyano, —C(O)OR$^7$, —CO$_2$H, —CONH$_2$, tetrazole, —CH$_2$NH$_2$ or halogen;

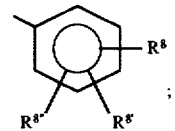

R$^3$ is hydrogen, alkyl, heterocycle or

R$^4$ is hydrogen, alkyl or B;

R$^5$, R$^{5'}$, R$^8$, R$^{8'}$ or R$^{8''}$ are independently hydrogen, alkoxy, lower alkyl, halogen, —OH, —CN, —(CH$_2$)$_n$NR$^6$COR$^7$, —CON(R$^6$)R$^{6'}$, —CON(R$^6$)OR$^{6'}$, —CO$_2$R$^6$, —SR$^7$, —SOR$^7$, —SO$_2$R$^7$, —N(R$^6$)SO$_2$R$^1$, —N(R$^6$)R$^{6'}$, —NR$^6$COR$^7$, —OCH$_2$CON(R$^6$)R$^{6'}$, —OCH$_2$CO$_2$R$^7$ or aryl; or R$^5$ and R$^{5'}$ or R$^8$ and R$^{8'}$ may together with the carbon atoms to which they are attached form an aryl or heterocycle;

R$^6$ and R$^{6'}$ are independently hydrogen or lower alkyl; and

R$^7$ is lower alkyl;

R$^9$ is hydrogen, lower alkyl, alkyl, cycloalkyl, arylalkyl, aryl, heteroaryl; or R$^9$ and R$^{9'}$ may together with the nitrogen atom to which they are attached form a heterocycle; with the proviso that when A is a bond or —(CH$_2$)$_n$ and R$^3$ is hydrogen or unsubstituted alkyl, then R$^4$ is B or substituted alkyl. These compounds are beta$_3$ adrenergic receptor agonists and are useful, therefore for example, in the treatment of diabetes, obesity and gastrointestinal diseases.

14 Claims, No Drawings

1

CATECHOLAMINE SURROGATES USEFUL AS β₃ AGONISTS

This application is a continuation-in-part of application Ser. No. 171,285, filed Dec. 21, 1993, now abandoned, which is incorporated by reference herein.

BRIEF DESCRIPTION OF THE INVENTION

The present invention is directed to compounds of the formula

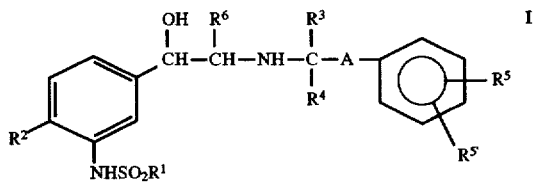

and pharmaceutically acceptable salts thereof. As used in formula I, and throughout the specification, the symbols have the following meanings:

A is a bond, —(CH$_2$)$_n$ or —CH(B)—, where n is an integer of 1 to 3 and B is —CN, —CON(R$^9$)R$^{9'}$ or —CO$_2$R$^7$;

R$^1$ is lower alkyl, aryl or arylalkyl;

R$^2$ is hydrogen, hydroxy, alkoxy, —CH$_2$OH, cyano, —C(O)OR$^7$, —CO$_2$H, —CONH$_2$, tetrazole, —CH$_2$NH$_2$ or halogen;

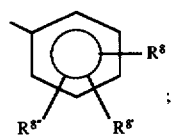

R$^3$ is hydrogen, alkyl, heterocycle or

R$^4$ is hydrogen, alkyl or B;

R$^5$, R$^{5'}$, R$^8$, R$^{8'}$ and R$^{8''}$ are independently hydrogen, alkoxy, lower alkyl, halogen, —OH, —CN, —(CH$_2$)$_n$NR$^6$COR$^7$, —CON(R$^6$)R$^{6'}$, —CON(R$^6$)OR$^{6'}$, —CO$_2$R$^6$, —SR$^7$, —SOR$^7$, —SO$_2$R$^7$, —N(R$^6$)SO$_2$R$^1$, —N(R$^6$)R$^{6'}$ —NR$^6$COR$^7$, —OCH$_2$CON(R$^6$)R$^{6'}$, —OCH$_2$CO$_2$R$^7$ or aryl; or R$^5$ and R$^{5'}$ or R$^8$ and R$^{8'}$ may together with the carbon atoms to which they are attached form an aryl or heterocycle;

R$^6$ and R$^{6'}$ are independently hydrogen or lower alkyl;

R$^7$ is lower alkyl; and

R$^9$ and R$^{9'}$ are independently hydrogen, alkyl, cycloalkyl, arylalkyl, aryl or heteroaryl; or R$^9$ and R$^{9'}$ may together with the nitrogen atom to which they are attached form a heterocycle; with the proviso that when A is a bond or —(CH$_2$)$_n$ and R$^3$ is hydrogen or unsubstituted alkyl, then R$^4$ is B or substituted alkyl.

The compounds of formula I possess activity at the beta 3 adrenergic receptor in mammals and are useful in the treatment of diabetes, obesity, gastrointestinal diseases and achalasia.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances) either individually or as part of a larger group.

The terms "alk" or "alkyl" refers to both straight and branched chain groups having 1 to 12 carbon atoms, preferably 1 to 8 carbons. It is understood, therefore, that the terms "alk" and "alkyl" denote both unsubstituted groups such as methyl, ethyl, n-propyl, iso-propyl, n-butyl, iso-butyl, sec-butyl, tert-butyl, n-pentyl, 1-methylbutyl, 2,2-dimethylbutyl, 2-methylpentyl, n-hexyl and the like as well as substituted groups. The term "substituted alkyl" specifically denotes an alkyl group as defined above having one or more of the following substituents: halo (especially to form trihaloalkyl, particularly trichloromethyl or trifluoromethyl); aryl; cycloalkyl; hydroxy; amino; thiol; or Y, where Y is —CN, alkoxy, —CON(R$^6$)R$^{6'}$, —CO$_2$R$^6$ or —N(R$^6$)SO$_2$R$^1$.

The term "lower alkyl" as employed herein includes such alkyl groups as described above containing 1 to 6 carbon atoms.

The term "alkoxy" refers to any of the above alkyl groups linked to an oxygen atom.

The term "lower alkoxy" refers to any of the above lower alkyl groups linked to an oxygen atom.

The term "aryl" refers to monocyclic or bicyclic aromatic groups containing from 6 to 10 carbons in the ring portion, such as phenyl, naphthyl, or such groups optionally substituted with one or more substituents selected from hydrogen, alkoxy, lower alkyl, halogen, —OH, —CN, —(CH$_2$)$_n$NR$^6$COR$^7$, —CON(R$^6$)R$^{6'}$, —CON(R$^6$)OR$^{6'}$, —CO$_2$R$^6$, —SR$^7$, —SOR$^7$, —SO$_2$R$^7$, —N(R$^6$)SO$_2$R$^1$, —N(R$^6$)R$^{6'}$ —NR$^6$COR$^7$, —OCH$_2$CON(R$^6$)R$^{6'}$, —OCH$_2$CO$_2$R$^7$ or aryl. Phenyl and substituted phenyl are preferred.

The term "halogen" or "halo" refers to chlorine, bromine, fluorine or iodine.

The term "heterocycle" refers to fully saturated or unsaturated rings of 5 or 6 atoms containing one or two oxygen and/or sulfur atoms and/or one to four nitrogen atoms provided that the total number of hetero atoms in the ring is four or less. Preferred monocyclic heterocycle groups include 2- and 3-thienyl, 2- and 3-furyl, 2-, 3- and 4-pyridyl and imidazolyl. The term heterocycle also includes bicyclic rings wherein the five- or six-membered ring containing oxygen and/or sulfur and/or nitrogen atoms as defined above is fused to a benzene ring and the bicyclic ring is attached by way of an available carbon atom. Preferred bicyclic heterocycle groups include 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl, 4-, 5-, 6- or 7-benzofuranzanyl, 4-, 5-, 6- or 7-benzodioxolyl and 4-, 5-, 6- or 7-benzofuran. The term "heterocycle" also includes such monocyclic and bicyclic rings wherein an available carbon atom is substituted with one or more substituents selected from nitro, keto, azo, thiazo, hydrogen, alkoxy, lower alkyl, halogen, —OH, —CN, —(CH$_2$)$_n$NR$^6$COR$^7$, —CON(R$^6$)R$^{6'}$, —CON(R$^6$) OR$^{6'}$, —CO$_2$R$^6$, —SR$^7$, —SOR$^7$, —SO$_2$R$^7$, —N(R$^6$) SO$_2$R$^1$, —N(R$^6$)R$^{6'}$ —NR$^6$COR$^7$, —OCH$_2$CON(R$^6$)R$^{6'}$, —OCH$_2$CO$_2$R$^7$ or aryl.

The compounds of formula I can be converted to salts, in particular pharmaceutically acceptable salts using art recognized procedures. If the compounds of formula I have at least one basic center, they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example trifluoroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as alkane- (of 1 to 4 carbon atoms) or arylsulfonic acids, for example methane- or p-toluenesulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form.

It should be understood that the present invention includes prodrug forms of the compounds of formula I.

The compounds of the instant invention may be in the free or hydrate form, and may be obtained by methods exemplified by the following descriptions.

Compounds of formula I can be prepared by coupling a compound having the formula II

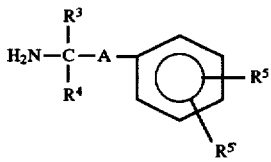

with a compound of formula III

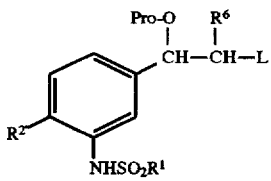

where $R^{2'}$ is hydrogen, halogen, CN, $CO_2R^7$, $CONH_2$, $CH_2OPro'$, $OR^7$ or O-Pro', optionally in the presence of an acid scavenger such as diisopropylethylamine to form a compound of formula IV

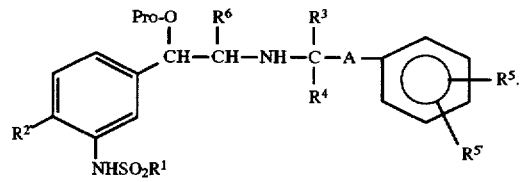

In formula III and throughout the specification, Pro is a suitable protecting group such as triethylsilyl, Pro' is a suitable protecting group such as benzyl or t-butyldimethylsilyl and L is a leaving group such as iodide, triflate, tosylate, or bromide.

Compounds of formula IV, where O-Pro is triethylsilyl are then sequentially deprotected to form compounds of formula I by first treatment with a source of fluoride such as tetrabutylammonium fluoride in a solvent such as tetrahydrofuran to remove the Pro moiety; and where $R^{2'}$ is O-benzyl, hydrogenolysis in a solvent such as methanol using a catalyst such as Pd or Raney nickel or alternatively treatment with a Lewis acid such as $BBr_3$ in a solvent such as methylene chloride to remove the O-benzyl group; and where $R^2$ is $CO_2R^7$, mild alkaline hydrolysis to generate compounds of formula I where $R^2$ is $CO_2H$; and where $R^{2'}$ is $CO_2R^7$, reduction with a reducing agent such as lithium borohydride in a solvent such as tetrahydrofuran to generate compounds of formula I where $R^2$ is $CH_2OH$; and where $R^{2'}$ is cyano, reduction with a reducing agent such as borane to generate compounds of formula I where $R^2$ is $CH_2NH_2$; and where $R^{2'}$ is cyano, treatment with an activated azide source such as trimethylsilyl azide to generate compounds of formula I where $R^2$ is tetrazole.

Alternatively, compounds of formula I may be prepared by stirring two equivalents of a compound of formula II with one equivalent of a compound of formula V

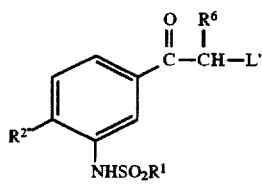

where L' is a leaving group such as bromide, iodide or chloride and $R^{2''}$ is hydrogen, hydroxyl, halogen, CN, $CO_2R^7$, $CONH_2$, $OR^7$ or O-benzyl, to form compounds of formula VI

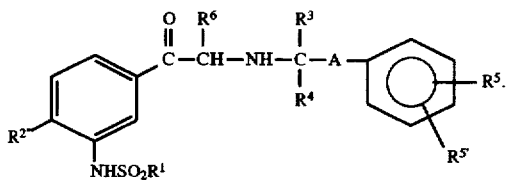

Compounds of formula VI are then converted to compounds of formula I by sequential treatment with a reducing agent such as sodium borohydride (and in the case where $R^{2''}$ is O-benzyl, subsequent hydrogenolysis using a catalyst such as Pd or Raney nickel to remove the O-benzyl group) in a solvent such as methanol; and where $R^{2''}$ is $CO_2R^7$, mild alkaline hydrolysis to generate compounds of formula I where $R^2$ is $CO_2H$; and where $R^{2''}$ is $CO_2R^7$, reduction with a reducing agent such as lithium borohydride in a solvent such as tetrahydrofuran to generate compounds of formula I where $R^2$ is $CH_2OH$; and where $R^{2''}$ is cyano, reduction with a reducing agent such as borane to generate compounds of formula I where $R^2$ is $CH_2NH_2$; and where $R^{2''}$ is cyano, treatment with an activated azide source such as trimethylsilyl azide to generate generate compounds of formula I where $R^2$ is tetrazole.

Compounds of formula I may also be prepared by sequentially heating compounds of formula II with compounds of formula IIIa

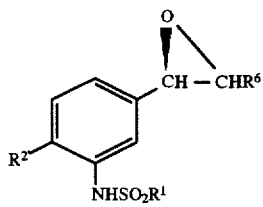

followed by, in the case where $R^{2'}$ is O-benzyl, subsequent hydrogenolysis using a catalyst such as Pd or Raney nickel to remove the O-benzyl group in a solvent such as methanol; and where $R^{2'}$ is $CO_2R^7$, mild alkaline hydrolysis to generate compounds of formula I where $R^2$ is $CO_2H$; and where $R^{2'}$ is $CO_2R^7$, reduction with a reducing agent such as lithium borohydride in a solvent such as tetrahydrofuran to generate compounds of formula I where $R^2$ is $CH_2OH$; and where $R^{2'}$ is cyano, reduction with a reducing agent such as borane to generate compounds of formula I where $R^2$ is $CH_2NH_2$; and where $R^{2'}$ is cyano, treatment with an activated azide source such as trimethylsilyl azide to generate generate compounds of formula I where $R^2$ is tetrazole.

Compounds of formula II where $R^4$ is hydrogen can be prepared by converting compounds of formula VII

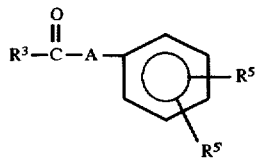

by sequential reactions entailing initial reduction using a reagent such as sodium borohydride in a solvent such as ethanol to generate compounds of formula VIII

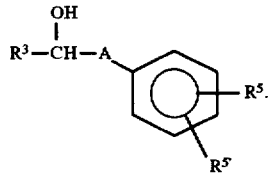

Subsequently, treatment of compounds of formula VIII with a reagent such as trimethylsilyl azide in a solvent such as methylene chloride followed by treatment with a reducing agent such as triphenylphosphine in a solvent such as tetrahydrofuran produces compounds of formula II where $R^4$ is hydrogen.

Alternatively, using standard chemistry known to those skilled in the art, compounds of formula VIII can be converted to the corresponding tosylate, chloride or bromide prior to 1) treatment with ammonia in a solvent such as tetrahydrofuran to directly produce compounds of formula II where $R^4$ is hydrogen; or 2) sequential treatment with an azide source such as lithium or sodium azide in a solvent such as aqueous ethanol followed by treatment with a reducing agent such as triphenylphosphine in a solvent such as tetrahydrofuran to produce compounds of formula II where $R^4$ is hydrogen.

Compounds of formula II where $R^3$ is

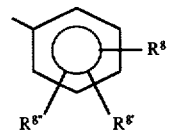

or heterocycle, A is a bond or $(CH_2)_n$ and $R^4$ is hydrogen can be prepared by fusion of a compound of formula VII with an aminating agent such as ammonium formate followed by heating with a strong mineral acid such as aqueous methanolic hydrochloric acid.

Alternatively, compounds of formula II where $R^3$ is

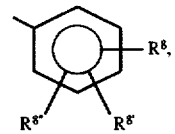

A is a bond or $(CH_2)_n$ and $R^4$ is hydrogen can be prepared by reducing compounds of formula IX

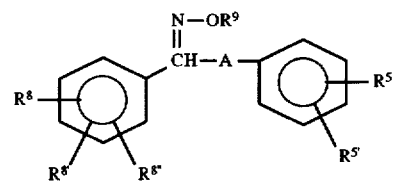

where $R^9$ in formula IX is alkyl or benzyl, with a reducing agent such as diborane.

Optically active compounds of formula II can be obtained by reduction of oxime ethers of formula IX with a preequilibrated complex of the borane and enantiomerically pure norephedrine following the procedure of Y. Sakito, Y. Yoneyoshi, G. Suzukamo, *Tet. Lett.*, 29, 223, (1988).

Compounds of formula II where $R^3$ and $R^4$ are hydrogen and A is —CH(B) are prepared by hydrogenation of compounds of formula X

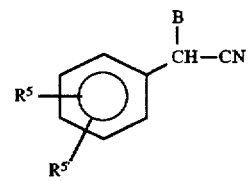

over a catalyst such as Pd in a solvent such as methanolic hydrochloric acid. Compounds of formula X may be prepared following the procedure of E. C. Horning et al., *Org. Syn. Coll.*, 4, 461 (1963).

Compounds of formula II where $R^3$ is

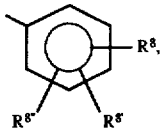

A is —CH(B), B is $CO_2Me$ and $R^4$ is hydrogen are prepared by condensation of aryl malonic acid with compounds of formula XI

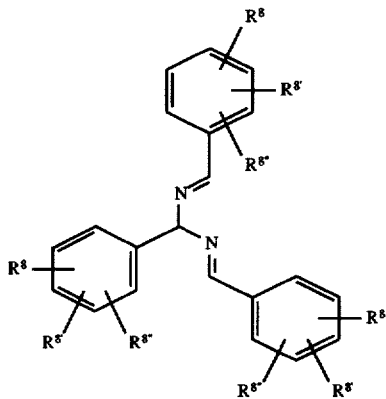

in a solvent such as ethanol followed by digestion in acidic methanol. Subsequently the above set of compounds where B is $CO_2Me$ can be converted to the corresponding set of compounds of formula II where B is —$CON(R^9)R^{9'}$ following the procedure of Weinreb et al., *Tet. Lett.*, 48, 4171 (1971) and in the case when $R^9$ and $R^{9'}$ are hydrogen, the latter ultimately to compounds of formula II where B is CN by a dehydrating agent such as phosphorous oxychloride.

Compounds of formula II where $R^3$ is

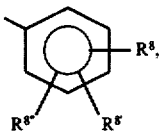

is a bond and $R^4$ is B, are prepared by treatment of benzylic acids of the formula XII

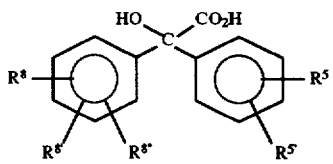

with a chlorinating agent such as thionyl chloride or phosphorous pentachloride (as described by E. Seeger, et al., U.S. Pat. No. 3,006,917) to produce compounds of formula XIII

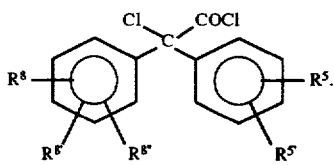

Compounds of XIII are then condensed with an amine or alcohol in a solvent such as pyridine or in diethyl ether in the presence of an acid scavenger such as a tertiary amine to produce compounds of formula XIV

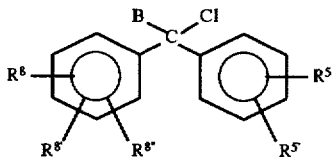

which is then treated with ammonia in a solvent such as dioxane to produce the compounds of formula II where $R^3$ is

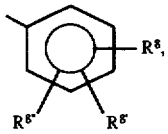

A is a bond and $R^4$ is B.

Compounds of formula II where A is a bond, $R^3$ is hydrogen and $R^4$ is B may be prepared upon sequential treatment of compounds of formula XV

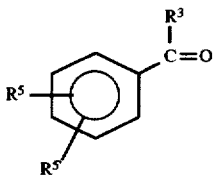

with aqueous basic ammonium cyanide followed by acid hydrolysis as described by L. B. Crast et al., U.S. Pat. No. 3,517,023 to produce compounds of formula XVI

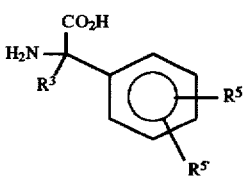

which are then converted to the compounds of formula II where A is a bond. $R^3$ is hydrogen and $R^4$ is B by using standard protocols for derivitization of amino acids.

Compounds of formula II where A is a bond, $R^3$ is alkyl and $R^4$ is B may be prepared upon sequential treatment of compounds of formula XV with aqueous sodium cyanide and ammonium carbonate followed by heating with aqueous barium hydroxide as described by C. Bernhart et al., U.S. Pat. No. 5,268,375 to produce compounds of formula XVI which are then converted to the compounds of formula II where A is a bond, $R^3$ is alkyl and $R^4$ is B by using standard protocols for derivitization of amino acids.

Compounds of formula II where $R^4$ is hydrogen, $R^3$ is a substituted alkyl, such as —$(CH_2)_pY$, where p is an integer of 3 to 7 and Y is —$CO_2R^6$ (where $R^6$ is a lower alkyl), can be prepared by heating compounds of formula XVII

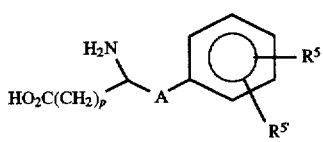

in the appropriate anhydrous alcohol in the presence of an acid catalyst such as hydrochloric acid.

Compounds of formula II. where $R^3$ is the substituted alkyl —$(CH_2)_pCH_2OH$ can be prepared from compounds of formula II where $R^3$ is —$(CH_2)_p$—$CO_2R^7$ by treatment with a reducing agent such as lithium aluminum hydride in a solvent such as tetrahydrofuran or diethyl ether.

Compounds of formula II where $R^3$ is —$(CH_2)_p$—$CON(R^6)R^{6'}$ can be prepared from compounds of formula II where $R^3$ is —$(CH_2)_p$—$CO_2R^6$ (where $R^6$ is a lower alkyl) by sequentially protecting the amine, conversion of the ester to an amide by treatment with the appropriate dimethylaluminum amide following the procedure of A. Basha, M. Lipton, S. M. Weinreb, *Tet. Lett.*, 48, 4171 (1977), and deprotection of the amine.

Alternatively, compounds of formula II where $R^4$ is hydrogen can be prepared by treating an aldehyde of formula XVIII

$R^3$—CHO sequentially with lithium hexamethyldisilazide and an organometallic compound of formula XIX

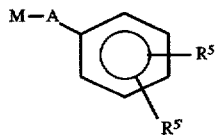

where M is a magnesium, lithium or sodium cation, in a solvent such as tetrahydrofuran following the procedure of D. Hart, et al., *J. Org. Chem.*, 48, 289 (1983).

Alternatively, following the procedures described in M.-J. Wu, et al., *J. Org. Chem.*, 56, 1340 (1991) and in M. K. Mokhallalati, et. al., *Synth. Comm.*, 23, 2055 (1993), optically active compounds of formula II where $R^4$ is hydrogen can be prepared from aldehydes of formula XVIII upon condensation with a chiral auxiliary such as optically active phenylglycinol in a solvent such as chloroform followed by addition in a solvent such as tetrahydrofuran to an organometallic of formula XX

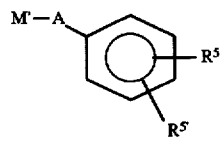

where M' is a magnesium cation which had been previously complexed with cerous chloride. Subsequent oxidation in a solvent such as methanol with an oxidant such as lead tetraacetate or sodium periodate followed by hydrolysis by heating in with a strong mineral acid such as aqueous methanolic hydrochloric acid yields compounds of formula II where $R^4$ is hydrogen.

All other compounds of formula II may be prepared by modification of the disclosed preparations using standard procedures known in the art.

Compounds of formula III where $R^6$ is hydrogen and L is bromide or iodide are prepared in high enantiomeric purity from compounds of formula V where $R^{2''}$ is hydrogen, halogen, $OR^7$, cyano, $CO_2R^7$ or O-benzyl by treatment with borane using a solvent such as tetrahydrofuran with a chiral auxillary agent such as the compound XXI

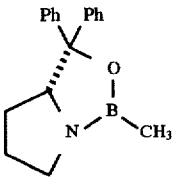

(prepared as reported by E. J. Corey et al., *J. Org. Chem.*, 56, 442 (1991)) to generate compounds of formula XXII

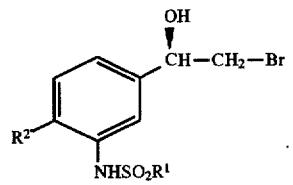

Subsequent treatment of compounds of formula XXII with an iodide source such as sodium iodide in a solvent such as hot acetone followed by reaction with a silylating agent such as triethylsilyl chloride in a solvent such as pyridine generates the compounds of formula III where L is iodide.

Compounds of formula III where $R^{2'}$ is $CH_2O$-Pro' can be prepared from compounds of formula III where $R^{2'}$ is $CO_2R^7$ upon reduction with a reducing agent such as lithium borohydride in a solvent such as tetrahydrofuran followed by treatment with a silylating agent such as t-butyldimethylsilyl chloride in a solvent such as dichloromethane in the presence of a base such as triethylamine.

Compounds of formula III where $R^6$ is hydrogen and L is triflate or tosylate may be prepared in high enantiomeric purity from compounds of formula XXIII

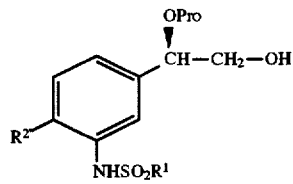

by treatment with trifluoromethanesulfonic anhydride or tosyl chloride in a solvent such as dichloromethane in the presence of a base such as pyridine.

Compounds of formula IIIa may be prepared as described hereinbelow.

Compounds of formula V where $R^{2''}$ is halogen, $OR^7$ or hydroxyl, can be obtained by treatment of a p-halophenyl alkyl ketone or p-alkoxyphenyl alkyl ketone, or p-hydroxyphenyl alkyl ketone, with a nitrating agent such as fuming nitric acid at a temperature of about −20° C. to 20° C. preferably at about −20° C. or 0° C. to generate a compound of formula XXIV

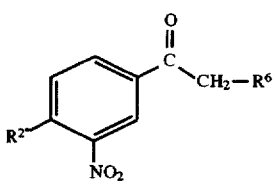

where $R^{2''}$ is hydroxy, $OR^7$, or halogen followed by, in the case of hydroxy, optional alkylation with benzyl chloride in a solvent such as dimethylformamide or acetone in the presence of a base such as potassium carbonate to generate compounds of formula XXV

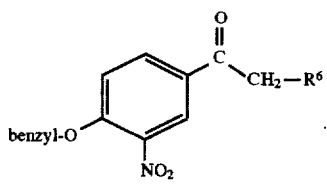

Compounds of formula XXIV where $R^{2''}$ is cyano can also be formed by heating compounds of formula XXIV where $R^{2''}$ is a halogen with cuprous cyanide in 1-methyl-2-pyrrolidinone. Compounds of formula XXIV where $R^{2''}$ is cyano can be transformed to compounds of formula XXIV where $R^{2''}$ is $CONH_2$ or $CO_2R^7$ employing procedures known to those skilled in the art.

Subsequent reduction of the compounds of formula XXIV or XXV 1) in a solvent such as methanol using hydrogen in the presence of a catalyst such as platinum oxide; or 2) heating with stannous chloride in a solvent such as ethyl acetate followed by condensation of the reaction product or of a commercially available 3-aminophenyl alkyl ketone with a sulfonyl chloride in a solvent such as pyridine, generates compounds of the formula XXVI

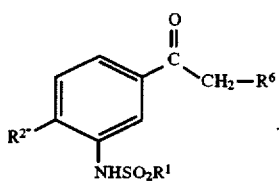

Compounds of formula XXVI where $R^{2''}$ is cyano, $CONH_2$ or $CO_2R^7$ can be prepared from compounds of formula XXVI where $R^{2''}$ is bromine by heating with a $Pd^{+2}$ catalyst and carbon monoxide in a solvent such as toluene/ aqueous NaOH as described by V. Grushin, H. Alper, *Organometallics*, 12, 1890–1901 (1993) to generate the corresponding carboxylic acid which in turn can be transformed to compounds of formula XXVI where $R^{2''}$ is cyano, $CONH_2$ or $CO_2R^7$ by employing procedures known to those skilled in the art. Compounds of formula XXVI where $R^{2''}$ is $CO_2R^7$ can be directly prepared from compounds of formula XXVI where $R^{2''}$ is bromine by the method of A. Schoenberg, I. Bartoletti, and R. F. Heck, *J. Org. Chem.*, 39, 3318–3326 (1974). Alternatively, compounds of formula XXVI where $R^{2''}$ is $OR^7$ can be prepared from compounds of formula XXVI where $R^{2''}$ is O-benzyl by sequential hydrogenolysis over a catalyst such as Pd in a solvent such as methanol, 2) conversion to the triflate upon reaction with trifluoromethanesulfonic anhydride in a solvent such as dichloromethane in the presence of a base such as pyridine, 3) heating with $Pd(OAc)_2$ and 1,2-bis(diphenyl)phosphino)

-ethane in an alcohol solvent containing a base such as triethyl amine as described by U. Gerlach, T. Wollmann, *Tetrahedron Letters*, 33, 5499–5502 (1992).

Heating of compounds of formula XXVI in a solvent such as ethyl acetate containing cupric bromide, or with bromine in tetrahydrofuran or methylene chloride generates all compounds of formula V where L' is bromine.

Compounds of formula V may also be prepared according to A. A. Larsen et al., *J. Med. Chem.*, 10, 462 (1967) or U.S. Pat. No. 3,574,741.

Compounds of formula VII where $R^3$ is

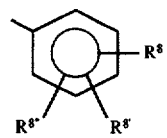

are either commercially available or may be directly prepared by coupling an arene (commercially available) represented by the formula XXVII

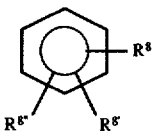

with an acid chloride of formula XXVIII

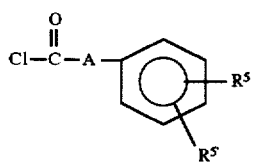

(commercially available or may be obtained by modifying commercially available compounds by art recognized procedures) in a solvent such as carbon disulfide containing a Lewis acid such as aluminum chloride or aluminum bromide.

Alternatively, the compounds of formula VII, where A is a bond or $(CH_2)_n$, may be prepared by treatment of the aldehyde of formula XVIII in a solvent such as tetrahydrofuran or diethyl ether with an organometallic compound of formula XIX to generate a compound of formula VIII which upon treatment with an oxidant such as chromic acid in a solvent such as aqueous acetone generates compounds of formula VII where A is a bond or $(CH_2)_n$.

Alternatively compounds of formula VII where A is a bond or $(CH_2)_n$ may be directly obtained by treatment of acid chlorides of formula XXIX

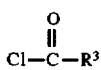

where $R^3$ is alkyl, heterocycle or

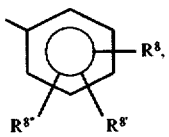

in a solvent such as tetrahydrofuran or diethyl ether with an organometallic compound of formula XXa

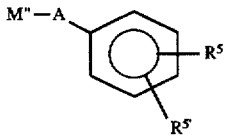

where M" is magnesium or cadmium.

Alternatively, compounds of formula XXIX can be coupled to compounds of formula XIXa

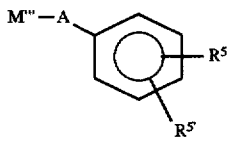

where M'" is bromide or chloride and A is $(CH_2)_n$ where n is the integer 1, in the presence of a palladium catalyst following the procedure of M. Iyoda et al., *Tet. Lett.*, 26, 4777 (1985) to produce compounds of formula VII.

Compounds of formula IX are obtained by condensation of the corresponding commercially available O-alkylated hydroxylamines with a ketone of formula VII in a solvent such as pyridine.

Compounds of formula XI were obtained by stirring compounds of formula XVIII in ethanolic ammonia (T. B. Johnson and J. E. Livak, *J. Amer. Chem. Soc.*, 58, 299, (1936)).

Compounds of formula XVII where A is $(CH_2)_n$ can be prepared by condensation of hydroxylamine with the commercially available ketones of formula XXX

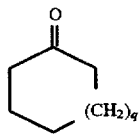

where q is an integer of 0 to 4, in a solvent such as pyridine to form compound of formula XXXI

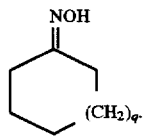

Compounds of formula XXXI are then sequentially treated in a solvent such as tetrahydrofuran with two equivalents of a strong base such as n-butyl lithium followed by compounds of formula XIXa as described by W. G. Kofron et al., *J. Org. Chem.*, 41, 439 (1976) to form compounds of formula XXXII

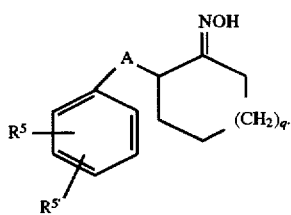

Compounds of formula XXXII are then heated in polyphosphoric acid to form compounds of formula XXXIII

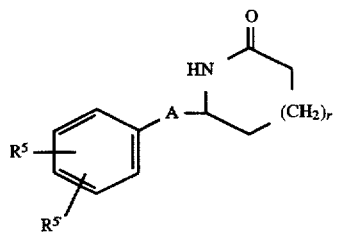

where r is an integer of 1 to 5, which are then heated in an aqueous mineral acid such as concentrated hydrochloric acid or 6M sulfuric acid to obtain the compounds of formula XVII.

Compounds of formula XVII where A is a bond can be prepared from either commercially available or readily prepared compounds of formula XXXIV

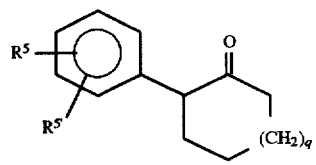

using the transformations described for conversion of XXX to XVII.

The aldehydes of formula XVIII are mostly commercially available, however, in the event that they are not available, as in the case of some heterocyclic aldehydes, the corresponding methyl substituted aromatic may be converted to the prerequisite aldehyde upon sequential bromination with a reagent such as N-bromosuccinamide, basic hydrolysis, followed by oxidation with a reagent such as manganese dioxide.

Compounds of formula XIX are commercially available or readily prepared from commercial precursors.

The compounds of formula XXIII are prepared from compounds of formula XXIV where $R^{2''}$ is not hydroxyl or compounds of formula XXV by reduction with a reducing agent such as sodium borohydride in a solvent such as ethanol, followed by alcohol elimination according to the methods described in N. A. Barba and K. F. Keptanaru, *Zhurnal Organicheskoi Khimii*, 14, 1002 (1978) to generate compounds of formula XXXV

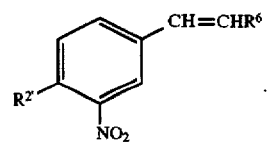

Alternatively, compounds of formula XXXV, where $R^{2''}$ is O-benzyl, can be prepared from commercially available 4-hydroxy-3-nitrobenzaldehyde by sequential benzylation and condensation with an appropriate alkylphosphorous ylid. Subsequent reduction of the nitro group forms compounds of formula XXXVI

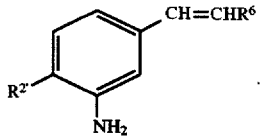

Compounds of formula XXXVI are then treated with a sulfonyl chloride in the presence of a base such as pyridine to produce the compounds of formula XXXVII

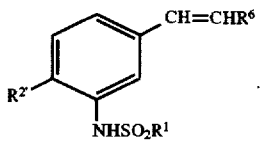

Compounds of formula XXXVII may alternatively be prepared from compounds of formula XXVI by ketone reduction and elimination as described above. Asymmetric dihydroxylation of compounds of formula XXXVII by methods of K. B. Sharpless, et al., described in *J. Org. Chem.*, 57, 2768 (1992) produces the compounds of formula XXXVIII

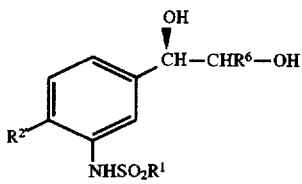

When $R^6$ is hydrogen, primary alcohol protection, for example by pivaloylation, followed by secondary alcohol protection, for example by triethylsilylation, followed by primary alcohol deprotection, for example depivaloylation by reduction with lithium aluminum hydride produces compounds of formula XXIII. Numerous general methods for alcohol protection and deprotection are described in "Protective Groups in Organic Synthesis" by T. W. Greene, John Wiley & Sons, Inc., 1981.

Alternatively, selective tosylation of the nonbenzylic alcohol of compound XXXVIII using tosyl chloride followed by benzylic alcohol protection, for example by triethylsilylation, generates the compounds of formula III.

Compounds of formula IIIa may be prepared by selective tosylation of the nonbenzylic alcohol of compound XXXVIII using tosyl chloride followed by treatment with a base such as lithium hexamethylsilazide in a solvent such as THF.

All other compounds of formula I made be prepared by modification of the above methods as known by those skilled in the art.

In any of the above reactions, it may be necessary to protect certain substituents by protecting groups as known by those skilled in the art.

Preferred compounds of formula I are those where:

A is a bond, —(CH$_2$)$_n$—, where n is 1 or —CH(B);

$R^3$ is hydrogen, alkyl or

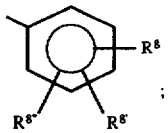

$R^5$ and $R^{5'}$ are independently hydrogen, halogen, lower alkyl, alkoxy, —CON(R$^6$)R$^{6'}$, or —CON(R$^6$)OR$^{6'}$; and the benzylic hydroxyl stereocenter has the (R) configuration.

The most preferred compounds of formula I are those where:

A is a bond;
$R^1$ is a lower alkyl;
$R^3$ is

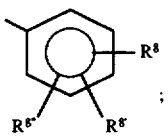

$R^4$ is hydrogen or alkyl;
$R^5$ and $R^8$ are both —CN, —CON(R$^6$)R$^{6'}$, —CON(R$^6$)OR$^{6'}$, hydroxy, alkoxy or —CH$_2$Y where Y is —CN, alkoxy, —CON(R$^6$)R$^{6'}$, —CO$_2$R$^7$ or —N(R$^6$)SO$_2$R$^1$; or
$R^5$, $R^{5'}$, $R^8$ and $R^{8'}$ together with the carbon atoms to which they are attached form an aryl or heterocycle; and the benzylic hydroxyl stereocenter has the (R) configuration;

or compounds of formula I where
A is a bond;
$R^1$ is a lower alkyl;
$R^3$ is hydrogen or alkyl;
$R^4$ is —CON(R$^9$)R$^{9'}$;
$R^5$ is —CN, —CON(R$^6$)R$^{6'}$, —CON(R$^6$)OR$^{6'}$, hydroxy or alkoxy; and the configuration of the stereocenter bearing the $R^3$ and $R^4$ substituents is (S) and the benzylic hydroxyl stereocenter has the (R) configuration;

or compounds of formula I where
A is —CH$_2$;
$R^1$ is a lower alkyl;
$R^3$ is

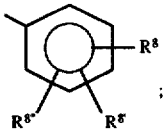

$R^4$ is hydrogen, alkyl, —CN, or —CON(R$^9$)R$^{9'}$;
$R^5$ is hydrogen, halogen or CF$_3$;
$R^8$ is —CN, —CON(R$^6$)R$^{6'}$, —CON(R$^6$)OR$^{6'}$, hydroxy, lower alkyl or alkoxy; or
$R^8$ and $R^{8'}$ together with the carbon atoms to which they are attached form an aryl or heterocycle; and the configuration of the stereocenter bearing the $R^3$ and $R^4$ substituents is (R) when $R^4$ is hydrogen and the benzylic hydroxyl stereocenter has the (R) configuration;

or compounds of formula I where

A is —CH(B), where B is —CN or —CON(R⁹)R⁹';

R¹ is a lower alkyl;

R³ and R⁴ are hydrogen or alkyl;

R⁵ is —CN, —CON(R⁶)R⁶', —CON(R⁶)OR⁶', hydroxy or alkoxy; and the benzylic hydroxyl stereocenter has the (R) configuration.

Preferred compounds of formula I are also those where the R⁶ substituent which is bonded to the group —CH(OH)—CH(R⁶)—NH— is hydrogen or unsubstituted lower alkyl.

The present compounds of formula I have activity at the beta 3 adrenergic receptor and are therefore useful, for example, in the treatment of diabetes, obesity, gastrointestinal diseases (such as inflammatory bowel disease, irritable bowel syndrome, nonspecific diarrhea, and peptic ulcer) and achalasia.

Thus a composition containing one (or a combination) of the compounds of this invention, may be administered to a species of mammal (e.g., humans) suffering from diabetes, obesity, an intestinal hypermotility disorder or achalasia as treatment therefor.

A single dose, or two to four divided daily doses, provided on a basis of about 0.1 to 100 mg per kilogram of body weight per day, preferably about 1 to 15 mg per kilogram of body weight per day is appropriate. The substance is preferably administered orally, but intranasal, transdermal and parenteral routes such as the subcutaneous, intramuscular, intravenous or intraperitoneal routes can also be employed.

The compounds of this invention can also be formulated in combination with beta₁/beta₂ adrenergic blockers such as propranolol and inadolol or stimulants such as salbutamol.

The compounds of formula I can be formulated for use in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Based on the literature, it is expected that these compounds may be useful for other indications such as treatment of depression and stress, regulation of intraocular pressure, treatment of conditions associated with increased protein breakdown such as during convalescence after surgery, treatment of triglyceridemia, hypercholesterolemia, atherosclerotic and cardiovascular diseases, and increasing high density lipoprotein levels. In addition, it is expected that these compounds may be useful as feed additives for fattening or improving weight gain or increasing lean body mass in animals and may therefore be used to decrease birth mortality and increase post-natal survival rates in animals.

In addition, based on the literature, compounds of formula I are expected to be useful for improving healing and preventing stomach ulcers (K. Kuratani et. al., *J. Pharmacol. Exp. Ther.*, 270, 559 (1994)). The compounds of formula I are also expected to be useful for regulating core temperature.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

N-|5-[2-||1-(3,4-Dimethoxyphenyl)-2-phenylethyl| amino|-1-hydroxyethyl|-2-hydroxyphenyl| methanesulfonamide

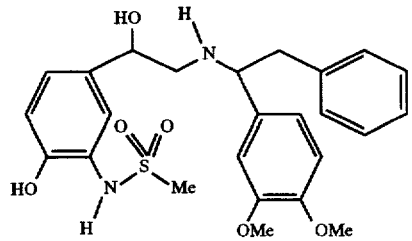

A. α-(3,4-Dimethoxyphenyl)benzeneethanol

To a 50° C. 2.0M solution of benzyl magnesium chloride in THF (9.0 mL) was added a solution of 3,4-dimethoxybenzaldehyde (3.0 g, 18.0 mmol) in THF (10 mL). After reflux for 20 minutes, the reaction mixture was quenched with an aq. NH₄Cl solution and the title compound was extracted with EtOAc (3×). The organic layer was washed with brine (2×), dried over anhydrous Na₂SO₄ and concentrated to obtain a pale yellow oil which was purified by SiO₂ column chromatography eluting with 20% EtOAc/hexanes to afford 4.2 g (16.26 mmol, 90% yield) of the title compound as a pale yellow gum which solidified upon standing at room temperature.

|   | Calc. | Found |
|---|-------|-------|
| C | 74.00 | 74.00 |
| H | 7.05  | 6.97  |

HPLC: 97% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=24.2 minutes.

B. 1-(3,4-Dimethoxyphenyl)-2-phenylethanone

To a solution of α-(3,4-dimethoxyphenyl)benzeneethanol (2.6 g, 10.06 mmol) in acetone (25 mL) was added Jones reagent (~7.0 mL) at room temperature. (The Jones reagent was prepared by dissolving CrO₃ (26.72 g) in conc. H₂SO₄ (23 mL) followed by dilution with H₂O to a volume of 100 mL). After stirring at room temperature for 20 minutes, the excess Jones reagent was quenched by the addition of i-PrOH and then diluted with EtOAc (50 mL). The solution was washed successively with 1N aq. HCl (2×), saturated aq. NaHCO₃ (2×), and brine (2×). The organic layer was dried over anhydrous Na₂SO₄ and then concentrated to obtain a pale yellow gummy material which was purified by SiO₂ column chromatography eluting with 20% EtOAc/hexanes to afford 2.3 g (8.97 mmol, 89% yield) of the title compound as a yellow solid.

|   | Calc. | Found |
|---|-------|-------|
| C | 74.38 | 74.38 |
| H | 6.33  | 6.19  |

HPLC: 94% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=25.3 minutes.

C. α-(3,4-Dimethoxyphenyl)benzeneethanamine

A mixture of 1-(3,4-dimethoxyphenyl)-2-phenylethanone (1.5 g, 5.85 mmol) and ammonium formate (3.0 g, 47.6 mmol) was heated at 160° C. for five hours. The mixture was diluted with $H_2O$ (30 mL) and the product N-[1-(3,4-dimethoxyphenyl)-2-phenylethyl]formamide was extracted with EtOAc (3×). The organic layer was washed with brine (2×), dried over anhydrous $Na_2SO_4$ and concentrated to obtain 1.75 g of material as a brown solid. This product was heated to 90° C. for 1.5 hours in MeOH (20 mL) and conc. HCl (10 mL). After cooling to room temperature, the pH was adjusted to 10.5 with an aq. NaOH solution and the compound was extracted with EtOAc (3×). The organic layer was washed with brine (3×), dried over anhydrous $Na_2SO_4$ and then concentrated to obtain a gummy material which was taken up in MeOH (5 mL) and cooled to 0° C. To this cooled solution was added a 4.0M solution of HCl in dioxane (1.5 mL) dropwise. To this mixture was added $Et_2O$ and the HCl salt of the title compound precipitated out. The precipitate was filtered, washed with $Et_2O$ and air dried to afford 1.33 g of white crystalline material (4.526 mmol, 77% yield) as the HCl salt of the title compound.

1.06 g (3.6 mmol) of the above HCl salt was dissolved in $H_2O$ (10 mL) and diluted with EtOAc (30 mL). It was then washed with a saturated solution of aq. $NaHCO_3$ (3×). The organic layer was again washed with brine (3×), dried over anhydrous $Na_2SO_4$ and then concentrated to afford 900 mg (3.497 mmol, 97% yield) of free amine (title compound) as a crystalline powder.

|   | Calc. | Found |
|---|-------|-------|
| C | 74.68 | 74.59 |
| H | 7.44  | 7.35  |
| N | 5.44  | 5.24  |

HPLC: 98% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% $H_2O$, 0.2% $H_3PO_4$) and B=90% MeOH, 10% $H_2O$, 0.2% $H_3PO_4$); retention time=16.8 minutes.

D. N-[5-[2-[[1-(3,4-Dimethoxyphenyl)-2-phenylethyl]amino]-1-hydroxyethyl]-2-(phenylmethoxy)phenyl]methanesulfonamide, trifluoroacetate salt To a solution of α-(3,4-dimethoxyphenyl)benzeneethanamine (250 mg, 0.97 mmol, 1.73 eq.) in anhydrous $CH_3CN$ (10 mL) was added a solution of 2-bromo-1-[4-phenylmethoxy-3-[(methylsulfonyl)amino]phenylethanone (prepared by a modifications (described in step F below of Example 1), of the procedure reported by A. A. Larsen et al., *J. Med. Chem.*, 10 462–472 (1967)) (360 mg, 0.56 mmol, 62% pure) in $CH_3CN$ (5 mL) at 0° C. under a nitrogen atmosphere. The mixture was then allowed to warm to room temperature (~22° C.) and stirred for 45 minutes (formation of a light brown ppt was observed). To this mixture was added a solution of $NaBH_4$ (110 mg, 2.9 mmol, 5.1 eq.) in abs. EtOH (10 mL) at room temperature. After one hour, the excess $NaBH_4$ was quenched with 1.0N HCl to pH 4.0 and then ethanolamine (0.28 mL, 4.5 mmol, ~8 eq.) was added. After stirring for ten minutes, the mixture was diluted with EtOAc (30 mL). The organic layer was washed with brine (3×), dried over anhydrous $Na_2SO_4$ and then concentrated to obtain 550 mg of material as a yellow gum which was passed through a $SiO_2$ column using 1:1 EtOAc/hexanes (v/v) to remove non-polar impurities and then 5% MeOH/$CH_2Cl_2$ to obtain 350 mg of a yellow gummy material which was contaminated with unreacted α-(3,4-dimethoxyphenyl)benzeneethanamine. This material was purified by prep HPLC eluting with 60% solvent B (Solution A=10% MeOH, 90% $H_2O$, 0.1% TFA; Solution B=90% MeOH, 10% $H_2O$, 0.1% TFA) to remove non-polar impurities and then with 90% solvent B to afford 240 mg (0.347 mmol, 62% yield) of the title compound as a yellow crystalline powder. The title compound is a racemic mixture of diastereomers.

Calculated for 1.40 mol $H_2O$ and 1.50 mol TFA:

|   | Calc. | Found |
|---|-------|-------|
| C | 54.39 | 54.20 |
| H | 5.25  | 5.25  |
| N | 3.62  | 3.91  |
| S | 4.15  | 4.15  |
| F | 11.06 | 11.06 |

HPLC: 95% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% $H_2O$, 0.2% $H_3PO_4$) and B=90% MeOH, 10% $H_2O$, 0.2% $H_3PO_4$); retention time=21.7 minutes.

E. N-[5-[2-[[1-(3,4-Dimethoxyphenyl)-2-phenylethyl]amino]-1-hydroxyethyl]-2-hydroxyphenyl]methanesulfonamide, trifluoroacetate salt N-[5-[2-[[1-(3,4-Dimethoxyphenyl)-2-phenylethyl]amino]-1-hydroxyethyl]-2-(phenylmethoxy)phenyl]methanesulfonamide, trifluoroacetate salt (220 mg, 0.38 mmol) was hydrogenated using 10% Pd/C (120 mg) and MeOH (25 mL, AR grade) at 40 psi of hydrogen in a Parr apparatus for one hour at room temperature. The catalyst was filtered through Celite and washed with MeOH. The filtrate and MeOH washings were combined and concentrated to afford 178 mg (0.37 mmol, 96% yield) of the title compound as a pale yellow crystalline powder. The title compound is a racemic mixture of diastereomers.

$^1$H NMR (270 MHz, $CD_3OD$): #33715-136-20, d 2.80–3.00 (m, 1H), 2.93 (s, 3H, $SO_2CH_3$), 3.19–3.28 (m, 1H), 3.37–3.54 (m, 2H), 3.83 (s, 3H, $OCH_3$), 3.86 (d, 3H, $OCH_3$), 4.16–4.30 (m, 1H), 4.83–5.32 (m, 1H), 6.73–6.83 (m, 3H), 6.89–7.04 (m, 4H), 7.16–7.28 (m, 4H), 7.33 (s, 2H).

$^{13}$C NMR (68 MHz, $CD_3OD$): #33715-136-20, d 39.9, 40.5, 41.0, 53.7, 53.9, 56.6, 56.8, 65.4, 66.2, 69.7, 70.2, 112.7, 112.9, 113.1, 117.0, 123.2, 124.2, 124.3, 125.6, 125.8, 126.2, 127.3, 127.6, 128.3, 129.8, 130.7, 130.9, 133.9, 137.2, 151.2, 151.6, 151.7, 151.8.

Calculated for 1.64 mol $H_2O$ and 1.50 mol TFA:

|   | Calc. | Found |
|---|-------|-------|
| C | 48.94 | 48.94 |
| H | 5.10  | 4.74  |
| N | 4.08  | 4.05  |
| S | 4.67  | 4.98  |
| F | 12.44 | 12.69 |

HPLC: 97% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% $H_2O$, 0.2% $H_3PO_4$) and B=90% MeOH, 10% $H_2O$, 0.2% $H_3PO_4$); retention time=6.1 minutes.

F. 2-Bromo-1-[4-phenylmethoxy-3-[(methylsulfonyl)amino]phenylethanone

1. 1-[4-Hydroxy-3-nitrophenyl]ethanone

To mechanically stirred conc. $H_2SO_4$ (700 mL) at 3° C. was added p-hydroxyacetophenone (66.0 g, 480 mmol)

followed by KNO$_3$ (48.3 g, 477 mmol) in two approximately equal portions about four minutes apart. An additional 3.76 g of KNO$_3$ was added after 1.67 hours to insure reaction completion. The reaction was slowly poured into 8 L crushed ice/water and extracted with 4 L ethyl acetate (EtOAc). The extract was concentrated in vacuo to a volume of ~1.25 L. 500 mL heptane were added and concentration was continued. Once a thick yellow suspension formed at 50° C., it was cooled to ~10° C. and filtered. The collected solids were washed with ~150 mL heptane and dried in vacuo at ~40° C. to give 81.8 g of the title compound.

2. 1-[4-Phenylmethoxy-3-nitrophenyl]ethanone

To a mechanically stirred DMF (260 mL) suspension of 1-[4-hydroxy-3-nitrophenyl]ethanone (51 g, 282 mmol) and K$_2$CO$_3$ (17 g, 847 mmol) was added benzyl bromide (68 mL, 572 mmol) followed by NaI (47 g, 313 mmol). After stirring overnight at 20° C., an additional 10 mL of benzyl bromide was added and stirred 15 minutes. The reaction was quenched by the addition of 1.6 L water. The resulting suspension was stirred overnight and then filtered. The collected solids were washed 3×250 mL=750 mL water and dried in vacuo at ~55° C. to give 75 g crude product which was slurried in 1.3 L toluene at ~75° C., filtered hot through a 5.0 µm membrane, concentrated in vacuo to a volume of ~300 mL, diluted with 250 mL heptane, and the suspension cooled from ~60° C. to ambient. After filtration, the collected solids were washed with heptane and dried in vacuo at ~55° C. to give 64 g (84%) of the title compound.

3. 1-[4-Phenylmethoxy-3-aminophenyl]ethanone

A mechanically stirred MeOH (3.8 L) suspension containing 1-[4-phenylmethoxy-3-nitrophenyl]ethanone (76.5 g, 282 mmol) was degassed with argon for 40 minutes at ~10° C. prior to addition of PtO$_2$ (2.34 g, 10 mmol). Hydrogen was sparged into the reaction mixture at 8°–10° C. via a subsurface gas inlet. After eight hours, the completed reaction was degassed with Ar while being warmed to ~15° C., diluted with CHCl$_3$ (250 mL) and filtered. The filtrate was stripped to give 70 g crude product which, after trituration for ten minutes with i-PrOH (450 mL) at 60° C., yielded 57.4 (84%) of the title compound.

4. 1-[4-Phenylmethoxy-3-[(methylsulfonyl)amino]phenyl]ethanone

To a mechanically stirred 16° C. pyridine (270 mL) solution of 1-[4-phenylmethoxy-3-aminophenyl]ethanone (57.4 g, 238 mmol) under N$_2$, was added methanesulfonyl chloride (18.6 mL, 240 mmol). After 39 minutes, the completed reaction was quenched with 1.8 L H$_2$O and the resulting suspension stirred for ~2 hours before filtration. The collected solids were washed with H$_2$O (2×250 mL=500 mL) and partially air dried. These solids were dissolved in CHCl$_3$ (450 mL), the water phase removed and heptane (475 mL) added with stirring. The resulting fine suspension was filtered after ~15 minutes, washed with hexane and dried in vacuo at 55° C. to give 59 g (78%) of the title compound.

5. 2-Bromo-1-[4-phenylmethoxy-3-[(methylsulfonyl)amino]phenyl]ethanone

To a mechanically stirred refluxing EtOAc (500 mL) suspension of CuBr$_2$ (41.5 g, 186 mmol) equipped with an Ar sparge was added a ~62° C. CHCl$_3$ (500 mL) solution of 1-[4-phenylmethoxy-3-[(methylsulfonyl)amino]phenyl]ethanone (25.5 g, 80 mmol). After 5.5 hours of reflux, HPLC showed 11.2 rel. area % unreacted starting material, 78.9 rel. area % of desired product and 9.8 rel. area % of dibrominated product. After cooling to 62° C. and dilution with 500 mL CHCl$_3$, the suspension was filtered hot and the filtrate concentrated to a volume of ~850 mL prior to addition of 250 mL heptane. The flocculent suspension was cooled to ~10° C. and filtered, washed with heptane and air-dried overnight to give 23.1 g (73%) of the title compound in 73% purity.

G. Alternative method for preparation of α-(3,4-dimethoxyphenyl)benzeneethanamine, hydrochloride salt 1. 1-(3,4-Dimethoxyphenyl)-2-phenylethanone, O-phenylmethyloxime A mixture of 1-(3,4-dimethoxyphenyl)-2-phenylethanone (2.3 g, 9 mmol) and O-(phenylmethyl)hydroxylamine, hydrochloride salt (1.57 g, 9.8 mmol) in pyridine (10 mL) and abs. EtOH (30 mL) was stirred at reflux for 1.5 hours. After concentration in vacuo, EtOAc (50 mL) was added. The organic layer was washed with brine (2×), dried over anhydrous Na$_2$SO$_4$ and concentrated to obtain a yellow gummy material which was purified by SiO$_2$ column chromatography eluting with 20% EtOAc/hexanes to afford 3.1 g (8.57 mmol, 96% yield) of the title compound as a yellow gum which solidified upon standing at room temperature for two hours.

Calculated for 0.42 mol H$_2$O:

|   | Calc. | Found |
|---|---|---|
| C | 74.85 | 74.49 |
| H | 6.51 | 6.28 |
| N | 3.80 | 4.16 |

HPLC: 69% pure, Shimadzu LC-6A, YMC S3 ODS (6.0× 150 mm); flow rate of 1.5 mL/minute; detection at 220 nm; gradient elution 0–100%: 10% MeOH, 90% H$_2$O, 0.2% H$_3$PO$_4$ to 90% MeOH, 10% H$_2$O, 0.2% H$_3$PO$_4$; 30 minutes; retention time=33.6 minutes.

2. α-(3,4-Dimethoxyphenyl)benzeneethanamine, hydrochloride salt

To a solution of 1-(3,4-dimethoxyphenyl)-2-phenylethanone, O-phenylmethyloxime (1.4 g, 3.87 mmol) in anhydrous THF (20 mL) was added a 1.0M solution of BH$_3$.THF complex (11.0 mL) at room temperature under N$_2$. After stirring at reflux for 1.25 hours, the reaction was quenched with 1.0N aq. HCl. The pH was adjusted to 10 with 1.0N NaOH and the amine was extracted with EtOAc (3×15 mL). The organic layer was washed with brine (3×), dried over anhydrous Na$_2$SO$_4$ and then concentrated to obtain a gummy residue which was dissolved in a minimum amount of MeOH. This solution was cooled to 0° C. and a 4.0M solution of HCl in dioxane (1.5 mL) was added dropwise. The resulting solution was diluted with anhydrous Et$_2$O. The precipitate was filtered, washed with Et$_2$O and air dried to afford 770 mg (2.62 mmol, 68% yield) of the title compound as a white crystalline powder.

|   | Calc. | Found |
|---|---|---|
| C | 64.83 | 65.28 |
| H | 6.83 | 6.91 |
| N | 4.73 | 4.28 |
| Cl | 12.80 | 12.97 |

HPLC: 96% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=16.7 minutes.

EXAMPLE 2

N-[5-[2-[(1,2-Diphenylethyl)amino]-1-hydroxyethyl]-2-hydroxyphenyl]methanesulfonamide, trifluoroacetate salt

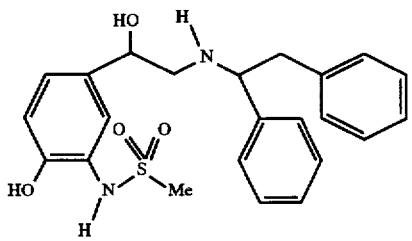

The title compound was prepared from commercially available 1,2-diphenylethylamine following the procedures described in steps D and E of Example 1, except for the following modifications: the solvent used during the prep HPLC purification of step D was 64% solvent B and after step E, the final product was purified by prep HPLC using 48% solvent B.

$^1$H NMR (270 MHz, CD$_3$OD): δ 2.80–3.00 (m, 1H), 2.93 (s, 3H, SO$_2$CH$_3$), 3.0–3.28 (m, 1H), 3.4–3.7 (m, 2H), 4.4–4.6 (m, 1H), 4.7–4.85 (m, 1H), 6.8–7.4 (m, 13H, aromatic).

$^{13}$C NMR (68 MHz, CD$_3$OD): δ 39.5, 40.664, 41.0, 53.586, 65.383, 66.02, 69.50, 69.969, 116.59, 118.57, 124.282, 124.37, 125.2, 125.4, 126.07, 128.09, 129.56, 129.67, 130.13, 130.33, 130.74, 133.512, 136.599, 154.511, 162.327.

Mass (M+H) 427

Calculated for 0.7 mol H$_2$O and 0.2 mol TFA:

|   | Calc. | Found |
|---|-------|-------|
| C | 52.97 | 52.97 |
| H | 5.00  | 4.74  |
| N | 4.86  | 4.74  |
| S | 5.57  | 5.37  |
| F | 11.87 | 11.83 |

HPLC: >99% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=18.8 minutes.

EXAMPLE 3

N-[5-[2-[[1-(1,3-Benzodioxol-5-yl)-2-phenylethyl]amino]-1-hydroxyethyl]-2-hydroxyphenyl]methanesulfonamide, trifluoroacetate salt

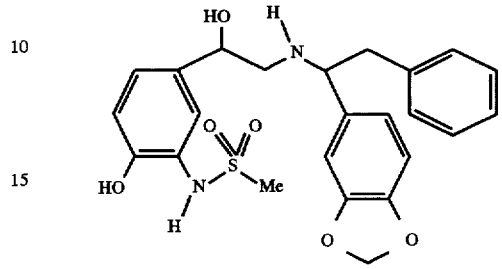

Commercially available 3,4-methylenedioxyphenylcarboxaldehyde was converted to the title compound following the procedures described in steps A–E of Example 1, except for the following modifications: 1) in step C, the amination reaction time was 16 hours. The acidic hydrolysis reaction, after dilution with H$_2$O, was extracted 2× with Et$_2$O prior to basification, extraction 3× with EtOAc and isolation of the desired amine after concentration; 2) the prep HPLC purification of step D used 65% solvent B; and 3) in step E, the final product was purified by prep HPLC using 47% solvent B as eluant.

$^1$H NMR (270 MHz, CD$_3$OD): δ 2.80–3.00 (m, 1H), 2.9 (s, 3H, SO$_2$CH$_3$), 3.1–3.28 (m, 1H), 3.2–3.7 (m, 2H), 4.4–4.6 (m, 1H), 4.5–4.7 (m, 1H), 6.0 (s, 2H), 6.8–7.4 (m, 11H, aromatic).

$^{13}$C NMR (68 MHz, CD$_3$OD): δ 41.77, 42.80, 43.01, 55.58, 67.7, 68.02, 72.6, 72.9, 105.17, 110.99, 111.68, 118.81, 126.34, 126.42, 127.46, 130.20, 130.32, 131.7, 132.51, 135.68.

Mass (M+H) 471

Calculated for 0.8 mol H$_2$O and 1.25 mol TFA:

|   | Calc. | Found |
|---|-------|-------|
| C | 50.73 | 50.72 |
| H | 4.63  | 4.48  |
| N | 4.46  | 4.64  |
| S | 5.11  | 4.86  |
| F | 11.35 | 11.27 |

HPLC: >99% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=18.5 minutes.

EXAMPLE 4

N-[5-[1-Hydroxy-2-[[1-(4-methoxyphenyl)-2-phenylethyl]amino]ethyl]-2-hydroxyphenyl]methanesulfonamide, trifluoroacetate salt

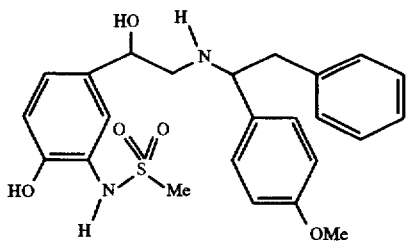

Commercially available 4-methoxybenzaldehyde was converted to the title compound following steps A–E described in Example 1, except for the following modifications: 1) in step C, the amination reaction time was 16 hours. The acidic hydrolysis reaction, after dilution with $H_2O$, was extracted 2× with $Et_2O$ prior to basification, extraction 3× with EtOAc and isolation of the desired amine after concentration; 2) the prep HPLC purification of step D used 65% solvent B; and 3) in step E, the final product was purified by prep HPLC using 47% solvent B as eluant.

$^1$H NMR (270 MHz, $CD_3OD$): δ 2.80–3.00 (m, 1H), 2.9 (s, 3H, $SO_2CH_3$), 3.2–3.28 (m, 1H), 3.2–3.7 (m, 2H), 3.8 (s, 3H), 4.4–4.6 (m, 1H), 4.7–5.0 (m, 1H), 6.8–7.4 (m, 12H, aromatic).

$^{13}$C NMR (68 MHz, $CD_3OD$): δ 38.03, 39.8, 52.5, 55.3, 63.25, 65.2, 66.2, 67.4, 114.3, 115.8, 121.4, 124.5, 124.9, 125.1, 126.3, 126.2, 127.11, 128.4, 129.8, 132.8, 135.1, 148.2, 161.4.

Mass (M+H) 457

Calculated for 0.75 mol $H_2O$ and 1.2 mol TFA:

|   | Calc. | Found |
|---|-------|-------|
| C | 52.25 | 52.30 |
| H | 5.10  | 5.04  |
| N | 4.62  | 4.85  |
| S | 5.28  | 5.54  |
| F | 11.27 | 11.48 |

HPLC: >99% pure, Shimadzu LC-6A, YMC S3 ODS (6.0×150 mm); flow rate of 1.5 mL/minute; detection at 220 nm; gradient elution 0–100% B over 30 minutes (A=10% MeOH, 90% $H_2O$, 0.2% $H_3PO_4$); B=90% MeOH, 10% $H_2O$, 0.2% $H_3PO_4$); retention time=18.9 minutes.

EXAMPLE 5

N-[5-[2-[[1-(3-Methoxyphenyl)-2-phenylethyl]amino]-1-hydroxyethyl]-2-hydroxyphenyl]methanesulfonamide, trifluoroacetate salt

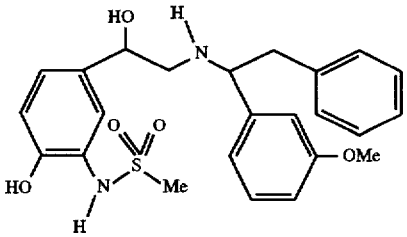

A. 2-Bromo-1-[4-hydroxy-3-[(methylsulfonyl)amino]phenyl]ethanone 1. 1-[3-Amino-4-hydroxy]phenylethanone, hydrochloride salt A stirred suspension of Raney nickel (11 g) in THF (170 mL) containing 1-[4-hydroxy-3-nitrophenyl]ethanone (16.5 g, 91 mmol; preparation described in step F of Example 1) was sparged with $H_2$ for several hours until the reaction was complete. The reaction suspension was filtered through celite, chilled to 0° C. and acidified by adding conc. HCl (8.3 mL). The precipitate was collected by filtration and air-dried to yield 13.2 g (77%).

2. 1-[4-Hydroxy-3-[(methylsulfonyl)amino]phenylethanone

To a stirred 15° C. pyridine (30 mL) solution of 1-[3-amino-4-hydroxyphenyl]ethanone, hydrochloride salt (13.0 g, 69.5 mmol) was added methanesulfonyl chloride (8.0 g, 69.5 mmol) over 50 minutes. After stirring overnight at 20° C., the reaction was poured into ice-water (250 mL) and the precipitate collected by filtration. The solid, after washing with $H_2O$ and i-PrOH, was air-dried to yield the title compound (9.9 g, 62%).

3. 2-Bromo-1-[4-hydroxy-3-[(methylsulfonyl)amino]phenyl]ethanone

To a stirred 60° C. dioxane (35 mL) solution of 1-[4-hydroxy-3-[(methylsulfonyl)amino]phenyl]ethanone (2.06 g, 8.7 mmol) was rapidly added $Br_2$ (1.48 g, 9.2 mmol). After one hour, the solution was cooled, concentrated and diluted with $H_2O$. After filtration, the product was washed thoroughly with $H_2O$, then with i-PrOH (9 mL), and air-dried to obtain the title compound (2.43 g, 84%).

$^1$H NMR (270 MHz, $CDCl_3$ with a little DMSO-$d_6$): δ 2.99 (s, 3H, $SO_2CH_3$), 4.47 (s, 2H), 7.02 (d, 1H), 7.71 (dd, 1H), 8.00 (d, 1H), 8.16 (s, 1H), 10.64 (s, 1H).

HPLC: Shimadzu, YMC S3 ODS (6.0×150 mm); flow rate of 1.5 mL/minute; detection at 217 nm; eluted with a 40 minutes linear gradient of 0% to 100% B solvent (A=10% MeOH, 90% $H_2O$, 0.2% $H_3PO_4$, B=90% MeOH, 10% $H_2O$, 0.2% $H_3PO_4$); retention time=19.1 minutes.

B. N-[5-[2-[[1-(3-Methoxyphenyl)-2-phenylethyl]amino]-1-hydroxyethyl]-2-hydroxyphenyl]methanesulfonamide, trifluoroacetate salt Commercially available 3-methoxybenzaldehyde was converted to α-(3-methoxyphenyl)benzeneethanamine following the procedures described in steps A–C of Example 1, except for the following modifications: 1) the reaction time in step A was three hours; 2) the column chromatography of step B was omitted; and 3) in step C, the acidic reaction mixture, after dilution with $H_2O$, was extracted 3× with EtOAc prior to basification, extraction 5× with $CH_2Cl_2$ and isolation of the desired amine after concentration.

To a stirred 60° C. MeCN (1 mL) containing α-(3-methoxyphenyl)benzene-ethanamine (800 mg, 3.5 mmol) was added 2-bromo-1-[4-hydroxy-3-|(methylsulfonyl)amino]phenyl]ethanone (522 mg, 1.7 mmol). After ten minutes, the completed reaction was cooled to 20° C. and an EtOH (30 mL) solution of NaBH$_4$ (665 mg, 17.5 mmol) added. After 30 minutes, the reaction was quenched with 1N aq. HCl to pH 1, then made alkaline and extracted 3× with CH$_2$Cl$_2$. After drying over Na$_2$SO$_4$ and concentration, the residue was chromatographed on silica gel using 5% of 10% conc. aq. NH$_4$OH/MeOH in CH$_2$Cl$_2$ as eluant. The title compound was isolated as the TFA salt (70 mg) after lyophilization.

$^1$H NMR (270 MHz, CD$_3$OD): δ 2.7–3.6 (m, 7H), 3.8 (s, 3H, OCH$_3$), 4.6–4.75 (m, 1H), 4.7–5.0 (m, 1H), 6.8–7.4 (m, 12H).

$^{13}$C NMR (68 MHz, CD$_3$OD): δ 40.1, 40.8, 41.2, 54.1, 54.3, 56.3, 65.8, 66.5, 70.0, 70.5, 115.5, 115.7, 116.6, 117.1, 122.7, 124.7, 124.9, 125.7, 125.9, 126.6, 128.6, 130.0, 130.8, 131.9, 134.1, 136.9, 137.2, 152.1, 162.2.

Mass (M+H) 457

Calculated for 1.1 mol TFA:

|   | Calc. | Found |
|---|-------|-------|
| C | 54.07 | 54.46 |
| H | 5.04  | 5.11  |
| N | 4.81  | 5.10  |
| F | 10.77 | 10.47 |
| S | 5.51  | 5.66  |

HPLC: >99% pure, Shimadzu LC-6A, YMC S3 ODS (6.0× 150 mm); flow rate of 1.5 mL/minute; detection at 217 nm; gradient elution 0–100% B over 25 minutes(A=10% MeOH, 90% H$_2$O, 0.2% H$_3$PO$_4$, B=90% MeOH, 10% H$_2$O, 0.2% H$_3$PO$_4$); retention time=17 minutes.

EXAMPLE 6

N-[5-[2-[[1-(2,4-Dimethoxyphenyl)-2-phenylethyl]amino]-1-hydroxyethyl]-2-hydroxyphenyl]methanesulfonamide

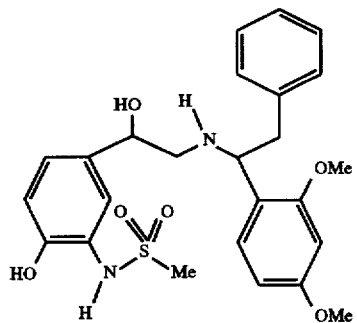

Commercially available 2,4-dimethoxybenzaldehyde was converted to α-(2,4-dimethoxyphenyl)benzeneethanamine following the procedures described in steps A–C of Example 1. The title compound was prepared from α-(2,4-dimethoxyphenyl)benzeneethanamine following the procedure described in step B of Example 5, except for isolation, after chromatography, as the free base.

$^1$H NMR (270 MHz, CDCl$_3$): δ 2.4–3.0 (m, 4H), 3.0–3.2 (m, 2H), 3.6–3.9 (m, 7H), 4.1–4.2 (m, 1H), 4.4–4.6 (m, 1H), 5.2–5.5 (s (broad), 4H, NH, OH), 6.3–6.4 (m, 2H), 6.7–7.2 (m, 9H).

$^{13}$C NMR (68 MHz, CDCl$_3$): δ 38.8, 41.4, 41.5, 53.4, 53.5, 55.29, 55.37, 55.43, 60.5, 70.1, 71.4, 77.5, 98.8, 104.3, 104.4, 116.9, 120.6, 121.3, 124.2, 124.4, 124.9, 126.2, 128.2, 129.6, 132.7, 132.8, 138.3, 138.5, 150.1, 158.2, 158.3, 160.2, 160.4.

Mass (M+H) 487

Calculated for 0.89 mol H$_2$O:

|   | Calc. | Found |
|---|-------|-------|
| C | 59.75 | 59.64 |
| H | 6.37  | 6.08  |
| N | 5.57  | 5.68  |
| S | 6.38  | 5.99  |

HPLC: >99% pure, Shimadzu LC-6A, YMC S3 ODS (6.0× 150 mm); flow rate of 1.5 mL/minute; detection at 217 nm; gradient elution 0–100% B over 25 minutes (A=10% MeOH, 90% H$_2$O, 0.2% H$_3$PO$_4$; B=90% MeOH, 10% H$_2$O, 0.2% H$_3$PO$_4$); retention time=18 minutes.

EXAMPLE 7

N-[5-[2-[[1-(3,4-Dichlorophenyl)-2-phenylethyl]amino]-1-hydroxyethyl]-2-hydroxyphenyl]methanesulfonamide, trifluoroacetate salt

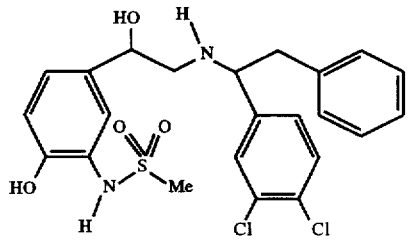

Commercially available 3,4-dichlorobenzaldehyde was converted to α-(3,4-dichlorophenyl)benzeneethanamine following the procedures described in steps A–C of Example 1 except for the following modifications of step C: the amination reaction was terminated after six days at 180° C. despite being incomplete. The formamide hydrolysis reaction time was four days. Upon completion, the acidic reaction mixture, after dilution with H$_2$O, was extracted 3× with EtOAc prior to basification, extraction 5× with CH$_2$Cl$_2$ and isolation of the desired amine after concentration.

The title compound was prepared from α-(3,4-dichlorophenyl)benzeneethanamine following the procedure described in step B of Example 5, except for reduction with excess NaCNBH$_4$ for five days at pH 2 and purification by prep HPLC using 75% solvent B as the eluant.

$^1$H NMR (270 MHz, CD$_3$OD): δ 2.8–3.0 (m, 4H), 3.1–3.6, (m, 3H), 4.5–4.6 (m, 1H), 4.7–5.0 (m, 1H), 6.8–6.9 (m, 1H), 7.0–7.1 (m, 3H), 7.1–7.4 (m, 5H), 7.5–7.7 (m, 2H).

Mass (M+H) 495

HPLC: ~82% pure, Shimadzu LC-6A, YMC S3 ODS (6.0× 150 mm); flow rate of 1.5 mL/minute; detection at 217 nm; gradient elution 0–100% B over 60 minutes (A=10% MeOH, 90% H$_2$O, 0.2% H$_3$PO$_4$; B=90% MeOH, 10% H$_2$O, 0.2% H$_3$PO$_4$); retention time=40 minutes.

EXAMPLE 8

N-[5-[2-[[1-(4-Methylsulfonylphenyl)-2-phenylethyl]amino]-1-hydroxyethyl]-2-hydroxyphenyl]methanesulfonamide

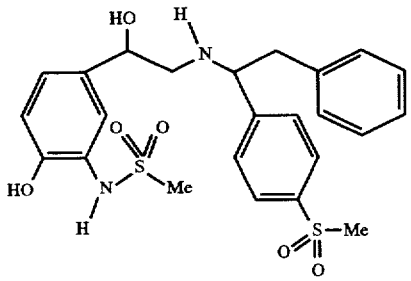

A. α-(4-Methylsulfonylphenyl)benzeneethanol

Commercially available 4-methylthiobenzaldehyde was converted to α-(4-methylthiophenyl)benzeneethanol, following the procedure described in step A of Example 1.

To a stirred pH 8 solution of $KH_2PO_4$ (5.0 g, 0.037 mmol) and $K_2HPO_4$ (42 g, 0.24 mmol) in $H_2O$ (500 mL) at 0° C., was added a $CH_2Cl_2$ (300 mL) solution containing α-(4-methylthiophenyl)benzeneethanol (14.2 g, 58 mmol). To this heterogeneous mixture was added m-chloroperbenzoic acid ~75% pure (42 g, 182 mmol). The reaction was complete after 20 minutes. The precipitate was filtered and washed with $CH_2Cl_2$. The combined organic layer of the filtrate was washed sequentially with 1M aq. $Na_2S_2O_3$ (200 mL), 1M aq. $NaHCO_3$ (100 mL), and 1M aq. NaOH (200 mL) prior to drying over $Na_2SO_4$. After concentration, 17.4 g (98%) of the title compound was obtained as a white solid.

B. N-[5-[2-[[1-(4-Methylsulfonylphenyl)-2-phenylethyl]amino]-1-hydroxyethyl]-2-(hydroxy)phenyl]methanesulfonamide The title compound was prepared from α-(4-methylsulfonylphenyl)benzeneethanol, following the procedures described in steps B–D of Example 1, except for the following modifications: the HPLC chromatographic purification of step D of Example 1 was omitted. The resulting N-[5-[2-[[1-(4-methylsulfonylphenyl)-2-phenylethyl]amino]-1-hydroxyethyl]-2-(phenylmethoxy)phenyl]methanesulfonamide was converted to N-[5-[2-[[1-(4-methylsulfonylphenyl)-2-phenylethyl]amino]-1-hydroxyethyl]-2-(hydroxy)phenyl]methanesulfonamide by treatment with $BBr_3$.

To a stirred −78° C. $CH_2Cl_2$ solution (10 mL) under argon containing N-[5-[2-[[1-(4-methylsulfonylphenyl)-2-phenylethyl]amino]-1-hydroxyethyl]-2-(phenylmethoxy)phenyl]methanesulfonamide 0.21 g, 0.34 mmol), was added a 1M $BBr_3/CH_2Cl_2$ solution (0.9 mL, 0.9 mmol). The solution was stirred for 20 minutes, warmed to 0° C., and stirred for 20 minutes. After quenching with $H_2O$, the pH was adjusted to ~9 and the mixture was extracted with EtOAc 5× before drying over $Na_2SO_4$. After concentration the crude product was chromatographed on silica gel using 2–10% of 10% conc. aq. $NH_4OH/MeOH$ in $CH_2Cl_2$ to elute 115 mg (67%) of the title compound.

$^1H$ NMR (270 MHz, $CD_3OD$): δ 2.40–2.65 (m, 2H), 2.80–3.10 (m, 2H), 2.90 (s, 3H, $SO_2CH_3$), 3.10 (s, 3H $SO_2CH_3$), 3.98–4.05 (m, 1H), 4.50–4.65 (m, 1H), 6.75–7.30 (m, 8H), 7.45–7.55 (m, 2H), 7.80–7.90 (m, 2H).

$^{13}C$ NMR (68 MHz, $CD_3OD$): δ 39.5, 44.4, 45.2, 45.3, 55.5, 56.0, 65.1, 65.9, 72.7, 73.4, 116.3, 124.3, 125.5, 125.6, 125.7, 127.5, 127.6, 128.4, 129.4, 129.5, 129.7, 130.3, 130.4, 135.8, 139.1, 140.7, 150.9.

Mass (M+H) 505
Calculated for 0.78 mol $H_2O$:

|   | Calc. | Found |
|---|-------|-------|
| C | 55.58 | 55.94 |
| H | 5.74  | 5.84  |
| N | 5.40  | 5.40  |
| S | 12.36 | 12.00 |

HPLC: >99% pure, Shimadzu LC-6A, YMC S3 ODS (6.0× 150 mm); flow rate of 1.5 mL/minute; detection at 220 nm; gradient elution 0–100% B over 40 minutes (A=10% MeOH, 90% $H_2O$, 0.2% $H_3PO_4$; B=90% MeOH, 10% $H_2O$, 0.2% $H_3PO_4$); retention time=18.7 minutes.

EXAMPLE 9

N-[5-[2-[[1-(3,4-Dimethylphenyl)-2-phenylethyl]amino]-1-hydroxyethyl]-2-hydroxyphenyl]methanesulfonamide, trifluoroacetate salt

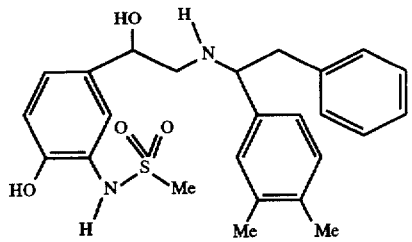

A. 1-(3,4-Dimethylphenyl)-2-phenylethanone

To a stirred suspension of $AlCl_3$ (7.0 g, 52 mmol) in $CS_2$ (20 mL) was added dropwise a $CS_2$ (10 mL) solution containing o-xylene (5.0 g, 47 mmol) and phenylacetyl chloride (7.29 g, 47 mmol) at such a rate that an ice bath could maintain the temperature at 20° C. After two hours, the reaction was poured onto mixture of 200 g of ice and NaOH (58 g) and extracted 2× with EtOAc (75 mL). The combined EtOAc fractions were washed 2× with $H_2O$ (50 mL), 2× with saturated aq. $Na_2CO_3$ (50 mL), and 2× with brine (50 mL). After drying over $Na_2SO_4$ and concentration, 10.1 g (96%) of the title compound was obtained as a yellow solid.

B. N-[5-[2-[[1-(3,4-Dimethylphenyl)-2-phenylethyl]amino]-1-hydroxyethyl]-2-hydroxyphenyl]methanesulfonamide 1-(3,4-dimethylphenyl)-2-phenylethanone was converted to the title compound following the procedures outlined in steps C–E of Example 1, except for the following modifications: 1) step C was modified to include chromatography on silica gel using 2:1 hexane/EtOAc elute the formamide prior to acid hydrolysis; 2) in step C, the acidic hydrolysis reaction, after dilution with $H_2O$, was extracted 2× with $Et_2O$ prior to basification, extraction 3× with EtOAc and isolation of the desired amine after concentration; and 3) in step D, the product was eluted from silica gel with 1:1 hexane/EtOAc; the prep HPLC purification utilized 75% solvent B as the eluant.

$^1H$ NMR (270 MHz, $CD_3OD$): δ 2.23 (s, 6H, —$CH_3$), 2.90 (d, 3H, —$SO_2CH_3$), 2.74–2.85 (m, 1H), 2.95–3.10 (m, 1H), 4.37–4.48 (m, 1H), 4.68 & 4.72 (dd, 1H), 6.82 & 6.87 (2d, 1H), 6.99–7.17 (m, 9H), 7.25 & 7.29 (2d, 1H).

$^{13}C$ NMR (67 MHz, $CD_3OD$): δ 19.6, 19.8, 39.6, 40.2, 40.6, 53.4, 53.7, 65.2, 65.9, 69.5, 70.0, 116.6, 124.3, 124.4, 125.2, 125.4, 126.1, 127.0, 128.1, 129.6, 130.4, 130.6, 130.8, 131.5, 132.1, 132.5, 133.6, 136.9, 139.0, 139.6, 151.6, 151.7.

Mass (M+H) 455

Calculated for 1.73 mol H$_2$O and 1.29 mol TFA:

|   | Calc. | Found |
|---|-------|-------|
| C | 52.37 | 52.37 |
| H | 5.54  | 4.90  |
| N | 4.43  | 4.39  |
| S | 5.07  | 5.39  |
| F | 11.58 | 11.57 |

HPLC: >99% pure. Shimadzu LC-6A, YMC S3 ODS (6.0× 150 mm); flow rate of 1.5 mL/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=24.0 minutes.

EXAMPLE 10

N-[5-[2-[[1-(3,4-Diethylphenyl)-2-phenylethyl]amino]-1-hydroxyethyl]-2-hydroxyphenyl]methanesulfonamide, trifluoroacetate salt

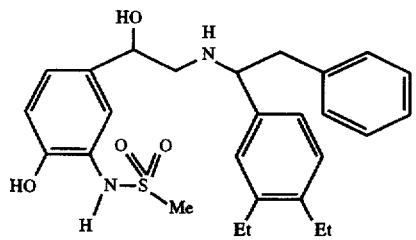

1-(3,4-Diethylphenyl)-2-phenylethanone was prepared from o-diethylbenzene using the method described in step A of Example 9. 1-(3,4-Diethylphenyl)-2-phenylethanone was converted to the title compound following the procedures outlined in steps C–E of Example 1, except for the following modifications: 1) in step C, the amination reaction time was 12 hours. The product was chromatographed on silica gel using 2:1 hexane/EtOAc elute the formamide prior to acid hydrolysis. The acidic hydrolysis reaction, after dilution with H$_2$O, was extracted 2× with Et$_2$O prior to basification, extraction 3× with EtOAc and isolation of the desired amine after concentration; and 2) in step D, the product was eluted from silica gel with 1:1 hexane/EtOAc; the prep HPLC purification utilized 98% solvent B as the eluant.

$^1$H NMR (270 MHz, CD$_3$OD): δ 1.08–1.20 (m, 6H, —CH$_2$CH$_3$), 2.55–2.65 (m, 4H, —CH$_2$CH$_3$), 2.85 (s, 3H, —SO$_2$CH$_3$), 2.75–3.1 (m, 2H), 3.45–3.55 (m, 1H), 4.35–4.51 (m, 1H), 4.70–4.80 (m, 1H), 6.80–7.30 (m, 11H).

$^{13}$C NMR (67 MHz, CD$_3$OD): δ 15.5, 15.8, 26.1, 26.3, 39.6, 40.8, 53.4, 65.2, 69.4, 116.6, 124.2, 125.2,126.8, 129.5, 129.6, 130.3, 130.4, 133.5, 136.4, 144.9, 145.2, 151.8.

Mass (M+H) 483

Calculated for 1.23 mol H$_2$O and 1.07 mol TFA:

|   | Calc. | Found |
|---|-------|-------|
| C | 55.84 | 55.83 |
| H | 6.03  | 6.05  |
| N | 4.47  | 4.19  |
| S | 5.11  | 4.74  |
| F | 9.73  | 9.72  |

HPLC: 100% pure. Shimadzu LC-6A, YMC S3 ODS (6.0× 150 mm); flow rate of 1.5 mL/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=27.1 minutes.

EXAMPLE 11

N-[5-[2-[[1-Phenyl-2-(3,4-dimethoxyphenyl)ethyl]amino]-1-hydroxyethyl]-2-hydroxyphenyl]methanesulfonamide, trifluoroacetate salt

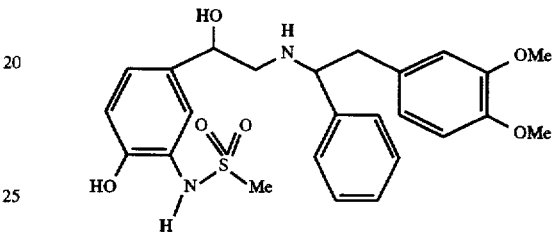

1-Phenyl-2-(3,4-dimethoxyphenyl)ethanone was prepared from benzene and 3,4-dimethoxyphenylacetyl chloride (prepared by heating the commercially available carboxylic acid in thionyl chloride and subsequent concentration) using the method described in step A of Example 9, except that the crude ketone was chromatographed on silica gel using 70% hexane/EtOAc as the eluant. 1-Phenyl-2-(3,4-dimethoxyphenyl)ethanone was converted to the title compound following the procedures outlined in steps C–E of Example 1, except for the following modifications: In step C the formamide was chromatographed on silica gel using EtOAc as eluant prior to acid hydrolysis thereby obviating the amine purification procedure. The prep HPLC purification was omitted in step D but the title compound obtained after step E was purified by prep HPLC using 38% solvent B as the eluant.

$^1$H NMR (270 MHz, CD$_3$OD): δ 2.80 (m, 1H)), 2.88 (s, 1.2H, —SO$_2$CH$_3$), 2.90 (s, 1.8H, —SO$_2$CH$_3$), 3.05 (m, 1H), 3.22 (m, 1H), 3.47 (m, 1H), 3.62 (s, 3H), 3.73 (s, 3H), 4.45 (m, 1H), 4.75–4.90 (m, 1H), 6.50 (m, 1H), 6.60 (m, 1H), 6.75 (m, 1H), 6.85 (m, 1H), 6.99 (m, 1H), 7.26–7.41 (m, 6H).

$^{13}$C NMR (67 MHz, CD$_3$OD): δ 38.06, 39.0, 52.0, 52.4, 54.74, 54.81, 62.6, 63.2, 65.6, 66.2, 111.3, 112.6, 115.0, 121.4, 122.9, 123.5, 124.2, 128.13, 128.19, 128.8, 129.2, 132.0, 148.0, 144.6.

Mass (M+H) 487

Calculated for 1.68 mol H$_2$O and 1.8 mol TFA:

|   | Calc. | Found |
|---|-------|-------|
| C | 47.57 | 47.57 |
| H | 4.91  | 4.67  |
| N | 3.88  | 3.89  |
| S | 4.44  | 4.42  |
| F | 14.21 | 14.13 |

HPLC: 96% pure. Shimadzu LC-6A, YMC S3 ODS (6.0× 150 mm); flow rate of 1.5 mL/minute; detection at 220 nm;

gradient elution 0–100% B over 30 minutes (A=10% MeOH, 90% H₂O, 0.2% H₃PO₄); B=90% MeOH, 10% H₂O, 0.2% H₃PO₄); retention time=16.6 minutes.

EXAMPLE 12

N-[5-[2-[[1-Phenyl-2-(4-methoxyphenyl)ethyl]amino]-1-hydroxyethyl]-2-hydroxyphenyl]methanesulfonamide, trifluoroacetate salt

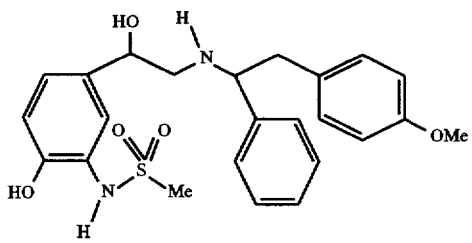

1-Phenyl-2-(4-methoxyphenyl)ethanone was prepared from benzene and 4-methoxyphenylacetyl chloride (prepared by heating the commercially available carboxylic acid in thionyl chloride and subsequent concentration) using the method described in step A of Example 9. 1-Phenyl-2-(4-methoxyphenyl)ethanone was converted to the title compound following the procedures outlined in steps C–E of Example 1, except for the following modifications: 1) in step C, the acidic hydrolysis reaction, after dilution with H₂O, was extracted 2× with Et₂O prior to basification, extraction 3× with EtOAc and isolation of the desired amine after concentration; 2) the prep HPLC purification of step D was omitted; and 3) in step E, the final product was purified by prep HPLC using 46% solvent B as eluant.

¹H NMR (270 MHz, CD₃OD): δ 2.80 (m, 1H)), 2.88 (s, 1.5H, —SO₂CH₃), 2.90 (s, 1.5H, —SO₂CH₃), 3.05 (m, 1H), 3.22 (m, 1H), 3.47 (m, 1H), 3.68 (s, 3H), 4.45 (m, 1H), 4.75–4.90 (m, 1H), 6.50 (m, 1H), 6.79 (dd, 4H), 6.85 (m, 1H), 6.99 (m, 1H), 7.26–7.41 (m, 6H).

¹³C NMR (67 MHz, CD₃OD): δ 37.95, 38.06,38.38, 52.08, 52.27, 54.05, 64.0, 64.7, 68.0, 68.5, 113.4, 115.0, 122.8,122.9, 123.7, 123.9, 124.5, 124.56, 126.9, 126.94, 128.1, 128.8, 129.2, 129.9, 132.0, 133.6, 133.9, 150.11, 150.16, 158.6.

Mass (M+H) 456

Calculated for 0.9 mol H₂O and 1.4 mol TFA:

|   | Calc. | Found |
|---|-------|-------|
| C | 50.90 | 50.90 |
| H | 4.97  | 4.77  |
| N | 4.43  | 4.46  |
| S | 5.07  | 5.34  |
| F | 12.62 | 12.29 |

HPLC: 93% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=18.3 minutes.

EXAMPLE 13

N-[5-[2-[[1-(4-Methoxyphenyl)-2-(4-methoxyphenyl)ethyl]amino]-1-hydroxyethyl]-2-hydroxyphenyl]methanesulfonamide, trifluoroacetate salt

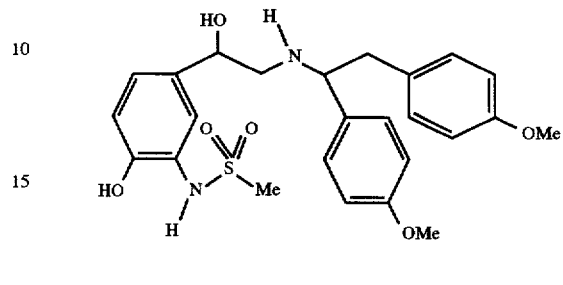

1-(4-Methoxyphenyl)-2-(4-methoxyphenyl)ethanone was prepared from anisole and 4-methoxyphenylacetyl chloride (prepared by heating the commercially available carboxylic acid in thionyl chloride and subsequent concentration) using the method described in step A of Example 9. After step A, the product was chromatographed on silica gel using 3:2 hexane/EtOAc as eluant. 1-(4-methoxyphenyl)-2-(4-methoxyphenyl)ethanone was converted to the title compound following the procedures described in steps C–E of Example 1, except for the following modifications: 1) in step C, the acidic hydrolysis reaction, after dilution with H₂O, was extracted 2× with Et₂O prior to basification, extraction 3× with EtOAc and isolation of the desired amine after concentration; and 2) the prep HPLC purification of step D utilized 65% solvent B as eluant.

¹H NMR (270 MHz, CD₃OD): δ 2.80 (m, 1H)), 2.88 (s, 1.6H, —SO₂CH₃), 2.90 (s, 1.4H, —SO₂CH₃), 3.05 (m, 1H), 3.22 (m, 1H), 3.47 (m, 1H), 3.69 (s, 3H), 3.776 (s, 1.6H), 3.77 (s, 1.4H), 4.45 (m, 1H), 4.75–4.90 (m, 1H), 6.77 (d, 1H), 6.9 (m, 6H), 7.26–7.41 (m, 3H).

¹³C NMR (67 MHz, CD₃OD): δ 37.86, 38.06,38.26, 51.85, 52.08, 54.05, 54.26, 63.55, 64.0, 67.94, 68.5, 113.4, 114.1, 115.0, 122.8, 122.9, 123.7, 123.9, 125.0, 125.2, 125.8, 126.1, 126.4, 127.2, 129.5, 129.6, 129.9, 132.1, 150.1, 158.6, 161.0.

Mass (M+H) 486

Calculated for 1.1 mol H₂O and 1.2 mol TFA:

|   | Calc. | Found |
|---|-------|-------|
| C | 51.16 | 51.17 |
| H | 5.23  | 4.92  |
| N | 4.36  | 4.22  |
| S | 4.98  | 4.79  |
| F | 10.63 | 10.65 |

HPLC: 99% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=18.8 minutes.

EXAMPLE 14

N-[5-[2-[[bis(4-Methoxyphenyl)methyl]amino]-1-hydroxyethyl]-2-hydroxyphenyl]methanesulfonamide, trifluoroacetate salt

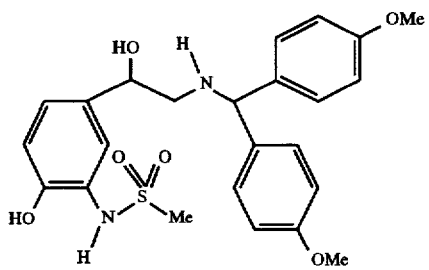

The title compound was prepared from commercially available 4,4'-dimethoxybenzophenone following the procedures described in steps C–E of Example 1, except for the following modifications: 1) in step C, the acidic hydrolysis reaction, after dilution with $H_2O$, was extracted 2× with $Et_2O$ prior to basification, extraction 3× with EtOAc and isolation of the desired amine after concentration; 2) in step D, the product was eluted from silica gel with 1:4 hexane/EtOAc; the prep HPLC purification was omitted; and 3) the product of step E was purified by prep HPLC utilizing 45% solvent B as the eluant.

$^1$H NMR (270 MHz, $CD_3OD$): δ 2.90 (s, 3H, —$SO_2CH_3$), 3.01 (d, J=6.45 Hz, 2H), 3.80 (d, 6H, —$OCH_3$), 5.5 (s, 1H), 6.85 (d, J=8.21 Hz, 1H), 7.00 (m,5H), 7.30 (d, 1H), 7.43 (m, 4H).

$^{13}$C NMR (67 MHz, $CD_3OD$): δ 39.6, 54.1, 55.9, 66.2, 69.6, 115.7, 115.8, 116.6, 124.3, 125.3, 126.1, 128.7, 129.1, 130.2, 130.5, 133.7, 151.7, 161.7.

Mass (M+H) 473

Calculated for 1.87 mol $H_2O$ and 1.08 mol TFA:

|   | Calc. | Found |
|---|-------|-------|
| C | 49.92 | 49.92 |
| H | 5.26  | 4.73  |
| N | 4.45  | 4.81  |
| S | 5.09  | 5.22  |
| F | 9.78  | 9.76  |

HPLC: 100% pure, Shimadzu LC-6A, YMC S3 ODS (6.0× 150 mm); flow rate of 1.5 mL/minute; detection at 220 nm; gradient elution 0–100% B over 35 minutes (A=10% MeOH, 90% $H_2O$, 0.2% $H_3PO_4$); B=90% MeOH, 10% $H_2O$, 0.2% $H_3PO_4$); retention time=20.6 minutes.

EXAMPLE 15

N-[5-[1-Hydroxy-2-[[(4-methoxyphenyl)phenylmethyl]amino]ethyl]-2-hydroxyphenyl]methanesulfonamide, trifluoroacetate salt

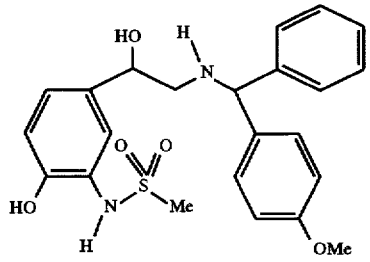

4-Methoxybenzophenone was prepared from anisole and benzoyl chloride following the procedure of step A of Example 9. The title compound was prepared from 4-methoxybenzophenone following the procedures described for steps C–E of Example 1, except for the following modifications: 1) in step C, the amination reaction time was nine hours. The acidic hydrolysis reaction, after dilution with $H_2O$, was extracted 2× with $Et_2O$ prior to basification, extraction 3× with EtOAc and isolation of the desired amine after concentration; 2) in step D, the product was eluted from silica gel with 1:1 hexane/EtOAc; the prep HPLC purification was omitted; and 3) the product of step E was purified by prep HPLC utilizing 41% solvent B as the eluant.

$^1$H NMR (270 MHz, $CD_3OD$): δ 2.90 (s, 3H, —$SO_2CH_3$), 3.02 (d, 2H), 3.80 (d, 3H, $OCH_3$), 5.75 (s, 1H), 6.85 (d,1H), 7.00 (m, 4H), 7.30 (d, 1H), 7.45 (m, 5H).

$^{13}$C NMR (67 MHz, $CD_3OD$): δ 39.5, 54.2, 56.0, 65.1, 69.5, 116.8, 117.7, 124.4, 125.3, 126.6, 128.6, 128.9, 130.1, 130.5, 131.3, 133.5, 137.2, 137.4, 152.3, 162.4.

Mass (M+H) 443

Calculated for 1.08 mol $H_2O$ and 1.15 mol TFA:

|   | Calc  | Found |
|---|-------|-------|
| C | 51.23 | 51.24 |
| H | 4.98  | 4.32  |
| N | 4.72  | 5.18  |
| S | 5.41  | 5.53  |
| F | 11.05 | 11.12 |

HPLC: 100% pure, Shimadzu LC-6A, YMC S3 ODS (6.0× 150 mm); flow rate of 1.5 mL/minute; detection at 220 nm; gradient elution 0–100% B over 35 minutes (A=10% MeOH, 90% $H_2O$, 0.2% $H_3PO_4$); B=90% MeOH, 10% $H_2O$, 0.2% $H_3PO_4$); retention time=19.8 minutes.

EXAMPLE 16

α-|||2-Hydroxy-2-|4-hydroxy-3-|(methylsulfonyl)
amino|phenyl|ethyl|amino]methyl|benzeneacetic
acid, ethyl ester, trifluoroacetate salt

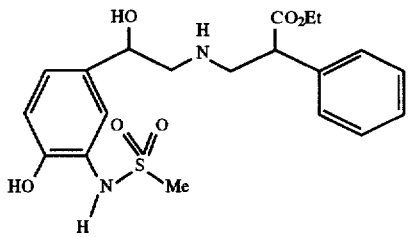

The title compound was prepared from α-(aminomethyl)
benzeneacetic acid, ethyl ester (preparation described in L.
Fontanella et al., Chem. Ber., 639, 157, (1961)) utilizing the
procedures described in steps D and E of Example 1. In step
D, the eluant for the prep HPLC was 55% solvent B. In step
E, the title compound was purified using prep HPLC using
50% solvent B as the eluant.

$^1$H NMR (270 MHz, CD$_3$OD): δ 1.173 (t, 1.5H), 1.179 (t, 1.5H), 2.90 (s, 3H), 3.1–3.345 (m, 3H), 3.80 (m, 1H), 4.2 (m, 3H), 4.93 (m, 1H), 6.90 (d, 1H), 7.13 (m, 1H), 7.38 (m, 5H).

$^{13}$C NMR (67 MHz, CD$_3$OD): δ 12.7,38.08, 54.0, 54.1, 61.5, 67.8, 115.1, 122.9, 124.0, 124.6, 127.5, 127.6, 128.1, 128.9, 131.9, 134.9, 135.0, 150.2, 171.4.

Mass (M+H) 422

Calculated for 0.3 mol H$_2$O and 1.0 mol TFA:

|   | Calc. | Found |
|---|-------|-------|
| C | 48.76 | 48.37 |
| H | 5.13  | 4.92  |
| N | 5.17  | 5.21  |
| S | 5.92  | 5.84  |
| F | 10.52 | 10.94 |

HPLC: 98% pure, Shimadzu LC-6A, YMC S3 ODS (6.0× 150 mm); flow rate of 1.5 mL/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention times=15.2 and 15.3 minutes.

EXAMPLE 17

α-|||2-Hydroxy-2-|4-hydroxy-3-|(methylsulfonyl)
amino|phenyl|ethyl]amino|methyl]-3,4-
dimethoxybenzeneacetic acid, methyl ester,
trifluoroacetate salt

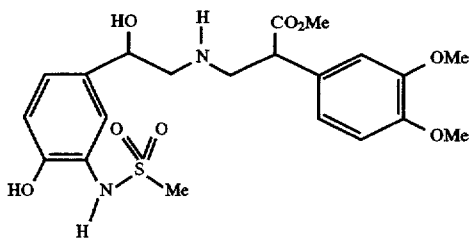

A. Methyl 3,4-dimethoxyphenylcyanoacetate

To a THF (10 mL) suspension of KH (1.8 g, 45 mmol) under N$_2$ was added dropwise a dimethyl carbonate (20 mL) solution of 3,4-dimethoxyphenylacetonitrile (5.3 g, 31 mmol) (preparation described by V. K. Mangla et al., Ind. J. Chem., 19, 748, (1980)). After five hours at 20° C., the reaction was quenched by addition of ice, diluted with H$_2$O, the pH adjusted to ~7, and extracted 4× with EtOAc. After drying over Na$_2$SO$_4$ prior to concentration, the product was chromatographed on silica gel using CH$_2$Cl$_2$ to elute 7.5 g (100%) of the title compound.

B. α-(Aminomethyl)-3,4-dimethoxybenzeneacetic acid, methyl ester

A MeOH solution (100 mL) containing methyl 3,4-dimethoxyphenylcyanoacetate (1.2 g, 5.1 mmol), TFA (1 mL), and 50 mg of 10% Pd/C was shaken on a Parr shaker for 20 hours under 30 psi of hydrogen. The reaction was filtered, concentrated, dissolved in H$_2$O, and extracted 2× with Et$_2$O. The pH was adjusted to ~10 and the mixture extracted 3× with EtOAc. The EtOAc fractions were dried over Na$_2$SO$_4$ and concentrated to yield 400 mg (32%) of the title compound.

C. α-[|[2-Hydroxy-2-[4-hydroxy-3-|(methylsulfonyl) amino|phenyl|ethyl]amino|methyl|-3,4- dimethoxybenzeneacetic acid, methyl ester The title compound was prepared from α-(aminomethyl)-3,4-dimethoxybenzeneacetic acid, methyl ester utilizing the procedures described in steps D and E of Example 1, except for the following modifications: 1) the prep HPLC purification of step D was omitted; and 2) in step E, the final product was purified by prep HPLC using 26% solvent B as eluant.

$^1$H NMR (270 MHz, CD$_3$OD): δ 2.90 (s, 3H), 3.1–3.35 (m, 3H), 3.7 (s, 3H), 3.75 (m, 1H), 3.811 (s, 3H), 3.813 (s, 3H), 4.1 (m, 1H), 4.90 (m, 1H), 6.86 (m, 4H), 7.13 (d, 1H), 7.38 (s, 1H).

$^{13}$C NMR (67 MHz, CD$_3$OD): δ 38.07, 51.07, 53.8, 53.81, 54.97, 55.0, 67.8, 111.2, 111.9, 115.1, 120.1, 120.2, 122.9, 124.0, 127.2, 149.9, 150.1, 151.2, 172.

Mass (M+H) 468

Calculated for 0.7 mol H$_2$O and 1.5 mol TFA:

|   | Calc. | Found |
|---|-------|-------|
| C | 44.20 | 44.23 |
| H | 4.78  | 4.76  |
| N | 4.30  | 4.45  |
| S | 4.92  | 5.10  |
| F | 13.11 | 12.79 |

HPLC: 98% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=12.3 minutes.

EXAMPLE 18

α-[[[2-Hydroxy-2-[4-hydroxy-3-[(methylsulfonyl)
amino]phenyl]ethyl]amino]methyl]-N,N-
dimethylbenzeneacetamide, trifluoroacetate salt

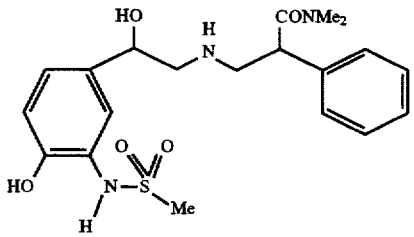

A. α-[[(Trifluoroacetyl)amino]methyl]benzeneacetic acid, ethyl ester

To a stirred EtOAc (20 mL) suspension of α-(aminomethyl)benzeneacetic acid, ethyl ester, HCl salt (1.2 g, 5.2 mmol) (preparation described in Example 16) was added sequentially trifluoroacetic anhydride (1.8 g, 9 mmol) and Et$_3$N (3 mL). After one hour, the reaction was quenched with H$_2$O and extracted 2× with EtOAc. The EtOAc fractions were washed pH 4 NaH$_2$PO$_4$ buffer, aq. NaHCO$_3$, brine, dried over Na$_2$SO$_4$, and concentrated to yield 1.4 g (94%) of the title compound.

B. α-(Aminomethyl)-N,N-dimethylbenzeneacetamide

To a stirred 4° C. CH$_2$Cl$_2$ solution (5 mL) containing HNMe$_2$ (180 mg, 4 mmol) under N$_2$, was added 2M AlMe$_3$ in toluene (2 mL, 4 mmol). The reaction was warmed to 20° C. and stirred for five minutes before adding a CH$_2$Cl$_2$ solution (4 mL) containing α-[[(trifluoroacetyl)amino] methyl]benzeneacetic acid, ethyl ester (600 mg, 2.1 mmol). After two days, the reaction was quenched with 1 N aq. HCl, and extracted 3× with EtOAc. The EtOAc fractions were washed with brine, dried over Na$_2$SO$_4$, and concentrated. The crude product was chromatographed on silica gel using 4:1 hexane/EtOAc to elute 380 mg (63%) of the desired trifluoroacetamide which was heated to 60° C. for five hours in MeOH (2 mL) containing 1N aq. NaOH (3 mL). The reaction was diluted with brine, extracted 4× with EtOAc, dried over Na$_2$SO$_4$, and concentrated to yield the title compound as a clear oil (280 mg, 74%).

C. α-[[[2-Hydroxy-2-[4-hydroxy-3-[(methylsulfonyl) amino]phenyl]ethyl]amino]methyl]-N,N-dimethylbenzeneacetamide The title compound was prepared from α-(aminomethyl)-N,N-dimethylbenzeneacetamide utilizing the procedures described in steps D and E of Example 1. The following modifications were made in steps D and E: The prep HPLC purification of step D was omitted. In step E, the final product was purified by prep HPLC using 27% solvent B as eluant.

$^1$H NMR (270 MHz, CD$_3$OD): δ 2.844 (s,1.5H), 2.85 (s, 1.5H), 2.90 (s, 3H), 2.96 (s, 1.5H), 2.98 (s, 1.5H), 3.1–3.345 (m, 3H), 3.63 (m, 1H), 4.4 (m, 1H), 4.93 (m, 1H), 6.90 (d, 1H), 7.13 (d, 1H), 7.29–7.45 (m, 6H).

$^{13}$C NMR (67 MHz, CD$_3$OD): δ 34.7, 35.9, 38.08, 45.6, 45.7, 50.7, 50.8, 54.0, 54.1, 67.76, 67.79, 115.1, 122.6, 124.0, 124.6, 127.5, 127.6, 128.0, 129.2, 131.9, 134.9, 150.6, 171.4.

Mass (M+H) 421
Calculated for 0.88 mol H$_2$O and 1.22 mol TFA:

|   | Calc. | Found |
|---|-------|-------|
| C | 46.75 | 46.76 |
| H | 5.24  | 5.08  |
| N | 7.29  | 7.29  |
| S | 5.56  | 5.47  |
| F | 12.06 | 12.08 |

HPLC: 100% pure. Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention times=13.1 and 13.2 minutes.

EXAMPLE 19

(R),(R)-N-[5-[1-(Hydroxy-2-[[1-(3,4-
dimethoxyphenyl)-2-phenylethyl]amino]ethyl]-2-
(hydroxy)phenyl]methanesulfonamide,
trifluoroacetate salt A. 1-(3,4-Dimethoxyphenyl)-2-phenylethanone, O-methyloxime A mixture of 1-(3,4-dimethoxyphenyl)-2-phenylethanone (7.3 g, 28.5 mmol) (preparation described in step B of Example 1) and O-methylhydroxylamine, hydrochloride salt (3.1 g, 37.11 mmol) in pyridine (20 mL) and abs. EtOH (100 mL) was stirred at reflux for 1.5 hours. After concentration in vacuo, the residue in EtOAc (200 mL) was washed with brine (2×), dried over anhydrous Na$_2$SO$_4$ and concentrated to obtain a 1:6 mixture of the syn/anti isomers, which were separated on a prep HPLC C$_{18}$ column eluting with 86% solvent B (solvent A=10% MeOH, 90% H$_2$O; solvent B=90% MeOH, 10% H$_2$O) to afford 1.1 g (3.85 mmol, 13.5% yield) of the syn oxime as a yellow gum and 6.34 g (22.22 mmol, 78% yield) of the anti oxime as a crystalline material.

Mass (M+H) 286; (M–H)$^-$@ 284.

|   | Calc. | Found |
|---|-------|-------|
| C | 71.56 | 71.31 |
| H | 6.71  | 6.67  |
| N | 4.91  | 4.79  |

HPLC: 98.8% pure. Shimadzu LC-6A, YMC S3 ODS (6.0×150 mm); flow rate of 1.5 mL/minute; detection at 220 nm; gradient elution 0–100% B over 30 minutes. (A=10% MeOH, 90% H$_2$O, 0.2% H$_3$PO$_4$); B=90% MeOH, 10% H$_2$O, 0.2% H$_3$PO$_4$); retention time=29.6 minutes.

B. (R)-α-(3,4-Dimethyoxyphenyl)benzeneethanamine

To a cooled (0° C.) solution of L-(+)-norephedrine (7.95 g, 52.6 mmol, 2.5 eq.) in anhydrous THF (75 mL) was added 1.0M solution of BH$_3$-THF complex (105 mL) under nitrogen. After warming to 20° C. and stirring for 15 minutes, anti-1-(3,4-dimethoxyphenyl)-2-phenylethanone, O-methyloxime (6.0 g, 21 mmol) in THF (10 mL) was added and the reaction refluxed for 25 minutes. The reaction was concentrated to dryness after sufficient 1.0N aq. HCl was added to adjust the pH to 2.5. The residue was dissolved in water, the pH was adjusted to 10 with 1.0N aq. NaOH and the solution was extracted with ether (4×). The organic layer was washed with brine (3×), dried over Na$_2$SO$_4$ and then concentrated to obtain 14 g of pale yellow gum. The residue, dissolved in minimum amount of MeOH, was cooled to 0°

C. and acidified to pH 2 with 4.0M solution of HCl in dioxane. After dilution with Et$_2$O, the precipitate was collected by filtration, dissolved in water and washed with Et$_2$O (4×). The pH of the aqueous phase was adjusted to 11 with aq. NaOH and extracted with EtOAc (3×). The organic layer was washed with brine, dried over anhydrous Na$_2$SO$_4$ and then concentrated to dryness to furnish 5.4 g of pale yellow gum. This gum was purified by SiO$_2$ column using 1:1 EtOAc/hexanes to obtain 2.6 g which upon recrystalization from hexanes gave 2.2 g (8.54 mmol, 40.5%) of the title compound with an ee of 89.18%.

Mass (M+H) 258, (M−H) 256, |α|$_D$=−72.9° (c=0.72, MeOH)

|   | Calc. | Found |
|---|---|---|
| C | 74.39 | 74.18 |
| H | 7.80 | 7.48 |
| N | 5.42 | 5.45 |

HPLC: 99.3% pure. Shimadzu LC-6A, YMC S3 ODS (6.0×150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=15.6 minutes.

C. (R)-N-[5-[2-Iodo-1-[(triethylsilyl)oxy]ethyl]-2-(phenylmethoxy)phenyl]methanesulfonamide 1. (R)-2-Bromo-1-[4-phenylmethoxy-3-[(methylsulfonyl)amino]phenyl]ethanol A 25 mL round bottom flask with magnetic stirbar and toluene-filled Dean-Stark trap with reflux condenser and gas bubbler, was charged with (R)-α,α-diphenyl-2-pyrrolidinemethanol (1.13 g, 4.46 mmol) and trimethylboroxine (418 μL, 2.99 mmol) in toluene (11 mL) under N$_2$. The reaction was stirred at ambient for ~30 minutes and then heated to reflux for 2.75 hours. Upon cooling, this solution was added to a stirred ~13° C. THF (185 mL) solution under N$_2$ containing 2-bromo-1-[4-phenylmethoxy-3-[(methylsulfonyl)amino]phenyl]ethanone (14.25 g, 36 mmol) prepared as described in step F of Example 1. To this was added 5.2 mL of 10.1M BH$_3$-Me$_2$S/THF (52 mmol) over ~5 minutes, keeping T≤−11.6° C. Upon completion of the reaction, HBr was bubbled through the solution until the pH was ~1 whereupon a solution of 50 mL MeOH in 100 mL methyl tert-butyl ether was carefully added. The mixture was washed with H$_2$O (4×100 mL=400 mL) (until final wash had pH~4–5), diluted with EtOAc (50 mL), dried over Na$_2$SO$_4$. After solvent removal in vacuo, 12.84 g (90%) of crude title compound was obtained in 86% purity with an ee of 96.9%.

2. (R)-2-Iodo-1-[4-phenylmethoxy-3-[(methylsulfonyl)amino]phenyl]ethanol

A mixture of (R)-2-bromo-1-[4-phenylmethoxy-3-[(methylsulfonyl)amino]phenyl]ethanol (12.4 g, 31 mmol) and NaI (52 g, 346 mmol) were refluxed in acetone (190 mL) for 1.75 hours. After filtration, the filtrate was concentrated to a pasty red-brown solid which was partitioned between CH$_2$Cl$_2$ (150 mL)/H$_2$O (190 mL). The organic phase was washed with 150 mL~23.5% w/w aq. sodium bisulfite and with H$_2$O (150 mL), dried over Na$_2$SO$_4$ and concentrated to give the title compound (12.72 g, 91%).

3. (R)-N-[5-[2-Iodo-1-[(triethylsilyl)oxy]ethyl]-2-(phenylmethoxy)phenyl]methanesulfonamide To a stirred DMF (65 mL) solution containing (R)-2-iodo-1-[4-phenylmethoxy-3-[(methylsulfonyl)amino]phenyl]ethanol (12.7 g, 28 mmol), imidazole (5.25 g, 77 mmol), and 4-dimethylaminopyridine (0.30 g, 2.46 mmol) was added triethylsilyl chloride (5.0 mL, 29.8 mmol). After 15 minutes the completed reaction was diluted with EtOAc (200 mL) and heptane (70 mL). The organic phase was washed 1×100 mL H$_2$O, 2×100 mL aq. sat. CuSO$_4$, 1×100 mL H$_2$O, 1×100 mL sat. brine, and dried over Na$_2$SO$_4$. The filtrate was concentrated in vacuo to give 15.81 g of tan solid which was dissolved in ~125 mL CH$_2$Cl$_2$ and diluted with 650 mL heptane. The mixture was concentrated in vacuo at 40°–42° C. until solids were seen (~105 mL distillate were collected), cooled to ~15° C. and filtered. The collected solids were washed with heptane and dried in vacuo at 45° C. to give 11.1 g (70%) of the title compound.

$^1$H NMR (270 MHz, CDCl$_3$): δ 0.50–0.68 (m, 6H), 0.90 (t, 3H), 2.90 (s, 3H, SO$_2$CH$_3$), 3.32 (m, 2H), 4.72 (t, 1H), 5.10 (s, 2H), 6.82 (bs, 1H), 6.99 (d, 1H), 7.12 (dd, 2H), 7.32–7.48 (m, 2H), 7.52 (d, 1H).

$^{13}$C NMR (68 MHz, CDCl$_3$): δ 4.7, 6.7, 15.1, 38.9, 71.0, 74.1, 111.9, 118.4, 122.8, 126.1, 127.8, 128.6, 128.7, 135.5, 136.5, 148.0.

Mass (M+NH$_4$) 579; (M−H) 560

HPLC: >99% pure, Shimadzu, YMC S3 ODS (6.0×150 mm); flow rate of 1.5 mL/minute; detection at 217 nm; gradient elution 0–100% B over 40 minutes (A=10% MeOH, 90% H$_2$O, 0.2% H$_3$PO$_4$ and B=90% MeOH, 10% H$_2$O, 0.2% H$_3$PO$_4$); retention time=45 minutes.

D. (R),(R)-N-[5-[1-(Triethylsilyl)oxy-2-[[1-(3,4-dimethoxyphenyl)-2-phenylethyl]amino]ethyl]-2-(phenylmethoxy)phenyl]methanesulfonamide A mixture of (R)-α-(3,4-dimethoxyphenyl) benzeneethanamine (1.75 g, 6.8 mmol), (R)-N-[5-[2-iodo-1-[(triethylsilyl)oxy]ethyl]-2-(phenylmethoxy)phenyl] methanesulfonamide (3.1 g, 5.52 mmol) and N,N-diisopropylethylamine (4.8 mL, 27.55 mmol) in THF (2 mL) was heated at 110° C. in a sealed flask for 58 hours. The reaction mixture was cooled, diluted with EtOAc and washed with brine (3×). The organic layer was dried over anhydrous Na$_2$SO$_4$ and concentrated to obtain a yellow gum which was purified by SiO$_2$ column eluting with 30% EtOAc/hexanes to obtain 2.64 g (3.82 mmol, 69%) of the title compound.

Mass (M+H) 691

Calculated for 1.92 mol of H$_2$O:

|   | Calc. | Found |
|---|---|---|
| C | 62.90 | 62.79 |
| H | 7.48 | 6.99 |
| N | 3.86 | 3.97 |
| S | 4.42 | 4.46 |

HPLC: 89% pure, Shimadzu LC-6A, YMC S3 ODS (6.0×150 mm); flow rate of 1.5 mL/minute; detection at 220 nm; gradient elution 0–100% B over 30 minutes (A=10% MeOH, 90% H$_2$O, 0.2% H$_3$PO$_4$) and (B=90% MeOH, 10% H$_2$O, 0.2% H$_3$PO$_4$); retention time=27.2 minutes.

E. (R),(R)-N-[5-[1-(Hydroxy-2-[[1-(3,4-dimethoxyphenyl)-2-phenylethyl]amino]ethyl]-2-(phenylmethoxy)phenyl] methanesulfonamide To a solution of compound (R),(R)-N-[5-[1-(triethylsilyl) oxy-2-[[1-(3,4-dimethoxyphenyl)-2-phenylethyl]amino] ethyl]-2-(phenylmethoxy)phenyl]methanesulfonamide (2.6 g, 3.76 mmol) in THF (50 mL) was added AcOH (0.9 mL) at room temperature followed by 1.0M solution of TBAF in THF (9.4 mL). After stirring at room temperature for 1.5 hours, the reaction was concentrated, diluted with EtOAc (100 mL), and washed successively with saturated aqueous solution of NaHCO$_3$ (2×) and brine (3×). The organic layer, after drying over anhydrous MgSO₄, was concentrated to a pale yellow gum which was purified by SiO₂ column using 1:1 of EtOAc/hexanes to remove nonpolar impurities and then by using 5% MeOH/CH₂Cl₂ to obtain 2.0 g (3.46 mmol, 92%) of the title compound.

Mass (M+H) 577

Calculated for 0.91 mol of water:

|   | Calc | Found |
|---|------|-------|
| C | 64.81 | 64.81 |
| H | 6.43 | 6.41 |
| N | 4.72 | 4.72 |
| S | 5.41 | 5.37 |

HPLC: 98% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=21.3 minutes.

F. (R),(R)-N-|5-|1-(Hydroxy-2-|[1-(3,4-dimethoxyphenyl)-2-phenylethyl|amino|ethyl|-2-(hydroxy)phenyl| methanesulfonamide, trifluoroacetate salt (R),(R)-N-|5-|1-(Hydroxy-2-|[1-(3,4-dimethoxyphenyl)-2-phenylethyl|amino|ethyl|-2-(phenylmethoxy)phenyl| methanesulfonamide, (1.9 g, 3.29 mmol) was hydrogenated using 10% Pd/C (300 mg) and MeOH (20 mL) at 40 psi of hydrogen in a Parr apparatus for 40 minutes at room temperature. The catalyst was filtered through Celite and washed with MeOH. The filtrate and MeOH washings were combined and concentrated to afford 1.7 g as a white foam. This material was chromatographed using a prep C₁₈ HPLC column eluting with 41% solvent B (solvent A=10% MeOH, 90% H₂O, 0.1% TFA; solvent B=90% MeOH, 10% H₂O, 0.1% TFA) to obtain 1.82 g (92%) of the title compound.

¹H NMR (270 MHz, CD₃OD): δ 2.88–2.93 (m, 1H), 2.90 (s, 3H, SO₂CH₃), 3.03–3.12 (m, 1H), 3.24–3.51 (m, 2H), 3.56–3.68 (dd, 1H), 3.77 (s, 6H, OCH₃), 4.39–4.45 (dd, 1H), 4.70–4.76 (dd, 1H), 6.83–6.91 (m, 3H), 6.98–7.04 (m, 4H), 7.12–7.19 (m, 4H), 7.30–7.31(d, 1H).

¹³C NMR (68 MHz, CD₃OD): δ 39.6, 40.2, 53.6, 56.3, 56.5, 65.9, 70.0, 112.8, 112.9, 116.6, 122.9, 124.3, 125.5, 126.1, 127.4, 128.1, 129.6, 130.5, 133.6, 137.0, 150.9, 151.5, 151.6.

Mass (M+H) 487 [a]_D=−32.77 (c=0.9, MeOH)

Calculated for 0.5 mol H₂O and 1.40 mol TFA:

|   | Calc. | Found |
|---|-------|-------|
| C | 50.96 | 50.79 |
| H | 4.98 | 4.99 |
| N | 4.28 | 4.32 |
| S | 4.89 | 4.88 |
| F | 12.18 | 12.28 |

HPLC: 91% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=17.6 minutes.

EXAMPLE 20

(R)-N-|5-[2-|[bis(4-Methoxyphenyl)methyl]amino|-1-hydroxyethyl|-2-hydroxyphenyl| methanesulfonamide, trifluoroacetate salt

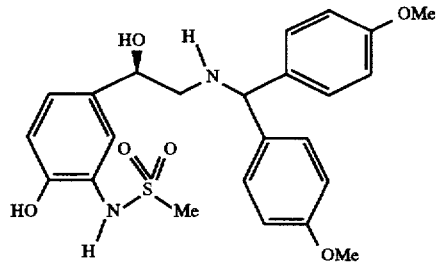

The title compound was prepared by coupling of 4,4'-dimethoxybenzhydrylamine (preparation described in Example 14) with (R)-N-|5-|2-iodo-1-|(triethylsilyl)oxy|ethyl|-2-(phenylmethoxy)phenyl|methanesulfonamide utilizing the procedures described in steps D–F of Example 19. In step F 44% solvent B was the eluant for the prep HPLC purification.

¹H NMR (270 MHz, CD₃OD): δ 2.91 (s, 3H, —SO₂CH₃), 3.02 (d, J=6.45 Hz, 2H), 3.79 (s, 3H, —OCH₃), 3.80 (s, 3H, —OCH₃), 5.51 (s, 1H), 6.86 (d, J=8.21, 1H), 6.99 (m, 5H), 7.31 (d, J=1.7, 1H), 7.44 (m, 4H).

¹³C NMR (67 MHz, CD₃OD): δ 39.6, 54.0, 55.8, 66.2, 69.6, 115.6, 115.7, 124.2, 125.3, 126.1, 128.7, 129.1, 130.2, 130.4, 133.7, 151.6, 161.7.

Mass (M+H) 473

Calculated for 0.95 mol H₂O and 1.25 mol TFA:

|   | Calc. | Found |
|---|-------|-------|
| C | 50.35 | 50.35 |
| H | 4.97 | 4.97 |
| N | 4.43 | 4.43 |
| S | 5.07 | 4.99 |
| F | 11.27 | 11.14 |

HPLC: 100% pure, Shimadzu LC-6A, YMC S3 ODS (6.0× 150 mm); flow rate of 1.5 mL/minute; detection at 220 nm; gradient elution 0–100% B over 35 minutes (A=10% MeOH, 90% H₂O, 0.2% H₃PO₄); B=90% MeOH, 10% H₂O, 0.2% H₃PO₄); retention time=20.7 minutes.

EXAMPLE 21

(R)-N-|5-[2-|[bis(4-Fluorophenyl)methyl]amino]-1-hydroxyethyl|-2-hydroxyphenyl| methanesulfonamide, trifluoroacetate salt

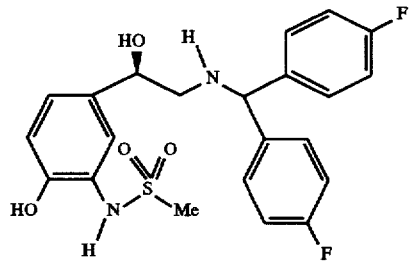

Commercially available 4,4'-difluorobenzophenone was converted to 4,4'-difluorobenzhydrylamine via the procedure described step C of Example 1, except for the following modifications. The amination reaction product was chromatographed on silica gel using 2:1 hexane/EtOAc to elute the formamide prior to acid hydrolysis. The acidic hydrolysis reaction, after dilution with H₂O, was extracted 2× with Et₂O prior to basification, extraction 3× with EtOAc and isolation of the desired amine after concentration. The title compound was prepared by coupling of 4,4'-difluorobenzhydrylamine with (R)-N-[5-[2-iodo-1-[(triethylsilyl)oxy]-ethyl]-2-(phenylmethoxy)phenyl] methanesulfonamide utilizing the procedures described in steps D–F of Example 19. In step F, 43% solvent B was the eluant for the prep HPLC purification.

¹H NMR (270 MHz, CD₃OD): δ 2.91 (s, 3H, —SO₂CH₃), 3.06 (m, 2H), 5.69 (s, 1H), 6.88 (d, J=8.21 Hz), 7.05 & 7.05 (2d, 1H), 7.24 (m, 4H), 7.29 (d, 1H), 7.47 (m, 4H).

¹³C NMR (67 MHz, CD₃OD): δ 39.7, 54.4, 65.6, 69.7, 116.7, 117.2, 117.3, 117.5, 117.6, 124.4, 125.4, 126.1, 131.1, 131.2, 131.4, 131.5, 132.8, 133.1, 133.6, 151.7, 162.7, 166.3.

Mass (M+H) 448

Calculated for 0.2 mol H₂O and 1.12 mol TFA:

|   | Calc. | Found |
|---|-------|-------|
| C | 50.22 | 50.12 |
| H | 4.09  | 3.78  |
| N | 4.83  | 4.57  |
| S | 5.53  | 6.08  |
| F | 17.56 | 17.12 |

HPLC: 97% pure, Shimadzu LC-6A, YMC S3 ODS (6.0× 150 mm); flow rate of 1.5 mL/minute; detection at 220 nm; gradient elution 0–100% B over 35 minutes (A=10% MeOH, 90% H₂O, 0.2% H₃PO₄); B=90% MeOH, 10% H₂O, 0.2% H₃PO₄); retention time=20.5 minutes.

EXAMPLE 22

(R),(S)-N-[5-[1-(Hydroxy-2-[[1-(3,4-dimethoxyphenyl)-2-phenylethyl]amino]ethyl]-2-(hydroxy)phenyl]methanesulfonamnide, trifluoroacetate salt

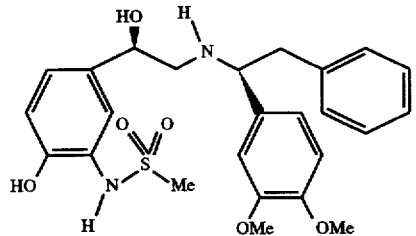

A. (R)-N-[5-[1-(Hydroxy-2-[[1-(3,4-dimethoxyphenyl)-2-phenylethyl]amino]ethyl]-2-(phenylmethoxy)phenyl] methanesulfonamide, cyclic urethane (R)-N-[5-[1-(Hydroxy-2-[[1-(3,4-dimethoxyphenyl)-2-phenyl ethyl]amino]ethyl]-2-(phenylmethoxy)phenyl] methanesulfonamide was prepared by condensation of α-(3, 4-dimethoxyphenyl)benzeneethanamine (prepared as described in steps A–C of Example 1) with (R)-N-[5-[2-iodo-1-[(triethylsilyl)oxy]ethyl]-2-(phenylmethoxy)phenyl] methane sulfonamide and subsequent reaction as described in steps D–E of Example 19.

To a solution of (R)-N-[5-[1-(hydroxy-2-[[1-(3,4-dimethoxyphenyl)-2-phenylethyl]amino]ethyl]-2-(phenylmethoxy)phenyl]methanesulfonamide (420 mg, 0.728 mmol) in anhydrous THF (20 mL) was added Et₃N (1.1 mL) followed by 1,1-carbonyldiimidazole (1.6 g, 9.87 mmol) at 20° C. under N₂. After stirring for 45 minutes, the reaction was diluted with EtOAc and washed successively with 1N aqueous HCl, saturated solution of aqueous NaHCO₃ and brine. The organic layer was dried over anhydrous Na₂SO₄ and then concentrated to obtain a white foam. By analytical HPLC Shimadzu LC-6A, YMC S3 ODS (6.0×150 mm); flow rate of 1.5 mL/minute; detection at 220 nm; gradient elution 0–100% B over 30 minutes (A=10% MeOH, 90% H₂O, 0.2% H₃PO₄) and B (B=90% MeOH, 10% H₂O, 0.2% H₃PO₄)] the retention time of the two diastereomers were 28.4 and 28.9 minutes. These two peaks were separated on preparative C₁₈ HPLC column using 78% solvent B (solvent A=90% H₂O/MeOH; solvent B=90% MeOH/H₂O) to obtain 205 mg (0.34 mmol, 47%) of diastereomer A as white foam (having R,R configuration) and 185 mg (0.31 mmol, 42%) of diastereomer B as colorless needles (having R,S configuration, confirmed by X-ray analysis).

Mass(M+H) 603

HPLC: 99% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=28.8 minutes. B. (R),(S)-N-[5-[1-(Hydroxy-2-[[1-(3,4-dimethoxyphenyl)-2-phenylethyl]amino]ethyl]-2-(phenylmethoxy)phenyl] methanesulfonamide A solution of (R),(S)-N-[5-[1-(hydroxy-2-[[1-(3,4-dimethoxyphenyl)-2-phenylethyl]amino]ethyl]-2-(phenylmethoxy)phenyl]methanesulfonamide, urethane (180 mg, 0.298 mmol) in EtOH (10 mL) and 5.0N NaOH (4 mL) was stirred at reflux overnight. The reaction mixture was cooled, diluted with EtOAc (30 mL) and then washed with brine. The organic layer was dried over anhydrous Na₂SO₄ and then concentrated to obtain 135 mg (78.5%) the title compound.

Mass (M+H) 577

HPLC: 100% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H₂O, 0.2% H₃PO₄); B=90% MeOH, 10% H₂O, 0.2% H₃PO₄); retention time=21.9 minutes.

C. (R),(S)-N-[5-[1-(Hydroxy-2-[[1-(3,4-dimethoxyphenyl)-2-phenylethyl]amino]ethyl]-2-(hydroxy)phenyl] methanesulfonanmide (R),(S)-N-[5-[1-(Hydroxy-2-[[1-(3,4-dimethoxyphenyl)-2-phenylethyl]amino]ethyl]-2-(phenylmethoxy)phenyl] methanesulfonamide (134 mg, 0.232 mmol) was hydrogenated using 10% Pd/C (90 mg) and MeOH (15 mL, AR grade) at 40 psi of hydrogen in a Parr apparatus for 40 minutes at room temperature. The catalyst was filtered through Celite and washed with MeOH. The filtrate and MeOH washings were combined and concentrated to obtain a white foam. This material was chromatographed on a prep C₁₈ HPLC eluting with 43% solvent B (solvent A=10% MeOH, 90% H₂O, 0.1% TFA; solvent B=90% MeOH, 10% H₂O, 0.1% TFA) to elute 102 mg (0.17 mmol, 73%) of the title compound.

¹H NMR (270 MHz, CD₃OD): δ 2.88–2.98 (m, 1H), 3.04 (s, 3H, SO₂CH₃), 3.17–3.26 (m, 1H), 3.38–3.50 (m, 2H), 3.58–3.70 (m, 1H), 3.92 (s, 6H, OCH₃), 4.58–4.68 (dd, 1H), 6.92–7.08 (m, 3H ), 7.12–7.22 (m, 4H), 7.26–7.38 (m, 3H ), 7.42 (s, 1H).

¹³C NMR (68 MHz, CD₃OD): δ 39.5, 40.7, 53.4, 56.3, 56.5, 65.2, 69.4, 112.4, 112.8, 116.6, 122.9, 124.1, 125.2, 126.0, 127.0, 128.0, 129.5, 130.4, 133.6, 136.9, 151.0, 151.4, 151.5.

Mass (M+H) 487

[α]$_D$=+2.0° (c=0.25, MeOH)

Calculated for 0.56 mol H$_2$O and 1.30 mol TFA:

|   | Calc. | Found |
|---|-------|-------|
| C | 51.34 | 51.41 |
| H | 5.50  | 5.34  |
| N | 4.43  | 4.36  |
| S | 5.08  | 5.10  |
| F | 11.49 | 11.11 |

HPLC: 99% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.3 minutes.

EXAMPLE 23

(threo)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer A

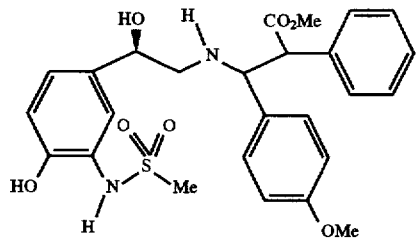

A. β-Amino-4-methoxy-α-phenylbenzenepropanoic acid, methyl ester

An ethanol solution (35 mL) containing anishydramide (2.5 g, 8.4 mmol) (T. B. Johnson et al., *J. Amer. Chem. Soc.*, 58, 299 (1936)) and phenylmalonic acid (4 g, 22 mmol) was refluxed for six hours. The reaction mixture, after concentration, was dissolved in methanol containing gaseous HCl and refluxed for six hours. The acidic solution was concentrated, diluted with H$_2$O (150 mL) and extracted 3× with Et$_2$O. Any solid that formed was collected by filtration. The Et$_2$O fractions were washed 1× with 1N aq. HCl and discarded. The combined aqueous layers after adjusting the pH to ~10 was extracted 3× with EtOAc. The EtOAc fraction was washed 1× with brine, dried over Na$_2$SO$_4$, and concentrated to yield 500 mg of an oil. Analytical HPLC using a MeOH gradient with a YMC S3 C$_{18}$ column revealed the solid was a 95:5 mixture of the HCl salts of the threo:erythro diastereomers of the title compound. The oil was a 55:45 mixture of threo and erythro free title amines. This mixture was separated by preparative HPLC using a YMC S10 C$_{18}$ column under isocratic conditions using 38% solvent B (A=10% MeOH, 90% H$_2$O, 0.1% TFA) and B (B=90% MeOH, 10% H$_2$O, 0.1% TFA) to elute racemic (threo)-β-amino]-4-methoxy-α-phenylbenzenepropanoic acid, methyl ester (165 mg, 9%) and (erythro)-β-amino]-4-methoxy-α-phenylbenzenepropanoic acid, methyl ester (130 mg, 7%).

B. (threo)-β-[[(R)-2-(Triethylsilyl)oxy-2-[4-phenylmethoxy-3-[(methylsulfonyl)amino]phenyl]ethyl]amino]-4-methoxy-α-phenylbenzenepropanoic acid, methyl ester A mixture of (threo)-β-amino-4-methoxy-α-phenylbenzenepropanoic acid (140 mg, 0.6 mmol), (R)-N-[5-[2-Iodo-1-[(triethylsilyl)oxy]ethyl]-2-(phenylmethoxy)phenyl]methanesulfonamide (350 mg, 0.67 mmol), and diisopropylethylamine (0.3 mL) in THF (1.3 mL) was heated in a sealed tube at 90° C. for 30 hours. After cooling, the product was extracted using EtOAc/aq. NaHCO$_3$. The EtOAc fractions were dried over Na$_2$SO$_4$ and concentrated. The resulting oil was chromatographed on silica gel using 4:1 hexane/EtOAc to elute the title compound as a 120 mg mixture of the R,R,R and R,S,S diastereomers. This mixture was separated by preparative reverse phase HPLC using a C$_{18}$ YMC S-5 column under isocratic conditions using 77% solvent B (A=10% MeOH, 90% H$_2$O) and B (B=90% MeOH, 10% H$_2$O) to elute 50 mg of diastereomer A of (threo)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester and 60 mg of diastereomer B of (threo)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester.

C. (threo)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer A A mixture of diastereomer A of (threo)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester (50 mg, 0.08 mmol) and 0.2 mL of 1M TBAF/THF in 0.75 mL of THF containing 4 drops of HOAc was stirred seven hours at 20° C. After removal of the solvents in vacuo, the residue in MeOH (80 mL) containing 0.2 mL TFA and 20 mg of 10% Pd/C was hydrogenated for 45 minutes at 40 psi H$_2$ using a Parr shaker. After filtration and concentration, the residue was purified via preparative HPLC using a YMC S10 C$_{18}$ column under isocratic conditions using 58% solvent B (A=10% MeOH, 90% H$_2$O, 0.1% TFA (B=90% MeOH, 10% H$_2$O, 0.1% TFA) to yield 19 mg of the title compound.

$^1$H NMR (270 MHz, CD$_3$OD): δ 2.25 (t, 1H), 2.74 (d, 1H), 2.92 (s, 3H ), 3.67 (s, 3H ), 3.7 (s, 3H ), 4.40 (dd, 2H), 4.43 (m, 1H), 6.80 (dd, 4H), 6.82 (d, 1H), 6.98 (m, 1H), 7.10–7.3 (m, 6H).

$^{13}$C NMR (67 MHz, CD$_3$OD): δ 38.8, 52.3, 54.98, 55.0, 59.0, 66.1, 72.1, 113.7, 116.6, 122.1, 123.7, 124.9, 127.3, 128.3, 128.4, 131.3, 134.3, 135.4, 148.9, 158.7,174.1.

Mass (M–H) 513

[α]$_D^{22}$=−56° (c=0.3, MeOH)

HPLC: 88% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=18.7 minutes.

EXAMPLE 24

(threo)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer B

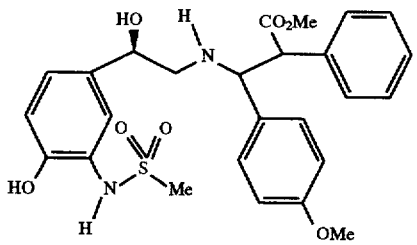

Using the procedure described in step C of Example 23, the title compound was prepared from 60 mg of diastereomer B of (threo)-β-[[(R)2-(triethylsilyl)oxy-2-[4-phenylmethoxy-3-[(methylsulfonyl)amino]phenyl]ethyl]amino]-4-methoxy-α-phenylbenzenepropanoic acid, methyl ester for which the preparation was described in step B of Example 23. The only difference was that 58% solvent B was employed during the preparative HPLC.

$^1$H NMR (270 MHz, CD$_3$OD): δ 2.4–2.75 (m, 2H), 2.91 (s, 3H,), 3.70 (s, 3H ), 3.71 (s, 3H), 4.40 (dd, 2H), 4.64 (m, 1H), 6.79 (d, 1H), 6.82 (dd, 4H), 6.92 (m, 1H), 7.10–7.3 (m, 6H).

$^{13}$C NMR (67 MHz, CD$_3$OD): δ 38.7, 52.3, 53.2, 55.0, 59.1, 63.7, 70.0, 113.7, 116.6, 122.0, 123.7, 124.9, 127.3, 128.3, 128.4, 130.9, 134.3, 135.5, 148.8, 158.7, 174.0.

Mass (M–H) 513

$[α]_D^{22}$=+11° (c=0.4, MeOH)

HPLC: 88% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=18.6 minutes.

EXAMPLE 25

(erythro)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer A

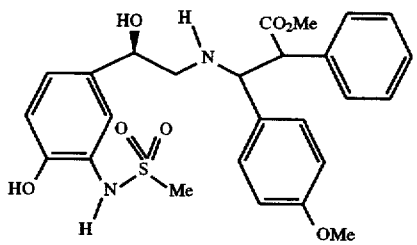

A. (erythro)-β-[[(R)-2-(Triethylsilyl)oxy-2-[4-phenylmethoxy-3-[(methylsulfonyl)amino]phenyl]ethyl]amino]-4-methoxy-α-phenylbenzenepropanoic acid, methyl ester.

The title compound was prepared from racemic (erythro)-β-amino-4-methoxy-α-phenylbenzenepropanoic acid, methyl ester (130 mg) for which the preparation was described in step A of Example 23. A mixture of (erythro)-β-amino-4-methoxy-α-phenylbenzene-propanoic acid (130 mg, 0.6 mmol), (R)-N-[5-[2-iodo-1-[(triethylsilyl)-oxy]ethyl]-2-(phenylmethoxy)phenyl]methanesulfonamide (310 mg, 0.67 mmol), and diisopropylethylamine (0.3 mL) in THF (1.3 mL) was heated in a sealed tube at 90° C. for 88 hours. The same isolation and purification procedures described in step B of Example 23 were employed to obtain 50 mg of diastereomer A of (erythro)-β-[[(R)-2-(triethylsilyl)-oxy-2-[4-phenylmethoxy-3-[(methylsulfonyl)amino]phenyl]ethyl]amino]-4-methoxy-α-phenylbenzenepropanoic acid, methyl ester and 60 mg of diastereomer B of (erythro)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester.

B. (erythro)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer A Diastereomer A of (erythro)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester was converted to the 25 mg of the title compound using the identical procedure described in step C of Example 23, except that 51% solvent B was employed during the preparative HPLC.

$^1$H NMR (270 MHz, CD$_3$OD): δ 2.35 (t, 1H), 2.5 (d, 1H), 2.79 (s, 3H ), 3.41 (s, 3H ), 3.78 (s, 3H ), 4.04 (dd, 2H), 4.12 (m, 1H), 6.77 (dd, 2H), 6.98 (s, 1H), 7.06 (dd, 4H), 7.30–7.45 (m, 5H).

$^{13}$C NMR (67 MHz, CD$_3$OD): δ 38.8, 51.8, 54.7, 55.1, 59.1, 64.9, 71.5, 113.9, 116.4, 121.6, 123.7, 124.6, 128.1, 128.6, 128.9, 132.1, 134.4, 135.5, 148.5, 159.1, 172.1.

Mass (M–H) 513

$[α]_D^{22}$=+41° (c=0.3, MeOH)

HPLC: 90% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.6 minutes.

EXAMPLE 26

(erythro)-β-[[(R)-2-Hydroxy-2-[4-hydroxy-3-[(methylsulfonyl)amino]phenyl]ethyl]amino]-4-methoxy-α-phenylbenzenepropanoic acid, methyl ester, trifluoroacetate salt, diastereomer B

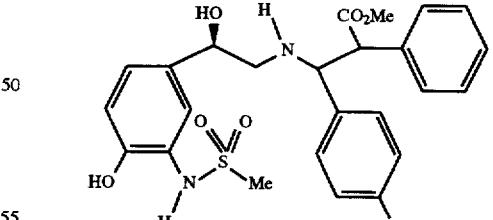

The title compound (32 mg) was prepared from 60 mg of diastereomer B of (erythro)-β-[[(R)-2-(triethylsilyl)oxy-2-[4-phenylmethoxy-3-[(methylsulfonyl)amino]phenyl]ethyl]amino]-4-methoxy-α-phenylbenzenepropanoic acid, methyl ester for which the preparation was described in step A of Example 25 using the procedure described in step C of Example 23. The only difference was that 51% solvent B was employed during the preparative HPLC.

$^1$H NMR (270 MHz, CD$_3$OD): δ 2.6–2.85 (m, 2H), 2.86 (s, 3H ), 3.45 (s, 3H ), 3.831 (s, 3H ), 4.54 (m, 1H), 4.82 (m,

1H), 5.0 (m, 1H), 6.84 (m, 2H), 7.18 (m, 1H), 7.28 (dd, 4H), 7.42–7.65 (m, 5H).

$^{13}$C NMR (67 MHz, CD$_3$OD): δ 38.7, 51.9, 53.3, 55.1, 59.1, 63.2, 70.4, 113.9, 116.4, 121.6, 123.7, 124.5, 128.1, 128.6, 128.9, 131.7, 134.0, 135.5, 148.5, 159.1, 172.2.

Mass (M–H) 513

[α]$_D^{22}$=–48° (c=0.6, MeOH)

HPLC: 84% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.5 minutes.

EXAMPLE 27

N-[3-[2-[[1-(3,4-Dimethoxyphenyl)-2-phenylethyl]amino]-1-hydroxyethyl]phenyl]methanesulfonamide, trifluoroacetate salt

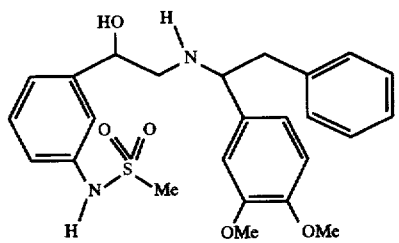

A. 2-Bromo-1-[3-[(methylsulfonyl)amino]phenyl]ethanone

Commercially available 3-aminoacetophenone was converted to 1-[3-[(methylsulfonyl)amino]phenyl]ethanone using the procedure for the preparation of 2-bromo-1-[4-phenylmethoxy-3-[(methylsulfonyl)amino]phenyl]ethanone described in step 4 of part F of Example 1.

To a 60° C. stirred dioxane (300 mL) solution of 1-[3-[(methylsulfonyl)amino]phenyl]ethanone (22.5 g, 105 mmol) was added Br$_2$ (17.5 g, 110 mmol). The solution was cooled to 20° C. after one hour, concentrated and diluted with 350 mL of H$_2$O. The resulting solid was filtered and recrystallized from EtOH to obtain 19.6 g (59%) of the title compound.

B. N-[3-[2-[[1-(3,4-Dimethoxyphenyl)-2-phenylethyl]amino]1-hydroxyethyl]phenyl]methanesulfonamide The title compound was prepared by coupling α-(3,4-dimethoxyphenyl)benzeneethanamine, prepared as described in step C of Example 1, with 2-bromo-1-[3-[(methylsulfonyl)amino]phenyl]ethanone via the procedure described in step D of Example 1. The title compound, after silica gel chromatography, was purified by preparative HPLC using 49% solvent B to elute the desired material from a YMC S10 C$_{18}$ column.

$^1$H NMR (270 MHz, CD$_3$OD): δ 2.74–3.17 (m, 3H ), 2.9 (s, 3H ), 3.52 (m, 1H), 3.76 (s, 3H ), 3.77 (s, 3H ), 4.46 (m, 1H), 4.82 (m, 1H), 6.86 (m, 2H), 7.0–7.4 (m, 10H).

$^{13}$C NMR (67 MHz, CD$_3$OD): δ 37.7, 38.7, 39.3, 51.9, 52.1, 54.8, 55.0, 63.8, 64.2, 68.7, 110.8, 111.1, 111.3, 117.1, 117.2, 119.6, 119.62, 121.3, 121.5, 125.5, 125.8, 126.5, 128.0, 128.9, 129.3, 135.4, 135.5, 138.4, 142.5, 149.4, 149.

Mass (M+H) 471
Calculated for 1.0 mol H$_2$O and 1.3 mol TFA:

|   | Calc. | Found |
|---|-------|-------|
| C | 52.06 | 51.96 |
| H | 5.27  | 5.11  |
| N | 4.40  | 4.31  |
| S | 5.03  | 4.92  |
| F | 11.63 | 11.72 |

HPLC: 93% pure, Shimadzu LC-6A, YMC S3 ODS (6.0× 150 mm); flow rate of 1.5 mL/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention times=18.0 and 18.1 minutes.

EXAMPLE 28

(R)-N-[3-[2-[[bis(4-Methoxyphenyl)methyl]amino]-1-hydroxyethyl]phenyl]methanesulfonamide

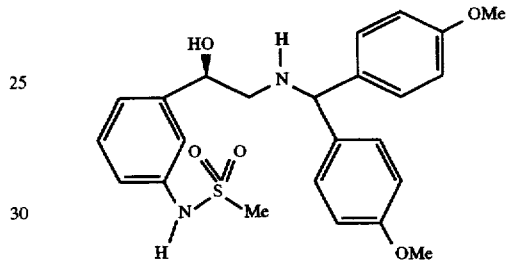

A. (R)-N-[3-[2-Iodo-1-[(triethylsilyl)oxy]ethyl]phenyl]methanesulfonamide

2-Bromo-1-[3-[(methylsulfonyl)amino]phenyl]ethanone (preparation described in Example 27) was converted to the title compound following the procedures described in steps 1–3 of part C of Example 19 for the preparation of (R)-N-[5-[2-iodo-1-[(triethylsilyl)oxy]ethyl]-2-(phenylmethoxy)phenyl]methanesulfonamide.

$^1$H NMR (270 MHz, CDCl$_3$): δ 0.49–0.62 (m, 6H), 0.88 (t, 3H ), 3.00 (s, 3H , SO$_2$CH$_3$), 3.32 (d, 2H), 4.73 (t, 1H), 7.10–7.35 (m, 5H).

$^{13}$C NMR (68 MHz, CDCl$_3$): δ 4.7, 6.7, 14.8, 39.2, 74.2, 118.1, 120.1, 122.9, 129.6, 136.8, 144.8.

Mass (M+H) 454

HPLC: Shimadzu, YMC S3 ODS (6.0×150 mm); flow rate of 1.5 mL/minute; detection at 217 nm; gradient elution 0–100% B over 40 minutes (A=10% MeOH, 90% H$_2$O, 0.2% H$_3$PO$_4$ and B=90% MeOH, 10% H$_2$O, 0.2% H$_3$PO$_4$); retention time=42.5 minutes.

B. (R)-N-[3-[2-[[bis(4-Methoxyphenyl)methyl]amino]-1-hydroxyethyl]phenyl]methanesulfonamide The title compound was prepared by coupling 4,4'-dimethoxybenzohydrylamine (preparation described in Example 14) with (R)-N-[3-[2-iodo-1-[(triethylsilyl)oxy]ethyl]phenyl]methanesulfonamide. The same procedures as described in steps D and E of Example 19 were employed for the condensation of 4,4'-dimethoxybenzohydrylamine with (R)-N-[3-[2-iodo-1-[(triethylsilyl)oxy]ethyl]phenyl]methanesulfonamide and subsequent deprotection. In step E, the eluant for column chromatography on silica gel was 5% of (10% conc aq. NH$_4$OH/MeOH) in CH$_2$Cl$_2$.

$^1$H NMR (270 MHz, CDCl$_3$): δ 2.6–2.9 (m, 2H), 2.9 (s, 3H, SO$_2$CH$_3$), 3.8 (s, 6H, OCH$_3$), 4.6–4.7 (m, 1H), 4.8 (s, 1H), 6.8–6.9 (m, 4H), 7.0–7.3 (m, 8H).

¹³C NMR (68 MHz, CDCl₃): δ 39.3, 55.1, 65.6, 71.8, 113.9, 117.9, 119.4, 122.7, 128.2, 129.6, 135.6, 136.9, 144.9, 158.6.

Calculated for 0.7 mol H₂O:

|   | Calc. | Found |
|---|-------|-------|
| C | 61.70 | 61.90 |
| H | 5.91  | 6.15  |
| N | 6.00  | 5.80  |
| S | 6.86  | 6.77  |

HPLC: >99% pure, Shimadzu LC-6A, YMC S3 ODS (6.0× 150 mm); flow rate of 1.5 mL/minute; detection at 217 nm; eluted with gradient conditions 0–100%B over 25 minutes (A=10% MeOH, 90% H₂O, 0.2% H₃PO₄ and B=90% MeOH, 10% H₂O, 0.2% H₃PO₄); retention time=17 minutes.

(M+H)+ @ 457

EXAMPLE 29

(R),(R)-N-[3-[2-[[1-(3,4-Dimethoxyphenyl)-2-phenylethyl]amino]-1-hydroxyethyl]phenyl] methanesulfonamide

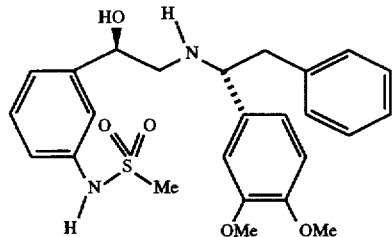

The title compound was prepared by coupling (R) α-(3,4-dimethyoxyphenyl)benzeneethanamine, prepared as described in step B of Example 19 with (R)-N-[3-[2-iodo-1-[(triethylsilyl)oxy]ethyl]phenyl]methanesulfonamide (preparation described in step A of Example 28). The same procedures as described in steps D and E of Example 19 were employed for the condensation and deprotection. The title compound was purified by column chromatography on silica gel using 2–6% of (10% conc. aq. NH₄OH/MeOH) in CH₂Cl₂ as the eluant.

¹H NMR (270 MHz, CDCl₃): δ 2.51 (dd, 1H), 2.68 (dd, 1H), 2.90 (s, 3H, SO₂CH₃), 2.80–3.00 (m, 2H), 3.70–4.20 (m, 3H), 3.80 (s, 3H, OCH₃), 3.82 (s, 3H, OCH₃), 4.45 (m, 1H), 6.70–6.82 (m, 3H), 6.90–7.30 (m, 10H).

¹³C NMR (68 MHz, CDCl₃): δ 39.2, 44.8, 55.0, 55.8, 55.8, 64.8, 71.8, 110.0, 111.0, 117.9, 119.3, 122.5, 126.3, 128.3, 129.2, 129.5, 135.5, 137.0, 138.4, 144.4, 148.1, 148.9.

Mass (M+H) 471

Calculated for 0.63 mol H₂O:

|   | Calc. | Found |
|---|-------|-------|
| C | 62.31 | 62.56 |
| H | 6.54  | 6.51  |
| N | 5.81  | 5.56  |
| S | 6.65  | 6.62  |

HPLC: >99% pure, Shimadzu LC-6A, YMC S3 ODS (6.0× 150 mm); flow rate of 1.5 mL/minute; detection at 217 nm; gradient elution 0–100% B over 40 minutes (A=10% MeOH, 90% H₂O, 0.2% H₃PO₄); B=90% MeOH, 10% H₂O, 0.2% H₃PO₄); retention time=22.6 minutes.

EXAMPLE 30

ε-||2-Hydroxy-2-|4-hydroxy-3-|(methylsulfonyl) amino|phenyl|ethyl|amino|benzeneheptanoic acid, methyl ester, trifluoroacetate salt

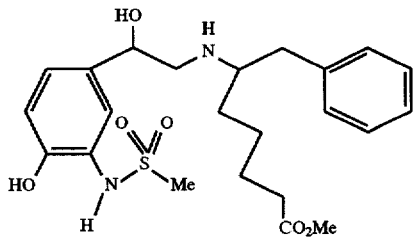

A. Hexahydro-7-(phenylmethyl)-2H-azepin-2-one

A mixture of polyphosphoric acid (150 g) and 2-(phenylmethyl)cyclohexanone, oxime (9 g, 45 mmol), which had been prepared as described by W. G. Kofron et al., J. Org. Chem., 41, 439 (1976), was heated with manual stirring to 120° C. for 20 minutes and then at 130° C. for ten minutes. The hot solution was poured onto 1000 g of ice, the pH adjusted to 4 with solid NaOH, and extracted 3× with EtOAc. After washing with brine, drying over Na₂SO₄, and concentration, the residue was chromatographed on silica gel using 1:1 EtOAc/hexane to elute a 1:1 mixture of the two isomeric lactams. The mixture was separated by prep HPLC using a C₁₈ reverse phase YMC S15 column with 68% solvent B as eluant to yield 2.3 g (26%) of the title compound and 1.8 g of the isomeric hexahydro-3-(phenylmethyl)-2H-azepin-2-one.

B. 6-Amino-7-benzeneheptanoic acid, methyl ester

A solution of hexahydro-7-(phenylmethyl)-2H-azepin-2-one (1.3 g, 6.4 mmol) in MeOH (15 mL) and conc. aq. HCl (15 mL) was heated at 75° C. for 36 hours. After cooling and concentration, the residue was dissolved in MeOH (50 mL). HCl gas was bubbled in briefly and the solution refluxed one hour. After cooling and concentration, a mixture of EtOAc and aq. Na₂CO₃ was added prior to 3 EtOAc extractions. After washing with brine, drying over Na₂SO₄, and concentration. 1.4 g (95%) of the title compound was obtained.

C. ε-[[2-Hydroxy-2-[4-hydroxy-3-[(methylsulfonyl)amino] phenyl]ethyl]amino]benzeneheptanoic acid, methyl ester, trifluoroacetate salt 6-Amino-7-benzeneheptanoic acid, methyl ester was converted to the title compound following the procedures outlined in steps D and E of Example 1, except for the following modifications: 1) the prep HPLC purification of step D was omitted; and 2) in step E, the final product was purified by prep HPLC using 46% solvent B as eluant.

¹H NMR (270 MHz, CDCl₃): δ 1.25–1.73 (m, 6H), 2.28 (t, 2H), 2.90 (m, 1H), 2.93 (s, 3H, SO₂CH₃), 3.06–3.26 (m, 3H), 3.56 (m, 1H), 3.63 (s, 3H, OCH₃), 4.84 (m, 1H), 6.90 (t, 1H), 7.1 (m, 1H) 7.25–7.42 (m, 6H).

¹³C NMR (68 MHz, CDCl₃): δ 23.77, 23.97, 24.0, 28.8, 29.8, 32.6, 36.3, 36.5, 38.1, 50.5, 50.7, 50.8, 59.17, 59.2, 68.1, 68.3, 115.1, 123.0, 124.0, 124.5, 126.9, 127.0, 128.55, 128.6, 128.9, 132.0, 132.1, 135.9, 150.2, 174.1.

Mass (M+H) 465

Calculated for 0.63 mol H$_2$O and 1.0 mol TFA:

|   | Calc. | Found |
|---|-------|-------|
| C | 48.99 | 49.22 |
| H | 6.08  | 5.45  |
| N | 4.97  | 4.74  |
| S | 6.65  | 6.62  |
| F | 10.11 | 11.22 |

HPLC: 100% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=18.0 minutes.

EXAMPLE 31

ε-[[2-Hydroxy-2-[4-hydroxy-3-[(methylsulfonyl) amino]phenyl]ethyl]amino]benzeneheptanoic acid

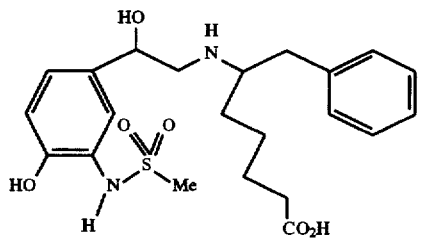

ε-[[2-Hydroxy-2-[4-hydroxy-3-[(methylsulfonyl)amino] phenyl]ethyl]amino]benzeneheptanoic acid, methyl ester, prepared in Example 30, was stirred at 20° C. under N$_2$ in 2:1 MeCN/H$_2$O containing 0.1N NaOH for one hour. After acidification with aq. HCl and concentration, the product was chromatographed on CHP-20 resin using 10% MeCN/H$_2$O to elute the title compound.

$^1$H NMR (270 MHz, CDCl$_3$): δ 1.4(m, 2H), 1.6 (m, 4H), 2.18 (t, 2H), 2.90 (m, 1H), 2.93 (s, 3H, SO$_2$CH$_3$), 2.95–3.1 (m, 3H), 3.3 (m, 1H), 4.76 (m, 1H), 6.87 (m, 1H), 7.04 (m, 1H) 7.2–7.38 (m, 6H).

$^{13}$C NMR (68 MHz, CDCl$_3$): δ 23.77, 23.97, 24.0, 28.8, 29.8, 32.6, 36.3, 36.5, 38.1, 50.5, 50.7, 50.8, 59.17, 59.2, 68.1, 68.3, 115.1, 123.0, 124.0, 124.5, 126.9, 127.0, 128.55, 128.6, 128.9, 132.0, 132.1, 135.9, 150.2, 174.1.

Mass (M+H) 451

Calculated for 0.53 mol H$_2$O:

|   | Calc. | Found |
|---|-------|-------|
| C | 57.42 | 57.37 |
| H | 6.80  | 6.68  |
| N | 6.09  | 6.14  |
| S | 6.97  | 6.96  |

HPLC: >99% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=16.0 minutes.

EXAMPLE 32

N-[5-[1-Hydroxy-2-[[6-hydroxy-1-(phenylmethyl) hexyl]amino]ethyl]-2-hydroxyphenyl] methanesulfonamide, trifluoroacetate salt

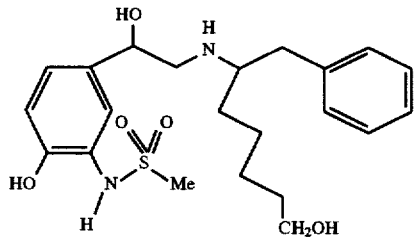

A. 6-Amino-7-benzeneheptanol

To a stirred THF (15 mL) containing 6-amino-7-benzeneheptanoic acid, methyl ester (450 mg, 1.95 mmol), described in part B of Example 30, was added 1M LiAlH$_4$ in THF (5 mL, 5 mmol). After six hours at 20° C., the reaction was quenched by dropwise addition of sat. aq. NH$_4$Cl, extracted 4× with EtOAc and dried over Na$_2$SO$_4$. The residue, obtained after concentration, was chromatographed on silica gel using 5% MeOH, 1% conc. NH$_4$OH, 94% CH$_2$Cl$_2$ to elute the title compound (250 mg, 60%).

B. N-[5-[1-Hydroxy-2-[[6-hydroxy-1-(phenylmethyl)hexyl] amino]ethyl]-2-hydroxyphenyl]methanesulfonamide 6-Amino-7-benzeneheptanol was converted to the title compound following the procedures outlined in steps D and E of Example 1, except for the following modifications: 1) the prep HPLC purification of step D was omitted; and 2) in step E, the final product was purified by prep HPLC using 38% solvent B as eluant.

$^1$H NMR (270 MHz, CDCl$_3$): δ 1.3–1.8 (m, 8H), 2.90 (m, 1H), 2.92 (s, 3H, SO$_2$CH$_3$), 3.06–3.26 (m, 3H), 3.50 (m, 3H), 4.88 (m, 1H), 6.91 (m, 1H), 7.1 (m, 1H) 7.25–7.42 (m, 6H).

$^{13}$C NMR (68 MHz, CDCl$_3$): δ 24.2, 24.3, 24.5, 24.8, 25.1, 27.3, 29.3, 30.2, 31.6, 36.4, 36.6, 38.1, 50.8, 50.9, 59.26, 59.3, 59.4, 61.1, 67.7, 68.1, 68.3, 115.1, 122.9, 124.0, 124.5, 126.9, 126.93, 128.5, 128.6, 128.9, 132.0, 132.1, 135.9, 136.0, 150.2.

Mass (M+H) 437

Calculated for 0.43 mol H$_2$O and 1.3 mol TFA:

|   | Calc. | Found |
|---|-------|-------|
| C | 49.86 | 49.87 |
| H | 5.81  | 5.58  |
| N | 4.73  | 4.42  |
| S | 5.41  | 4.97  |
| F | 12.5  | 12.92 |

HPLC: 95% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=16.0 minutes.

EXAMPLE 33

ε-[[2-Hydroxy-2-[4-hydroxy-3-[(methylsulfonyl)amino]phenyl]ethyl]amino]-N,N-dimethylbenzeneheptanamide, trifluoroacetate salt

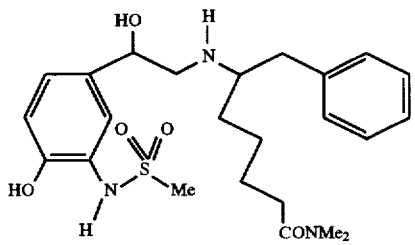

A. 6-Amino-N,N-dimethyl-7-benzeneheptanoamide

6-Amino-7-benzeneheptanoic acid, methyl ester was converted to 6-amino-N,N-dimethyl-7-benzeneheptanoamide following the procedures described in steps A and B of Example 18, except for the following modifications: 1) the product of step A was chromatographed on silica gel using 1:1 hexane/EtOAc; and 2) the intermediary bis-amide counterpart of step B was chromatographed using EtOAc as the eluant.

B. ε-[[2-Hydroxy-2-[4-hydroxy-3-[(methylsulfonyl)amino]phenyl]ethyl]amino]-N,N-dimethylbenzeneheptanamide 6-Amino-N,N-dimethyl-7-benzeneheptanoamide was converted to the title compound following the procedures outlined in steps D and E of Example 1, except for the following modifications: 1) the prep HPLC purification of step D was omitted; and 2) in step E, the final product was purified by prep HPLC using 37% solvent B as eluant.

$^1$H NMR (270 MHz, CDCl$_3$): δ 1.25–1.73 (m, 6H), 2.32 (t, 2H), 2.90 (s, 3H), 2.92 (s, 3H), 2.95 (m, 1H), 2.99 (s, 3H), 3.06–3.26 (m, 3H), 3.55 (m, 1H), 4.86 (m, 1H), 6.88 (t, 1H), 7.08 (m, 1H) 7.26–7.42 (m, 6H).

$^{13}$C NMR (68 MHz, CDCl$_3$): δ 23.9, 24.0, 24.1, 28.9, 29.8, 31.8, 34.3, 36.3, 36.4, 36.6, 38.1, 50.7, 50.9, 50.8, 59.1, 68.1, 68.3, 115.1, 122.9, 124.0, 124.5, 126.9, 128.5, 128.6, 128.8, 128.9, 129.1, 132.0, 132.1, 135.9, 136.0, 150.1, 173.7.

Mass (M+H) 478

Calculated for 0.59 mol H$_2$O and 2.0 mol TFA:

|   | Calc. | Found |
|---|-------|-------|
| C | 46.95 | 46.95 |
| H | 5.37  | 5.39  |
| N | 5.87  | 6.08  |
| F | 15.91 | 16.25 |

HPLC: >99% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=16.1 minutes.

EXAMPLE 34

ε-[[2-Hydroxy-2-[4-hydroxy-3-[(methylsulfonyl)amino]phenyl]ethyl]amino]-N-methylbenzeneheptanamide, trifluoroacetate salt

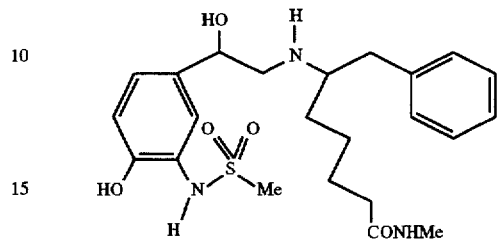

A. 6-Amino-N-methyl-7-benzeneheptanamide

6-Amino-7-benzeneheptanoic acid, methyl ester was converted to 6-amino-N-methyl-7-benzeneheptanamide following the procedures described in steps A and B of Example 18, except for the substitution of H$_2$NMe for HNMe$_2$ in step B.

B. ε-[[2-Hydroxy-2-[4-hydroxy-3-[(methylsulfonyl)amino]phenyl]ethyl]amino]-N-methylbenzeneheptanamide 6-Amino-N-methyl-7-benzeneheptanamide was converted to the title compound following the procedures outlined in steps D and E of Example 1, except for the following modifications: 1) the prep HPLC purification of step D was omitted; and 2) in step E, the final product was purified by prep HPLC using 37% solvent B as eluant.

$^1$H NMR (270 MHz, CDCl$_3$): δ 1.25–1.73 (m, 6H), 2.15 (t, 2H), 2.68 (s, 3H), 2.93 (s, 3H), 2.94 (m, 1H), 3.06–3.26 (m, 3H), 3.53 (m, 1H), 4.84 (m, 1H), 6.91 (t, 1H), 7.08 (m, 1H) 7.26–7.42 (m, 6H).

$^{13}$C NMR (68 MHz, CDCl$_3$): δ 25.6, 25.7, 26.4, 26.5, 30.7, 31.7, 37.1, 38.7, 38.8, 40.2, 52.2, 52.3, 61.0, 70.4, 70.5, 117.0, 125.0, 126.0, 126.5, 128.5, 130.0, 130.2, 130.3, 134.0, 137.5, 152.4, 176.6.

Mass (M+H) 464

Calculated for 1.0 mol H$_2$O and 1.5 mol TFA:

|   | Calc. | Found |
|---|-------|-------|
| C | 47.85 | 47.83 |
| H | 5.64  | 5.45  |
| N | 6.44  | 6.36  |
| S | 4.91  | 4.57  |
| F | 13.10 | 13.10 |

HPLC: 100% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention times=1.5 and 15.7 minutes.

EXAMPLE 35

ε-[[2-Hydroxy-2-[4-hydroxy-3-[(methylsulfonyl)amino]phenyl]ethyl]amino]-3,4-dimethoxybenzeneheptanoic acid, methyl ester, trifluoroacetate salt

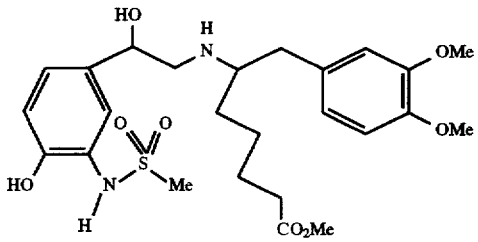

A. 6-Amino-7-(3,4-dimethoxybenzene)heptanoic acid, methyl ester

Following the procedure described by W. G. Kofron et al., *J. Org. Chem.*, 41, 439 (1976), 2-(3,4-dimethoxyphenylmethyl)-cyclohexanone, oxime was prepared from commercially available cyclohexanone, oxime and 3,4-dimethoxyphenylmethylchloride, freshly prepared by treatment of commercial 3,4-dimethoxyphenylmethanol with thionyl chloride. 2-(3,4-dimethoxyphenyl-methyl)cyclohexanone, oxime was converted to 6-amino-7-(3,4-dimethoxybenzene)heptanoic acid, methyl ester as described in steps A and B of Example 30.

B. ε-[[2-Hydroxy-2-[4-hydroxy-3-[(methylsulfonyl)amino]phenyl]ethyl]amino]-3,4-dimethoxybenzeneheptanoic acid, methyl ester 6-Amino-7-(3,4-dimethoxybenzene)heptanoic acid, methyl ester was converted to the title compound following the procedures outlined in steps D and E of Example 1, except for the following modifications: the prep HPLC purification of step D utilized 56% solvent B.

$^1$H NMR (270 MHz, CDCl$_3$): δ 1.25–1.73 (m, 6H), 2.31 (t, 2H), 2.92 (s, 3H), 2.99 (m, 3H), 3.15 (m, 1H), 3.63 (m, 1H), 3.63 (s, 3H), 3.81 (s, 3H), 3.84 (s, 3H), 4.83 (m, 1H), 6.88 (m, 4H), 7.1 (m, 1H), 7.35 (m, 1H).

$^{13}$C NMR (68 MHz, CDCl$_3$): δ 23.9, 24.0, 24.1, 30.0, 32.7, 36.3, 38.1, 50.6, 50.7, 50.9, 55.0, 59.3, 68.3, 68.4, 111.7, 111.8, 112.5, 115.1, 121.3, 122.9, 123.98, 124.0, 124.7, 128.3, 128.4, 131.8, 148.0, 149.2, 150.2, 174.1.

Mass (M+H) 524

Calculated for 2.65 mol H$_2$O and 1.5 mol TFA:

|   | Calc. | Found |
|---|-------|-------|
| C | 45.30 | 45.30 |
| H | 5.67  | 5.36  |
| N | 3.77  | 3.84  |
| S | 4.32  | 3.81  |
| F | 11.52 | 11.89 |

HPLC: 92% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.6 minutes.

EXAMPLE 36

N-[2-Hydroxy-5-[(R)-1-hydroxy-2-[[2-phenyl-1-(4-pyridinyl)ethyl]amino]ethyl]phenyl]methanesulfonamide, trifluoroacetate salt

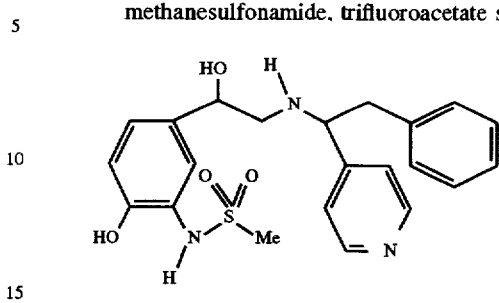

A. α-Pyridyl-benzeneethanamine

Commercially available 4-pyridinecarboxaldehyde was converted to the title compound using the procedures described in steps A–C of Example 1, except for the following modifications: 1) the chromatography of step B was omitted; 2) in step C, the intermediary formamide was purified by silica gel chromatography using 5% MeOH/EtOAc as eluant; and 3) the acidic hydrolysis reaction, after dilution with H$_2$O, was extracted 2× with Et$_2$O prior to basification, extraction 3× with EtOAc and isolation of the title compound after concentration.

B. N-[2-Hydroxy-5-[(R)-1-hydroxy-2-[[2-phenyl-1-(4-pyridinyl)ethyl]amino]ethyl]phenyl]methanesulfonamide α-Pyridyl-benzeneethanamine was converted to the title compound following the procedures outlined in steps D–F of Example 19, except for the following modifications: 1) the chromatographic purification of step D was omitted; and 2) in step F, the final product was purified by prep HPLC using 15% solvent B as eluant.

$^1$H NMR (270 MHz, CD3OD): δ 2.90 & 2.92 (2 s, 3H, —SO2CH3), 3.00–3.06 (m, 1H), 3.15–3.25 (m, 2H), 3.58–3.70 (m, 1H), 4.68–4.78 (m, 1H), 6.85 & 6.89 (2 d, 1H), 7.00–7.23 (m, 6H), 7.30–7.35 (m, 1H), 7.60 (1, H).

$^{13}$C NMR (67 MHz, CD3OD): δ 40.0, 40.5, 54.6, 64.6, 65.0, 70.1, 70.4, 117.0, 124.8, 125.7, 125.9, 126.6, 128.9, 130.2, 130.8, 133.7, 133.8, 136.0, 136.1, 149.9, 152.1.

Mass (M+H) 427

HPLC: >99% pure, Shimadzu LC-6A, YMC S3 ODS (6.0× 150 mm); flow rate of 1.5 mL/minute; detection at 217 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention times=8.2 and 8.7 minutes.

EXAMPLE 37

α-[[(R)-2-Hydroxy-2-[4-hydroxy-3-[(methylsulfonyl)amino]phenyl]ethyl]amino]-4-methoxybenzeneacetamide, isomer A

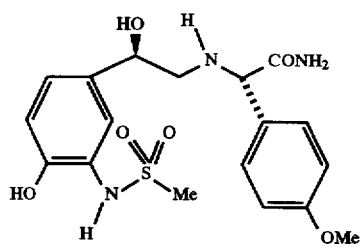

A. α-[[(R)-2-(Triethylsilyl)oxy-2-[4-phenylmethoxy-3-[(methylsulfonyl)amino]phenyl]ethyl]amino]-4-methoxybenzeneacetamide, isomer A α-Amino-4-methoxybenzeneacetamide (prepared as described in Y. B. Lee et al., *Tet. Lett.*, 31, 1169 (1990)) was converted to the title compound following the procedure described in step D of Example 19, except for the following modification: in step D after silica gel chromatography, the diastereomeric mixture was separated by prep TLC using 5% i-PrOH/CHCl₃ to obtain two diastereomers A and B of the title compound.

B. α-|[(R)-2-Hydroxy-2-|4-hydroxy-3-|(methylsulfonyl) amino|phenyl|ethyl|amino|-4-methoxybenzeneacetamide, isomer A α-|[(R)-2-(Triethylsilyl)oxy-2-[4-phenylmethoxy-3-|(methylsulfonyl)amino|phenyl|ethyl|amino|-4-methoxybenzeneacetamide, isomer A was converted to the title compound following the procedures described in steps E and F of Example 19, except for the following modifications: 1) the product of step E was purified by prep TLC using a 1:9:90 mixture of conc. NH₃/MeOH/CH₂Cl₂; 2) in step F the hydrogenolysis was run under 1 atmosphere H₂ for ten minutes; and 3) the product was purified by prep TLC using a 1:9:90 mixture of conc. NH₃/MeOH/CH₂Cl₂.

¹H NMR (270 MHz, CD₃OD): δ 7.34–7.28 (m, 3H), 7.05 (dd, J=2.34, 8.21 Hz, 1H), 6.90–6.83 (m, 3H), 4.65 (m, 1H), 4.16 (s, 1H), 3.77 (s, 3H), 2.91 (s, 3H), 2.77–2.66 (m, 2H).

¹³C NMR (68 MHz, CD₃OD): δ 178.01, 161.05, 151.03, 135.88, 132.45, 129.77, 125.77, 125.71, 124.50, 116.36, 115.03, 73.39, 67.00, 56.20, 55.71, 39.50.

Mass (M+H) 410

Calculated for 2.9 mol H₂O:

|   | Calc. | Found |
|---|-------|-------|
| C | 46.83 | 47.19 |
| H | 6.29  | 4.81  |
| N | 9.10  | 8.74  |

HPLC: 100% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H₂O, 0.2% H₃PO₄); B=90% MeOH, 10% H₂O, 0.2% H₃PO₄); retention time=9.9 minutes.

EXAMPLE 38

α-|[(R)-2-Hydroxy-2-|4-hydroxy-3-|(methylsulfonyl)amino|phenyl|ethyl|amino|-4-methoxybenzeneacetamide, isomer B

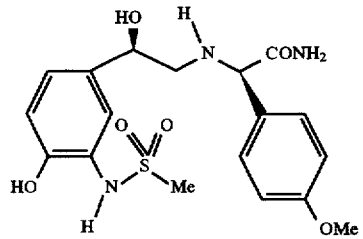

α-|[(R)-2-(Triethylsilyl)oxy-2-[4-phenylmethoxy-3-|(methylsulfonyl)amino|phenyl|ethyl|amino|-4-methoxybenzeneacetamide, isomer B of step A of Example 37 was converted to the title compound utilizing the procedure described in step B of Example 37.

¹H NMR (270 MHz, CD₃OD): δ 7.32–7.29 (m, 3H), 7.02 (dd, J=1.76, 8.21 Hz, 1H), 6.89–6.82 (m, 3H), 4.68 (m, 1H), 4.16 (s, 1H), 3.77 (s, 3H), 2.91 (s, 3H), 2.74–2.64 (m, 2H).

¹³C NMR (68 MHz, CD₃OD): δ 178.08, 161.06, 151.10, 135.95, 132.41, 129.82, 125.81, 125.58, 124.49, 116.45, 115.07, 73.37, 67.12, 56.15, 55.78, 39.51.

Mass (M+H) 410

Calculated for 1.54 mol H₂O:

|   | Calc. | Found |
|---|-------|-------|
| C | 49.46 | 49.54 |
| H | 6.01  | 4.43  |
| N | 9.61  | 9.53  |

HPLC: 100% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H₂O, 0.2% H₃PO₄); B=90% MeOH, 10% H₂O, 0.2% H₃PO₄); retention time=9.6 minutes.

EXAMPLE 39

(R)-α-|[2-Hydroxy-2-|4-hydroxy-3-|(methylsulfonyl)amino|phenyl|ethyl|amino|-α-(4-methoxyphenyl)-4-methoxybenzeneacetamide

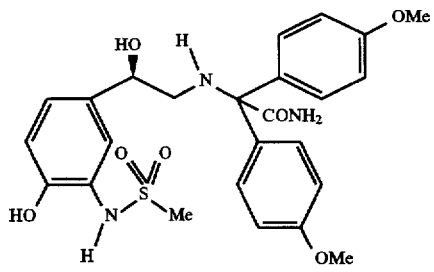

A. α-Amino-bis-(4-methoxyphenyl)acetamide

α-Chloro-bis-(4-methoxyphenyl)acetyl chloride (2.2 g, 6.8 mmol) prepared, as described in U.S. Pat. No. 3,006,917, from α-hydroxy-bis-(4-methoxyphenyl)acetic acid (see T. Ohwada et al., *J. Amer. Chem. Soc.*, 110, 1862 (1988) for preparation) in dry dioxane (30 mL) was converted to the title compound by bubbling NH₃ through the solution for three hours. After filtration of the NH₄Cl and concentration, the residue was recrystallized 2× from EtOAc prior to chromatography on silica gel using EtOAc to 5% MeOH/EtOAc to elute the title compound (468 mg, 24%).

B. (R)-α-[[2-Hydroxy-2-|4-hydroxy-3-|(methylsulfonyl) amino|phenyl]ethyl|amino|-α-(4-methoxyphenyl)-4-methoxybenzeneacetamide α-Amino-bis-(4-methoxyphenyl)acetamide was converted to the title compound following the procedures described in steps D–F of Example 19, except for the following modifications: 1) after step D, the chromatographic solvent for the first silica gel column was 3% MeOH/CH₂Cl₂ and 1:1 EtOAc/hexane for the second; 2) after step E, the product was eluted from silica gel with 2% MeOH/CH₂Cl₂; 3) in step F the hydrogenolysis was run under 1 atmosphere H₂ for ten minutes; and 4) the title compound was purified by prep TLC using 10% MeOH/CH₂Cl₂.

¹HNMR (CD₃OD, 400 MHz): δ 2.31 (m, 2H), 2.90 (s, 3H), 3.77 (s, 6H), 4.57 (m, 1H), 6.80–7.40 (m, 11H, aromatic).

¹³CNMR (CD₃OD): δ 39.57, 53.13, 55.75, 72.80, 74.06, 114.19, 116.35, 124.83, 125.64, 131.14, 135.88, 136.00, 136.25, 150.90, 160.21, 178.76.

MS (M+H) 516
Calculated for 0.76 mol H$_2$O:

|   | Calc | Found |
|---|------|-------|
| C | 56.74 | 56.94 |
| H | 5.81  | 5.68  |
| N | 7.94  | 7.74  |

HPLC: 100% pure. Shimadzu LC-6A. YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=15.4 minutes.

EXAMPLE 40

4-[[[5-[2-[[2-(3,4-Dimethoxyphenyl)ethyl]amino]-1-hydroxyethyl]-2-hydroxyphenyl]amino]sulfonyl] benzoic acid, methyl ester

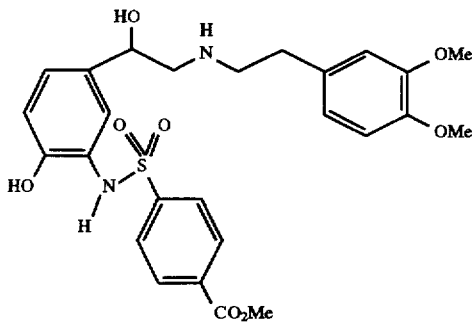

A. 5-Bromoacetyl-2-phenylmethoxyphenyl]amino] sulfonyl]benzoic acid, methyl ester The title compound was prepared by bromination of 5-acetyl-2-phenylmethoxyphenyl]amino]sulfonyl]benzoic acid, methyl ester which in turn was prepared by coupling 1-[4-phenylmethoxy-3-amino]phenylethanone (described in part 3 of step F of Example 1) with 4-(chlorosulfonyl) benzoic acid, methyl ester (prepared by titration of commercially available 4-(chlorosulfonyl)benzoic acid with diazomethane in Et$_2$O) following the procedure described in part 4 of step F of Example 1, except for the following modifications: the coupled product was chromatographed on silica gel using 40% EtOAc/hexane and then recrystallized from EtOAc/hexane.

A 1:3 HOAc/THF (20 mL) solution of 5-acetyl-2-phenylmethoxyphenyl]amino]sulfonyl]benzoic acid, methyl ester (608 mg, 1.38 mmol) and Br$_2$ (221 mg, 1.38 mmol) was stirred at 20° C. overnight whereupon 70 mg of additional Br$_2$ was added and stirred for 24 hours. After dilution with EtOAc, the solution was washed with aq. NaHCO$_3$, brine, and dried over Na$_2$SO$_4$. The residue, upon after concentration, was chromatographed on silica gel using 30% EtOAc/hexane as eluant to obtain the title compound (536 mg, 75%).

B. 4-[[[5-[2-[[2-(3,4-Dimethoxyphenyl)ethyl]amino]-1-hydroxyethyl]-2-hydroxyphenyl]amino]sulfonyl]benzoic acid, methyl ester The title compound was prepared by coupling of commercially available 2-(3,4-dimethoxybenzene)ethylamine with 5-bromoacetyl-2-phenylmethoxyphenyl]amino] sulfonyl]benzoic acid, methyl ester and subsequent reactions described in steps D and E of Example 1, except for the following modifications: 1) the prep HPLC purification of step D was omitted; and 2) the catalyst of step E was Pd(OH)$_2$.

$^1$H NMR (270 MHz, DMSO-d$_6$): δ 2.6–2.7 (m, 3H), 2.8–2.9 (m, 2H), 3.72 (s, 3H, OCH$_3$), 3.73 (s, 3H, OCH$_3$), 3.83 (s, 3H, CO$_2$CH$_3$), 4.49 (br t, 1H), 6.60 (d, 1H, J=8.21 Hz), 6.72 (m, 2H), 6.80 (s, 1H), 6.86 (d, 1H, J=8.21 Hz), 7.06 (s, 1H), 7.82 (d, 2H, J=8.8 Hz), 8.00 (d, 2H, J=8.8 Hz).

$^{13}$C NMR (67.7 MHz, DMSO-d$_6$): δ 33.9, 48.6, 49.9, 52.4, 55.4, 55.5, 56.0, 70.2, 111.9, 112.5, 113.4, 120.4, 120.7, 121.0, 126.9, 127.8, 129.3, 131.6, 131.7, 133.8, 147.2, 148.6, 149.4, 165.4.

MS (M+H) 531

|   | Calc. | Found |
|---|-------|-------|
| C | 58.86 | 58.65 |
| H | 5.70  | 5.67  |
| N | 5.28  | 5.37  |
| S | 6.04  | 5.91  |

HPLC: 100% pure. Shimadzu LC-6A. YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.7 minutes.

EXAMPLE 41

N-[5-[2-[[2-(3,4-Dimethoxyphenyl)ethyl]amino]-1-hydroxyethyl]-2-hydroxyphenyl] benzenemethanesulfonamide, trifluoroacetate salt

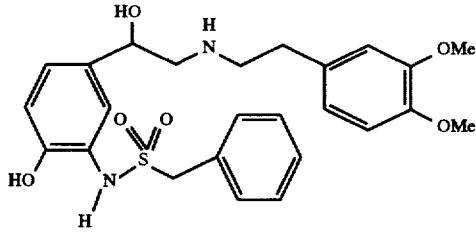

A. 2-Bromo-1-[4-phenylmethoxy-3-(benzenemethylsulfonyl)amino]phenylethanone

Following the procedure described in step A of Example 40, the title compound was prepared by bromination of 1-[4-phenylmethoxy-3-(benzenemethylsulfonyl)amino] phenylethanone which in turn was prepared by coupling 1-[4-phenylmethoxy-3-amino]phenylethanone (described in part 3 of step F of Example 1) with commercially available benzenemethylsulfonyl chloride following the procedure described in part 4 of step F of Example 1.

B. N-[5-[2-[[2-(3,4-Dimethoxyphenyl)ethyl]amino]-1-hydroxyethyl]-2-hydroxyphenyl] benzenemethanesulfonamide The title compound was prepared by coupling of commercially available 2-(3,4-dimethoxybenzene)ethylamine with 2-bromo-1-[4-phenylmethoxy-3-(benzenemethylsulfonyl)amino]phenylethanone and subsequent reactions described in steps D and E of Example 1, except for the following modifications: 1) the prep HPLC purification of step D was omitted; and 2) the catalyst of step E was Pd(OH)$_2$ and the final product was purified by prep HPLC using 41% solvent B.

$^1$H NMR (270 MHz, CD$_3$OD): δ 2.9–3.0 (m, 2H), 3.0–3.3 (m, 4H), 3.80 (s, 3H, OCH$_3$), 3.83 (s, 3H, OCH$_3$), 4.38 (s, 2H), 4.82 (m, 1H), 6.8–6.95 (m, 4H), 7.05–7.10 (dd, 1H), 7.31 (s, 5H), 7.38 (d, 1H).

$^{13}$C NMR (67.7 MHz, CD$_3$OD): δ 32.7, 50.1, 55.1, 56.5, 58.8, 69.7, 113.5, 113.7, 116.5, 122.2, 124.6, 126.6, 129.5, 130.5, 130.7, 132.1, 133.6, 149.8, 150.4, 150.9.

MS (M+H) 487

Calculated for 1.21 moles of H$_2$O and 1.0 moles of TFA:

|   | Calc. | Found |
|---|-------|-------|
| C | 52.11 | 52.11 |
| H | 5.41  | 5.15  |
| N | 4.50  | 4.40  |
| F | 9.16  | 9.06  |
| S | 5.15  | 5.25  |

HPLC: >97% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.0 minutes.

EXAMPLE 42

N-[5-[2-[[2-(3,4-Dimethoxyphenyl)ethyl]amino]-1-hydroxyethyl]-2-hydroxyphenyl]-4-methylbenzenesulfonamide, trifluoroacetate salt

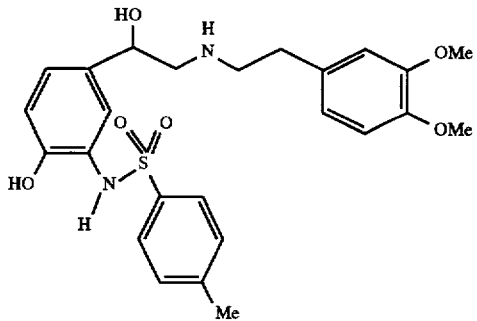

A. 2-Bromo-1-[4-phenylmethoxy-3-(4-methylbenzenesulfonyl)amino]phenylethanone

Following the procedure described in step A of Example 40, the title compound was prepared by bromination of 1-[4-phenylmethoxy-3-(4-methylbenzenesulfonyl)amino] phenylethanone except for the following modifications: 1) the reaction was run for six hours in CH$_2$Cl$_2$; 2) the crude product was purified by 2 recrystallizations from 95% EtOH. 1-[4-phenylmethoxy-3-(4-methylbenzenesulfonyl) amino]phenylethanone in turn was prepared by coupling 1-[4-phenylmethoxy-3-amino]phenylethanone (described in part 3 of step F of Example 1) with commercially available 4-methylbenzenesulfonyl chloride following the procedure described in part 4 of step F of Example 1.

B. N-[5-[2-[[2-(3,4-Dimethoxyphenyl)ethyl]amino]-1-hydroxyethyl]-2-hydroxyphenyl]-4-methylbenzenesulfonamide, trifluoroacetate salt Utilizing the procedures described in steps D and E of Example 1, the title compound was prepared by the coupling of commercially available 2-(3,4-dimethoxybenzene) ethylamine with 2-bromo-1-[4-phenylmethoxy-3-(4-methylbenzenesulfonyl)amino]phenylethanone and subsequent reactions except for the following modifications: 1) the preparative HPLC purification of step D was omitted; and 2) the catalyst of step E was Pd(OH)$_2$ and the final product was purified by preparative HPLC using 41% solvent B.

$^1$H NMR (270 MHz, CD$_3$OD): δ 2.35 (s, 3H), 2.9–3.0 (m, 2H), 3.0–3.2 (m, 2H), 3.22–3.28 (brd, 2H), 3.81 (s, 3H, OCH$_3$), 3.83 (s, 3H, OCH$_3$), 3.75–3.85 (m, 1H), 6.70 (d, 1H, J=8.2 Hz), 6.8–7.02 (m, 4H), 7.28 (d, 2H, J=8.2 Hz), 7.44 (d, 1H, J=2.4 Hz), 7.62 (d, 2H, J=8.8 Hz).

$^{13}$C NMR (67.7 MHz, CD$_3$OD): δ 21.4, 32.7, 50.0, 55.1, 56.5, 69.7, 113.5, 113.7, 116.3, 122.2, 122.8, 124.7, 126.1, 128.3, 130.3, 130.5, 133.3, 138.4, 144.8, 149.8, 150.9, 150.9, 175.9.

MS (M+H) 487

Calculated for 0.27 moles of H$_2$O and 1.1 moles of TFA:

|   | Calc. | Found |
|---|-------|-------|
| C | 52.96 | 52.96 |
| H | 5.17  | 5.11  |
| N | 4.54  | 4.31  |
| F | 10.16 | 10.08 |
| S | 5.20  | 5.26  |

HPLC: >98% pure, Shimadzu LC-6A, YMC S3 ODS (6.0× 150 mm); flow rate of 1.5 mL/minute; detection at 217 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=17.6 minutes.

EXAMPLE 43

N-[5-[2-[[bis(4-Methoxymethylphenyl)methyl]amino]-1-hydroxyethyl]-2-hydroxyphenyl]methanesulfonamide, trifluoroacetate salt

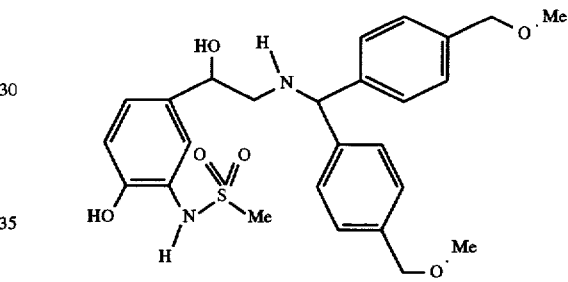

A. 4,4'-bis-Bromomethylbenzophenone

A suspension of NBS (11 g, 62 mmol) in CH$_2$Cl$_2$ (100 mL) containing commercially available 4,4'-dimethylbenzophenone (6.3 g, 30 mmol) was refluxed for five hours while being irradiated with a sun lamp. After concentration, the resulting solid was triterated sequentially once with 1:1 hexane/CCl$_4$ and three times with 1N aq. NaOH. The resulting solid was then recrystallized from 30% hexane/CCl$_4$ to yield 8.4 (76%) of the title compound.

B. 4,4'-bis-Methoxymethylbenzophenone

A solution of 0.46M NaOMe/MeOH (30 mL) containing 4,4'-bis-bromomethylbenzophenone (2.1 g, 5.7 mmol) was refluxed 42 hours. After cooling, the reaction was partitioned between EtOAc and 5% aq. KHSO$_4$. The organic layer was washed with brine, dried over Na$_2$SO$_4$ and concentrated. The resulting residue was chromatographed on silica gel using 1:4 EtOAc/hexane to elute 1.11 g (70%) of the title compound.

C. N-[5-[2-[[bis(4-Methoxymethylphenyl)methyl]amino]-1-hydroxyethyl]-2-hydroxyphenyl]methanesulfonamide, trifluoroacetate salt 4,4'-bis-Methoxymethylbenzophenone was converted to 4,4'-bis-methoxymethylbenzhydrylamine following the procedure described in step C of Example 1, except for the following modifications: 1) the amination reaction was run for 18 hours at 175° C.; and 2) the acidic hydrolysis reaction, after dilution with H$_2$O, was extracted 2× with Et$_2$O prior to basification, extraction 3× with EtOAc and isolation of the desired amine.

The title compound was prepared by coupling 2-bromo-1-[4-hydroxy-3-[(methylsulfonyl)amino]phenyl]ethanone with 4,4'-bis-methoxymethylbenzhydrylamine and subsequent reaction as described in step B of Example 5, except for the following modifications: the crude product, after conversion to the TFA salt was purified by prep HPLC utilizing 40% solvent B as the eluant.

$^1$H NMR (270 MHz, CD$_3$OD): δ 2.89 (s, 3H), 3.0–3.1 (m, 2H), 3.36 (s, 3H), 3.37 (s, 3H), 4.45 (s, 2H), 4.47 (s, 2H), 4.9 (1H,), 5.62 (s, 1H), 6.84 (d, 1H), 7.01 (dd, 1H), 7.29 (d, 1H), 7.4–7.55 (m, 8H).

$^{13}$C NMR (67 MHz, CD$_3$OD): δδ 39.6, 54.3, 58.5, 66.6, 69.7, 74.9, 116.6, 124.4, 125.3, 126.1, 128.8, 129.1, 129.4, 129.6, 129.7, 130.1, 133.6, 136.1, 136.4, 141.0, 141.1, 151.7.

Mass (M+H) 501

Calculated for 2.35 mole H$_2$O and 1.2 mole TFA:

|   | Calc. | Found |
|---|-------|-------|
| C | 50.18 | 50.18 |
| H | 5.62  | 5.22  |
| N | 4.12  | 4.37  |
| S | 4.72  | 4.77  |
| F | 10.06 | 10.22 |

HPLC: >98% pure, Shimadzu LC-6A, YMC S3 ODS (6.0× 150 mm); flow rate of 1.5 ml/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=17.4 minutes.

EXAMPLE 44

(R),(R)-N-[5-[2-[[1-(1,3-Benzodioxol-5-yl)-2-phenylethyl]amino]-1-hydroxyethyl]-2-hydroxyphenyl]methanesulfonamide, trifluoroacetate salt

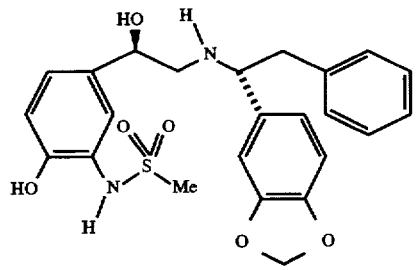

A. N-[5-[(R)-1-(Hydroxy-2-[[1-(1,3-benzodioxol-5-yl)-2-phenylethyl]amino]ethyl]-2-(phenylmethoxy)phenyl]methanesulfonamide, cyclic urethane The title compound was prepared by condensation of α-(1,3-benzodioxol-5-yl)benzeneethanamine (see Example 3 for preparation) with (R)-N-[5-[2-iodo-1-[(triethylsilyl)oxy]ethyl]-2-(phenylmethoxy)phenyl]methanesulfonamide and subsequent reaction as described in steps D–E of Example 19 to generate N-[5-[(R)-1-(hydroxy-2-[[1-(1,3-benzodioxol-5-yl)-2-phenylethyl]amino]ethyl]-2-(phenylmethoxy)phenyl]methanesulfonamide. Subsequently, the N-[5-[(R)-1-(hydroxy-2-[[1-(1,3-benzodioxol-5-yl)-2-phenylethyl]amino]ethyl]-2-(phenylmethoxy)phenyl]methanesulfonamide so formed was transformed to the title compound following the procedure described in step A of Example 22, except that the two diastereomeric products were separated on a preparative HPLC C$_{18}$ HPLC column using 86% solvent B (solvent A=90% H$_2$O/MeOH; solvent B=90% MeOH/H$_2$O) to elute diastereomers A and B.

B. (R),(R)-N-[5-[2-[[1-(1,3-Benzodioxol-5-yl)-2-phenylethyl]amino]-1-hydroxyethyl]-2-hydroxyphenyl]methanesulfonamide, trifluoroacetate salt The title compound was prepared from N-[5-[(R)-1-(hydroxy-2-[[1-(1,3-benzodioxol-5-yl)-2-phenylethyl]amino]ethyl]-2-(phenylmethoxy)phenyl]methanesulfonamide, cyclic urethane, diastereomer A following the procedures described in steps B and C of Example 22, except for final HPLC purification using 46% solvent B.

$^1$H NMR (270 MHz, CD$_3$OD): δ 2.9 (s, 3H), 3.04 (m, 1H), 3.2–3.3 (m, 2H), 3.52 (m, 1H), 4.43 (m, 1H), 4.77 (m, 1H), 5.94 (s, 2H), 6.75 (s, 2H), 6.86–7.4 (m, 9H).

$^{13}$C NMR (68 MHz, CD$_3$OD): δ 39.6, 40.1, 53.5, 65.8, 69.96, 103.0, 109.0, 109.5, 124.2, 124.27, 125.45, 126.0, 128.0, 128.48, 129.5, 130.3, 133.57, 136.8, 149.96, 150.1, 151.6.

Mass (M+H) 471

[α]$_D$=−38.0° (c=0.51, MeOH)

Calculated for 1.0 mole H$_2$O and 1.13 mole TFA:

|   | Calc. | Found |
|---|-------|-------|
| C | 51.09 | 51.09 |
| H | 4.76  | 4.32  |
| N | 4.54  | 4.43  |
| S | 5.19  | 5.05  |
| F | 10.43 | 10.05 |

HPLC: 94% pure, Shimadzu LC-6A, YMC S3 ODS (6.0× 150 mm); flow rate of 1.5 ml/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=18.5 minutes.

EXAMPLE 45

(R),(S)-N-[5-[2-[[1-(1,3-Benzodioxol-5-yl)-2-phenylethyl]amino]-1-hydroxyethyl]-2-hydroxyphenyl]methanesulfonamide, trifluoroacetate salt

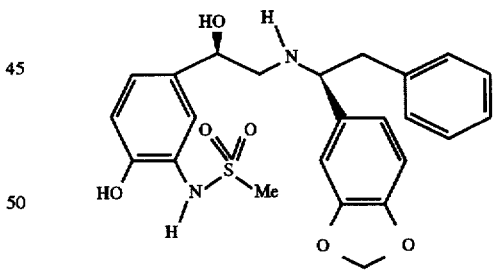

The title compound was prepared from N-[5-[(R)-1-(hydroxy-2-[[1-(1,3-benzodioxol-5-yl)-2-phenylethyl]amino]ethyl]-2-(phenylmethoxy)phenyl]methanesulfonamide, cyclic urethane, diastereomer B (see step A of Example 44 for preparation) following the procedures described in steps B and C of Example 22, except for final HPLC purification using 46% solvent B.

$^1$H NMR (270 MHz, CD$_3$OD): δ 2.80 (m, 1H), 2.9 (s, 3H), 3.03 (m, 1H), 3.24 (m, 1H), 3.43 (m, 1H), 4.46 (m, 1H), 4.88 (m, 1H), 5.97 (s, 2H), 6.75 (s, 2H), 6.84–7.4 (m, 9H).

$^{13}$C NMR (68 MHz, CD$_3$OD): δ 39.6, 40.5, 53.5, 65.2, 69.5, 103.0, 108.85, 109.5, 116.6, 124.25 125.26, 126.1, 128.1, 129.6, 130.37, 133.57, 136.7, 150.07, 150.18, 151.6.

Mass (M+H) 471

$[\alpha]_D$=+2.7° (c=0.55, MeOH)

Calculated for 1.0 mole H$_2$O and 1.13 mole TFA:

|   | Calc. | Found |
|---|-------|-------|
| C | 57.91 | 57.92 |
| H | 4.43  | 4.12  |
| N | 4.08  | 3.97  |
| S | 4.67  | 4.62  |
| F | 14.11 | 13.82 |

HPLC: 95% pure, Shimadzu LC-6A, YMC S3 ODS (6.0× 150 mm); flow rate of 1.5 ml/minute; detection at 220 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=18.5 minutes.

EXAMPLE 46

N-[5-[2-[[bis(4-Methoxyphenyl)methyl]amino]-1-hydroxyethyl]-2-fluorophenyl]methanesulfonamide

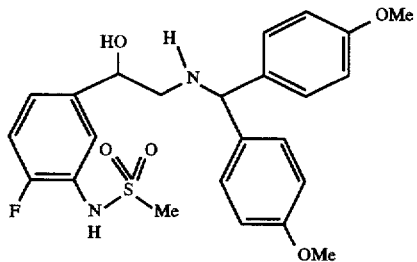

A. 1-[4-Fluoro-3-[(methylsulfonyl)amino]phenyl]ethanone

The title compound was prepared from commercially available 4-fluoroacetophenone utilizing the procedures employed in step F parts 1, 3, and 4 of Example 1, except for the following modifications: 1) in part 1, fuming nitric acid was both the solvent and reagent; the reaction was begun at −5° C. and then run for 20 hours at 20° C.; 2) the product, after isolation, was chromatographed on silica gel using 10% EtOAc/hexane as the eluant; 3) in part 3 the reduction employed PtO$_2$ as catalyst with 40 psi H$_2$ using a Parr shaker; and 4) the isolated product was chromatographed on silica gel using 20% EtOAc/hexane as eluant to yield the title compound.

B. 2-Bromo-1-[4-fluoro-3-[(methylsulfonyl)amino]phenyl]ethanone

To a stirred 20° C. solution (4 mL) of 40% HOAc/THF containing 1-[4-fluoro-3-[(methylsulfonyl)amino]phenyl]ethanone (1.0 g, 4.3 mmol) was added bromine (223 mL, 4.3 mmol). After stirring one hour, a second equivalent of bromine was added and the reaction run for 3.5 hours whereupon the reaction was judged complete by TLC (1:1 EtOAc/hexane). After dilution with EtOAc, the organic layer was washed with aq. NaHCO$_3$ and then brine before drying over Na$_2$SO$_4$. After concentration, 0.58 g (44%) of the title compound was isolated after recrystallization from EtOH.

C. N-[5-[2-[[bis(4-Methoxyphenyl)methyl]amino]-1-hydroxyethyl]-2-fluorophenyl]methanesulfonamide The title compound was prepared by coupling of 2-bromo-1-[4-fluoro-3-[(methylsulfonyl)amino]phenyl]ethanone with 4,4'-dimethoxybenzhydrylamine (preparation described in Example 14) following the procedure described in step D of Example 1, except for the following modification: the crude product after coupling and reduction was chromatographed on silica gel using 75% EtOAc/hexane to elute pure title compound.

$^1$H NMR (270 MHz, CDCl$_3$): δ 2.6 (m, 1H), 2.8 (m, 1H), 2.98 (s, 3H), 3.76 (s, 6H), 4.6 (dd, 1H), 4.77 (s, 1H), 7.03 (dd, 8H), 7.05–7.23 (m, 2H), 7.49 (d, 1H).

$^{13}$C NMR (68 MHz, CDCl$_3$): δ 39.76, 55.22, 65.55, 71.38, 113.89, 115.42, 115.71, 120.99, 123.76, 123.87, 124.22, 124.39, 128.14, 135.58, 135.84, 139.74, 151.42, 155.02, 158.63.

Mass (M−H) 473

Calculated for 0.52 mole H$_2$O:

|   | Calc. | Found |
|---|-------|-------|
| C | 59.58 | 59.70 |
| H | 5.84  | 5.62  |
| N | 5.79  | 5.67  |
| S | 6.63  | 6.43  |
| F | 3.93  | 4.21  |

HPLC: >98% pure, Shimadzu LC-6A, YMC S3 ODS (6.0× 150 mm); flow rate of 1.5 ml/minute; detection at 220 nm; gradient elution 0–100% B over 30 minutes (A=10% MeOH, 90% H$_2$O, 0.2% H$_3$PO$_4$); B=90% MeOH, 10% H$_2$O, 0.2% H$_3$PO$_4$); retention time=21.4 minutes.

EXAMPLE 47

N-[2-Hydroxy-5-[(R)-1-hydroxy-2-[[2-phenyl-1-(3-thienyl)ethyl]amino]ethyl]phenyl]methanesulfonamide, trifluoroacetate salt

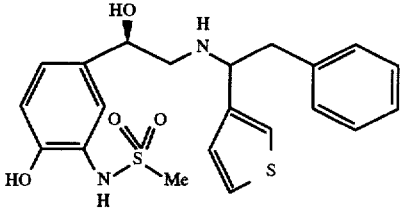

A. α-Thienylbenzeneethanamine

Commercially available 3-thiophenecarboxaldehyde was converted to the title compound using the procedures described in steps A–C of Example 1, except for the following modifications: 1) the chromatography of step A utilized 10% EtOAc/hexane as eluant; 2) the chromatography of step B was omitted; and 3) in step C, the acidic hydrolysis reaction, after dilution with H$_2$O, was extracted 2× with Et$_2$O prior to basification, extraction 3× with EtOAc and isolation of the title compound after concentration.

B. N-[2-Hydroxy-5-[(R)-1-hydroxy-2-[[2-phenyl-1-(3-thienyl)ethyl]amino]ethyl]phenyl]methanesulfonamide α-Thienylbenzeneethanamine was converted to the title compound following the procedures outlined in steps D–E of Example 19, except for the following modifications: 1) the chromatographic purification of step D used 20% EtOAc/hexane as eluant; 2) the chromatographic purification of step E was omitted; and 3) the benzyl ether protecting group was removed following the procedure described in step B of Example 8, (except for the following modifications: the reaction was run at 0° C. and the final product was purified by prep HPLC using 44% solvent B as eluant).

$^1$H NMR (270 MHz, CD$_3$OD): δ 2.76–2.9 (m, 1H), 2.899 (s, 1.8H), 2.908 (s, 1.2H), 3.00–3.08 (m, 1H), 3.19–3.34 (m, 2H), 3.4–3.5 (m, 1H), 4.67 (m, 1H), 6.85 (m, 1H), 7.03 (m, 3H), 7.15–7.23 (m, 4H), 7.30 (m, 1H), 7.39 (m, 1H), 7.54 (1, H).

$^{13}$C NMR (67 MHz, CD$_3$OD): δ 39.63, 40.1, 40.5, 53.38, 53.53, 57.16, 57.48, 60.51, 61.09, 69.51, 70.1, 70.3, 116.6, 124.3, 124.4, 125.26, 125.4, 126.1, 127.1, 127.97, 128.06, 128.14, 129.0, 129.59, 130.3, 133.6, 135.6, 134.0, 136.8, 151.65.

Mass (M+H) 433

HPLC: 100% pure, Shimadzu LC-6A, YMC S3 ODS (6.0× 150 mm); flow rate of 1.5 ml/minute; detection at 217 nm; gradient elution 0–100% B over 35 minutes (A=10% MeOH, 90% H$_2$O, 0.2% H$_3$PO$_4$); B=90% MeOH, 10% H$_2$O, 0.2% H$_3$PO$_4$); retention time=19.6 minutes.

EXAMPLE 48

(R),(R)-N-[5-[1-(Hydroxy-2-[[1-(4-methoxyphenyl)- 2-(4-fluorophenyl)ethyl]amino]ethyl]-2-(hydroxy) phenyl]methanesulfonamide, trifluoroacetate salt

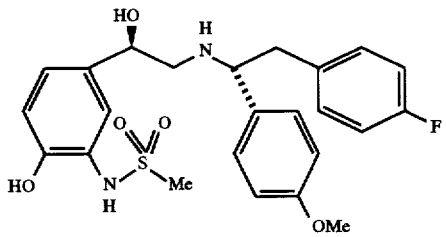

A. α-(4-Methoxyphenyl)-4-fluorobenzeneethanamine

Commercially available 4-fluorophenylacetic acid, after conversion to the corresponding acid choride upon reflux in thionyl chloride, was converted to 1-(4-methoxyphenyl)-2-(4-fluorophenyl)ethanone using the procedure described in step A of Example 9. 1-(4-methoxyphenyl)-2-(4-fluorophenyl)ethanone was converted to (α-(4-methoxyphenyl)4-fluorobenzeneethanamine using the procedure described in step C of Example 1, except for the following modification: the acidic hydrolysis reaction, after dilution with H$_2$O, was extracted 2× with Et$_2$O prior to basification, extraction 3× with EtOAc and isolation of the title compound after concentration.

B. (R),(R)-N-[5-[1-(Hydroxy-2-[[1-(4-methoxyphenyl)-2-(4-fluorophenyl)ethyl]amino]ethyl]-2-(hydroxy)phenyl] methanesulfonamide α-(4-Methoxyphenyl)-4-fluorobenzeneethanamine was converted to (R)-N-[5-[1-(triethylsilyl)oxy-2-[[1-(4-methoxyphenyl)-2-(4-fluorophenyl)ethyl]amino]ethyl]-2-(phenylmethoxy)phenyl]methanesulfonamide following the procedure outlined in step D of Example 19, except for the following modifications: 1) 20% EtOAc/hexane eluted the product from silica gel as a mixture of two diastereomers; and 2) rechromatography on silica gel using 16% EtOAc/hexane eluted first the R,R diastereomer A followed by the R,S diastereomer B.

Diastereomer A, (R),(R)-N-[5-[1-(triethylsilyl)oxy-2-[[1-(4-methoxyphenyl)-2-(4-fluorophenyl)ethyl]amino]ethyl]-2-(phenylmethoxy)phenyl]methanesulfonamide, was desilylated as described in step E of Example 19, except for omission of chromatographic purification. The benzyl ether protecting group was removed by hydrogenation in MeOH (100 mL) containing 0.4 mL TFA for one hour at 20 psi using a Parr shaker. After HPLC verification that the reaction was complete, the reaction was filtered through a 0.5 micron filter and concentrated. The crude product was purified by preparative HPLC chromatography using a C$_{18}$ HPLC column eluting with 52% solvent B (solvent A=10% MeOH, 90% H$_2$O, 0.1% TFA; solvent B=90% MeOH, 10% H$_2$O, 0.1% TFA) to obtain the title compound after concentration and lyophilization.

$^1$H NMR (270 MHz, CD$_3$OD): δ 2.84–2.93 (m, 1H), 2.9 (s, 3H), 3.05 (t, 1H), 3.22 (t, 1H), 3.5 (dd, 1H), 3.78 (s, 3H), 4.42 (dd, 1H), 4.70 (dd, 1H), 6.84–7.04 (m, 8H), 7.29 (d, 2H), 7.31 (d, 1H).

$^{13}$C NMR (68 MHz, CD$_3$OD): δ 38.95, 39.3, 53.33, 55.49, 65.21 69.74, 115.36, 115.73, 116.0, 116.27, 124.08, 125.1, 125.8, 126.21, 130.8, 131.84, 131.95, 132.4, 133.1, 151, 161.8.

Mass (M+H) 475

$[\alpha]_D^{22}$=−31° (c=0.28, MeOH)

HPLC: 93% pure, retention time 19.4 minutes, protocol described in Example 1.

EXAMPLE 49

(R),(S)-N-[5-[1-(Hydroxy-2-[[1-(4-methoxyphenyl)-2-(4-fluorophenyl)ethyl]amino]ethyl]-2-(hydroxy) phenyl]methanesulfonamide, trifluoroacetate salt

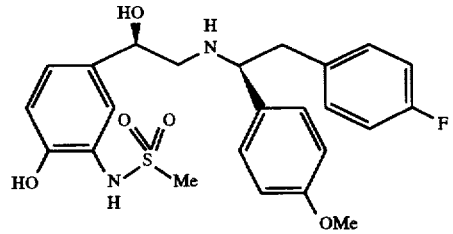

Diastereomer B described in step B of Example 48, (R),(S)-N-[5-[1-(triethylsilyl)oxy-2-[[1-(4-methoxyphenyl)-2-(4-fluorophenyl)ethyl]amino]ethyl]-2-(phenylmethoxy)-phenyl]methanesulfonamide, was converted to the title compound using the procedure described in step B of Example 48.

$^1$H NMR (270 MHz, CD$_3$OD): δ 2.84–2.93 (m, 1H), 2.9 (s, 3H), 3.05 (t, 1H), 3.22 (t, 1H), 3.5 (dd, 1H), 3.78 (s, 3H), 4.42 (dd, 1H), 4.70 (dd, 1H), 6.84–7.04 (m, 8H), 7.29 (d, 2H), 7.31 (d, 1H).

$^{13}$C NMR (68 MHz, CD$_3$OD): δ 39.27, 39.36, 53.1, 55.49, 65.0 69.2, 115.38, 115.74, 116.03, 116.28, 124.2, 124.91, 125.7, 130.71, 130.80, 131.85, 131.95, 132.6, 133.28, 150, 161.

Mass (M+H) 475

$[\alpha]_D^{22}$=+4.7° (c=1.9, MeOH)

HPLC: 98% pure, retention time 19.4 minutes, protocol described in Example 1.

EXAMPLE 50

(R),(R)-N-[5-[1-(Hydroxy-2-[[1-(4-hydroxyphenyl)-2-(4-fluorophenyl)ethyl]amino]ethyl]-2-(hydroxy)phenyl]methanesulfonamide, trifluoroacetate salt

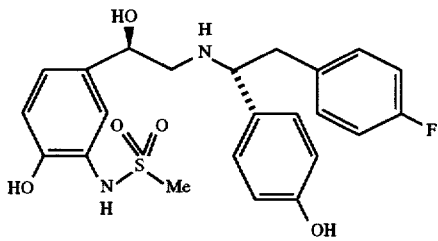

A. α-(4-Phenylmethoxyphenyl)-4-fluorobenzeneethanamine

To a −20° C. CH$_2$Cl$_2$ (100 mL) solution of N-[1-(4-methoxyphenyl)-2-(4-fluorophenyl)ethyl]formamide (1.6 g, 5.86 mmol) (for preparation see step A of Example 48) was added 11 mL of 1N BBr$_3$ in hexane. After warming to 0° C. and stirring for one hour, an additional 5 mL of BBr$_3$ solution was added. After 40 minutes, the reaction was complete by HPLC analysis. The reaction was quenched upon transferal into a stirred 4° C. aqueous NaHCO$_3$ solution and extracted with CH$_2$Cl$_2$ (3×). The organic phases were washed with pH 4 NaH$_2$PO$_4$, brine, dried over Na$_2$SO$_4$ and concentrated to yield 1.4 g of N-[1-(4-hydroxyphenyl)-2-(4-fluorophenyl)ethyl]formamide as a yellow solid. To a 50° C. DMF (10 mL) containing benzyl bromide (400 mg, 2.3 mmol) and N-[1-(4-hydroxyphenyl)-2-(4-fluorophenyl)ethyl]formamide (450 mg, 1.7 mmol) under N$_2$ was added 60% NaH (200 mg, 5 mmol). After one hour the reaction was quenched with H$_2$O, extracted with EtOAc (3×). The organic phases were washed with H$_2$O (3×), brine, dried over Na$_2$SO$_4$ and concentrated to yield 1 g of crude product. Flash chromatography on silica gel using 1:1 EtOAc/hexane eluted 300 mg of N-[1-(4-phenylmethoxyphenyl)-2-(4-fluorophenyl)ethyl]formamide. A 1:1 ETOH/H$_2$O solution (10 mL) containing N-[1-(4-phenylmethoxyphenyl)-2-(4-fluorophenyl)ethyl]formamide (300 mg, 0.86 mmol) and NaOH (200 mg, 5 mmol) was refluxed for 40 hours, diluted with H$_2$O and extracted 3× with EtOAc. The organic phases were washed with H$_2$O (3×), brine, dried over Na$_2$SO$_4$ and concentrated to yield 290 mg of α-(4-phenylmethoxyphenyl)-4-fluorobenzeneethanamine.

B. (R),(R)-N-[5-[1-(Hydroxy-2-[[1-(4-hydroxyphenyl)-2-(4-fluorophenyl)ethyl]amino]ethyl]-2-(hydroxy)phenyl]methanesulfonamide Following the procedure described in step A of Example 48, α-(4-phenylmethoxyphenyl)4-fluorobenzeneethanamine was converted to (R)-N-[5-[1-(triethylsilyl)oxy-2-[[1-(4-phenylmethoxyphenyl)-2-(4-fluorophenyl)ethyl]amino]ethyl]-2-(phenylmethoxy)phenyl]methanesulfonamide. After chromatographic separation of the R,R and R,S diastereomers, the R,R diastereomer was converted as described to the title compound except that 38% solvent B was employed for the final HPLC purification.

$^1$H NMR (270 MHz, CD$_3$OD): δ 2.87 (dd, 1H), 2.9 (s, 3H), 3.05 (t, 1H), 3.25 (t, 1H), 3.5 (dd, 1H), 4.33 (dd, 1H), 4.71 (dd, 1H), 6.77 (d, 2H), 6.84–6.92(m, 3H), 6.98–7.03 (m, 3H), 7.15 (d, 2H), 7.31 (d, 1H).

$^{13}$C NMR (68 MHz, CD$_3$OD): δ 39.0, 39.32, 53.29, 65.36, 69.74, 115.71, 115.96, 116.3, 116.74, 124.04, 124.93, 125.1, 125.8, 130.8, 131.85, 131.95, 132.6, 133.33, 151, 159.65.

Mass (M+H) 461

[α]$_D^{22}$=−28.6° (c=0.95, MeOH)

Calculated for 0.25 mol H$_2$O and 1.4 mol TFA:

|   | Calc. | Found |
|---|---|---|
| C | 49.61 | 49.58 |
| H | 4.34 | 4.35 |
| N | 4.48 | 4.46 |
| S | 5.13 | 5.24 |
| F | 15.82 | 15.90 |

HPLC: 99% pure, retention time 16.0 minutes, protocol described in Example 1.

EXAMPLE 51

(R),(S)-N-[5-[1-(Hydroxy-2-[[1-(4-hydroxyphenyl)-2-(4-fluorophenyl)ethyl]amino]ethyl]-2-(hydroxy)phenyl]methanesulfonamide, trifluoroacetate salt

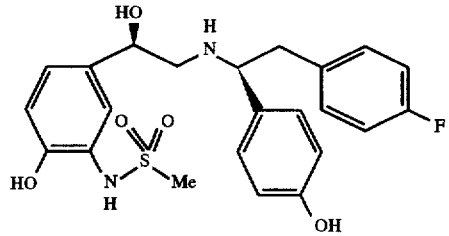

Diastereomer B described in step B of Example 50, (R),(S)-N-[5-[1-(triethylsilyl)oxy-2-[[1-(4-phenylmethoxyphenyl)-2-(4-fluorophenyl)-ethyl]amino]ethyl]-2-(phenylmethoxy)phenyl]methanesulfonamide, was converted to the title compound using the procedure described in step B of Example 50.

$^1$H NMR (270 MHz, CD$_3$OD): δ 2.78 (t, 1H), 2.89 (s, 3H), 2.99 (t, 1H), 3.28 (t, 1H), 3.43 (dd, 1H), 4.39 (dd, 1H), 4.88 (m, 1H), 6.78 (d, 2H), 6.84–6.92 (m, 3H), 6.98–7.03 (m, 3H), 7.15 (d, 2H), 7.28 (d, 1H).

$^{13}$C NMR (68 MHz, CD$_3$OD): δ 39.3, 39.4, 53.03, 64.65, 69.2, 115.72, 116.0, 116.33, 116.76, 123.96, 124.61, 124.95, 125.76, 130.73, 131.86, 131.96, 132.68, 133.31, 151, 159.61.

Mass (M+H) 461

[α]$_D^{22}$=−2.9° (c=0.8, MeOH)

Calculated for 0.25 mol H$_2$O and 1.4 mol TFA:

|   | Calc. | Found |
|---|---|---|
| C | 49.61 | 49.59 |
| H | 4.34 | 4.15 |
| N | 4.48 | 4.42 |
| S | 5.13 | 5.25 |
| F | 15.82 | 15.71 |

HPLC: 97% pure, retention time 16.0 minutes, protocol described in Example 1.

EXAMPLE 52

(R),(S)-N-[5-[1-(Hydroxy-2-[[1-(4-phenylmethoxyphenyl)-2-(4-fluorophenyl)ethyl]amino]ethyl]-2-(hydroxy)phenyl]methane sulfonamide, trifluoroacetate salt

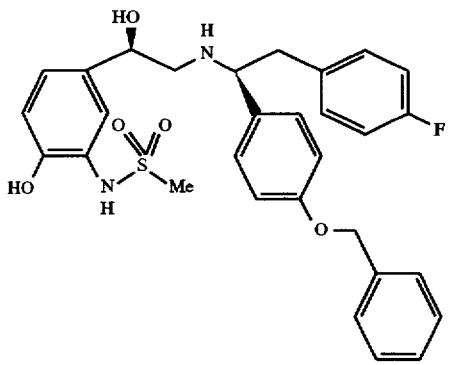

Diastereomer B described in step B of Example 50, (R),(S)-N-[5-[1-(triethylsilyl)oxy-2-[[1-(4-phenylmethoxyphenyl)-2-(4-fluorophenyl)ethyl]amino]ethyl]-2-(phenylmethoxy)phenyl]methanesulfonamide, was converted to the title compound using the procedure described in step B of Example 48 except that: 1) the Parr hydrogenation was closely monitored by HPLC to insure the reaction was terminated after hydrogenolysis of one benzyl ether; and 2) 68% solvent B was employed for the final HPLC purification.

$^1$H NMR (270 MHz, CD$_3$OD): δ 2.78 (t, 1H), 2.89 (s, 3H), 3.0 (dd, 1H), 3.28 (t, 1H), 3.43 (dd, 1H), 4.46 (dd, 1H), 4.88 (m, 1H), 5.07 (s, 2H), 6.87 (m, 3H), 6.98–7.02 (m, 5H), 7.24–7.4 (m, 8H).

$^{13}$C NMR (68 MHz, CD$_3$OD): δ 39.3, 39.35, 53.1, 64.8, 69.2, 70.79, 115.77, 116.03, 116.29, 116.46, 124.0, 124.89, 125.15, 125.22, 128.41, 128.72, 129.23, 130.71, 131.83, 131.95, 132.5, 133.25, 151, 160.

Mass (M+H) 551.

$[α]_D^{22}$=+5.8° (c=0.4, MeOH)

HPLC: 95% pure, retention time 24.0 minutes, protocol described in Example 1.

EXAMPLE 53

(R),(R)-N-[5-[1-(Hydroxy-2-[[1-(4-methoxyphenyl)-2-(3-trifluoromethylphenyl)ethyl]amino]ethyl]-2-(hydroxy)phenyl]methanesulfonamide, trifluoroacetate salt

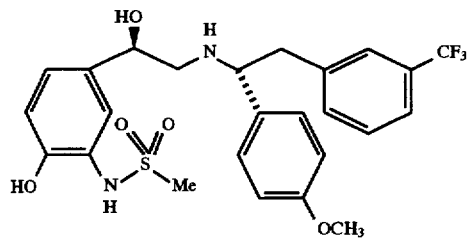

A. α-(4-Methoxyphenyl)-3-trifluoromethylbenzeneethanamine

Commercially available 3-trifluoromethylphenylacetic acid, after conversion to the corresponding acid choride upon reflux in thionyl chloride, was converted to 1-(4-methoxyphenyl)-2-(3-trifluoromethylphenyl)ethanone using the procedure described in step A of Example 9, except that the crude ketone was chromatographed on silica gel using 4:1 hexane/EtOAc. 1-(4-Methoxyphenyl)-2-(3-trifluoromethylphenyl)ethanone was converted to α-(4-methoxyphenyl)-3-trifluoromethylbenzeneethanamine using the procedure described in step C of Example 1, except for the following modifications: 1) the amination reaction required 43 hours; and 2) the acidic hydrolysis reaction, after dilution with H$_2$O, was extracted 2× with Et$_2$O prior to basification, extraction 3× with EtOAc and isolation of the title compound after concentration.

B. (R),(R)-N-[5-[1-(Hydroxy-2-[[1-(4-methoxyphenyl)-2-(3-trifluoromethyl-phenyl)ethyl]amino]ethyl]-2-(hydroxy)phenyl]methanesulfonamide, trifluoroacetate salt Following the procedure described in step B of Example 48, α-(4-phenylmethoxyphenyl)-3-trifluoromethylbenzeneethanamine was converted to (R)-N-[5-[1-(triethylsilyl)oxy-2-[[1-(4-phenylmethoxyphenyl)-2-(4-fluorophenyl)ethyl]amino]ethyl]-2-(phenylmethoxy)phenyl]methanesulfonamide. After chromatographic separation of the R,R and R,S diastereomers entailing multiple developments of 20×20 analytical silica gel plates with 1% MeOH/CH$_2$Cl$_2$, the R,R diastereomer was converted to the title compound as described in step B of Example 48, except that 57% solvent B was employed for the final HPLC purification.

$^1$H NMR (270 MHz, CD$_3$OD): δ 2.95 (m, 1H), 3.01 (s, 3H), 3.19 (t, 1H), 3.45 (m, 1H), 3.71 (dd, 1H), 3.87 (s, 3H), 4.55 (dd, 1H), 4.85 (dd, 1H), 6.95–7.15 (m, 4H), 7.35–7.53 (m, 7H).

$^{13}$C NMR (68 MHz, CD$_3$OD): δ 39.32, 39.44, 53.39, 55.53, 64.89, 69.76, 115.44, 116.29, 124.1, 124.47, 125.13, 125.78, 125.89, 126.84, 126.89, 129.99, 130.83, 133.3, 133.99, 138.05, 151.38, 162.

Mass (M+H) 525

$[α]_D^{22}$=−30.2° (c=0.53, MeOH)

Calculated for 0.12 mol H$_2$O and 1.25 mol TFA:

|   | Calc. | Found |
|---|---|---|
| C | 49.35 | 49.36 |
| H | 4.29 | 3.93 |
| N | 4.19 | 4.06 |
| S | 4.79 | 4.93 |
| F | 19.16 | 19.20 |

HPLC: 99% pure, retention time 21.5 minutes, protocol described in Example 1.

EXAMPLE 54

(R),(S)-N-[5-[1-(Hydroxy-2-[[1-(4-methoxyphenyl)-
2-(3-trifluoromethylphenyl)ethyl]amino]ethyl]-2-
(hydroxy)phenyl]methanesulfonamide,
trifluoroacetate salt

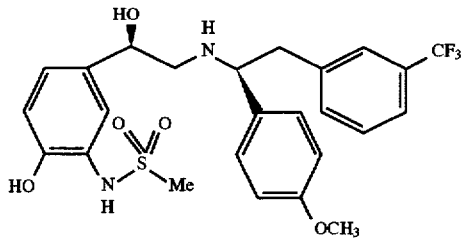

Diastereomer B described in step B of Example 53, (R),(S)-N-[5-[1-(triethylsilyl)oxy-2-[[1-(4-methoxyphenyl)-2-(3-trifluoromethylphenyl)ethyl]amino]ethyl]-2-(phenylmethoxy)phenyl]methanesulfonamide, was converted to the title compound using the procedure described in step B of Example 48, except that 60% solvent B was employed for the final HPLC purification.

$^1$H NMR (270 MHz, CD$_3$OD): δ 2.89 (t, 1H), 3.00 (s, 3H), 3.13 (m, 1H), 3.49 (m, 1H), 3.65 (dd, 1H), 3.87 (s, 3H), 4.61 (dd, 1H), 4.97 (dd, 1H), 6.94–7.12 (m, 4H), 7.36–7.54 (m, 7H).

$^{13}$C NMR (68 MHz, CD$_3$OD): δ 39.29, 39.85, 53.19, 55.55, 64.15, 69.22, 115.46, 116.32, 123.98, 124.51, 124.56, 124.97, 125.59, 125.74, 126.85, 126.89, 130.01, 130.73, 133.28, 134.0, 138.01, 151.33, 161.9.

Mass (M+H) 525

$[\alpha]_D^{22}$=+0.5° (c=0.55, MeOH)

Calculated for 0.3 mol H$_2$O and 1.22 mol TFA:

|   | Calc. | Found |
|---|---|---|
| C | 49.26 | 49.26 |
| H | 4.34 | 4.05 |
| N | 4.19 | 4.07 |
| S | 4.79 | 5.00 |
| F | 18.91 | 18.87 |

HPLC: 99% pure, retention time 21.6 minutes, protocol described in Example 1.

EXAMPLE 55

(R),(R)-N-[5-[1-(Hydroxy-2-[[1-(4-
difluoromethoxyphenyl)-2-(4-fluorophenyl)ethyl]
amino]ethyl]-2-(hydroxy)phenyl]
methanesulfonamide, trifluoroacetate salt

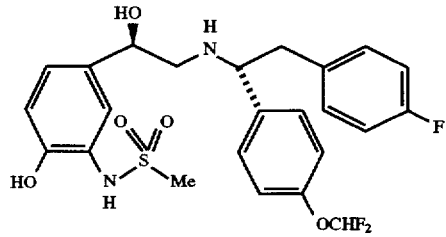

A. 4-Difluoromethoxybenzoic Acid

Difluorochloromethane was bubbled through a 75° C. i-PrOH (100 mL) solution containing commercially available methyl 4-hydroxybenzoate (7.5 g, 5.0 mmol) and t-BuOK (5.6 g, 5 mmol). After two hours, 4 additional g of t-BuOK was added and the reaction continued two hours. The reaction was diluted with H$_2$O and extracted with EtOAc (3×). The organic phases were washed with H$_2$O (3×), brine, dried over Na$_2$SO$_4$ and concentrated to yield 12 g of methyl 4-difluoromethoxybenzoate as an oil. The crude methyl 4-difluoromethoxybenzoate was refluxed two hours in 2:1 MeOH/H$_2$O containing KOH (3.4 g, 61 mmol) followed by dilution with H$_2$O. After washing the aqueous phase 2× with 1:1 Et$_2$O/hexane and then acidification to pH 1 with 2.5N H$_2$SO$_4$, the title compound was collected by filtration as a white solid (8.6 g).

B. α-(4-Difluoromethoxyphenyl)-4-fluorobenzeneethanamine

To a stirred suspension of Zn pwder (3.3 g, 50 mmol) and Pd(PPh$_3$)$_4$ (1.45 g, 1.25 mmol) in DME (20 mL) under N$_2$, was added 10 mL of DME containing 4-fluorobenzyl bromide (4.9 g, 26 mmol) and 4-difluoromethoxybenzoyl chloride (4.7 g, 25 mmol) (prepared by refluxing 4-difluoromethoxybenzoic acid in SOCl$_2$). After stirring 40 hours at 20° C., the reaction was diluted with EtOAc and H$_2$O, filtered through celite, and then concentrated. The crude product was dissolved in EtOAc, washed with brine, dried over Na$_2$SO$_4$, and then concentrated to 10 g of crude product. Chromatography on silica gel using 1:2 CH$_2$Cl$_2$/hexane eluted 4 g of 1-(4-difluoromethoxyphenyl)-2-(4-fluorophenyl)ethanone which was converted to the title compound using the procedure described in step C of Example 1, except for the following modifications: 1) the acidic hydrolysis reaction, after dilution with H$_2$O, was extracted 2× with Et$_2$O prior to basification, extraction 3× with EtOAc and isolation of the title compound after concentration; and 2) the title amine was purified from dealkylated α-(4-hydroxyphenyl)-4-fluorobenzeneethanamine by preparative HPLC chromatography using a C$_{18}$ HPLC column eluting with 50% solvent B (solvent A=10% MeOH, 90% H$_2$O, 0.1% TFA; solvent B=90% MeOH, 10% H$_2$O, 0.1% TFA).

C. (R),(R)-N-[5-[1-(Hydroxy-2-[[1-(4-difluoromethoxyphenyl)-2-(4-fluorophenyl)ethyl]amino]ethyl]-2-(hydroxy)phenyl]methanesulfonamide, trifluoroacetate salt Following the procedure described in step B of Example 48, α-(4-difluoromethoxyphenyl)-4-fluorobenzeneethanamine was converted to (R)-N-[5-[1-(triethylsilyl)oxy-2-[[1-(4-phenylmethoxyphenyl)-2-(4-fluorophenyl)ethyl]amino]ethyl]-2-(phenylmethoxy)phenyl]methanesulfonamide. After a chromatographic separation of the R,R and R,S diastereomers entailing multiple developments of 0.25 mm silica gel plates with CH$_2$Cl$_2$, the R,R diastereomer was converted to the title compound as described in step B of Example 48, except that 60% solvent B was employed for the final HPLC purification.

$^1$H NMR (270 MHz, CD$_3$OD): δ 2.88 (m, 1H), 2.92 (s, 3H), 3.11 (t, 1H), 3.24 (t, 1H), 3.58 (dd, 1H), 4.52 (dd, 1H), 4.78 (dd, 1H), 6.85 (t, 1H), 6.86–7.07 (m, 6H), 7.27 (ABq, 4H), 7.33 (d, 1H).

$^{13}$C NMR (68 MHz, CD$_3$OD): δ 40.58, 41.02, 55.18, 66.57, 71.39, 115.06, 117.51, 117.83, 118.03, 118.87, 121.92, 122.67, 125.73, 126.88, 127.49, 133.00, 133.17, 133.55, 133.66, 133.95, 134.01, 134.93, 153.07, 155.18.

Mass (M+H) 511

[α]$_D^{22}$=−33.4° (c=0.47, MeOH)

Calculated for 0.48 mol H$_2$O and 1.37 mol TFA:

|   | Calc. | Found |
|---|-------|-------|
| C | 47.55 | 47.55 |
| H | 4.08  | 3.77  |
| N | 4.15  | 4.12  |
| S | 4.75  | 4.86  |
| F | 20.00 | 19.98 |

HPLC: 97% pure, retention time 20.1 minutes, protocol described in Example 1.

EXAMPLE 56

(R),(S)-N-[5-[1-(Hydroxy-2-[[1-(4-difluoromethoxyphenyl)-2-(4-fluorophenyl)ethyl]amino]ethyl]-2-(hydroxy)phenyl] methanesulfonamide, trifluoroacetate salt

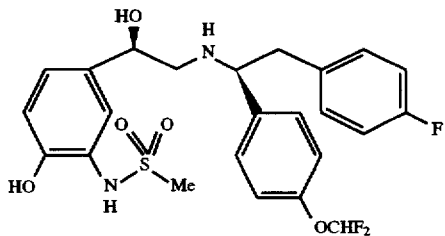

The R,S diastereomer described in step C of Example 55, (R),(S)-N-[5-[1-(triethylsilyl)oxy-2-[[1-(4-difluoromethoxyphenyl)-2-(4-fluorophenyl)ethyl]amino]ethyl]-2-(phenyl-methoxy)phenyl]methanesulfonamide, was converted to the title compound using the procedure described in step C of Example 55.

$^1$H NMR (270 MHz, CD$_3$OD): δ 2.78 (t, 1H), 2.90 (s, 3H), 3.05 (dd, 1H), 3.26 (t, 1H), 3.52 (dd, 1H), 4.55 (dd, 1H), 4.84 (m, 1H), 6.85 (t, 1H), 6.86–7.11 (m, 6H), 7.28 (ABq, 4H), 7.29 (d, 1H).

$^{13}$C NMR (68 MHz, CD$_3$OD): δ 39.60, 53.64, 64.58, 69.54, 113.70, 116.15, 116.47, 116.61, 117.50, 120.56, 121.31, 124.23, 125.29, 126.07, 131.49, 132.16, 132.27, 132.56, 133.51, 151.63, 153.82.

Mass (M+H) 511

[α]$_D^{22}$=+1.25° (c=0.95, MeOH)

Calculated for 0.59 mol H$_2$O and 1.28 mol TFA:

|   | Calc. | Found |
|---|-------|-------|
| C | 47.82 | 47.82 |
| H | 4.15  | 3.73  |
| N | 4.20  | 3.91  |
| S | 4.81  | 5.10  |
| F | 19.48 | 19.47 |

HPLC: 98% pure, retention time 20.3 minutes, protocol described in Example 1.

EXAMPLE 57

(R),(R)-N-[5-[1-(Hydroxy-2-[[1-(4-difluoromethoxyphenyl)-2-(phenyl)ethyl]amino]ethyl]-2-(hydroxy)phenyl]methanesulfonamide, trifluoroacetate salt

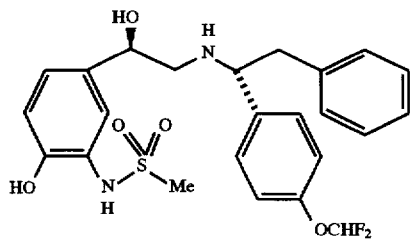

The title compound was prepared from 4-difluoromethoxybenzoic acid, preparation described in step A of Example 55, following the procedures described in steps B and C of Example 55, except for the following modifications: 1) the Pd coupling employed benzyl bromide; 2) the preparative TLC separation of the R,R and R,S diastereomers of (R)-N-[5-[1-(triethylsilyl)oxy-2-[[1-(4-phenylmethoxyphenyl)-2-(phenyl)ethyl]amino]ethyl]-2-(phenylmethoxy)phenyl]methanesulfonamide required multiple developments in 1:4 EtOAc/hexane; and 3) final HPLC purification of the title compound derived from the R,R diastereomer utilized 54% solvent B.

$^1$H NMR (270 MHz, CD$_3$OD): δ 2.89 (m, 1H), 2.90 (s, 3H), 3.15 (t, 1H), 3.27 (t, 1H), 3.56 (dd, 1H), 4.53 (dd, 1H), 4.75 (dd, 1H), 6.84 (d, 1H), 6.87 (t, 1H), 7.01–7.05 (m, 3H), 7.12–7.18 (m, 5H), 7.3 (d, 1H), 7.39 (d, 2H).

$^{13}$C NMR (68 MHz, CD$_3$OD): δ 39.31, 39.76, 53.45, 64.87, 69.7, 115.44, 116.28, 117.18, 120.18, 124.13, 125.81, 127.87, 129.36, 130.08, 131.18, 131.26, 131.68, 133.22, 136.27, 150, 153.

Mass (M+H) 493

[α]$_D^{22}$=−30.7° (c=0.98, MeOH)

Calculated for 1.56 mol TFA:

|   | Calc. | Found |
|---|-------|-------|
| C | 48.59 | 48.64 |
| H | 4.14  | 4.37  |
| N | 4.18  | 4.24  |
| S | 4.78  | 5.09  |
| F | 18.93 | 19.07 |

HPLC: 100% pure, retention time 19.9 minutes, protocol described in Example 1.

EXAMPLE 58

(R),(S)-N-[5-[1-(Hydroxy-2-[[1-(4-difluoromethoxyphenyl)-2-(phenyl)ethyl]amino]ethyl]-2-(hydroxy)phenyl]methanesulfonamide, trifluoroacetate salt

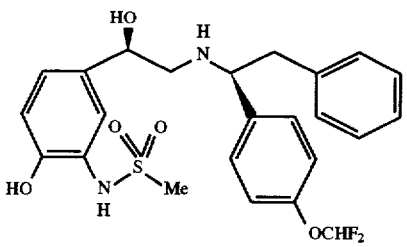

The R,S diastereomer described in Example 57, (R),(S)-N-[5-[1-(triethylsilyl)oxy-2-[[1-(4-difluoromethoxyphenyl)-2-(phenyl)ethyl]amino]ethyl]-2-(phenylmethoxy)phenyl]methanesulfonamide, was converted to the title compound using the procedure described in Example 57.

$^1$H NMR (270 MHz, CD$_3$OD): δ 2.77 (t, 1H), 2.89 (s, 3H), 3.05 (dd, 1H), 3.26 (t, 1H), 3.50 (dd, 1H), 4.57 (dd, 1H), 4.89 (m, 1H), 6.84 (d, 1H), 6.86 (t, 1H), 6.99–7.03 (m, 3H), 7.12–7.21 (m, 5H), 7.27 (d, 1H), 7.39 (d, 2H).

$^{13}$C NMR (68 MHz, CD$_3$OD): δ 39.28, 40.22, 53.34, 64.33, 69.25, 116.30, 117.23, 120.17, 123.98, 124.94, 125.76, 127.90, 129.36, 130.10, 131.16, 131.33, 133.22, 136.21, 151.34, 154.

Mass (M+H) 493

$[\alpha]_D^{22}$=−2.9° (c=0.44, MeOH)

Calculated for 0.22 mol H$_2$O and 1.45 mol TFA:

|   | Calc. | Found |
|---|-------|-------|
| C | 48.82 | 48.82 |
| H | 4.25  | 4.26  |
| N | 4.23  | 4.17  |
| S | 4.84  | 5.19  |
| F | 18.23 | 18.31 |

HPLC: 100% pure, retention time 20.0 minutes, protocol described in Example 1.

EXAMPLE 59

(R)-N-[5-[2-[[bis-(4-Difluoromethoxyphenyl)methyl]amino]-1-hydroxyethyl]-2-hydroxyphenyl]methanesulfonamide, trifluoroacetate salt

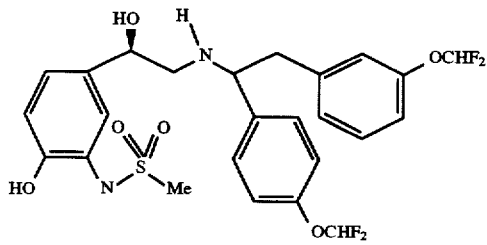

Following the procedure described in step A of Example 55, commercially available 4,4'-bishydroxybenzophenone was alkylated with difluorochloromethane to generate 4,4'-bisdifluoromethoxybenzophenone which was converted to 4,4'-bisdifluoromethoxybenzhydryl amine using the procedure described in step C of Example 1, except for the following modifications: 1) the amination reaction product was chromatographed on silica gel using 2:1 hexane/EtOAc; and 2) the acidic hydrolysis reaction, after dilution with H$_2$O, was extracted 2× with Et$_2$O prior to basification, extraction 3× with EtOAc and, isolation of 4,4'-bisdifluoromethoxybenzhydryl amine after concentration. This amine was converted to the title compound following the procedure described in step B of Example 48.

$^1$H NMR (270 MHz, CD$_3$OD): δ 2.90 (s, 3H), 3.06 (m, 2H), 4.9 (m, 1H), 5.69 (s, 1H), 6.85 (d, 1H), 6.87 (t, 1H), 6.88 (t, 1H), 7.03 (dd, 1H), 7.31 (d, 1H), 7.39 (ABq, 4H), 7.44 (ABq, 4H).

$^{13}$C NMR (68 MHz, CD$_3$OD): δ 39.59, 54.37, 65.62, 69.67, 114.05, 114.08, 116.51, 117.47, 117.5, 120.79, 120.87, 124.29, 125.37, 126.08, 130.66, 132.03, 133.34, 133.52, 133.63, 151.67, 153.46.

Mass (M+H) 545.

$[\alpha]_D^{22}$=−8.6° (c=0.73, MeOH)

Calculated for 3.1 mol H$_2$O and 0.7 mol TFA:

|   | Calc. | Found |
|---|-------|-------|
| C | 44.85 | 44.82 |
| H | 4.58  | 4.50  |
| N | 4.12  | 4.07  |
| S | 4.71  | 4.48  |
| F | 17.04 | 16.89 |

HPLC: 99% pure, retention time 20.4 minutes, protocol described in Example 1.

EXAMPLE 60

(R),(R)-N-[3-[2-[[1-(1,3-Benzodioxol-5-yl)-2-phenylethyl]amino]-1-hydroxyethyl]phenyl]methanesulfonamide, trifluoroacetate salt

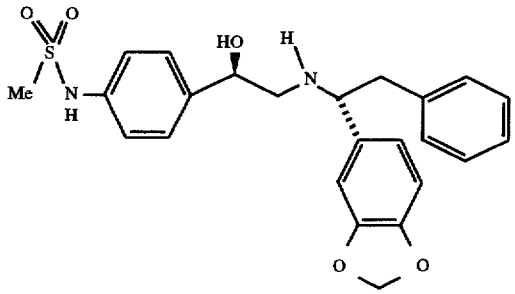

A. (R),(R)-N-[-2-[1-(1,3-benzodioxol-5-yl)-2-phenylethyl]amino]benzeneethanol, hydrochloride salt Following the general procedure described in M.-J. Wu et al., *JOC*, 56, 1340 (1991), commercially available piperonal (12.0 g, 80.0 mmol) and (R)phenylglycinol (11.0 g, 80.0 mmol) were condensed upon stirring in CHCl$_3$ for 18 hours at 20° C. under Ar. The reaction after concentration was repeatedly dissolved in toluene and concentrated to yield 21.4 g of dry imine. The imine in THF (50 mL) was added over 40 minutes to a −45° C. solution prepared by addition under Ar of 120 mL of 2M benzylmagnesium chloride/THF to a −45° C. suspension of anhydrous CeCl$_3$ (60.0 g, 243 mmol) in THF (300 mL) which had previously been stirred for 18 hours at 20° C. After warming to 20° C., the reaction was quenched with 800 mL of water and extracted with CH$_2$Cl$_2$. The free base of the title compound, isolated initially as a 11:1 diastereomeric mixture after drying over $Na_2SO_4$ and concentration, was purified by precipitation at 0° C. from $Et_2O$ (500 mL) upon addition of methanolic HCl made by cautious addition of AcCl (12.5 g, 160 mmol, to ~40 mL of methanol at 0° C. Recrystallization from ~400 mL of MeOH and 1.5 L of ether followed by filtration at 0° C. yielded 23.3 g of the title compound.

B. (R) α-(1,3-benzodioxol-5-yl)benzeneethanamine

Following the general procedure described in M. K. Mokhallalati et al., *Synth. Comm.*, 23, 2055 (1993), (R),(R) -N-|-2-|1-(1,3-benzodioxol-5-yl)-2-phenylethyl]amino] benzeneethanol, freshly generated from 21.1 g (R),(R)-N-[-2-|1-(1,3-benzodioxol-5-yl)-2-phenylethyl]amino] benzeneethanol, hydrochloride salt after 3 $CH_2Cl_2$ extracts from aq. $NaHCO_3$, drying over $Na_2SO_4$ and concentration, in 400 mL of $CH_2Cl_2$ was added over ~35 minutes to 800 mL of MeOH containing $Pb(OAc)_4$ (30.6 g, 69.1 mmol) at 0° C. under argon. Upon completion of the addition, the reaction, after dilution with 200 mL of $CH_2Cl_2$ and 10% aq. $Na_2CO_3$ (600 mL), was extracted 3× with $CH_2Cl_2$. The oil obtained, after drying the $CH_2Cl_2$ extracts over $Na_2SO_4$ and concentrating, was stirred at 60° C. for six hours in a solution of 150 mL of water and 50 mL of MeOH containing 12 mL of conc. aq. HCl. After cooling and basification to pH 12 with 1M aq. NaOH, the mixture was extracted 3 times with $CH_2Cl_2$ (~200 mL). The combined organic extracts were dried over $Na_2SO_4$ and then concentrated to a thick oil. To the resulting oil, after dissolution in 500 mL of ether, was added 4M methanolic HCl (40 mL). The resulting white precipitate was collected by filtration at 0° C., treated with aq. $NaHCO_3$, and extracted with $CH_2Cl_2$ to yield the title compound, after drying over $Na_2SO_4$ and concentration.

C. (R),(R)-N-[3-[2-[[1-(1,3-Benzodioxol-5-yl)-2-phenylethyl]amino]-1-hydroxyethyl]phenyl] methanesulfonamide The title compound was prepared by coupling (R) α-(1, 3-benzodioxol-5-yl)benzeneethanamine with (R)-N-[3-[2-iodo-1-|(triethylsilyl)oxy]ethyl]phenyl] methanesulfonamide (preparation described in step A of Example 28) following the procedures described in steps D and E of Example 19. After removal of the triethylsilyl group as described in step E of Example 19, the crude product was purified by preparative HPLC chromatography using a $C_{18}$ HPLC column eluting with 60% solvent B (solvent A=10% MeOH, 90% $H_2O$, 0.1% TFA; solvent B=90% MeOH, 10% $H_2O$, 0.1% TFA) to obtain the title compound after concentration and lyophilization.

$^1$H NMR (270 MHz, $CD_3OD$): δ 2.90 (m, 1H), 2.93 (s, 3H), 3.07 (t, 1H), 3.26 (t, 1H), 3.52 (dd, 1H), 4.42 (dd, 1H), 4.85 (d, 1H), 5.96 (s, 2H), 6.76 (s, 2H), 6.94 (s, 1H), 7.03–7.31 (m, 8H).

$^{13}$C NMR (68 MHz, $CD_3OD$): δ 39.25, 40.11, 53.50, 65.85, 70.20, 103.02, 109.05, 109.54, 118.71, 121.14, 122.90, 124.34, 128.06, 128.46, 129.56, 130.37, 130.83, 136.80, 139.97, 143.98, 149.98, 150.15.

Mass (M+H) 455

$[α]_D^{22}$=-34.3° (c=0.61, MeOH)

Calculated for 0.5 mol $H_2O$ and 1.14 mol TFA:

|   | Calc. | Found |
|---|---|---|
| C | 53.18 | 53.11 |
| H | 4.78 | 4.72 |
| N | 4.72 | 4.59 |
| S | 5.40 | 5.50 |
| F | 10.95 | 10.92 |

HPLC: 99% pure, retention time 19.1 minutes, protocol described in Example 1.

EXAMPLE 61

(R),(R)-N-[3-|2-|| 1-(4-Difluoromethoxyphenyl)-2-(4-fluorophenyl)ethyl]amino|-1-hydroxyethyl] phenyl]methanesulfonamide, trifluoroacetate salt

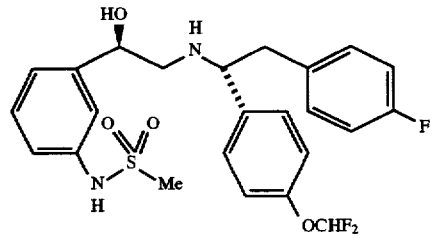

The title compound was prepared by coupling α-(4-difluoromethoxyphenyl)-4-fluorobenzeneethanamine, preparation described in step B of Example 55, with (R)-N-[3-[2-iodo-1-|(triethylsilyl)oxy]ethyl]phenyl] methanesulfonamide (preparation described in step A of Example 28) following the procedures described in steps D and E of Example 19 with the following modifications: 1) chromatography on silica gel using 25% EtOAc/hexane followed by preparative TLC entailing multiple developments of 0.25 mm silica plates using 0.3% $MeOH/CH_2Cl_2$ separated the R,R and R,S diastereomers of the initial coupled product (R)-N-[3-[1-(triethylsilyl)oxy-2-[[1-(4-phenylmethoxyphenyl)-2-(4-fluorophenyl)ethyl]amino] ethyl]phenyl]methanesulfonamide; and 2) the R,R diastereomer was converted to the title compound as described in step F of Example 60, except that 56% solvent B was employed for the final HPLC purification.

$^1$H NMR (270 MHz, $CD_3OD$): δ 2.93 (s, 3H), 2.97 (m, 1H), 3.10 (t, 1H), 3.23 (t, 1H), 3.58 (dd, 1H), 4.52 (dd, 1H), 4.84 (m, 1H), 6.80–6.92 (m, 2H), 6.84 (t, 1H), 7.00–7.16 (m, 4H), 7.25 (ABq, 4H), 7.28 (m, 1H).

$^{13}$C NMR (68 MHz, $CD_3OD$): δ 39.15, 39.27, 53.69, 65.19, 70.20, 116.13, 116.42, 117.45, 118.71, 120.51, 121.19, 122.90, 130.85, 131.60, 131.72, 132.12, 132.24, 143.91.

Mass (M+H) 494

$[α]_D^{22}$=-31.5° (c=0.54, MeOH)

Calculated for 0.99 mol $H_2O$ and 1.0 mol TFA:

|   | Calc. | Found |
|---|---|---|
| C | 49.86 | 49.90 |
| H | 4.50 | 4.16 |
| N | 4.47 | 4.41 |

HPLC: 99% pure, retention time 20.8 minutes, protocol described in Example 1.

EXAMPLE 62

(R),(S)-N-[3-[2-[[1-(4-Difluoromethoxyphenyl)-2-(4-fluorophenyl)ethyl]amino]-1-hydroxyethyl]phenyl]methanesulfonamide, trifluoroacetate salt

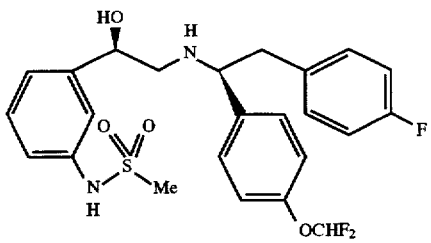

The R,S diastereomer of (R)-N-[3-[1-(triethylsilyl)oxy-2-[[1-(4-phenylmethoxyphenyl)-2-(4-fluorophenyl)ethyl]amino]ethyl]phenyl]methanesulfonamide, preparation described in Example 61, was converted to the title compound using the procedure described in Example 61.

$^1$H NMR (270 MHz, CD$_3$OD): δ 2.78 (m, 1H), 2.90 (s, 3H), 3.13 (dd, 1H), 3.28 (t, 1H), 3.5 (dd, 1H), 4.56 (dd, 1H), 5.0 (d, 1H), 6.83–7.16 (m, 7H), 6.84 (t, 1H), 7.26 (ABq, 4H).

$^{13}$C NMR (68 MHz, CD$_3$OD): δ 39.24, 39.6, 53.59, 65.0, 69.76, 116.0, 116.2, 117.3, 118.57, 120.52, 121.1, 122.78, 130.83, 131.43, 131.47, 132.14, 132.25, 143.86.

Mass (M+H) 545

$[\alpha]_D^{22}$=+7.0° (c=0.57, MeOH)

Calculated for 0.69 mol H$_2$O and 1.1 mol TFA:

|   | Calc. | Found |
|---|-------|-------|
| C | 49.76 | 49.80 |
| H | 4.38  | 4.25  |
| N | 4.43  | 4.30  |
| S | 5.07  | 5.25  |
| F | 18.93 | 19.08 |

HPLC: 98% pure, retention time 20.6 minutes, protocol described in Example 1.

EXAMPLE 63

(R),(R)-N-[5-[2-[[1-(4-Difluoromethoxyphenyl)-2-(4-fluorophenyl)ethyl]amino]-1-hydroxyethyl]-2-fluorophenyl]methanesulfonamide, trifluoroacetate salt

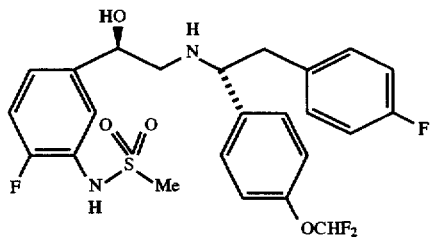

The title compound was prepared by coupling α-(4-difluoromethoxyphenyl)-4-fluorobenzeneethanamine, preparation described in step B of Example 55, with (R)-N-[3-[2-iodo-1-[(triethylsilyl)oxy]ethyl]-2-fluorophenyl]methanesulfonamide (prepared from 2-bromo-1-[4-fluoro-3-[(methylsulfonyl)amino]phenyl]ethanone, preparation described in step B of Example 46, utilizing the procedure described in step A of Example 28 for (R)-N-[3-[2-iodo-1-[(triethylsilyl)oxy]ethyl]phenyl]methanesulfonamide) following the procedures described in steps D and E of Example 19, with the following modifications: 1) chromatography on silica gel using 20% EtOAc/hexane followed by preparative TLC entailing multiple developments of 0.25 mm silica plates using CH$_2$Cl$_2$ separated the R,R and R,S diastereomers of the initial coupled product (R)-N-[5-[1-(triethylsilyl)oxy-2-[[1-( 4-phenylmethoxyphenyl)-2-(4-fluorophenyl)ethyl]amino]ethyl]-2-fluorophenyl]methanesulfonamide; 2) the R,R diastereomer was converted to the title compound as described in step F of Example 60, except that 58% solvent B was employed for the final HPLC purification.

$^1$H NMR (270 MHz, CD$_3$OD): 2.93 (m, 1H), δ2.98 (s, 3H), 3.11 (t, 1H), 3.23 (t, 1H), 3.58 (dd, 1H), 4.52 (dd, 1H), 4.86 (m, 1H), 6.85 (t, 1H), 6.86–7.23 (m, 6H), 7.26 (ABq, 4H), 7.51 (d, 1H).

$^{13}$C NMR (68 MHz, CD$_3$OD): δ 39.12, 40.13, 53.61, 65.21, 69.65, 116.13, 116.44, 117.02, 117.31, 117.45, 120.56, 121.25, 124.28, 125.25, 125.37, 126.66, 131.59, 131.73, 132.14, 132.25, 132.54, 139.19, 153.79.

Mass (M-H) 511

$[\alpha]_D^{22}$=-28.1° (c=0.72 MeOH)

HPLC: 99% pure, retention time 21.2 minutes, protocol described in Example 1.

EXAMPLE 64

(R),(S)-N-[5-[2-[[1-(4-Difluoromethoxyphenyl)-2-(4-fluorophenyl)ethyl]amino]-1-hydroxyethyl]-2-fluorophenyl]methanesulfonamide, trifluoroacetate salt

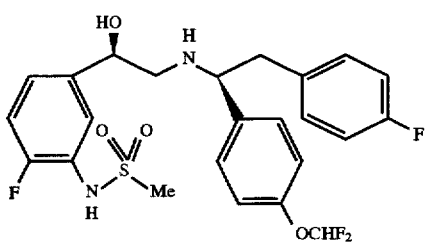

The R,S diastereomer, (R),(S)-N-[5-[1-(triethylsilyl)oxy-2-[[1-(4-phenylmethoxyphenyl)-2-(4-fluorophenyl)ethyl]amino]ethyl]-2-fluorophenyl]methanesulfonamide, preparation described in Example 63, was converted to the title compound using the procedure described in Example 63.

$^1$H NMR (270 MHz, CD$_3$OD): δ 2.78 (t, 1H), δ2.97 (s, 3H), 3.11 (dd, 1H), 3.27 (t, 1H), 3.50 (dd, 1H), 4.55 (dd, 1H), 4.99 (dd, 1H), 6.85 (t, 1H), 6.88–7.21 (m, 6H), 7.28 (ABq, 4H), 7.46 (d, 1H).

$^{13}$C NMR (68 MHz, CD$_3$OD): δ 39.61, 40.16, 53.49, 64.66, 69.27, 116.18, 116.50, 117.05, 117.36, 117.51, 120.62, 124.22, 125.11, 125.22, 126.69, 131.50, 132.16, 131.28, 132.50, 139.16, 153.85.

Mass (M−H) 511

$[\alpha]_D^{22} = +0.5°$ (c=0.81, MeOH)

Calculated for 0.6 mol H₂O and 1.25 mol TFA:

|   | Calc. | Found |
|---|-------|-------|
| C | 47.80 | 47.80 |
| H | 4.00  | 4.01  |
| N | 4.21  | 4.12  |
| S | 4.81  | 4.87  |
| F | 22.11 | 22.12 |

HPLC: 99% pure, retention time 21.2 minutes, protocol described in Example 1.

EXAMPLE 65

N-[5-[2-[[1,2-Diphenyl-1-(trifluoromethyl)ethyl]amino]-1-hydroxyethyl]-2-hydroxyphenyl]methanesulfonamide, trifluoroacetate salt

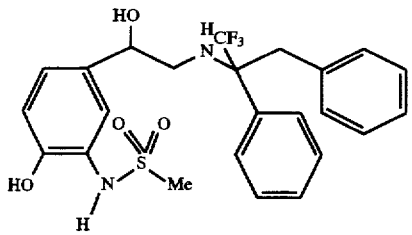

A. α-(Phenyl)-α-(trifluoromethyl)benzeneethanamine

To a 0.4M lithium hexamethyldisilazide in THF (10 mL) at 4° C. under N₂, was added 2,2,2-trifluoroacetophenone (0.66 g, 3.9 mmol). The solution was stirred two hours at 20° C., cooled to 4° C. and 2 mL of 2M benzylmagnesium chloride/THF was added. After three hours, the reaction was quenched with sat. aq. NH₄Cl, diluted with H₂O and extracted with EtOAc (3×). The organic layers were washed with H₂O, then with brine, dried over Na₂SO₄ and concentrated. Chromatography on silica gel using 4:1 hexane/EtOAc yielded the title compound.

B. N-[5-[2-[[1,2-Diphenyl-1-(trifluoromethyl)ethyl]amino]-1-hydroxyethyl]-2-hydroxyphenyl]methanesulfonamide A mixture of 2-bromo-1-[4-phenylmethoxy-3-[(methylsulfonyl)amino]phenylethanone (133 mg, 0.44 mmol), preparation described in step F of Example 1, and α-(phenyl)-α-(trifluoromethyl)benzeneethanamine (150 mg, 0.6 mmol) in 2 mL of CH₃CN containing 200 mg of NaI was refluxed for six hours under N₂. Upon cooling the suspension was transferred to stirred a EtOH (10 mL) suspension of NaBH₄ (250 mg). After 48 hours, the reaction was quenched with 1N HCl, diluted with H₂O and extracted with EtOAc (3×) after adjusting the pH to 10. The organic extracts were washed with brine, dried over Na₂SO₄ and concentrated. Chromatography on silica gel using 2:1 hexane/EtOAc eluted N-[5-[2-[[1,2-diphenyl-1-(trifluoromethyl)ethyl]amino]-1-hydroxyethyl]-2-phenylmethoxy-phenyl]methanesulfonamide (22 mg) which was converted to the title compound as described in step B of Example 48, except that 88% solvent B was employed for the final HPLC purification.

¹H NMR (270 MHz, CD₃OD): δ 2.58 (dd, 0.5H), 2.7–2.9 (m, 1.5H), 2.86 (s, 1.5H), 2.87 (s, 1.5H), 3.08 (m, 1H), 3.18 (m, 1H), (4.62 (m, 1H), 4.85 (dd, 1H), 6.8–7.4 (m, 13H).

¹³C NMR (68 MHz, CD₃OD): δ 39.41, 45.08, 51.08, 52.0, 73.77, 74.49, 116.21, 116.33, 124.4, 124.68, 125.69, 125.74, 126.03, 127.93, 128.65, 128.77, 129.05, 129.2, 129.31, 132.08, 135.39, 135.50, 135.76, 137.55, 151.0.

Mass (M+H) 495

HPLC: 100% pure, retention time 29.2 minutes, protocol described in Example 1.

EXAMPLE 66

α-[[[(R)-2-Hydroxy-2-[4-hydroxy-3-[(methylsulfonyl)amino]phenyl]ethyl]amino]methyl]-3,4-dimethoxy-N,N-dimethylbenzeneacetamide, trifluoroacetate salt, diastereomer A

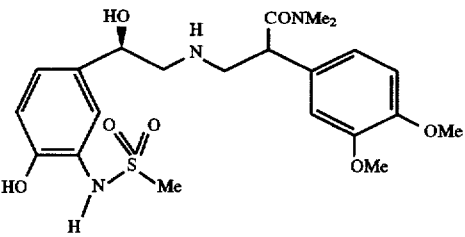

A. α-(Aminomethyl)-3,4-dimethoxy-N,N-dimethyl benzeneacetamide

The title compound was prepared by conversion of α-(aminomethyl)-3,4-dimethoxybenzeneacetic acid, methyl ester, preparation described in step B of Example 17, to α-(aminomethyl)-3,4-dimethoxy-N,N-dimethylbenzeneacetamide following the procedures described in steps A and B of Example 18.

B. α-[[[(R)-2-Hydroxy-2-[4-hydroxy-3-[(methylsulfonyl)amino]phenyl]ethyl]amino]methyl]-3,4-dimethoxy-N,N-dimethylbenzeneacetamide, diastereomer A Following the procedure outlined in step D of Example 19, α-(aminomethyl)-3,4-dimethoxy-N,N-dimethylbenzeneacetamide was converted to α-[[[(R)-2-(triethylsilyl)oxy-2-[4-phenylmethoxy-3-[(methylsulfonyl)amino]phenyl]ethyl]amino]methyl]-3,4-dimethoxy-N,N-dimethylbenzeneacetamide. The coupled product, after chromatographic purification on silica gel using EtOAc, was treated with an excess of TFAA in CH₂Cl₂ for one hour whereupon the reaction was quenched with aq. NaHCO₃ and extracted 3× with CH₂Cl₂. After drying over Na₂SO₄ and concentration, chromatography on silica gel using 2:1 hexane/EtOAc separated diastereomers A and B of α-[[[(R)-2-(triethylsilyl)oxy-2-[4-phenylmethoxy-3-[(methylsulfonyl)amino]phenyl]ethyl](trifluoroacetyl)amino]methyl]-3,4-dimethoxy-N,N-dimethylbenzeneacetamide. Diastereomer A was stirred with TBAF in CH₂Cl₂/THF containing 0.3% HOAc for 40 hours. After workup as described in step E of Example 19, the crude product was stirred six hours in 3:2 MeOH/H₂O containing Na₂CO₃, whereupon the reaction was diluted with H₂O and extracted 3× with EtOAc. After drying over Na₂SO₄ and concentration, the crude α-[[[(R)- 2-hydroxy-2-[4-phenylmethoxy-3-[(methylsulfonyl)amino]phenyl]ethyl]amino]methyl]-3,4-dimethoxy-N,N-dimethylbenzeneacetamide was converted to the title compound as described in step B of Example 48, except that 24% solvent B was employed for the final HPLC purification.

¹H NMR (270 MHz, CD₃OD): δ 2.87 (s, 3H), 2.90 (m, 1H), 2.92 (s, 3H), 2.97 (s, 3H), 3.10 (t, 1H), 3.18 (m, 1H), 3.58 (t, 1H), 3.81 (s, 3H), 3.82 (3H), 4.32 (m, 1H), 4.85 (m, 1H), 6.81–6.91 (m, 3H), 6.97 (d, 1H), 7.10 (dd, 1H), 7.38 (d, 1H).

¹³C NMR (68 MHz, CD₃OD): δ 36.2, 37.46, 39.57, 46.64, 51.98, 55.34, 56.47, 69.27, 112.37, 113.54, 115.36, 116.69, 121.59, 124.3, 125.49, 126.11, 128.69, 133.4, 150.63, 151.3, 151.65, 172.65.

Mass (M+H) 482.

$[\alpha]_D^{22} = -82.0°$ (c=0.24, MeOH)

Calculated for 1.5 mol TFA:

|   | Calc. | Found |
|---|---|---|
| C | 46.01 | 45.93 |
| H | 5.02 | 5.03 |
| N | 6.44 | 6.44 |
| S | 4.91 | 5.05 |
| F | 13.10 | 13.13 |

HPLC: 98% pure, retention time 11.9 minutes, protocol described in Example 1.

EXAMPLE 67

α-[[[(R)-2-Hydroxy-2-|4-hydroxy-3-|(methylsulfonyl)amino]phenyl]ethyl]amino]methyl]-3,4-dimethoxy-N,N-dimethylbenzeneacetamide, trifluoroacetate salt, diastereomer B

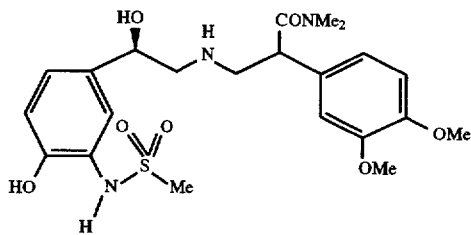

Diastereomer B of α-[[[(R)-2-(triethylsilyl)oxy-2-|4-phenylmethoxy-3-|(methylsulfonyl)amino]phenyl]ethyl](trifluoroacetyl)amino]methyl]-3,4-dimethoxy-N,N-dimethylbenzeneacetamide, preparation described in Example 66, was converted to the title compound using the procedure described in step B of Example 66.

$^1$H NMR (270 MHz, CD$_3$OD): δ 2.88 (s, 3H), 2.92 (s, 3H), 2.94 (m, 1H), 2.97 (s, 3H), 3.10 (t, 1H), 3.22 (dd, 1H), 3.60 (m, 1H), 3.81 (s, 3H), 3.82 (3H), 4.33 (m, 1H), 4.86 (m, 1H), 6.81–6.91 (m, 3H), 6.97 (d, 1H), 7.11 (dd, 1H), 7.39 (d, 1H).

$^{13}$C NMR (68 MHz, CD$_3$OD): δ 36.18, 37.46, 39.57, 46.46, 52.24, 55.58, 56.46, 56.48, 69.30, 112.42, 113.54, 116.68, 121.51, 121.59, 124.37, 125.46, 126.11, 128.62, 133.44, 150.64, 151.31, 151.62, 172.73.

Mass (M+H) 482.

$[\alpha]_D^{22} = +16.7°$ (c=0.52, MeOH)

Calculated for 0.8 mol H$_2$O and 1.5 mol TFA:

|   | Calc. | Found |
|---|---|---|
| C | 45.02 | 45.05 |
| H | 5.15 | 4.75 |
| N | 6.30 | 6.15 |
| S | 4.81 | 4.82 |
| F | 12.82 | 12.72 |

HPLC: 99% pure, retention time 11.9 minutes, protocol described in Example 1.

EXAMPLE 68

N-[5-[2-[[(R)1-(3,4-Dimethoxyphenyl)-2-phenylethyl]amino]-1-hydroxyethyl]-2-fluorophenyl]methanesulfonamide, trifluoroacetate salt

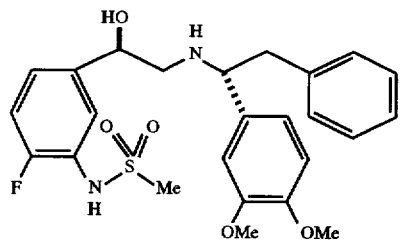

The title compound was prepared by coupling of 2-bromo-1-[4-fluoro-3-[(methylsulfonyl)amino]phenyl]ethanone (preparation described in step B of Example 46) with (R)-α-(3,4-dimethoxyphenyl)benzeneethanamine (preparation described in step B of Example 19) following the procedure described in step D of Example 1, except for the following modifications: 1) the crude product after coupling and reduction was chromatographed on silica gel using 8:1 EtOAc/hexane as elutant; and 2) the title compound was isolated after preparative HPLC using 36% solvent B.

$^1$H NMR (270 MHz, CD$_3$OD): δ 2.76 (t, 1H), 2.96 (s, 1.5H), 2.97 (s, 1.5H), 3.1 (m, 1H), 3.28 (m, 1H), 3.46 (t, 1H), 3.79 (s, 3H), 3.80 (s, 3H), 4.46 (m, 1H), 4.85 (m, 1H), 6.80–6.92 (m, 2H), 6.96–7.06 (m, 3H), 7.10–7.20 (m, 5H), 7.45 (dd, 1H).

$^{13}$C NMR (67 MHz, CD$_3$OD): δ 40.15, 40.26, 40.75, 53.33, 53.53, 56.36, 56.59, 65.30, 66.02, 69.16, 69.68, 112.47, 112.75, 112.92, 117.01, 117.33,122.90, 124.17, 124.25, 125.06, 125.18, 125.32, 126.91, 127.28, 128.09, 129.56, 130.40, 136.83, 139.22,151.02, 151.51,154.48, 158.12.

Mass (M+H) 489

HPLC: 98% pure, retention times 19.5 and 19.6 minutes, protocol described in Example 9.

EXAMPLE 69

N-[5-[2-[[(R)1-(1-(1,3-Benzodioxol-5-yl)-2-phenylethyl]amino]-1-hydroxyethyl]-2-chlorophenyl]methanesulfonamide, trifluoroacetate salt

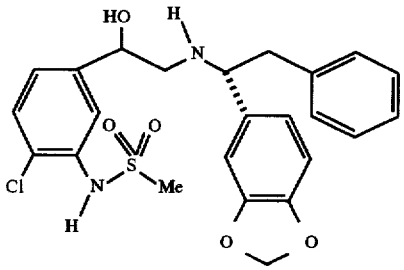

Following the procedure described in step D of Example 1, the title compound was prepared by coupling of 2-bromo-1-[4-chloro-3-[(methylsulfonyl)amino]phenyl]ethanone (preparation analogous to that reported in steps A and B of Example 46 beginning with 4-chloroacetophenone, except that the nitro group was reduced with SnCl$_2$ as described in step A of Example 128) with (R)-α-(1,3-benzodioxol-5-yl)benzeneethanamine (preparation described in step B of Example 60) except for the following modifications: the crude product after coupling and reduction was chromatographed on silica gel using 1:2 EtOAc/hexane as elutant. The title compound was isolated after preparative HPLC using 52% solvent B.

$^1$H NMR (270 MHz, CD$_3$OD): δ 2.78 T, 1H), 2.97 (s, 1.5H), 2.98 (s, 1.5H), 3.08 (m, 1H), 3.24 (t,1H), 3.428 (t, 1H), 4.46 (t, 1H), 4.9 (m, 1H), 5.97 (s, 1H), 5.98 (s, 1H), 6.76 (q, 2H), 6.95 (s, 1H), 7.02–7.06 (m, 2H), 7.15–7.24 (m, 4H), 7.45–7.55 (m, 2H).

$^{13}$C NMR (67 MHz, CD$_3$OD): δ 40.08, 40.55, 40.72, 53.15, 53.27, 65.27, 65.87, 103.08, 108.79, 108.99, 109.57, 124.28, 125.06, 125.18, 125.38, 125.55, 128.06, 128.12, 128.44, 128.72, 129.62, 130.37, 131.29, 135.73, 135.79, 136.69, 136.74, 142.57, 150.04, 150.09, 150.21.

Mass (M+H) 489

HPLC: 100% pure, retention time 22.5 minutes, protocol described in Example 9.

EXAMPLE 70

N-|5-|2-|[(R)1-(1-(1,3-Benzodioxol-5-yl)-2-phenylethyl]amino]-1-hydroxyethyl]-2-methoxyphenyl]methanesulfonamide, trifluoroacetate salt

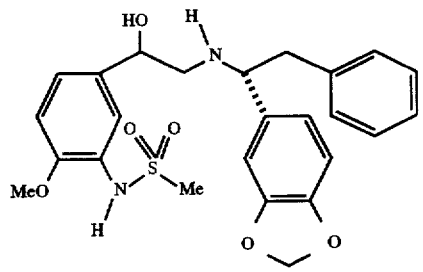

Following the procedure described in step D of Example 1, the title compound was prepared by coupling of 2-bromo-1-[4-methoxy-3-|(methylsulfonyl)amino]phenyl]ethanone (preparation analogous to that described in steps A and B of Example 46 beginning with 4-methoxyacetophenone) with (R)-α-(1,3-benzodioxol-5-yl)benzeneethanamine (preparation described in step B of Example 60) except for the following modification: the crude product after coupling and reduction was purified by preparative HPLC using 49% solvent B to yield the title compound.

$^1$H NMR (270 MHz, CD$_3$OD): δ 2.93 (t, 1H), 3.03 (s, 1.5H), 3.04 (s, 1.5H), 3.17–3.40 (m, 2H), 3.58–3.63 (m, 1H), 4.02 (s, 1.5H), 4.03 (s, 1.5H), 4.55–4.63 (m, 1H), 4.9 (m, 1H), 6.1 (s, 2H), 6.90 (d, 2H), 7.08 (d, 1H), 7.15–7.19 (m, 3H), 7.28–7.33 (m, 4H), 7.50 & 7.54 (2 d, J=5.86 & 10.55 Hz, 1H).

$^{13}$C NMR (67 MHz, CD$_3$OD): δ 39.63, 40.11, 40.58, 53.44, 53.56, 56.44, 65.21, 65.82, 69.39, 69.94, 103.08, 108.85, 109.02, 109.57, 112.51, 123.27, 123.39, 124.28, 124.98, 125.15, 127.51, 127.57, 128.12, 128.49, 129.59, 130.37, 134.75, 136.74, 150.07, 150.18, 153.18.

Mass (M+H) 485

Calculated for 0.96 mol H$_2$O and 1.21 mol TFA:

|   | Calc. | Found |
|---|-------|-------|
| C | 51.47 | 51.47 |
| H | 4.90  | 4.72  |
| N | 4.38  | 4.19  |
| S | 5.01  | 5.02  |
| F | 10.78 | 10.79 |

HPLC: 100% pure, retention time 21.5 minutes, protocol described in Example 9.

EXAMPLE 71

(R),(R)-N-|5-|2-|[1-(1-(1,3-Benzodioxol-5-yl)-2-phenylethyl]amino]-1-hydroxyethyl]-2-fluorophenyl]methanesulfonamide, trifluoroacetate salt

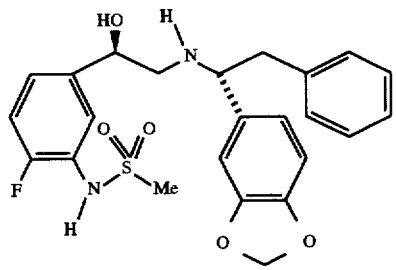

Following the procedure described in Example 63, (R)-α-(1,3-benzodioxol-5-yl)benzeneethanamine (preparation described in step B of Example 60) was converted to the title compound with the following modifications: 1) the preparative TLC chromatography was omitted; 2) 52% solvent B was utilized for the HPLC purification.

$^1$H NMR (270 MHz, CD$_3$OD): δ 2.93 (m, 1H), 2.98 (s, 3H), 3.03–3.25 (m, 2H), 3.49 (dd, 1H), 4.43 (dd, 1H), 4.82 (dd, 1H), 5.96 (s, 1H), 5.97 (s, 1H), 6.77 (s, 2H), 6.94 (s, 1H), 7.03–7.06 (m, 2H), 7.17–7.20 (m, 5H), 7.49 (d, 1H).

$^{13}$C NMR (67 MHz, CD$_3$OD): δ 40.1, 53.43, 65.88, 69.69, 103.06, 109.05, 109.57, 117.0, 117.31, 124.31, 125.23, 125.35, 126.87, 128.08, 128.49, 129.59, 130.36, 136.78, 139.23, 150.03, 150.20.

Mass (M+H) 473

HPLC: 99% pure, retention time 21.2 minutes, protocol described in Example 9.

EXAMPLE 72

(R),(R)-N-[5-[2-[[1-(1-(3,4-Dimethoxyphenyl)-2-phenylethyl]amino]-1-hydroxyethyl]-2-fluorophenyl]methanesulfonamide, trifluoroacetate salt

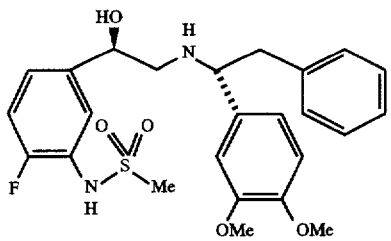

Following the procedure described in Example 71, (R)-α-(3,4-dimethoxyphenyl)benzeneethanamine (preparation described in step B of Example 19) was converted to the title compound with the following modifications: 1) the title compound was eluted from silica gel using 1:2 EtOAc/hexane; and 2) 45% solvent B was utilized for the HPLC purification.

¹H NMR (270 MHz, CD₃OD): δ 2.92 (m, 1H), 2.98 (s, 3H), 3.085 (t, 2H), 3.25 (td, 1H), 3.53 (dd, 1H), 3.79 (s, 3H), 3.80 (s, 3H), 4.40 (dd, 1H), 4.8 (m, 1H), 6.84–6.94 (m, 2H), 6.99–7.06 (m, 3H), 7.14–7.20 (m, 5H), 7.49 (d, 1H).

¹³C NMR (67 MHz, CD₃OD): δ 40.14, 40.26, 53.53, 56.38, 56.59, 66.02, 69.68, 112.77, 112.95, 117.01, 117.33, 122.93, 124.28, 125.23, 125.35, 126.88, 127.31, 128.06, 129.56, 130.97, 136.92, 139.22, 151.02, 151.54.

Mass (M+H) 547

Calculated for 1.06 mol H₂O and 1.48 mol TFA:

|   | Calc. | Found |
|---|-------|-------|
| C | 49.65 | 49.65 |
| H | 4.84  | 4.41  |
| N | 4.14  | 4.06  |
| S | 4.74  | 4.61  |
| F | 15.28 | 15.24 |

HPLC: 98% pure, retention time 19.7 minutes, protocol described in Example 9.

EXAMPLE 73

(R)-N-[5-[2-[[bis-(4-Difluoromethoxyphenyl)methyl]amino]-1-hydroxyethyl]-2-fluorophenyl]methanesulfonamide, trifluoroacetate salt

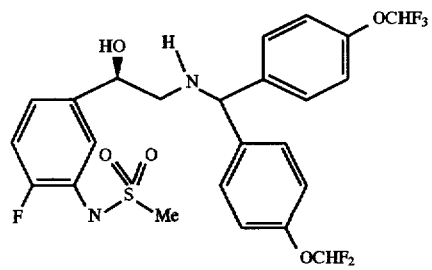

Following the procedure described in Example 63, 4,4'-bisdifluoromethoxybenzhydryl amine (preparation described in Example 59) was converted to the title compound with the following modifications: 1) the coupling step required heating at 110° C. for 135 hours; 2) the preparative TLC chromatography was omitted; and 3) 52% solvent B was utilized for the HPLC purification.

¹H NMR (270 MHz, CD₃OD): δ 2.97 (s, 3H), 3.04–3.16 (m, 2H), 5.01 (dd, 1H), 5.07 (s, 1H), 6.87 (t, 1H), 6.88 (t, 1H), 7.15–7.28 (m, 6H), 7.45–7.65 (m, 5H).

¹³C NMR (67 MHz, CD₃OD): δ 40.21, 54.28, 65.82, 69.49, 113.73, 117.14, 117.42, 117.58, 120.94, 121.03, 121.38, 124.35, 125.24, 125.36, 130.75,131.01, 133.32, 133.63, 139.23, 153.56.

Mass (M+H) 489

HPLC: 99% pure, retention time 23.2 minutes, protocol described in Example 9.

EXAMPLE 74

α-[[[(R)-2-Hydroxy-2-[4-hydroxy-3-[(methylsulfonyl)amino]phenyl]ethyl]amino]methyl]-3,4-dimethoxy-N-(phenyl)benzeneacetamide, trifluoroacetate salt

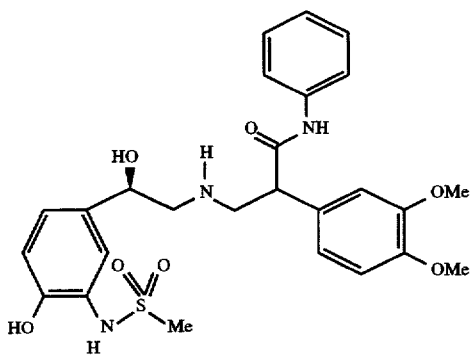

Following the procedure described in Example 66, α-(aminomethyl)-3,4-dimethoxybenzeneacetic acid, methyl ester, (preparation described in step B of Example 17), was converted first to α-(aminomethyl)-3,4-dimethoxy-N-(phenyl)benzeneacetamide and then to the title compound with the following modifications: 1) the initial coupled product, α-[[[(R)-2-(triethylsilyl)oxy-2-[4-phenylmethoxy-3-[(methylsulfonyl)amino]phenyl]ethyl]amino]methyl]-3,4-dimethoxy-N-(phenyl)benzeneacetamide was eluted from silica gel using 9:1 EtOAc/hexane as a mixture of the R, R and R, S diastereomers; and 2) 37% solvent B was employed for the HPLC purification of the title compound.

¹H NMR (270 MHz, CD₃OD): δ 2.90 (s, 1.5H), 2.91 (s, 1.5H), 3.10–3.29 (m, 2H), 3.42 (dd, 1H), 3.75 (m, 1H), 3.82 (s, 3H), 3.85 (s, 3H), 4.11–4.18 (m, 1H), 4.82 (m, 1H), 6.89 (d, 1H), 6.98–7.14 (m, 5H), 7.26–7.40 (m, 3H), 7.52–7.56 (m, 1H).

¹³C NMR (67 MHz, CD₃OD): δ 39.98, 51.26, 51.58, 55.68, 55.96, 56.92, 69.61, 69.72, 113.13, 113.91, 117.03, 121.79, 122.02, 122.13, 124.84, 125.88, 125.99, 126.54, 129.98, 130.24, 133.81, 139.87, 151.18, 151.49, 152.07, 171.8.

Mass (M+H) 530

Calculated for 1.45 mol H₂O and 1.45 mol TFA:

|   | Calc. | Found |
|---|-------|-------|
| C | 48.14 | 48.15 |
| H | 4.94  | 4.81  |
| N | 5.83  | 5.73  |
| S | 4.45  | 4.54  |
| F | 11.46 | 11.66 |

HPLC: 100% pure, retention time 18.6 minutes, protocol described in Example 9.

EXAMPLE 75

α-[[[(R)-2-Hydroxy-2-[4-hydroxy-3-[(methylsulfonyl)amino]phenyl]ethyl]amino]methyl]-3,4-dimethoxy-N-(phenylmethyl)benzeneacetamide, trifluoroacetate salt

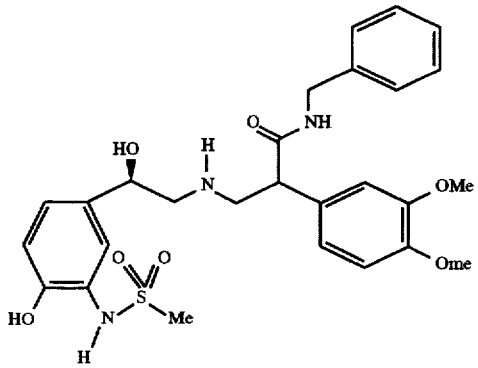

Following the procedure described in Example 66, α-(aminomethyl)-3,4-dimethoxybenzeneacetic acid, methyl ester, preparation described in step B of Example 17, was converted first to α-(aminomethyl)-3,4-dimethoxy-N-(phenylmethyl)benzeneacetamide and then to the title compound following the procedure described in Example 74.

$^1$H NMR (270 MHz, CD₃OD): δ 2.92 (s, 3H), 3.06–3.22 (m, 2H), 3.4 (m, 1H), 3.70 (m, 1H), 3.77 (s, 3H), 3.82 (s, 3H), 3.98 (m, 1H), 4.01 (m, 1H), 4.24 (d, 1H), 4.49 (dd, 1H), 4.9 (m, 1H), 6.85–6.98 (m, 4H), 7.07–7.29 (m, 6H), 7.39 (d, 1H).

$^{13}$C NMR (67 MHz, CD₃OD): δ 40.01, 44.57, 51.20, .51.46, 55.53, 55.73, 56.86, 56.92, 69.66, 69.72, 113.04, 113.85, 117.02, 122.33, 122.45, 124.81, 125.85, 126.54, 128.62, 128.88, 129.86, 130.00, 130.09, 133.81, 140.10, 151.15, 151.47, 152.07, 17365, 173.70.

Mass (M+H) 544

Calculated for 1.8 mol H₂O and 1.45 mol TFA:

|   | Calc. | Found |
|---|-------|-------|
| C | 51.03 | 50.78 |
| H | 5.30  | 4.99  |
| N | 5.83  | 6.06  |
| S | 4.45  | 4.45  |
| F | 10.29 | 10.22 |

HPLC: 100% pure, retention time 17.7 minutes, protocol described in Example 9.

EXAMPLE 76

α-[[[(R)-2-Hydroxy-2-[4-hydroxy-3-[(methylsulfonyl)amino]phenyl]ethyl]amino]methyl]-3,4-dimethoxy-N-(2-phenylethyl)benzeneacetamide, trifluoroacetate salt

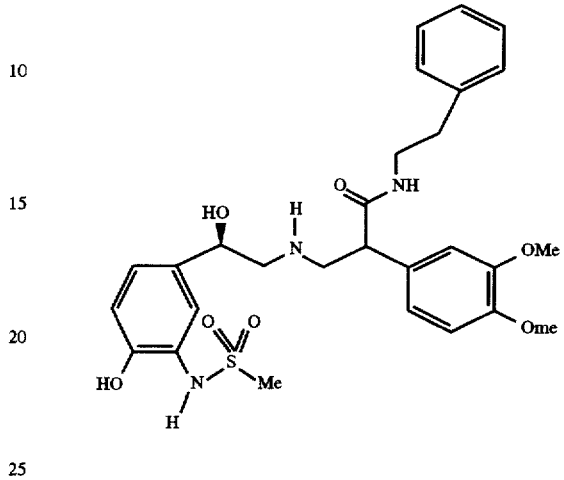

Following the procedure described in Example 66, α-(aminomethyl)-3,4-dimethoxybenzeneacetic acid, methyl ester, (preparation described in step B of Example 17), was converted first to α-(aminomethyl)-3,4-dimethoxy-N-(2-phenylethyl)benzeneacetamide and then to the title compound following the procedure described in Example 74, except that 40% solvent B was employed for the final HPLC purification.

$^1$H NMR (270 MHz, CD₃OD): δ 2.71 (t, 2H), 2.92 (s, 3H), 3.16–3.27 (m, 3H), 3.35 (m, 1H), 3.54–3.70 (m, 2H), 3.81 (s, 3H), 3.84 (s, 3H), 3.88 (m, 1H), 4.85 (m, 1H), 6.80–7.15 (m, 10H), 7.39 (d, 1H).

$^{13}$C NMR (67 MHz, CD₃OD): δ 36.19, 39.63, 42.05, 50.64, 50.87, 55.11, 55.29, 56.53, 69.31, 112.77, 113.49, 116.64, 121.74, 121.86, 124.43, 125.47, 126.16, 127.28, 129.39, 129.62, 129.79, 133.43, 140.20, 150.76, 151.08, 151.64, 173.23, 173.32.

Mass (M+H) 558

HPLC: 100% pure, retention time 19.1 minutes, protocol described in Example 9.

EXAMPLE 77

(R),(R)-N-[5-[1-(Hydroxy-2-[[1-(3,4-dimethylphenyl)-2-phenylethyl]amino]ethyl]-2-(hydroxy)phenyl]methanesulfonamide, trifluoroacetate salt

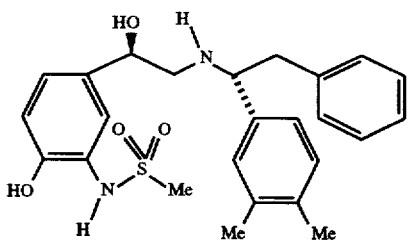

The title compound was prepared from 1-(3,4-dimethylphenyl)-2-phenylethanone (preparation described in Example 9) utilizing the procedure described in Example 19, except for the following modifications: 1) in step A, chromatography on silica gel using 4:1 hexane/CH₂Cl₂ separated the anti oxime from the minor syn contaminant; 2) the chromatography of step E was omitted; and 3) the title compound was purified via prep HPLC using 53% solvent B.

¹H NMR (270 MHz, CD₃OD): δ 2.3 (s, 6H), 2.94 (m, 1H), 3.00 (s, 3H), 3.15 (t, 1H), 3.35 (t, 1H), 3.61 (dd, 1H), 4.49 (dd, 1H) 4.81 (m, 1H), 6.95 (d, 1H), 7.08–7.23 (m, 9H), 7.39 (d, 1H).

¹³C NMR (67 MHz, CD₃OD): δ 19.54, 19.77, 39.64, 40.19, 53.6, 65.88, 69.96, 116.64, 124.30, 125.43, 126.06, 127.04, 128.02, 129.52, 130.38, 130.78, 131.42, 132.40, 133.58, 136.90, 138.90, 139.59, 151.53.

Mass (M+H) 568

$[\alpha]_D^{22} = -35.0°$ (c=1.00, MeOH)

Calculated for 0.02 mol H₂O and 1.4 mol TFA:

|   | Calc. | Found |
|---|-------|-------|
| C | 54.33 | 54.33 |
| H | 5.16  | 4.42  |
| N | 4.56  | 4.31  |
| S | 5.22  | 5.20  |
| F | 12.98 | 12.97 |

HPLC: 97% pure, retention time 23.6 minutes, protocol described in Example 9

EXAMPLE 78

(R)-N-[5-[1-(Hydroxy-2-[[1-(4-hydroxyphenyl)-2-(2-thienyl)ethyl]amino]ethyl]-2-(hydroxy)phenyl] methanesulfonamide, trifluoroacetate salt

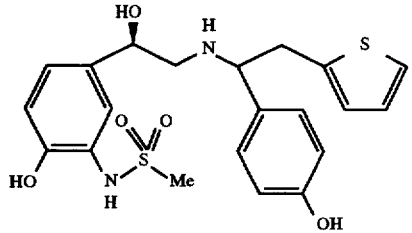

A. α-(4-Methoxyphenyl)-2-thiopheneethanamine

Commercially available 2-thienylacetic acid, after conversion to the corresponding acid choride upon reflux in thionyl chloride, was converted to 1-(4-methoxyphenyl)-2-(2-thienyl)ethanone using the procedure described in step A of Example 9. 1-(4-Methoxyphenyl)-2-(2-thienyl)ethanone was converted to α-(4-methoxyphenyl)-2-thiopheneethanamine using the procedure described in step C of Example 1 except for the following modification. The acidic hydrolysis reaction, after dilution with H₂O, was extracted 2× with Et₂O prior to basification, extraction 3× with EtOAc and isolation of the title compound after concentration.

B. (R)-N-[5-[1-(Hydroxy-2-[[1-(4-hydroxyphenyl)-2-(2-thienyl)ethyl]-amino]ethyl]-2-(hydroxy)phenyl]methane sulfonamide α-(4-Methoxyphenyl)-2-thiopheneethanamine was converted to (R)-N-[5-[1-hydroxy-2-[[1-(4-methoxyphenyl)-2-(2-thienyl)ethyl]amino]ethyl]-2-(phenylmethoxy)phenyl] methanesulfonamide following the procedure outlined in steps D and E described in Example 19 except for the following modifications: 10 In step D, 20% EtOAc/hexane eluted the product from silica gel as a mixture of two diastereomers. 2) In step E, the chromatographic purification was omitted.

Addition of 4 equivalents of BBr₃ to a −75° CH₂Cl₂ solution of (R)-N-[5-[1-hydroxy-2-[[1-(4-methoxyphenyl)-2-(2-thienyl)ethyl]amino]ethyl]-2-(phenylmethoxy)phenyl] methanesulfonamide followed by warming to −40° over 1 hour prior to quenching with aq NaHCO₃ and extraction 3× with EtOAc generated crude title compound. After drying over Na₂SO₄ and concentration, the crude product was purified by preparative HPLC chromatography eluting with 33% solvent B (see Example 1 for HPLC protocol) to obtain the title compound after concentration and lyophilization.

¹H NMR (270 MHz, CD₃OD): δ 2.70–2.9 (m, 1H), 2.89 (s, 1.5H), 2.90 (s, 1.5H), 3.00–3.1 (m, 1H), 3.45–3.75 (m, 2H), 4.3–4.48 (m, 1H), 4.70 (d, 1H), 6.72 (d, 1H), 6.80–6.9 (m, 4H), 6.98–7.04 (m, 2H), 7.15–7.34 (m, 3H).

¹³C NMR (68 MHz, CD₃OD): δ 34.23, 34.64, 39.66, 53.33, 53.59, 64.75, 65.42 69.51, 70.06, 116.64, 117.16, 124.40, 124.92, 125.27, 125.41, 125.99, 126.13, 127.86, 128.1, 131.21, 131.3, 133.60, 138.42, 151.75, 161.23.

Mass (M+H) 449

HPLC: 93% pure, retention time 19.4 minutes, protocol described in Example 1

EXAMPLE 79

(R)-N-[5-[2-[[bis[4-(2-Methoxy-2-oxoethoxy) phenyl]methyl]amino]-1-hydroxyethyl]-2-hydroxyphenyl]methanesulfonamide, trifluoroacetate salt

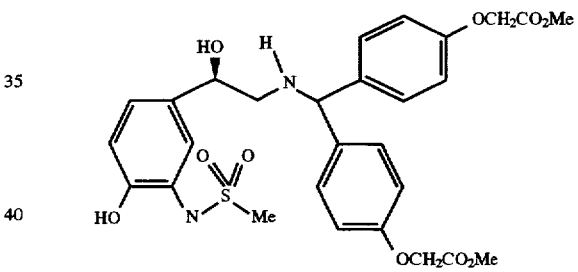

A. bis-(4-(2-Methoxy-2-oxoethoxy)phenyl)methanamine

Following the procedure in step C of Example 1, 4,4'-dimethoxybenzophenone was converted to N-[bis-(4-methoxyphenyl)methyl]formamide. To a solution of the above formamide (2.2 g, 8.1 mmol) in anhydrous CH₂Cl₂ (50 ml) at 0° C. under N₂ was added 1.0M solution of BBr₃ in CH₂Cl₂ (20.0 ml). After warming to 20° C. and stirring for one hour, the reaction mixture was quenched with aq. NaHCO₃ and extracted with EtOAc. The EtOAc fractions were washed with brine, dried over MgSO₄ and then stripped to obtain 1.9 g of N-[bis-(4-hydroxyphenyl)methyl] formamide.

To a stirred solution of the above bis-phenol (1.01 g, 4.1 mmol) in dry DMF (5 mL) was added 60% NaH in mineral oil (460 mg, 11.5 mmol) at 20° C. under N₂ and subsequently, after 15 minutes, methyl bromoacetate (1.06 mL, 11.2 mmol). After stirring for one hour, the reaction was quenched with H₂O and then extracted with EtOAc. The organic layer was washed with brine (5×), dried over MgSO₄ and concentrated to yield 1.2 g of N-[bis-(4-(2-methoxy-2-oxoethoxy)phenyl)methyl]formamide after elution from silica gel using 70% EtOAc/hexanes. The title compound was obtained by refluxing the above bis-ester (1.1 g, 2.8 mmol) for 45 minutes in methanol (25 mL)

containing conc. HCl (1.0 mL). After cooling, pH adjustment to 11, concentration, and extraction with EtOAc (3×), the EtOAc layers were washed with brine, dried over MgSO₄ and then concentrated to obtain the title compound (305 mg).

B. (R)-N-[5-[2-[[bis[4-(2-Methoxy-2-oxoethoxy)phenyl] methyl]amino]-1-hydroxyethyl]-2-hydroxyphenyl] methanesulfonamide Following the procedure described in step B of Example 48, bis-(4-(2-methoxy-2-oxoethoxy)phenyl)methanamine was converted to the title compound except for the following modifications: 1) the triethylsilyl ether was eluted from silica gel with 1:1 EtOAc/toluene; and 2) the title compound was isolated using 41% solvent B for HPLC purification.

$^1$H NMR (270 MHz, CD₃OD): δ 3.0 (s, 3H), 3.24–3.51 (m, 2H), 3.86 (s, 6H), 4.85 (s, 4H), 5.64 (s, 1H) 6.95–7.25 (m, 6H), 7.41(s, 1H), 7.45–7.65(m, 4H).

$^{13}$C NMR (68 MHz, CD₃OD): δ 39.58, 52.67, 54.13, 59.42, 65.90, 66.02, 69.62, 116.36, 116.44, 116.59, 124.16, 125.31, 126.06, 129.66, 130.0, 130.26, 130.52, 133.63, 151.55, 159.87, 171.1.

Mass (M+Na) 611

$[\alpha]_D$=−7.14 (c=0.56, MeOH)

HPLC: 82% pure, retention time 17.1 minutes, protocol described in Example 1.

EXAMPLE 80

(R),(R)-N-[5-[2-[[1-(1,3-Benzodioxol-5-yl)-2-phenylethyl]amino]-1-hydroxyethyl]-2-chlorophenyl]methanesulfonamide, trifluoroacetate salt

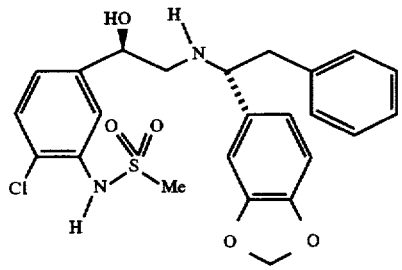

The title compound was prepared by coupling (R)-α-(1, 3-benzodioxol-5-yl)benzeneethanamine (preparation described in Step B of Example 60) with (R)-N-[3-[2-iodo-1-[(triethylsilyl)oxy]ethyl]-2-chlorophenyl] methanesulfonamide (prepared from 2-bromo-1-[4-chloro-3-[(methylsulfonyl)amino]phenyl]ethanone, preparation described in Example 69, utilizing the procedures described in step A–C of Example 19) following the procedure described in steps D and E of Example 19 with the following modifications. 1) Chromatography on silica gel using 25% EtOAc/hexane yielded (R), (R)-N-[5-[1-(triethylsilyl)oxy-2-[[1-(1,3-benzodioxol-5-yl)-2-phenylethyl]amino]ethyl]-2-chlorophenyl]methanesulfonamide. 2) In step E the title compound was eluted from silica gel using 1:1 EtOAc/hexane prior to final preparative HPLC purification (see Example 1 for HPLC protocol) eluting with 52% solvent B.

$^1$H NMR (270 MHz, CD₃OD), δ2.94 (m, 1H), 2.98 (s, 3H), 3.06 (m, 1H), 3.21 (t,1H), 3.50 (dd, 1H), 4.43 (dd, 1H), 4.83 (m, 1H), 5.97 (s, 1H), 5.98 (s, 1H), 6.76 (s, 2H), 6.93 (s, 1H), 7.02–7.06 (m, 2H), 7.15–7.24 (m, 4H), 7.46 (d, 1H), 7.54 (d, 1H)

$^{13}$C NMR (67 MHz, CD₃OD) δ40.12, 40.72, 53.30, 65.94, 69.66, 103.11, 109.06, 109.60, 124.35, 125.18, 125.44, 125.61, 128.15, 128.47, 128.79, 129.65, 130.40, 131.33, 135.83, 136.81, 142.63, 150.07, 150.28.

Mass (M+H) 489

$[\alpha]_D^{22}$=−28.0° (c=1.0, MeOH)

Calculated for 0.55 H₂O and 1.1 mol TFA:

|    | Calc. | Found |
|----|-------|-------|
| C  | 50.41 | 50.41 |
| H  | 4.39  | 4.30  |
| N  | 4.49  | 4.49  |
| S  | 5.14  | 5.21  |
| P  | 10.04 | 10.24 |
| Cl | 5.68  | 5.71  |

HPLC: 100% pure, retention time 20.0 minutes, protocol described in Example 1

EXAMPLE 81

(R),(S)-N-[5-[1-(Hydroxy-2-[[1-(2,4-dimethoxy-3-pyridinyl)-2-phenylethyl]amino]ethyl]-2-hydroxyphenyl]methanesulfonamide

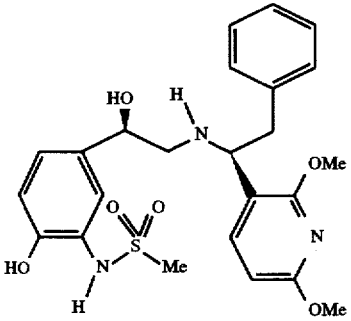

The title compound was prepared from (R),(S)-N-[5-[1-(triethylsilyl)oxy-2-[[1-(2,4-dimethoxy-3-pyridinyl)-2-phenylethyl]amino]ethyl]-2-(phenylmethoxy)phenyl] methanesulfonamide, preparation described in step B of Example 125, following the procedure described in step B of Example 125.

$^1$H NMR (270 MHz, CDCl₃): δ 2.41–2.46 (m, 1H), 2.63 (dd, 1H), 2.91 (s, 3H), 2.89–3.07 (m, 2H), 3.19–3.60 (br. s, 1H), 3.90 (s, 3H), 3.93 (s, 3H), 4.08 (t, 1H), 4.51 (dd, 1H), 6.23 (d, 1H), 6.78 (d, 1H), 6.93 (dd, 1H), 7.09–7.31 (m, 7H).

$^{13}$C NMR (68 MHz, CD₃OD): δ 38.8, 42.0, 53.4, 53.6, 53.9, 58.1, 70.4, 100.7, 114.0, 117.1, 122.2, 124.5, 126.6, 128.3, 129.2, 134.5, 138.7, 139.7, 149.3,160.0, 162.1.

Mass (M+H) 488

$[\alpha]_D^{22}$=−4.7° (c=0.17, MeOH)

Calculated for 1.00 H₂O:

|   | Calc. | Found |
|---|-------|-------|
| C | 57.02 | 57.38 |
| H | 6.18  | 5.86  |
| N | 8.31  | 8.16  |
| S | 6.34  | 5.91  |

HPLC: 99% pure, retention time 19.8 minutes, protocol described in Example 1.

EXAMPLE 82

(R),(R)-4-[1-[[2-Hydroxy-2-[4-hydroxy-3-[(methylsulfonyl)amino]phenyl]ethyl]amino]-2-phenylethyl]benzoic acid, methyl ester, trifluoroacetate salt

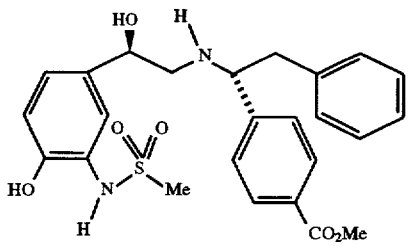

A. α-(4-Carbomethoxyphenyl)benzeneethanamine

The title compound was prepared from 4-carbomethoxybenzoyl chloride, prepared by refluxing commercially available 4-carbomethoxybenzoic acid in $SOCl_2$, following the procedure described in step B of Example 55, except for the following modifications: 1) the Pd coupling employed benzyl bromide to generate 1-(4-carbomethoxyphenyl)-2-phenylethanone which was eluted from silica gel using 5% EtOAc/hexane; and 2) refluxing a solution of N-[1-(4-carbomethoxyphenyl)-2-phenylethyl] formamide in methanolic HCl containing 1% $H_2O$ yielded the title compound.

B. (R),(R)-4-[1-[[2-Hydroxy-2-[4-hydroxy-3-[(methylsulfonyl)amino]phenyl]ethyl]amino]-2-phenylethyl] benzoic acid, methyl ester The title compound was prepared from α-(4-carbomethoxyphenyl)benzeneethanamine following the procedures described in steps D, E, and F of Example 19, except for the following modifications: 1) separation of the R,R and R,S diastereomers of (R)-4-[1-[[2-triethylsilyl)oxy-2-[4-phenylmethoxy-3-[(methylsulfonyl)amino]phenyl] ethyl]amino]-2-phenylethyl]benzoic acid, methyl ester required three column chromatographies on silica gel using 0.5–2% acetone/$CH_2Cl_2$ as eluant; (R),(R)-4-[1-[[2-triethylsilyl)oxy-2-[4-phenylmethoxy-3-[(methylsulfonyl) amino]phenyl]ethyl]amino]-2-phenylethyl]benzoic acid, methyl ester was converted to the title compound; 2) in step E, 70% EtOAc/hexane was the eluant; and 3) in step F, 48% solvent B was employed for the final HPLC purification.

$^1$H NMR (270 MHz, $CD_3OD$): δ 2.90 (s, 3H), 2.95 (d, 1H), 3.1–3.3 (m, 2H), 3.61 (dd, 1H), 3.89 (s, 3H), 4.62 (dd, 1H), 4.77 (dd, 1H), 6.86 (d, 1H), 7.0–7.1 (m, 3H), 7.1–7.2 (m, 3H), 7.32 (d, 1H), 7.45 (d, 2H), 8.00 (d, 2H).

$^{13}$C NMR (68 MHz, $CD_3OD$): δ 39.6, 40.1, 52.8, 54.0, 65.5, 69.9, 116.6, 124.4, 125.4, 126.1, 128.3, 129.7, 129.9, 130.4, 131.2, 132.5, 133.5, 136.3, 140.4, 151.7, 167.7.

Mass (M+H) 485

$[α]_D$=−46.9° (c=0.5, MeOH)

Calculated for 1.29 mol $H_2O$ and 1.12 mol TFA:

| | Calc. | Found |
|---|---|---|
| C | 51.48 | 51.49 |
| H | 5.03 | 4.62 |
| N | 4.41 | 4.33 |
| S | 5.04 | 5.12 |
| F | 10.04 | 10.07 |

HPLC: >97% pure, retention time 18.7 minutes, protocol described in Example 1.

EXAMPLE 83

(R),(S)-4-[1-[[2-Hydroxy-2-[4-hydroxy-3-[(methylsulfonyl)amino]phenyl]ethyl]amino]-2-phenylethyl]benzoic acid, methyl ester, trifluoroacetate salt

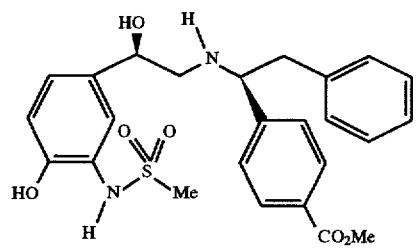

(R),(S)-4-[1-[[2-Triethylsilyl)oxy-2-[4-phenylmethoxy-3-[(methylsulfonyl)amino]phenyl]ethyl]amino]-2-phenylethyl]benzoic acid, methyl ester (described in step B of Example 82) was converted to the title compound following the procedure described in step B of Example 82.

$^1$H NMR (270 MHz, $CD_3OD$): δ 2.79 (dd, 1H), 2.88 (s, 3H), 3.09 (dd, 1H), 3.29 (m, 1H), 3.55 (dd, 1H), 3.89 (s, 3H), 4.65 (dd, 1H), 4.9 (m, 1H), 6.84 (dd, 1H), 6.9–7.1 (m, 3H), 7.1–7.2 (m, 3H), 7.27 (d, 1H), 7.45 (d, 2H), 8.00 (d, 2H).

$^{13}$C NMR (68 MHz, $CD_3OD$): δ 39.6, 40.5, 52.8, 53.8, 65.0, 69.6, 116.6, 124.3, 125.2, 126.1, 128.3, 129.7, 129.8, 130.4, 131.3, 132.5, 133.5, 136.2, 140.1, 151.7, 167.7.

Mass (M+H) 485

$[α]_D$=+13.1° (c=0.5, MeOH)

Calculated for 0.85 mol $H_2O$ and 1.16 mol TFA:

| | Calc. | Found |
|---|---|---|
| C | 51.91 | 51.67 |
| H | 4.92 | 4.63 |
| N | 4.43 | 4.44 |
| S | 5.04 | 5.12 |
| F | 10.46 | 10.56 |

HPLC: >99% pure, retention time 18.8 minutes, protocol described in Example 1.

EXAMPLE 84

(R),(R)-4-[1-[[2-Hydroxy-2-[4-hydroxy-3-[(methylsulfonyl)amino]phenyl]ethyl]amino]-2-phenylethyl]benzoic acid, trifluoroacetate salt

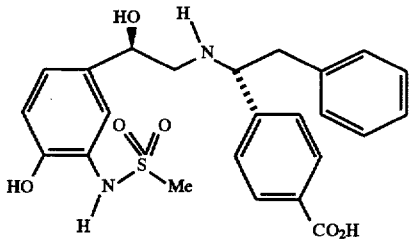

(R),(R)-4-[1-[[2-Hydroxy-2-[4-hydroxy-3-[(methylsulfonyl)amino]phenyl]ethyl]amino]-2-phenylethyl] benzoic acid, methyl ester (preparation described in Example 82) was stirred under Ar in MeOH containing 1N NaOH. Upon completion, the reaction was acidified with TFA, concentrated and the title compound was isolated by preparative HPLC using 39% solvent B (protocol described in Example 1).

$^1$H NMR (270 MHz, CD$_3$OD): δ 2.91 (s, 3H), 2.95 (d, 1H), 3.1–3.3 (m, 2H), 3.60 (dd, 1H), 4.60 (dd, 1H), 4.77 (dd, 1H), 6.86 (d, 1H), 6.9–7.1 (m, 3H), 7.1–7.2 (m, 3H), 7.33 (d, 1H), 7.44 (d, 2H), 8.00 (d, 2H).

$^{13}$C NMR (68 MHz, CD$_3$OD): δ 39.6, 40.2, 54.0, 65.5, 70.0, 116.6, 124.4, 125.4, 126.1, 128.2, 129.7, 129.8, 130.4, 131.4, 133.5, 136.4, 140.2, 151.7, 169.0.

Mass (M+H) 471

$[\alpha]_D = -43.4°$ (c=0.5, MeOH)

Calculated for 2.17 mol H$_2$O and 1.0 mol TFA:

|   | Calc. | Found |
|---|-------|-------|
| C | 50.08 | 49.78 |
| H | 5.06  | 4.71  |
| N | 4.49  | 4.79  |
| S | 5.14  | 5.22  |
| F | 9.14  | 9.51  |

HPLC: >98% pure, retention time 16.2 minutes, protocol described in Example 1.

EXAMPLE 85

(R),(S)-4-[1-[[2-Hydroxy-2-[4-hydroxy-3-[(methylsulfonyl)amino]phenyl]ethyl]amino]-2-phenylethyl]benzoic acid, trifluoroacetate salt

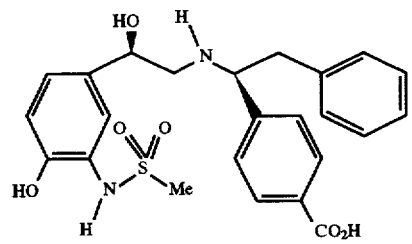

(R),(S)-4-[1-[[2-Hydroxy-2-[4-hydroxy-3-[(methylsulfonyl)amino]phenyl]ethyl]amino]-2-phenylethyl] benzoic acid, methyl ester, trifluoroacetate salt (preparation described in Example 83) was converted to the title compound following the procedure described in Example 84, except that 37% solvent B was employed for preparative HPLC.

$^1$H NMR (270 MHz, CD$_3$OD): δ 2.80 (dd, 1H), 2.89 (s, 3H), 3.10 (dd, 1H), 3.28 (m, 1H), 3.55 (dd, 1H), 4.65 (dd, 1H), 6.85 (d, 1H), 7.0–7.1 (m, 3H), 7.1–7.2 (m, 3H), 7.29 (d, 1H), 7.44 (d, 2H), 8.01 (d, 2H).

$^{13}$C NMR (68 MHz, CD$_3$OD): δ 39.6, 40.6, 53.8, 65.0, 69.6, 116.6, 124.3, 125.3, 126.1, 128.3, 129.7, 129.7, 130.4, 131.5, 133.3, 133.5, 136.3, 140.0, 151.7, 169.0.

Mass (M+H) 471$^+$ $[\alpha]_D = +8.6°$ (c=0.5, MeOH)

Calculated for 3.4 mol H$_2$O and 2.0 mol TFA:

|   | Calc. | Found |
|---|-------|-------|
| C | 44.26 | 44.23 |
| H | 4.62  | 4.25  |
| N | 3.69  | 3.30  |
| S | 4.22  | 4.53  |
| F | 15.00 | 12.73 |

HPLC: >99% pure, retention time 15.7 minutes, protocol described in Example 1.

EXAMPLE 86

(R),(R)-4-[1-[[2-Hydroxy-2-[4-hydroxy-3-[(methylsulfonyl)amino]phenyl]ethyl]amino]-2-phenylethyl]-N-methylbenzamide, trifluoroacetate salt

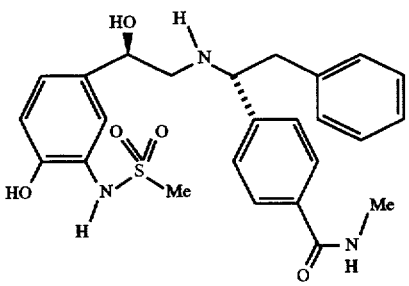

To a 0° C. solution of (R),(R)-4-[1-[[2-hydroxy-2-[4-hydroxy-3-[(methylsulfonyl)amino]phenyl]ethyl]amino]-2-phenylethyl]benzoic acid (74.1 mg, 0.12 mmol; preparation described in Example 84) and 62.1 mL (0.36 mmol) of Hunigs base in 3 mL of dry DMF was added MeNH$_2$.HCl (8.0 mg, 0.12 mmol) of followed by hydroxybenztriazole (17.7 mg, 0.13 mmol) and then 1-(3-dimethylaminopropyl)-3-ethylcarbodiimide.HCl (22.8 mg, 0.12 mmol). After stirring 16 hours, the reaction, after dilution with H$_2$O, was extracted with EtOAc (3×). The organic layers were washed with H$_2$O (2×), saturated NaHCO$_3$ solution (1×), H$_2$O (1×) and brine, dried (Na$_2$SO$_4$) and concentrated. The title compound was isolated by preparative HPLC, eluting with 35% B using the protocol described in Example 1.

$^1$H NMR (270 MHz, CD$_3$OD): δ 2.89 (s, 3H), 2.90 (s, 3H), 2.91 (m, 1H), 3.1–3.3 (m, 2H), 3.60 (dd, 1H), 4.61 (dd, 1H), 4.77 (dd, 1H), 6.86 (d, 1H), 7.0–7.1 (m, 3H), 7.1–7.2 (m, 3H), 7.31 (d, 1H), 7.44 (d, 2H), 7.79 (d, 2H).

$^{13}$C NMR (68 MHz, CD$_3$OD): δ 26.9, 39.7, 40.1, 54.0, 65.5, 70.1, 116.6, 124.5, 125.5, 126.2, 128.3, 129.1, 129.7, 130.0, 130.5, 133.5, 136.4, 137.0, 138.7, 151.8, 169.9.

Mass (M+H)484 and (M−H) 482

$[\alpha]_D = -40.0°$ (c=0.5, MeOH)

Calculated for 2.4 mol H$_2$O and 1.4 mol TFA:

|   | Calc. | Found |
|---|-------|-------|
| C | 48.64 | 48.59 |
| H | 5.17  | 4.73  |
| N | 6.12  | 5.97  |
| S | 4.67  | 4.58  |
| F | 11.62 | 11.29 |

HPLC: >99% pure, retention time 14.7 minutes, protocol described in Example 1.

EXAMPLE 87

(R),(R)-N-[5-[1-(Hydroxy-2-[[1-(2-naphthalenyl)-2-(phenyl)ethyl]amino]ethyl]-2-(hydroxy)phenyl] methanesulfonamide, trifluoroacetate salt

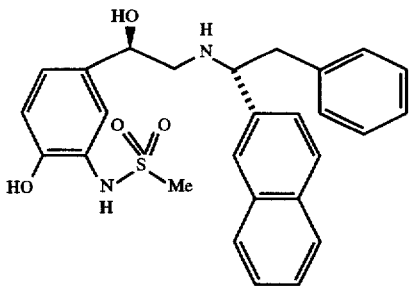

The title compound was prepared from commercially available naphthoyl chloride following the procedures described in steps B and C of Example 55, except for the following modifications: 1) the Pd coupling employed benzyl bromide; 2) 5% EtOAc/CH$_2$Cl$_2$ separated the R,R and R,S diastereomers of (R)-N-[5-[1-(triethylsilyl)oxy-2-[[1-(2-naphthalenyl)-2-(phenyl)ethyl]amino]ethyl]-2-(phenylmethoxy)phenyl]methanesulfonamide on 0.25 mm silica TLC plates; and 3) Final HPLC purification of the title compound derived from the R,R diastereomer utilized 59% solvent B.

$^1$H NMR (270 MHz, CD$_3$OD): δ 2.86 (s, 3H), 2.92 (dd, 1H), 3.15 (dd, 1H), 3.4 (dd, 1H), 3.63 (dd, 1H), 4.66 (dd, 1H), 4.75 (dd, 1H), 6.82 (d, 1H), 6.9–7.0 (m, 3H), 7.1–7.2 (m, 3H), 7.31 (d, 1H), 7.5–7.6 (m, 3H), 7.75 (s, 1H), 7.8 (m, 1H), 7.9 (m, 1H), 7.94 (d, 1H).

Mass (M+H) 477

$[\alpha]_D^{22}$=-46.5° (c=0.5, MeOH)

Calculated for 0.93 H$_2$O and 1.2 mol TFA:

|   | Calc. | Found |
|---|-------|-------|
| C | 56.04 | 56.04 |
| H | 4.97  | 4.54  |
| N | 4.45  | 4.21  |
| S | 5.09  | 5.10  |
| F | 10.85 | 10.57 |

HPLC: 100% pure, retention time 21.6 minutes, protocol described in Example 1.

EXAMPLE 88

(R),(S)-N-[5-[1-(Hydroxy-2-[[1-(2-naphthalenyl)-2-(phenyl)ethyl]amino]ethyl]-2-(hydroxy)phenyl] methanesulfonamide, trifluoroacetate salt

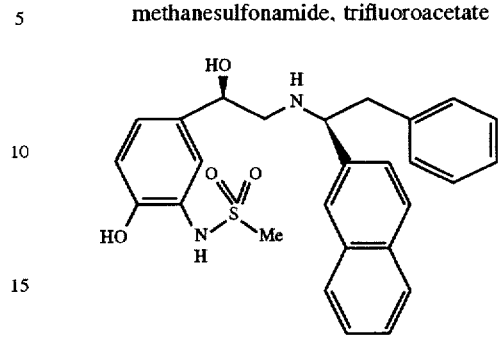

(R),(S)-N-[5-[1-(triethylsilyl)-oxy-2-[[1-(2-naphthalenyl)-2-(phenyl)ethyl]amino]ethyl]-2-(phenylmethoxy)phenyl] methanesulfonamide, described in Example 87, was converted to the title compound using the procedure described in Example 87, except that the final HPLC purification employed 62% solvent B.

$^1$H NMR (270 MHz, CD$_3$OD): δ 2.77 (t, 1H), 2.89 (s, 3H), 3.05 (dd, 1H), 3.26 (t, 1H), 3.50 (dd, 1H), 4.57 (dd, 1H), 4.89 (m, 1H), 6.84 (d, 1H), 6.86 (t, 1H), 6.99–7.03 (m, 3H), 7.12–7.21 (m, 5H), 7.27 (d, 1H), 7.39 (d, 2H).

Mass (M+H) 477

$[\alpha]_D^{22}$=+20.5° (c=0.5, MeOH)

Calculated for 1.02 H$_2$O and 1.35 mol TFA:

|   | Calc. | Found |
|---|-------|-------|
| C | 54.97 | 54.97 |
| H | 4.88  | 4.44  |
| N | 4.32  | 4.11  |
| S | 4.94  | 5.10  |
| F | 11.86 | 11.53 |

HPLC: >99% pure, retention time 21.5 minutes, protocol described in Example 1.

EXAMPLE 89

(R),(S)-4-[1-[[2-Hydroxy-2-[4-hydroxy-3-[(methylsulfonyl)amino]phenyl]ethyl]amino]-2-phenylethyl]benzeneacetic acid, methyl ester, trifluoroacetate salt

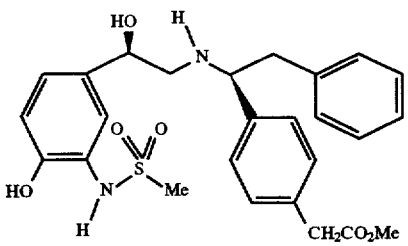

A. Methyl 4-(1-amino-2-phenylethyl)benzeneacetate

A suspension of 4-bromomethylbenzoic acid (25.26 g, 0.12 mol) and KCN (20 g, 0.31 mol) in 5:7 H$_2$O/EtOH (60 mL) was heated to 75°–80° C. for four hours. The cooled reaction was partially concentrated, H$_2$O added, and extracted 1× with EtOAc. After acidification of the aqueous layer, the resulting precipitate was filtered and washed well with H₂O to yield 13.6 g; 4 EtOAc extractions of the filtrate yielded an additional 2.7 g. Recrystallization of the combined solids from H₂O/EtOH using activated charcoal and filtering through Celite afforded 15.20 g of 4-cyanomethylbenzoic acid.

A solution of 4-cyanomethylbenzoic acid (10.0 g, 62.2 mmol) in thionyl chloride (65 mL) containing DMF (1 mL) was refluxed for three hours, cooled, concentrated, dissolved in hot EtOAc, treated with activated charcoal, filtered through Celite, and concentrated to yield 4-cyanomethylbenzoyl chloride. 4-Cyanomethylbenzoyl chloride was converted to the title compound following the procedure described in step A of Example 82 with the following modifications: 1) 1-(4-cyanomethylphenyl)-2-phenylethanone was chromatographed on silica gel using 2:3 EtOAc/hexane; 2) purification of N-[1-(4-cyanomethylphenyl)-2-phenylethyl]formamide entailed treatment with activated charcoal in EtOAc followed by recrystallization from EtOAc/hexane; and 3) the title compound was chromatographed on silica gel eluting with 10% acetone/EtOAc.

B. (R),(S)-4-[1-[[2-Hydroxy-2-[4-hydroxy-3-[(methylsulfonyl)amino]phenyl]ethyl]amino]-2-phenylethyl]benzeneacetic acid, methyl ester The title compound was prepared from methyl 4-(1-amino-2-phenylethyl)benzeneacetate following the procedures described in steps D, E, and F of Example 19, except for the following modifications: 1) separation of the R,R and R,S diastereomers of (R)-4-[1-[[2-triethylsilyl)oxy-2-[4-phenylmethoxy-3-[(methylsulfonyl)amino]phenyl]ethyl]amino]-2-phenylethyl]benzoic acid, methyl ester on 0.25 mm silica TLC plates required multiple developments using 0.5% MeOH/CH₂Cl₂; (R),(S)-4-[1-[[2-triethylsilyl)oxy-2-[4-phenylmethoxy-3-[(methylsulfonyl)amino]phenyl]ethyl]amino]-2-phenylethyl]benzeneacetic acid, methyl ester was converted to the title compound; 2) in step E, 70% EtOAc/hexane was the eluant; and 3) in step F, 44% solvent B was employed for the final HPLC purification.

¹H NMR (270 MHz, CD₃OD): δ 2.75–2.83 (m, 1H), 2.89 (s, 3H), 3.02 (dd, 1H), 3.23–3.32 (m, 1H), 3.48 (dd, 1H), 3.66 (s, 2H), 3.67 (s, 3H), 4.54 (dd, 1H), 4.83–4.89 (m, 1H), 6.84 (d, 1H), 6.98–7.03 (m, 3H), 7.14–7.18 (m, 3H), 7.27 (d, 1H), 7.31 (s, 4H).

¹³C NMR (68 MHz, CD₃OD): δ 39.6, 40.5, 41.1, 52.5, 53.5, 65.0, 69.5, 116.6, 124.2, 125.2, 126.0, 128.1, 129.6, 129.8, 130.4, 131.3, 133.5, 133.7, 136.6, 137.4, 151.6, 173.6, 174.7.

Mass (M+H) 499

[α]$_D$=+0.3° (c=0.5, MeOH)

Calculated for 0.3 mol H₂O and 1.12 mol TFA:

|   | Calc. | Found |
|---|-------|-------|
| C | 53.69 | 53.70 |
| H | 5.06  | 5.15  |
| N | 4.43  | 4.28  |
| S | 5.08  | 5.02  |
| F | 10.11 | 10.12 |

HPLC: >98% pure, retention time 19.5 minutes, protocol described in Example 1.

EXAMPLE 90

(R),(R)-4-[1-[[2-Hydroxy-2-[4-hydroxy-3-[(methylsulfonyl)amino]phenyl]ethyl]amino]-2-phenylethyl]benzeneacetic acid, methyl ester, trifluoroacetate salt

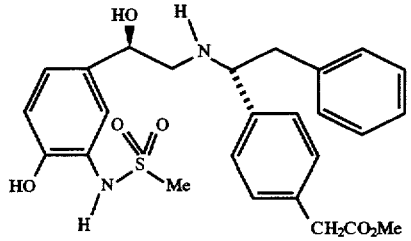

(R),(R)-4-[1-[[2-Triethylsilyl)oxy-2-[4-phenylmethoxy-3-[(methylsulfonyl)amino]phenyl]ethyl]amino]-2-phenylethyl]benzeneacetic acid, methyl ester (described in step B of Example 89) was converted to the title compound following the procedure described in step B of Example 89.

¹H NMR (270 MHz, CD₃OD): δ 2.90 (s, 3H), 3.05–3.25 (m, 2H), 3.54 (dd, 1H), 3.66 (s, 5H), 4.49 (dd, 1H), 4.70 (dd, 1H), 6.85 (d, 1H), 6.99–7.03 (m, 3H), 7.13–7.19 (m, 3H), 7.30 (d, 1H), 7.31 (s, 4H).

¹³C NMR (68 MHz, CD₃OD): δ 39.7, 40.2, 41.2, 52.6, 53.8, 65.7, 70.0, 116.6, 124.4, 125.5, 126.1, 128.1, 129.6, 129.9, 130.4, 131.4, 133.6, 134.0, 136.7, 137.5, 151.7, 173.6.

Mass (M+H) 499

[α]$_D$=−34.4° (c=0.5, MeOH)

Calculated for 0.6 mol H₂O and 1.12 mol TFA:

|   | Calc. | Found |
|---|-------|-------|
| C | 53.24 | 53.24 |
| H | 5.11  | 5.07  |
| N | 4.40  | 4.41  |
| S | 5.03  | 4.85  |
| F | 10.02 | 10.06 |

HPLC: >98% pure, retention time 19.5 minutes, protocol described in Example 1.

EXAMPLE 91

(R),(R)-4-[1-[[2-Hydroxy-2-[4-hydroxy-3-[(methylsulfonyl)amino]phenyl]ethyl]amino]-2-phenylethyl]benzeneacetic acid, trifluoroacetate salt

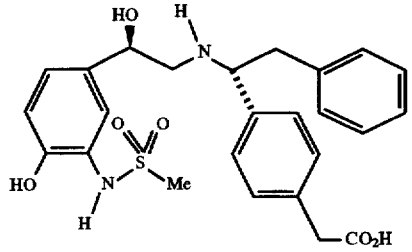

(R),(R)-4-[1-[[2-Hydroxy-2-[4-hydroxy-3-[(methylsulfonyl)amino]phenyl]ethyl]amino]-2-phenylethyl]benzeneacetic acid, methyl ester, trifluoroacetate salt (preparation described in Example 90) was converted to the title compound following the procedure described in Example 84, except that 37% solvent B was employed for preparative HPLC.

¹H NMR (270 MHz, CD₃OD): δ 2.9–3.0 (m, 1H), 2.95 (s, 3H), 3.05–3.26 (m, 2H), 3.45 (dd, 1H), 3.54 (s, 2H), 4.43 (dd, 1H), 4.65–4.8 (m, 1H), 6.86–7.3 (m, 12H).

¹³C NMR (68 MHz, CD₃OD): δ 39.3, 39.9, 41.0, 52.4, 65.1, 69.4, 117.5, 124.4, 125.1, 125.9, 126.7, 128.2, 129.7, 130.3, 131.3, 132.7, 132.9, 136.2, 136.8, 151.5, 177.2.

Mass (M+H) 485⁺

[α]$_D$=−31.6° (c=0.5, MeOH)

Calculated for 2.35 mol H₂O and 0.93 mol TFA:

|   | Calc. | Found |
|---|-------|-------|
| C | 50.97 | 50.68 |
| H | 5.36  | 4.97  |
| N | 4.43  | 4.37  |
| S | 5.07  | 5.02  |
| F | 8.37  | 8.06  |

HPLC: >97% pure, retention time 18.1 minutes, protocol described in Example 1.

EXAMPLE 92

(R),(S)-4-[1-[[2-Hydroxy-2-[4-hydroxy-3-[(methylsulfonyl)amino]phenyl]ethyl]amino]-2-phenylethyl]benzeneacetic acid, sodium salt

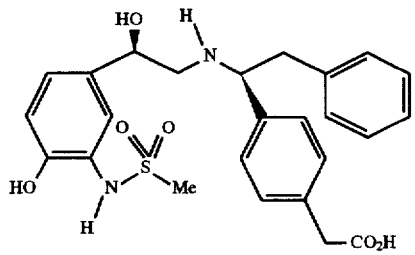

(R),(S)-4-[1-[[2-Hydroxy-2-[4-hydroxy-3-[(methylsulfonyl)amino]phenyl]ethyl]amino]-2-phenylethyl]benzeneacetic acid, methyl ester, trifluoroacetate salt (preparation described in Example 89) was hydrolyzed to the title compound following the procedure described in Example 84, except that 37% solvent B was employed for preparative HPLC. After lyophilization, the TFA salt of the title compound was converted to the sodium salt and the product chromatographed on CHP-20P resin using 10% and 25% CH₃CN/H₂O to elute the title compound.

¹H NMR (270 MHz, D₂O): δ 2.49–2.55 (m, 1H), 2.65–2.73 (m, 1H), 2.86 (br s, 5H), 3.43 (s, 2H), 3.82 (m, 1H), 4.54 (m, 1H), 6.70–7.18 (m, 12H).

¹³C NMR (68 MHz, D₂O): δ 40.3, 43.9, 46.0, 54.4, 65.3, 73.1, 118.5, 124.0, 126.0, 128.4, 128.7, 129.6, 130.4, 130.9, 131.2, 133.0, 138.7, 139.6, 140.4, 154.4, 182.7.

Mass (M+H) 485⁺

[α]$_D$=−4.2° (c=0.5, MeOH)

Calculated for 3.19 mol H₂O:

|   | Calc. | Found |
|---|-------|-------|
| C | 53.23 | 52.97 |
| H | 5.97  | 5.59  |
| N | 4.97  | 4.71  |
| S | 5.68  | 5.59  |

HPLC: >97% pure, retention time 17.9 minutes, protocol described in Example 1.

EXAMPLE 93

(R, R)-4-[1-[[2-Hydroxy-2-[4-hydroxy-3-[(methylsulfonyl)amino]phenyl]ethyl]-amino]-2-phenylethyl]-N-phenylmethylbenzamide, trifluoroacetate salt

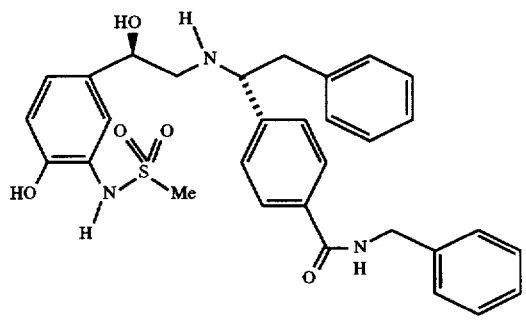

(R, R)-4-[1-[[2-Hydroxy-2-[4-hydroxy-3-[(methylsulfonyl)amino]phenyl]ethyl]amino]-2-phenylethyl] benzoic acid, trifluoroacetate salt (preparation described in Example 84) and benzylamine were converted to the title compound following the procedure described in Example 86 except that 54% solvent B was employed for the final HPLC purification.

¹H NMR (270 MHz, CD₃OD): δ 2.89 (s, 3H), 2.9 (dd, 1H), 3.11 (br t, 1H), 3.26 (br t, 1H), 3.61 (dd, 1H), 4.54 (s, 2H), 4.61 (dd, 1H), 4.77 (dd, 1H), 6.86 (d, 1H), 7.0 (m, 3H), 7.1 (m, 3H), 7.2–7.4 (m, 6H), 7.45 (d, 2H), 7.84 (d, 2H)

¹³C NMR (68 MHz, CD₃OD): δ 39.6, 40.1, 44.5, 53.9, 65.4, 70.0, 116.6, 124.3, 125.4, 126.1, 128.2, 128.5, 129.2, 129.5, 129.6, 130.0, 130.4, 133.5, 136.4, 136.9, 138.7, 139.9, 151.7, 169.3

Mass (M+H) 560

[α]$_D^{22}$=−43.0° (c=0.5, MeOH)

Calculated for 1.7 H₂O and 1.10 mol TFA:

|   | Calc. | Found |
|---|-------|-------|
| C | 55.71 | 55.70 |
| H | 5.28  | 5.01  |
| N | 5.87  | 5.62  |
| S | 4.48  | 4.59  |
| F | 8.76  | 6.38  |

HPLC: 100% pure, retention time 20.4 minutes, protocol described in Example 1

EXAMPLE 94

(R, R)-N-(2-Hydroxyethyl)-4-[1-[[2-hydroxy-2-[4-hydroxy-3-[(methylsulfonyl)amino]-phenyl]ethyl]amino]-2-phenylethyl]-benzamide, trifluoroacetate salt

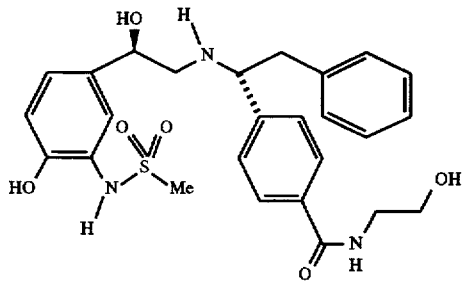

(R, R)-4-[1-[[2-Hydroxy-2-[4-hydroxy-3-[(methylsulfonyl)amino]phenyl]ethyl]amino]-2-phenylethyl] benzoic acid, trifluoroacetate salt (preparation described in Example 84) and ethanolamine were converted to the title compound following the procedure described in Example 86 except that 33% solvent B was employed for the final HPLC purification.

$^1$H NMR (270 MHz, CD$_3$OD): δ 2.90 (s, 3H), 2.9 (dd, 1H), 3.11 (br t, 1H), 3.25 (br t, 1H), 3.47 (t, 2H), 3.61 (dd, 1H), 3.68 (t, 2H), 4.61 (dd, 1H), 4.78 (dd, 1H), 6.86 (d, 1H), 7.0 (m, 3H), 7.1 (m, 3H), 7.31 (d, 1H), 7.45 (d, 2H), 7.82 (d, 2H).

$^{13}$C NMR (68 MHz, CD$_3$OD): δ 39.6, 40.1, 43.6, 53.8, 61.5, 65.5, 69.9, 116.6, 124.2, 125.5, 126.0, 128.1, 129.1, 129.6, 129.9, 130.4, 133.5, 136.4, 136.9, 138.6, 151.6, 169.6.

Mass (M+H) 514

[α]$_D^{22}$=−41.4° (c=0.5, MeOH)

Calculated for 1.18 H$_2$O and 1.13 mol TFA:

|   | Calc. | Found |
|---|-------|-------|
| C | 51.14 | 51.19 |
| H | 5.24  | 5.15  |
| N | 6.33  | 6.32  |
| S | 4.83  | 5.24  |
| F | 9.70  | 9.75  |

HPLC: 100% pure, retention time 14.0 minutes, protocol described in Example 1

EXAMPLE 95

(R),(R)-N-[5-[2-[[1-(1,3-Benzodioxol-5-yl)-2-(4-fluorophenyl)ethyl]amino]-1-hydroxyethyl]-2-hydroxyphenyl]methanesulfonamide

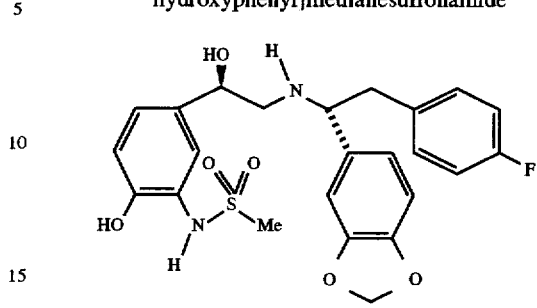

A. (R),(R)-N-[-2-[1-(1,3-Benzodioxol-5-yl)-2-(-4-fluorophenyl)ethyl]amino]benzeneethanol, trifluoroacetate salt The title compound was prepared following the procedure described in step A of Example 60 with the following modifications: 1) freshly prepared 4-fluorobenzylmagnesium chloride was employed; and 2) the 11:1 mixture of the R,R and R,S diastereomers of (R)-N-[-2-[1-(1,3-benzodioxol-5-yl)-2-(4-fluorophenyl)ethyl]amino]benzeneethanol were separated by preparative HPLC using 60% solvent B (see Example 1 for HPLC protocol).

B. (R)-α-(1,3-Benzodioxol-5-yl)-4-fluorobenzeneethanamine

Following the general procedure described in C. K. Miao et al., Tet. Lett., 34, 2259 (1993), a solution of (R),(R)-N-[-2-[1-(1,3-benzodioxol-5-yl)-2-(4-fluorophenyl)ethyl]amino]benzeneethanol (4.0 g, 8.1 mmol) and NaIO$_4$ (4.5 g, 21.1 mmol) in a mixture of 40 mL water, 10 mL MeOH and 10 mL conc. aq. HCl was stirred at 20° C. for 48 hours. After partial concentration, the mixture was diluted with 200 mL of water, stirred for six hours at 35° C., washed three times with 100 mL of hexane, and then basified to pH 10 by addition of 1M aq. NaHCO$_3$. The aqueous mixture was extracted 3× with 200 mL of CH$_2$Cl$_2$; the extracts were dried over Na$_2$SO$_4$ and concentrated. Chromatography on silica gel eluting with 2% (10% conc. aq. NH$_4$OH/MeOH)/CH$_2$Cl$_2$ yielded 213 mg of the title compound.

C. (R),(R)-N-[5-[2-[[1-(1,3-Benzodioxol-5-yl)-2-(4-fluorophenyl)ethyl]amino]-1-hydroxyethyl]-2-hydroxyphenyl]methanesulfonamide (R)-α-(1,3-Benzodioxol-5-yl)-4-fluorobenzeneethanamine was converted to (R),(R)-N-[5-[2-[[1-(1,3-benzodioxol-5-yl)-2-(4-fluorophenyl)ethyl]amino]-1-hydroxyethyl]-2-phenylmethoxyphenyl]methanesulfonamide following the procedures described in steps D and E of Example 19, except that 5% (10% conc. aq. NH$_4$OH/MeOH)/CH$_2$Cl$_2$ eluted the product of step E from silica gel. Hydrogenolysis over 10% Pd/C in 1% HOAc/MeOH sparged with H$_2$ followed by filtration and concentration produced the title compound which was isolated after silica gel chromatography eluting with 3% (10% conc. aq. NH$_4$OH/MeOH)/CH$_2$Cl$_2$.

$^1$H NMR (270 MHz, CDCl$_3$): δ 2.5–2.7 (m, 2H), 2.90 (s, 3H), 2.7–3.0 (m, 2H), 3.75 (m, 1H), 4.41 (m, 1H), 5.94 (s, 2H), 6.5–7.2 (m, 11H).

$^{13}$C NMR (68 MHz, CDCl$_3$): δ 38.9, 43.1, 54.5, 66, 71.5, 101.0, 107.1, 108.1, 115.0, 115.3, 116.5, 121.0, 121.7, 124.3, 124.6, 130.6, 130.7, 133.5, 133.9, 135.3, 146.9, 147.9, 149.2, 159.7, 163.3.

Mass (M+H) 489⁺
Calculated for 0.53 H₂O and 0.17 Et₂O:

|   | Calc. | Found |
|---|-------|-------|
| C | 58.05 | 58.04 |
| H | 5.48  | 5.27  |
| N | 5.49  | 5.23  |
| F | 3.72  | 4.06  |
| S | 6.28  | 5.84  |

HPLC: >99% pure. Shimadzu LC-6A. YMC S3 ODS (6.0× 150 mm); flow rate of 1.5 mL/minute; detection at 217 nm; gradient elution 0–100% B over 25 minutes (A=10% MeOH, 90% H₂O, 0.2% H₃PO₄); B=90% MeOH, 10% H₂O, 0.2% H₃PO₄); retention time=17.5 minutes.

EXAMPLE 96

(R),(S)-N-(1,1-Dimethylethyl)-α-|[2-hydroxy-2-[4-hydroxy-3-[(methylsulfonyl)amino]phenyl]ethyl]amino]-4-methoxybenzeneacetamide

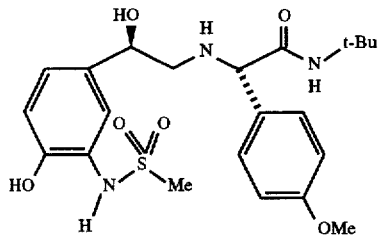

A. (S)-N-(1,1-Dimethylethyl)-α-amino-4-methoxybenzene acetamide

A suspension of NaHCO₃ (184 mg, 2.2 mmol), commercially available N-(benzyloxycarbonyloxy)succinamide (548 mg, 2.2 mmol) and (S)-α-amino-4-methoxybenzeneacetic acid (360 mg, 2 mmol), synthesis described in U.S. Pat. No. 3,517,023, in 1:1 acetone/H₂O was stirred for 18 hours at 20° C. After partial concentration and extraction with CH₂Cl₂, the pH was adjusted to 1.5 and the solution extracted with EtOAc (3×). The EtOAc extracts were washed with brine, dried over MgSO₄ and concentrated to yield (S)-α-[N-[(phenylmethoxy)carbonyl]amino]-4-methoxybenzeneacetic acid. A solution of 1-(3-dimethylaminopropyl)-3-ethylcarbodiimide.HCl (608 mg, 3.2 mmol), hydroxybenztriazole (643 mg, 4.76 mmol) and (S)-α-|N-(phenylmethoxy)carbonyl]amino-4-methoxybenzeneacetic acid (1 g, 3.17 mmol) in CH₂Cl₂ (10 mL) was stirred one hour at 0° C. whereupon N-methylmorpholine (0.7 mL, 6.4 mmol) and t-butylamine (0.5 mL, 4.8 mmol) were added and the reaction stirred at 20° C. for 18 hours. The reaction was diluted with EtOAc, washed with H₂O, aq. NaHCO₃, brine, dried over MgSO₄, and concentrated. Pure (S)-N-(1,1-dimethylethyl)-α-[N-[(phenylmethoxy)carbonyl]amino]-4-methoxybenzeneacetamide was obtained after chromatography on silica gel using 35% EtOAc/hexane as eluant. Hydrogenation of (S)-N-(1,1-dimethylethyl)-α-[N-[(phenylmethoxy)carbonyl]amino]-4-methoxybenzeneacetamide over 10% Pd(OH)₂/C at 1 atom of H₂ in 1:1 MeOH/EtOAc generated the title compound which required no further purification following filtration and concentration.

B. (R),(S)-N-(1,1-Dimethylethyl)-α-[[2-hydroxy-2-[4-hydroxy-3-[(methylsulfonyl)amino]phenyl]ethyl]amino]-4-methoxy benzeneacetamide Following the procedure described in step D of Example 19, a solution of (S)-N-(1,1-dimethylethyl-α-amino-4-methoxybenzeneacetamide and (R)-N-|5-[2-iodo-1-| (triethylsilyl)oxy]ethyl]-2-(phenylmethoxy)phenyl] methanesulfonamide was heated at 110° C. for 20 hours. After isolation of the crude coupled product and cleavage of the triethylsilyl ether as described in step E of Example 19, chromotography on silica gel eluting with 1:3:96 conc. NH₄OH/MeOH/CH₂Cl₂ yielded a diastereomeric mixture of predominantly (R),(S)-N-(1,1-dimethylethyl)-α-|[2-hydroxy-2-[4-phenylmethoxy-3-[(methylsulfonyl)amino] phenyl]ethyl]amino]-4-methoxybenzeneacetamide. The desired R,S diastereomer, purified by preparative HPLC using 55% solvent B (protocol described in Example 1), was converted to the title compound upon hydrogenation as the free base over 10% Pd/C at 1 atom of H₂ in 1:1 MeOH/EtOAc. After filtration and concentration, the title compound was purified by chromatography on 0.5 mm silica TLC plates using 1:9:96 conc. NH₄OH/MeOH/CH₂Cl₂.

¹H NMR (400 MHz, CDCl₃): δ 7.29–7.21 (m, 3H), 6.96 (m, 1H), 6.85–6.82 (m, 3H), 6.78 (s, 1H), 4.61 (dd, 1H), 4.03 (s, 1H), 3.78 (s, 3H), 2.93 (s, 3H), 2.74–2.69 (m, 2H), 1.31 (s, 9H).

¹³C NMR (75 MHz, CDCl₃): δ 172.35, 159.37, 148.79, 134.34, 130.76, 128.42, 124.31, 124.10, 121.67, 116.35, 114.21, 71.68, 66.41, 55.20, 55.04, 51.21, 38.91, 28.49.

Mass (M+H) 466
$[\alpha]_D^{22}$=+11.5° (c=0.34, MeOH)
Calculated for 0.40 H₂O:

|   | Calc. | Found |
|---|-------|-------|
| C | 55.90 | 56.03 |
| H | 6.78  | 6.78  |
| N | 8.89  | 8.76  |

HPLC: 100% pure, Shimadzu LC-6A. YMC S3 ODS (6.0× 150 mm); flow rate of 1.5 ml/minute; detection at 254 nM; gradient elution 0–100% B over 30 minutes (A=10% MeOH, 90% H₂O, 0.2% H₃PO₄); B=90% MeOH, 10% H₂O, 0.2% H₃PO₄); retention time=17.5 minutes.

EXAMPLE 97

(R),(S)-α-[[2-Hydroxy-2-[4-hydroxy-3-[(methylsulfonyl)amino]phenyl]ethyl]amino]-4-methoxy-N-phenylbenzeneacetamide

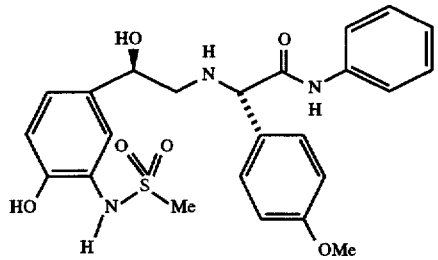

Following the procedure described in step A of Example 96, aniline was converted to (S)-α-amino-4-methoxy-N-phenylbenzeneacetamide. The title compound was prepared from (S)-α-amino-4-methoxy-N-phenylbenzene-acetamide following the procedure in step B of Example 96 with the following modifications: 1) racemization was a major side-reaction during the coupling to (R)-N-|5-[2-iodo-1-[ (triethylsilyl)oxy]ethyl]-2-(phenylmethoxy)phenyl]

methanesulfonamide necessitating chromatographic separation of the two diastereomers on silica gel; and 2) (R),(S)-α-[[2-hydroxy-2-[4-hydroxy-3-[(methylsulfonyl)amino]phenyl]ethyl]amino]-4-methoxy-N-phenylbenzeneacetamide was purified by preparative HPLC using 60% solvent B.

$^1$H NMR (400 MHz, CD$_3$OD): δ 7.47 (d, 2H), 7.44–7.35 (m, 5H), 7.07 (m, 2H), 6.91–6.85 (m, 3H), 4.72 (dd, 1H), 4.32 (s, 1H), 3.76 (s, 3H), 2.88 (s, 3H), 2.84 (dd, 1H), 2.75 (dd, 1H).

$^{13}$C NMR (100 MHz, CD$_3$OD): δ 173.13, 161.23, 151.07, 139.21, 135.84, 131.91, 129.91, 129.84, 125.83, 125.77, 125.53, 124.64, 121.48, 116.43, 115.24, 73.31, 67.71, 56.18, 55.78, 39.61.

Mass (M+H) 486

$[α]_D^{22}$=+13.3° (c=0.36, MeOH)

Calculated for 1.26 H$_2$O:

| | Calc. | Found |
|---|---|---|
| C | 56.72 | 56.87 |
| H | 5.85 | 5.34 |
| N | 8.27 | 8.12 |

HPLC: 99% pure, retention time 18.2 minutes, protocol described in Example 96.

EXAMPLE 98

(R),(S)-α-[[2-Hydroxy-2-[4-hydroxy-3-[(methylsulfonyl)amino]phenyl]ethyl]amino]-4-methoxy-N-methyl-N-phenylbenzeneacetamide

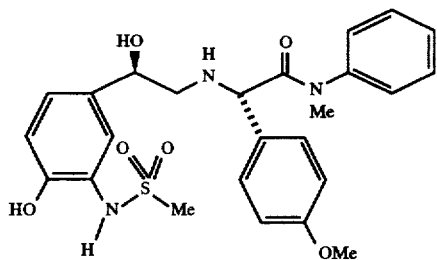

A. (S)-α-Amino-4-methoxy-N-methyl-N-phenylmethylbenzeneacetamide

To a 4° C. solution of (S)-α-amino-4-methoxybenzeneacetic acid (1.8 g, 10 mmol), synthesis described in U.S. Pat. No. 3,517,023, in 1:2 1N NaOH/dioxane was added commercially available di-t-butyl dicarbonate (2.4 g, 11 mmol). After stirring 1.5 hours at 20° C., the reaction was partially concentrated, adjusted to pH 2, and extracted with EtOAc (3×). The EtOAc extracts were washed with brine, dried over MgSO$_4$ and concentrated to yield (S)-α-[N-[(1,1-dimethylethyl)-carbonyl]amino]-4-methoxybenzeneacetic acid. A solution of 2-ethoxy-1-ethoxycarbonyl-1,2-dihydroquinoline (660 mg, 2.7 mmol), (S)-α-[N-(1,1-dimethylethyl)carbonyl]amino]-4-methoxybenzeneacetic acid (600 mg, 2.14 mmol) in CH$_2$Cl$_2$ (10 mL) and N-methylaniline (2.13 mmmol) was stirred at 20° C. for 18 hours. After concentration, the reaction was diluted with EtOAc, washed with aq. NaHCO$_3$, H$_2$O, 1N HCl, brine, dried over MgSO$_4$, and concentrated. Pure (S)-α-[N-[(1,1-dimethylethyl)carbonyl]amino]-4-methoxy-N-methyl-N-phenylbenzeneacetamide was obtained after chromatography on silica gel using 30% EtOAc/hexane as eluant. (S)-α-[N-[(1,1-Dimethylethyl)carbonyl]amino]-4-methoxy-N-methyl-N-phenylbenzeneacetamide was stirred 1.5 hours at 20° C. in 4N HCl/dioxane to generate (S)-α-amino-4-methoxy-N-methyl-N-phenylbenzeneacetamide which was used directly following isolation after concentration, dilution with EtOAc, washing sequentially with aq. NaHCO$_3$ (2×) and brine, drying over MgSO$_4$, and concentration.

B. (R),(S)-α-[[2-Hydroxy-2-[4-hydroxy-3-[(methylsulfonyl)amino]phenyl]ethyl]amino]-4-methoxy-N-methyl-N-phenylbenzeneacetamide.

(S)-α-Amino-4-methoxy-N-methyl-N-phenylbenzeneacetamide was converted to the title compound following the procedures described in steps D, E and F of Example 19 with the following modifications: 1) in step D, the reaction was heated at 70° C. for 40 hours to generate primarily the R, S diastereomer which was separated by silica gel chromatography from the R, R isomer; 2) in step E, the R, S diastereomer was further purified by preparative HPLC from the R, R isomer using 60% solvent B (protocol described in Example 1); and 3) in step F, the HPLC purification was omitted after hydrogenolysis at 1 atom. H$_2$.

$^1$H NMR (270 MHz, CD$_3$OD): δ 7.39–7.30 (m, 4H), 7.03–6.83 (m, 8H), 4.96 (s, 1H), 4.82 (m, 1H), 3.78 (s, 3H), 3.29 (s, 3H), 2.94 (m, 1H), 2.90 (s, 3H), 2.76 (m, 1H).

$^{13}$C NMR (68 MHz, CD$_3$OD): δ 168.22, 162.69, 151.63, 142.47, 133.72, 131.79, 131.01, 129.95, 128.94, 126.12, 125.40, 124.36, 122.92, 116.59, 115.75, 70.02, 63.34, 55.91, 52.66, 39.61, 38.32.

Mass (M+H) 500

$[α]_D^{22}$=+42.3° (c=0.35, MeOH)

HPLC: 99% pure, retention time 18.4 minutes, protocol described in Example 96.

EXAMPLE 99

(R),(S)-N-(1,3-Benzodioxol-5-yl)-α-[[2-hydroxy-2-[4-hydroxy-3-[(methylsulfonyl)amino]phenyl]ethyl]amino]-4-methoxybenzeneacetamide

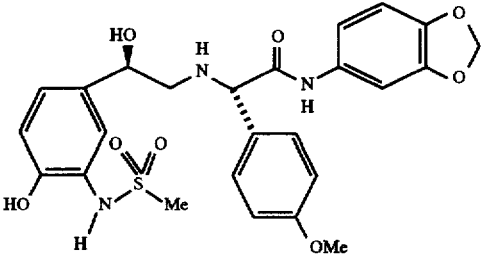

A. (S)-α-N-[(1,3-Benzodioxol-5-yl)amino]-4-methoxybenzene acetamide

To a 0° C. DMF (5 mL) solution of (S)-α-[N-(1,1-dimethylethyl)carbonyl]amino]-4-methoxybenzeneacetic acid (600 mg, 2.14 mmol; preparation described in step A of Example 98), 1-hydroxy-7-azabenzotriazole (290 mg, 2.13 mmol) and 3,4-(methylenedioxy)aniline (366 mg, 2.7 mmol) was added 1-(3-dimethyl-aminopropyl)-3-ethylcarbodiimide.HCl (409 mg, 2.13 mmol) under Ar. After stirring 18 hours at 20° C., the reaction was diluted with EtOAc, washed with aq. NaHCO$_3$, H$_2$O, 1N HCl, brine, dried over MgSO$_4$, and concentrated. Pure (S)-N-(1,3-benzodioxol-5-yl)-α-[N-[(1,1-dimethylethyl)carbonyl]amino]-4-methoxybenzeneacetamide, obtained after chromatography on silica gel using 30% EtOAc/hexane as eluant, was converted to the title compound following the procedure described in step A of Example 98.

117

B. (R),(S)-N-(1,3-Benzodioxol-5-yl)-α-[[2-hydroxy-2-[4-hydroxy-3-[(methylsulfonyl)amino]phenyl]ethyl]amino]-4-methoxy benzeneacetamide (S)-α-N-[(1,3-Benzodioxol-5-yl)amino]-4-methoxybenzeneacetamide was converted to the title compound following the procedures described in steps D, E and F of Example 19 with the following modifications: 1) in step D, the reaction was heated at 70° C. for 60 hours to generate primarily the R, S diastereomer; separation from the R, R isomer required a second chromatography on silica gel eluting with 40% EtOAc in toluene; and 2) in step F, the HPLC purification was omitted after hydrogenolysis as the free base under 1 atom. $H_2$; the title compound was chromatographed on silica gel eluting with 5–10% MeOH/$CH_2Cl_2$.

$^1$H NMR (400 MHz, $CD_3OD$): δ 7.38 (d, 1H), 7.33 (d, 2H), 7.12 (d, 1H), 7.05 (dd, 1H), 6.90–6.81 (m, 3H), 6.79 (d, 1H), 6.71 (d, 1H), 5.89 (s, 2H), 4.69 (dd, 1H), 4.24 (s, 1H), 3.76 (s, 3H), 2.90 (s, 3H), 2.83 (dd, 1H), 2.72 (dd, 1H).

$^{13}$C NMR (68 MHz, $CD_3OD$): δ 173.21, 161.12, 151.07, 149.05, 145.80, 135.89, 133.41, 132.35, 129.79, 125.78, 124.66, 116.34, 115.19, 114.70, 108.88, 103.73, 73.46, 67.79, 56.33, 55.75, 39.60.

Mass (M+H) 530

$[\alpha]_D^{22}$=+7.3° (c=0.30, MeOH)

HPLC: 99% pure, retention time 18.5 minutes, protocol described in Example 96.

EXAMPLE 100

(R),(S)-N-(4-Chlorophenyl)-α-[[2-hydroxy-2-[4-hydroxy-3-[(methylsulfonyl)amino]phenyl]ethyl]amino]-4-methoxybenzeneacetamide

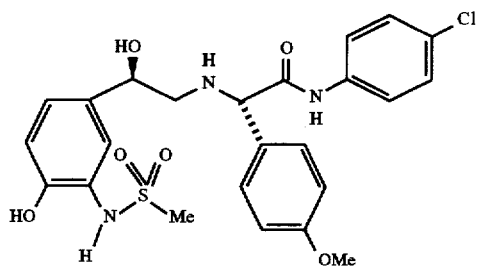

(S)-α-Amino-N-(4-chlorophenyl)-4-methoxybenzeneacetamide (prepared from p-chloroaniline via a procedure analogous to that described in step A of Example 99) was converted to the title compound following the procedure described in step B of Example 99, except for the following modifications: 1) after elution from silica gel with 2% MeOH/$CH_2Cl_2$, (R),(S)-N-(4-chlorophenyl)-α-[[2-phenylmethoxy-2-[4-hydroxy-3-[(methylsulfonyl)amino]phenyl]ethyl]amino]-4-methoxybenzeneacetamide was further purified by preparative HPLC using 58% solvent B; and 2) the title compound after silica gel chromatography was purified by by preparative HPLC using 57% solvent B and isolated as the free base.

$^1$H NMR (400 MHz, $CD_3OD$): δ 7.48 (dd, 2H), 7.46–7.28 (m, 3H), 7.27 (dd, 2H), 7.07 (dd, 1H), 6.90 (d, 2H), 6.85 (d, 1H), 4.70 (dd, 1H), 4.27 (s, 1H), 3.76 (s, 3H), 2.91 (s, 3H), 2.85 (dd, 1H), 2.73 (dd, 1H).

$^{13}$C NMR (68 MHz, $CD_3OD$): δ 173.43, 161.13, 151.03, 138.07, 135.85, 132.11, 130.26, 129.75, 125.71, 124.59, 122.72, 116.36, 115.18, 73.42, 67.78, 56.26, 55.74, 39.58.

Mass (M+H) 520

118

$[\alpha]_D^{22}$=+8.3° (c=0.30, MeOH)

HPLC: 99% pure, retention time 21.7 minutes, protocol described in Example 96.

EXAMPLE 101

(R),(S)-α-[[2-Hydroxy-2-[4-hydroxy-3-[(methylsulfonyl)amino]phenyl]ethyl]amino]-4-methoxy-α-methyl-N-phenylbenzeneacetamide

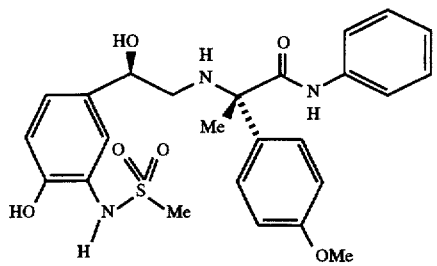

A. (S)-α-Amino-4-methoxy-α-methyl-N-phenylbenzeneacetamide (S)-α-Amino-4-methoxy-α-methylbenzeneacetic, ethyl ester (446 mg, 2 mmol; prepared from 4-methoxyacetophenone as described in U.S. Pat. No. 5,268,375) in 1:1 2N aq. NaOH/EtOH was heated at 75° C. for two hours, cooled, and concentrated. (S)-α-[N-[(1,1-Dimethylethyl)carbonyl]amino]-4-methoxy-α-methylbenzeneacetic acid, obtained upon treatment of the crude acid with excess di-t-butyl dicarbonate as described in step A of Example 98, was converted to the title compound following:

1) coupling to aniline utilizing the procedure described in step A of Example 96; and 2) removal of the BOC protecting group as described in step A of Example 98.

B. (R),(S)-α-[[2-Hydroxy-2-[4-hydroxy-3-[(methylsulfonyl)amino]phenyl]ethyl]amino]-4-methoxy-α-methyl-N-phenylbenzeneacetamide Following the procedures described in steps D, E, and F of Example 19, (S)-α-amino-4-methoxy-α-methyl-N-phenylbenzeneacetamide was converted to the title compound with the following modifications: 1) in step E, the desilylated material eluted from silica gel with 2:3 EtOAc/toluene; 2) in step F, after hydrogenolysis as the free base under 1 atom. $H_2$, the title compound was purified by silica gel chromatography eluting with 4% MeOH/$CH_2Cl_2$.

$^1$H NMR (270 MHz, $CD_3OD$): δ 1.72 (s, 3H), 2.58 (dd, 1H), 2.78 (dd, 1H), 2.86 (s, 3H), 3.77 (s, 3H), 4.68 (dd, 1H), 6.88 (m, 3H), 7.07 (m, 2H), 7.27 (m, 2H), 7.42 (m, 5H).

$^{13}$C NMR (68 MHz, $CD_3OD$): δ 22.7, 39.6, 52.4, 55.8, 65.7, 74.1, 114.8, 116.4, 121.5, 124.7, 125.4, 125.7, 125.8, 128.6, 129.8, 136.2, 139.3, 151.0, 160.5, 176.0.

Mass (M+H) 500

$[\alpha]_D^{22}$=−48.2° (c=0.9 MeOH)

HPLC: 99% pure, retention time 17.1 minutes, protocol described in Example 96.

EXAMPLE 102

(R),(R)-α-[[2-Hydroxy-2-[4-hydroxy-3-[(methylsulfonyl)amino]phenyl]ethyl]amino]-4-methoxy-N-phenylbenzeneacetamide

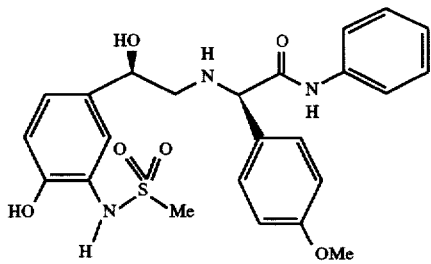

(R)-α-Amino-4-methoxybenzeneacetic acid (1.8 g, 10 mmol), synthesis described in U.S. Pat. No. 3,517,023, was converted to the title compound following a reaction series analogous to that described in Example 98, except for the following modifications: in step B, the desilylated material was chromatographed on silica gel using 1% MeOH/CH$_2$Cl$_2$ prior to the preparative HPLC purification using 60% solvent B and subsequently was converted to the free base prior to the hydrogenolysis reaction to generate the title compound.

$^1$H NMR (270 MHz, CD$_3$OD): δ 7.48 (d, 2H), 7.45–7.24 (m, 5H), 7.08 (m, 2H), 6.92–6.84 (m, 3H), 4.72 (dd, 1H), 4.31 (s, 1H), 3.77 (s, 3H), 2.88 (s, 3H), 2.86–2.67 (m,2H).

$^{13}$C NMR (68 MHz, CD$_3$OD): δ 173.30, 161.18, 151.01, 139.26, 136.01, 132.09, 129.87, 125.81, 125.58, 125.52, 124.55, 121.49, 116.45, 115.21, 73.37, 67.84, 56.24, 55.78, 39.57.

Mass (M+H) 486

$[\alpha]_D^{22}$=−53.3° (c=0.22, MeOH)

HPLC: 98.5% pure, retention time 18.9 minutes, protocol described in Example 96.

EXAMPLE 103

(R),(S)-α-[[2-Hydroxy-2-[4-hydroxy-3-[(methylsulfonyl)amino]phenyl]ethyl]amino]-N-phenylbenzeneacetamide

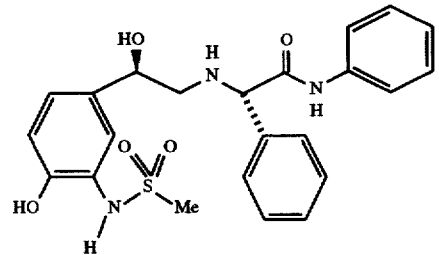

Following the procedure described in step A of Example 98, (S)-phenylglycine was converted to α-amino-N-phenylbenzeneacetamide. The title compound was prepared from α-amino-N-phenylbenzeneacetamide following the procedure described in step B of Example 99 with the following modification: the desilylated material was purified by preparative HPLC using 56% solvent B and subsequently was converted to the free base prior to the hydrogenolysis reaction to generate the title compound.

$^1$H NMR (400 MHz, CD$_3$OD): δ 7.47 (d, 2H), 7.46 (d, 2H), 7.45–7.25 (m, 6H), 7.10–7.05 (m, 2H), 6.86 (d, 1H), 4.72 (dd, 1H), 4.34 (s, 1H), 2.89 (s, 3H), 2.87–84 (m, 2H), 2.77 (dd, 2H).

$^{13}$C NMR (68 MHz, CD$_3$OD): δ 173.15, 151.07, 140.35, 139.20, 135.92, 129.87, 129.30, 128.69, 125.78, 125.55, 124.69, 121.49, 116.43, 73.49, 68.51, 56.44, 39.60.

Mass (M+H) 456

$[\alpha]_D^{22}$=+8.3° (c=0.20, MeOH)

Calculated for 0.42 H$_2$O:

|   | Calc. | Found |
|---|-------|-------|
| C | 59.65 | 59.93 |
| H | 5.62  | 5.43  |
| N | 9.07  | 8.79  |

HPLC: 97% pure, retention time 15.8 minutes, protocol described in Example 96.

EXAMPLE 104

(R),(S)-α-[[2-Hydroxy-2-[4-hydroxy-3-[(methylsulfonyl)amino]phenyl]ethyl]amino]-4-methoxy-N-(phenylmethyl)benzeneacetamide

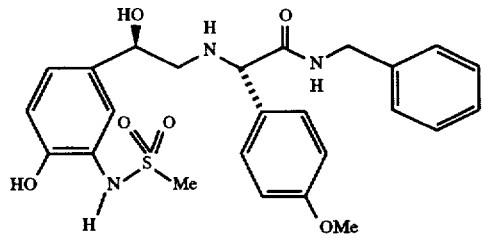

(S)-α-Amino-4-methoxy-N-(phenylmethyl)benzeneacetamide (prepared from benzylamine via a procedure analogous to that described in step A of Example 98, except for omission of chromatography on silica gel) was converted to the title compound following the procedure described in step B of Example 98, except for the following modification: separation of the R, R and R, S diastereomers of α-[[2-(triethylsilyl)oxy-2-[4-phenylmethoxy-3-[(methylsulfonyl)amino]phenyl]ethyl]amino]-4-methoxy-N-(phenylmethyl)benzeneacetamide required a second chromatography on silica gel eluting with 30% EtOAc in toluene.

$^1$H NMR (400 MHz, CD$_3$OD): δ 7.47 (d, 2H), 7.33 (d, 1H), 7.27–7.15 (m, 5H), 7.02 (m, 3H), 6.87 (d, 1H), 5.00 (s, 1H), 4.83 (m, 1H), 4.41 (q, 2H), 3.82 (s, 3H), 3.02–2.86 (m, 2H), 2.91 (s, 3H).

$^{13}$C NMR (68 MHz, CD$_3$OD): δ 168.56, 162.80, 151.75, 139.31, 133.66, 131.68, 129.57, 128.51, 128.42, 126.15, 125.45, 124.50, 124.13, 116.61, 115.89, 69.85, 64.26, 55.94, 53.00, 44.31, 39.64.

Mass (M+H) 500

$[\alpha]_D^{22}$=+45.9° (c=0.31 MeOH)

HPLC: 99.9% pure, retention time 18.1 minutes, protocol described in Example 96.

EXAMPLE 105

(R),(S)-N-(Cyclohexyl)-α-[[2-Hydroxy-2-[4-hydroxy-3-[(methylsulfonyl)amino]phenyl]ethyl]amino]-4-methoxybenzeneacetamide

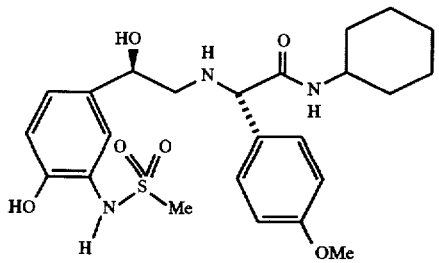

(S)-N-(Cyclohexyl)-α-amino-4-methoxybenzeneacetamide (prepared from cyclohexylamine via procedure analogous to that described in step A of Example 98) was converted to the title compound following the procedure described in step B of Example 98, except for the following modifications: 1) separation of the R, R and R, S diastereomers of N-(cyclohexyl)-α-[[2-(triethylsilyl)oxy-2-[4-phenylmethoxy-3-[(methylsulfonyl)amino]phenyl]ethyl]amino]-4-methoxybenzeneacetamide required a second chromatography on silica gel eluting with 40% EtOAc/toluene; 2) in step E, the residual R, R diastereomer was separated by preparative HPLC from the R, S isomer using 65% solvent B (protocol described in Example 1); and 3) in step F, following HPLC purification using 50% solvent B, the title compound was further purified as the free base by flash chromatography on silica gel using 8% MeOH/CH$_2$Cl$_2$.

$^1$H NMR (270 MHz, CD$_3$OD): δ 7.37 (d, 1H), 7.29 (dd, 2H), 7.03 (dd, 1H), 6.89 (m, 3H), 4.66 (dd, 1H), 4.11 (s, 1H), 3.77 (s, 3H), 3.60 (m, 1H), 2.93 (s, 3H), 2.92–2.62 (m, 2H), 1.81–1.56 (m, 5H), 1.35–1.11 (m, 5H).

$^{13}$C NMR (68 MHz, CD$_3$OD): δ 174.04, 161.02, 150.91, 135.91, 132.54, 129.69, 125.86, 125.66, 124.36, 116.33, 115.03, 73.30, 67.14, 56.23, 55.74, 39.61, 33.68, 33.54, 26.57, 26.05.

Mass (M+H) 492

$[\alpha]_D^{22}$=+9.2° (c=0.10, MeOH)

Calculated for 1.62 H$_2$O:

|   | Calc. | Found |
|---|-------|-------|
| C | 55.34 | 55.57 |
| H | 7.01  | 6.83  |
| N | 8.07  | 7.84  |

HPLC: 98% pure, retention time 19.8 minutes, protocol described in Example 96.

EXAMPLE 106

(R, R)-N-Hydroxy-4-[1-[[2-hydroxy-2-[4-hydroxy-3-[(methylsulfonyl)amino]phenyl]ethyl]amino]-2-phenylethyl]benzamide, trifluoroacetate salt

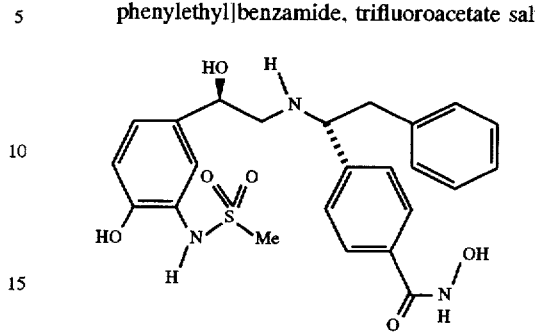

(R, R)-4-[1-[[2-Hydroxy-2-[4-hydroxy-3-[(methylsulfonyl)amino]phenyl]ethyl]amino]-2-phenylethyl]benzoic acid, trifluoroacetate salt (preparation described in Example 84) and hydroxylamine were converted to the title compound following the procedure described in Example 86 except that 28% solvent B was employed for the final HPLC purification.

$^1$H NMR (270 MHz, CD$_3$OD): δ 2.90 (s, 3H), 2.9 (m, 1H), 3.0–3.3 (m, 2H), 3.61 (br d, 1H), 4.61 (br d, 1H), 4.82 (m, 1H), 6.86 (d, 1H), 7.01 (br s, 3H), 7.14 (br s, 3H), 7.32 (br s, 1H), 7.46 (br s, 2H), 7.72 (br s, 2H)

$^{13}$C NMR (68 MHz, CD$_3$OD): δ 39.6, 40.1, 53.9, 65.4, 70.0, 116.6, 124.4, 125.4, 126.1, 128.2, 129.1, 129.6, 130.1, 130.4, 133.5, 136.3, 138.9, 151.7

Mass (M+H) 486

$[\alpha]_D^{22}$=−43.2° (c=0.5, MeOH)

HPLC: >99% pure, retention time 12.5 minutes, protocol described in Example 1

EXAMPLE 107

(R),(S)-α-[[2-Hydroxy-2-[4-hydroxy-3-[(methylsulfonyl)amino]phenyl]ethyl]amino]-4-methoxy-N-phenylbenzenepropanamide

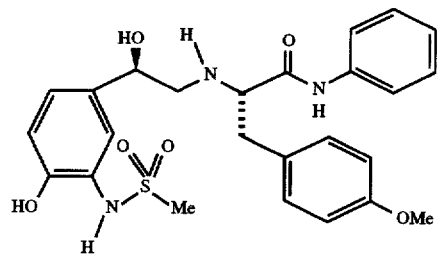

Following the procedure described in step A of Example 96, commercially available N-(benzyloxycarbonyloxy)succinamide and (S)-α-amino-4-methoxybenzenepropanoic acid was converted to (S)-α-[N-[(phenylmethoxy)carbonyl]amino]-4-methoxybenzenepropanoic acid. A DMF (5 mL) solution of (S)-α-[N-[(phenylmethoxy)carbonyl]amino]-4-methoxybenzenepropanoic acid (500 mg, 1.5 mmol), 1-benzotriazolyloxytris(dimethylamino)phosphonium hexaflourophosphate (672 mg, 1.5 mmol), N-methylmorpholine (167 mL, 1.5 mmol), and aniline (140 mg, 1.5 mmol) was stirred for 18 hours at 20° C., diluted with EtOAC, washed with H$_2$O, aq. NaHCO$_3$, and brine, and dried over MgSO$_4$.

After concentration, the product was chromatographed on silica gel using 1% MeOH/CH₂Cl₂ to elute (S)-α-[N-[(phenylmethoxy)carbonyl]amino]-4-methoxy-N-phenylbenzenepropanamide (84%) which was converted to (S)-α-amino]-4-methoxy-N-phenylbenzenepropanamide as described in step A of Example 96.

The title compound was prepared from (S)-α-amino]-4-methoxy-N-phenylbenzenepropanamide following the procedures described: 1) in steps D and E of Example 19; and 2) the hydrogenolysis conditions described in step B of Example 99.

¹H NMR (270 MHz, CD₃OD): δ 7.41–7.24 (m, 5H), 7.13–7.01 (m, 4H), 6.84–6.79 (m, 3H), 4.65 (t, 1H), 3.74 (s, 3H), 3.45 (t, 1H), 3.04–2.97 (m, 1H), 2.90–2.68 (m, 3H), 2.86 (s, 3H).

¹³C NMR (68 MHz, CD₃OD): δ 174.13, 160.14, 150.95, 138.92, 135.66, 131.31, 130.19, 129.79, 125.78, 125.61, 124.46, 121.55, 116.34, 115.07, 73.09, 65.63, 56.38, 55.64, 39.54, 39.39.

Mass (M+H) 500

$[\alpha]_D^{22}$=−34.6° (c=0.35 MeOH)

HPLC: 99% pure, retention time 18.7 minutes, protocol described in Example 96.

EXAMPLE 108

(R),(R)-α-[[2-Hydroxy-2-[4-hydroxy-3-[(methylsulfonyl)amino]phenyl]ethyl]amino]-4-methoxy-N-phenylbenzenepropanamide

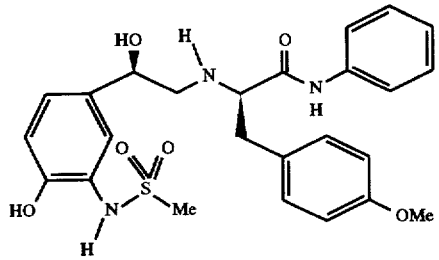

A mixture of commercial (R)-N-(t-butoxycarbonyl)tyrosine (2.0 g, 6.35 mmol), dimethyl sulfate (1.3 mL, 14 mmol), K₂CO₃ (1.93 g, 14 mmol), and 18-crown-6-ether (185 mg, 0.7 mmol) was refluxed in 30 mL of toluene for five hours. After cooling and dilution with H₂O, the organic layer was washed with H₂O, dried over MgSO₄, and concentrated. Chromatography of the residue on silica gel eluting with 20% EtOAc/hexane yielded methyl (R)-α-[N-[(phenylmethoxy)carbonyl]amino]-4-methoxybenzenepropanoate which was hydrolyzed by stirring three hours at 0° C. with NaOH (185 mg, 4.6 mmol) in 6 mL of 2:1 MeOH/H₂O. After concentration, adjustment to pH 2, extraction with EtOAc (2×), and concentration, the crude acid was converted to (R)-α-amino-4-methoxy-N-phenylbenzenepropanamide by coupling to aniline under the conditions described in step A of Example 98 and utilizing the hydrogenolysis conditions described in Step A of Example 96. The title compound was prepared from (R)-α-amino]-4-methoxy-N-phenylbenzenepropanamide following the procedures described in steps D, E, and F of Example 19 with the following modifications: 1) the product of step D was not purified; 2) in step E, the product was chromatographed twice on silica gel eluting with 1.5% MeOH/CH₂Cl₂; and 3) in step F, after hydrogenolysis as the free base under 1 atom. H₂, the title compound was purified by preparative HPLC using 48% solvent B prior to isolation as the free base.

¹H NMR (270 MHz, CD₃OD): δ 7.44–7.25 (m, 5H), 7.11–6.97 (m, 3H), 7.01 (dd, 1H), 6.83–6.78 (m, 3H), 4.63 (t, 1H), 3.74 (s, 3H), 3.45 (dd, 1H), 3.02–2.95 (m, 1H), 2.87 (s, 3H), 2.85–2.69 (m, 3H).

¹³C NMR (68 MHz, CD₃OD): δ 174.59, 160.11, 150.90, 139.03, 135.63, 131.34, 130.39, 129.82, 125.90, 125.58, 124.26, 121.61, 116.40, 115.07, 73.37, 66.06, 56.59, 55.72, 39.54, 39.39.

Mass (M+H) 500

$[\alpha]_D^{22}$=+4.2° (c=0.15 MeOH)

HPLC: 99% pure, retention time 19.0 minutes, protocol described in Example 96.

EXAMPLE 109

(R),(S)]-N-[5-[1-Hydroxy-2-[[1-(4-methoxyphenyl)-2-oxo-2-(1-piperidinyl)ethyl]amino]ethyl]-2-hydroxyphenyl]methanesulfonamide

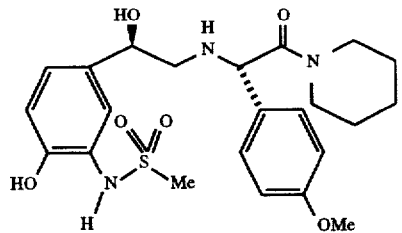

(S)-α-[(1-Piperidinyl)carbonyl]-4-methoxybenzenemethanamine (prepared from piperdine via a procedure analogous to that described in step A of Example 99) was converted to the title compound following the procedures described in steps D, E, and F of Example 19, except for the following modifications: 1) in step D, the reaction was heated to 75° C. for 60 hours; and 2) in step F, the desilylated product was hydrogenated under 1 atom. of H₂ as the free base to generate the title compound which was purified by silica gel chromatography eluting with 8% MeOH/CH₂Cl₂.

¹H NMR (270 MHz, CD₃OD): δ 0.90 (m, 1H), 1.38 (m, 2H), 1.53 (m, 3H), 2.60 (dd, 1H), 2.77 (dd, 1H), 2.92 (s, 3H), 3.35 (m, 1H), 3.73 (m, 1H), 3.78 (s, 3H), 4.60 (dd, 1H), 6.84 (d, 1H), 6.91 (d, 2H), 7.02 (dd, 1H), 7.25 (d, 1H), 7.30 (d, 1H).

¹³C NMR (68 MHz, CD₃OD): δ 25.3, 26.7, 26.9, 39.6, 44.7, 47.5, 55.7, 55.8, 62.9, 73.5, 115.5, 116.5, 124.3, 125.7, 126.0, 130.3, 131.3, 135.8, 151.1, 161.2, 171.6.

Mass (M+H) 478

$[\alpha]_D^{22}$=+53.9° (c=0.3 MeOH)

HPLC: 99% pure, retention time 17.2 minutes, protocol described in Example 96.

EXAMPLE 110

(R),(S)-N-(1,3-Benzodioxol-5-yl)-α-[[2-hydroxy-2-[4-hydroxy-3-[(methylsulfonyl)amino]phenyl]ethyl]amino]-4-methoxy-α-methylbenzeneacetamide

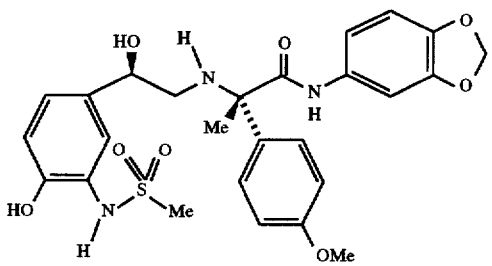

A. (S)-α-N-[(1,3-Benzodioxol-5-yl)amino]-4-methoxy-α-methylbenzeneacetamide (S)-α-[N-[(1,1-Dimethylethyl)carbonyl]amino]-4-methoxy-α-methylbenzeneacetic acid (preparation described in step A of Example 101) was condensed with 3,4-(methylenedioxy)aniline following the procedure described in step A of Example 99. Pure (S)-N-(1,3-benzodioxol-5-yl)-α-[N-[(1,1-dimethylethyl)carbonyl]]amino]-4-methoxy-α-methyl-benzeneacetamide, obtained after chromatography on silica gel using 30% EtOAc/hexane as eluant, was converted to the title compound following the procedure described in step A of Example 98.

B. (R),(S)-N-(1,3-Benzodioxol-5-yl)-α-[[2-hydroxy-2-[4-hydroxy-3-[(methylsulfonyl)amino]phenyl]ethyl]amino]-4-methoxy-α-methylbenzeneacetamide Following the procedures described in steps D, E, and F of Example 19, (S)-α-N-[(1,3-benzodioxol-5-yl)amino]-4-methoxy-α-methyl-benzeneacetamide was converted to the title compound with the following modifications: 1) in step D, the coupling reaction was heated at 115° C. for 96 hours to give a mixture of expected silylated product and its desilylated counterpart which were eluted from silica gel using 0.5% MeOH/CH$_2$Cl$_2$ and 1.5% respectively; 2) in step E, after desilylation and chromatography on silica gel, all fractions of (R),(S)-N-(1,3-benzodioxol-5-yl)-α-[[2-hydroxy-2-[4-phenylmethoxy-3-[(methylsulfonyl)amino]phenyl]ethyl]amino]-4-methoxy-α-methylbenzeneacetamide, formed in either step D or E, were combined and further purified by preparative HPLC using 56% solvent B; and 3) in step F, after hydrogenolysis as the free base under 1 atom. H$_2$, the title compound was purified by silica gel chromatography eluting with 5% MeOH/CH$_2$Cl$_2$.

$^1$H NMR (400 MHz, CD$_3$OD): δ 7.40 (d, 2H), 7.39 (d, 1H), 7.10 (d, 1H), 7.07 (dd, 1H), 6.87 (m, 3H), 6.73 (m, 2H), 5.89 (s, 2H), 4.66 (dd, 1H), 3.77 (s, 3H), 2.89 (s, 3H), 2.77 (dd, 1H), 2.56 (dd, 1H), 1.70 (s, 3H).

$^{13}$C NMR (100 MHz, CD$_3$OD): δ 175.76, 160.44, 150.94, 148.98, 145.70, 136.14, 133.55, 128.59, 125.69, 124.74, 116.36, 114.77, 108.84, 103.74, 102.53, 74.02, 65.56, 55.71, 52.40, 39.58, 22.57.

Mass (M+H) 544

[α]$_D^{22}$=−64.8° (c=0.20, MeOH)

Calculated for 0.46 H$_2$O:

|   | Calc. | Found |
|---|---|---|
| C | 56.68 | 56.73 |
| H | 5.47 | 5.41 |
| N | 7.61 | 7.46 |

HPLC: 99% pure, retention time 17.1 minutes, protocol described in Example 96.

EXAMPLE 111

(R),(R),(R)-N-[5-[2-[[1-(1,3-Benzodioxol-5-yl)-2-phenylethyl]amino]-1-hydroxypropyl]-2-hydroxyphenyl]methanesulfonamide

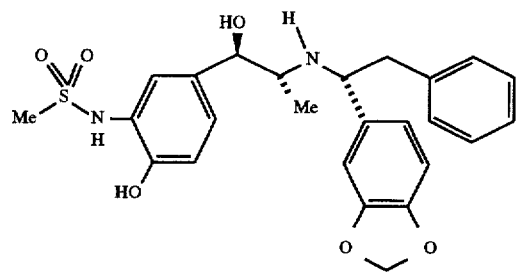

A. 4-Phenylmethoxy-3-nitrobenzaldehyde

To 4-hydroxy-3-nitrobenzaldehyde (50.6 g, 300 mmol) stirring in 250 mL of dry DMF under Ar at 20° C., was added 60% NaH oil dispersion (14.6 g, 360 mmol) and, after 30 minutes, benzyl bromide (79 g, 460 mmol). The mixture was heated to 70° C. for four hours until complete, cooled, quenched with H$_2$O and then diluted with 1.3 L of ice water. The resulting yellow precipitate was filtered, washed with water, and air-dried to provide 69.7 g of of the title compound, after recrystallization from 30% toluene/hexane.

B. 1-[4-Phenylmethoxy-3-nitrophenyl]propene

To a stirred suspension of (ethyl)triphenylphosphonium bromide (63.3 g, 170.5 mmol) in 270 mL of dry THF under Ar at 20° C., was added 91 mL of 1.8M phenyllithium in 70% cyclohexane/Et$_2$O solution (163 mmol). After 30 minutes the reaction was cooled to −78° C., and a solution of 4-phenylmethoxy-3-nitrobenzaldehyde (38.96 g, 151.6 mmol) in 138 mL of THF was added by cannula over 25 minutes. The reaction was maintained at −78° C. for 60 minutes and stirred at 20° C. overnight prior to addition of 400 mL hexane. The supernatant was decanted and the solids stirred twice with additional THF/hexane which was also decanted. After concentration of the combined supernatants, the title compound (11.33 g, 1:1 trans to cis ratio) was eluted from silica gel by 0% to 25% EtOAc/hexane.

C. trans-1-[3-(Methylsulfonyl)amino-4-phenylmethoxyphenyl]propene

A solution of 1-[4-phenylmethoxy-3-nitrophenyl]propene (12.74 g, 47.3 mmol) and SnCl$_2$.2H$_2$O (53.4 g, 237 mmol) in 200 mL of EtOAc was refluxed for one hour. After cooling, 100 mL of hexane and then a solution of 41 g of K$_2$CO$_3$ (297 mmol) in 35 mL H$_2$O were added with vigorous stirring, whereupon 300 mL of CH$_2$Cl$_2$ and 100 g Na$_2$SO$_4$ were added prior to filtration through Celite. After concentration, the residue was chromatographed twice on silica gel eluting with 7% to 17% Et$_2$O/hexane to obtain 3.66 g of 1-[3-amino-4-phenylmethoxyphenyl]propene as a 98:2 mixture of trans to cis isomers. The title compound was prepared from 1-[3-amino-4-phenylmethoxyphenyl]propene following the procedure described in part 4 of step F of Example 1, except that the crude product was chromatographed on silica gel eluting with 50% EtOAc/hexane and then recrystallized from EtOAc/hexane to obtain 3.11 g.

D. (R),(R)-1-[3-(Methylsulfonyl)amino-4-phenylmethoxyphenyl]-1,2-propanediol

Following the procedure described by K. B. Sharpless et al., *J. Org. Chem.*, 57, 2768 (1992), trans-1-[3-(methylsulfonyl)-amino-4-phenylmethoxyphenyl]propene (1.88 g, 5.8 mmol) was added to a stirred mixture of 0.55 g of MeSO$_2$NH$_2$ (5.8 mmol), 8.1 g of AD-mix-β, 45 mL of water, and 45 mL of t-butanol at 20° C. After 16 hours, the reaction was stirred with 9.6 g of Na$_2$SO$_3$ for 30 minutes, diluted with H$_2$O and extracted 4× with CH$_2$Cl$_2$ whereupon the organic layers were dried over Na$_2$SO$_4$ and concentrated. Chromatography on silica gel eluting with 50% to 100% EtOAc/hexane provided the title compound (1.71 g, 98.6% ee).

E. (R),(S)-1-[3-(Methylsulfonyl)amino-4-phenylmethoxyphenyl]-2-methyloxirane (R),(R)-1-[3-(Methylsulfonyl)amino-4-phenylmethoxyphenyl]-1,2-propanediol (0.83 g, 2.36 mmol) and p-toluenesulfonyl chloride (1.0 g, 5.24 mmol) in 4 mL of pyridine were stirred under Ar at 0° C. for four hours. After addition of H$_2$O (6 drops) and then toluene, the reaction was concentrated at 0° C. under high vacuum and chromatographed 2× on silica gel eluting with 20% to 50% EtOAc/hexane to obtain 0.39 g of (R),(R)-1-hydroxy-1-[3-(methylsulfonyl)amino-4-phenylmethoxyphenyl]-2-propyl tosylate. To a stirred 0° C. solution of (R),(R)-1-hydroxy-1-[3-(methylsulfonyl)amino-4-phenylmethoxyphenyl]-2-propyl tosylate (0.16 g, 0.32 mmol) in 3 mL of dry THF under Ar, was added 0.72 mL of 1.0M LiN(TMS)$_2$ in THF solution (0.72 mmol). After three hours at 0° C., the reaction was diluted with 10 volumes of hexane and CH$_2$Cl$_2$, and without evaporation chromatographed on silica gel eluting with 10% to 25% EtOAc/hexane to provide 72 mg of the title compound (98% pure, containing 2% trans epoxide).

F. (R),(R),(R)-N-[5-[2-[[1-(1,3-Benzodioxol-5-yl)-2-phenylethyl]amino]-1-hydroxypropyl]-2-hydroxyphenyl]methane sulfonamide.

A mixture of (R),(S)-1-[3-(methylsulfonyl)amino-4-phenylmethoxyphenyl]-2-methyloxirane (72 mg, 0.21 mmol) and (R)-1-(1,3-benzodioxol-5-yl)-2-benzeneethanamine (0.40 g, 1.66 mmol) (preparation described in step B of Example 60) was heated under Ar at 130° C. for 16 hours. After cooling, the product was chromatographed 4× on silica gel eluting first with 1% [10% conc. aq. NH$_3$/MeOH]/CH$_2$Cl$_2$, then 5% to 8% acetone in toluene, then 4% to 8% acetone in toluene, then 0.5 to 1% [10% conc. aq. NH$_3$/MeOH]/CH$_2$Cl$_2$ to obtain 32 mg of (R),(R),(R)-N-[5-[2-[[1-(1,3-benzodioxol-5-yl)-2-phenylethyl]amino]-1-hydroxypropyl]-2-phenylmethoxyphenyl]methanesulfonamide which, was converted to the title compound (18 mg) by hydrogenolysis, as described in step C of Example 95.

$^1$H NMR (270 MHz, 5% CD$_3$OD/CDCl$_3$): δ 0.79 (d, 3H), 2.66 (m, 1H), 2.92 (s, 3H), 2.8–3.0 (m, 2H), 3.67 (t, 1H), 4.02 (d, 1H), 5.94 (s, 2H), 6.66 (dd, 1H), 6.7 (m, 2H), 6.80 (d, 1H), 6.91 (d, 1H), 7.05 (m, 2H), 7.1–7.4 (m, 4H).

$^{13}$C NMR (68 MHz, 5% CD$_3$OD/CDCl$_3$): δ 148.2, 147.6, 146.5, 138.5, 137.9, 133.9, 129.2, 128.1, 126.1, 124.7, 123.9, 122.0, 120.3, 115.3, 107.9, 106.9, 100.8, 76.5, 63.4, 57.9, 44.5, 38.5, 17.7.

Mass (M–H) 483

HPLC: 97% pure, Shimadzu, YMC S3 ODS (6.0×150 mm); flow rate of 1.5 mL/minute; detection at 217 nM; eluted with a 40 minutes linear gradient of 0% to 100% B solvent (A=10% MeOH, 90% H$_2$O, 0.2% H$_3$PO$_4$, B=90% MeOH, 10% H$_2$O, 0.2% H$_3$PO$_4$); retention time=23.8 minutes.

EXAMPLE 112

(R),(S),(R)-N-[5-[2-[[1-(1,3-Benzodioxol-5-yl)-2-phenylethyl]-amino]-1-hydroxypropyl]-2-hydroxyphenyl]methanesulfonamide, trifluoroacetate salt

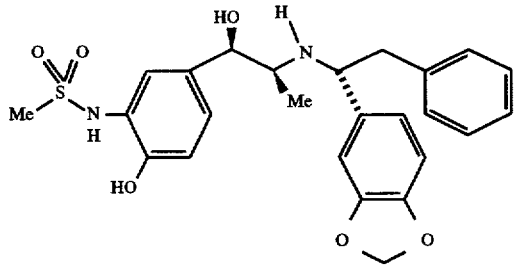

A. (R),(S),(R)-N-[5-[2-[[1-(1,3-Benzodioxol-5-yl)-2-phenylethyl]amino]-1-(triethylsilyl)oxypropyl]-2-phenylmethoxyphenyl]methanesulfonamide A solution of (R),(R)-1-hydroxy-1-[3-(methylsulfonyl)amino-4-phenylmethoxyphenyl]-2-propyl tosylate (0.39 g, 0.77 mmol, prepared in step E of Example 111), imidazole (0.20 g, 2.9 mmol), DMAP (15 mg, 0.12 mmol), and 0.35 mL of triethylsilyl chloride (0.34 g, 2.3 mmol) in 5 mL of dry DMF under Ar was stirred at 20° C. for several hours and then diluted with 25% EtOAc/hexane. The organic layer was concentrated after washing with H$_2$O, sat. aq. CuSO$_4$ (2×), and H$_2$O (2×), prior to drying over Na$_2$SO$_4$. Chromatography on silica gel eluting with 15% to 25% EtOAc/hexane generated 0.47 g of (R),(R)-1-(triethylsilyl)oxy-1-[3-(methylsulfonyl)-amino- 4-phenylmethoxyphenyl]-2-propyl tosylate which was heated with (R)-1-(1,3-benzodioxol-5-yl)-2-benzeneethanamine (preparation described in step B of Example 60) at 144° C. under Ar for five hours. After cooling, chromatography 2× on silica gel eluting first with 0.4% to 9% [10% conc. aq. NH$_3$/MeOH]/CH$_2$Cl$_2$, then with 15% EtOAc/hexane yielded the title compound (84% purity).

B. (R),(S),(R)-N-[5-[2-[[1-(1,3-Benzodioxol-5-yl)-2-phenylethyl]amino]-1-hydroxypropyl]-2-hydroxyphenyl]methanesulfonamide Following the procedure described in step E of Example 19, (R),(S),(R)-N-[5-[2-[[1-(1,3-benzodioxol-5-yl)-2-phenylethyl]amino]-1-(triethylsilyl)oxypropyl]-2-phenylmethoxyphenyl]methanesulfonamide was desilylated using TBAF except for the following modifications: 1) the reaction required heating at 60° C. for two hours; and 2) chromatography twice on silica gel eluting with 25% to 50% EtOAc/hexane provided (R),(S),(R)-N-[5-[2-[[1-(1,3-benzodioxol-5-yl)-2-phenylethyl]amino]-1-hydroxypropyl]-2-phenylmethoxyphenyl]methanesulfonamide (93% purity) which, upon hydrogenolysis as described in step C of Example 95, was converted to the free base of the title compound which was purified by elution from silica gel with EtOAc and isolated as the TFA salt.

$^1$H NMR (270 MHz, CDCl$_3$) of the free base: δ 0.71 (d, 3H), 2.84 (s, 3H), 2.6–3.0 (m, 3H), 3.88 (t, 1H), 4.33 (d, 1H), 4.8 (s, 3H), 5.91 (s, 2H), 6.6–6.9 (m, 5H), 7.0–7.3 (m, 6H).

$^{13}$C NMR (68 MHz, CDCl$_3$) of the free base: δ 148.8, 148.0, 146.9, 138.0, 136.5, 133.0, 129.1, 128.4, 126.5, 125.2, 123.7, 122.2, 120.8, 116.2, 108.1, 107.1, 101.0, 74.3, 62.0, 55.5, 44.9, 38.7, 14.4.

129

Mass (M−H) 483; (M+H) 485

HPLC: 97% pure, retention time 24.3 minutes, protocol described in Example 128.

EXAMPLE 113

(R), (S)-N-(4-Chlorophenyl)-α-||2-hydroxy-2-|4-hydroxy-3-|(methylsulfonyl)-amino|phenyl|ethyl| amino]-α-methyl-4-methoxybenzeneacetamide

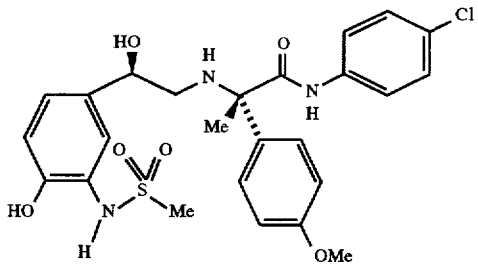

A. (S)-N-(4-Chlorophenyl)-[α-amino]-α-methyl-4-methoxybenzene-acetamide (S)-α-[N-[(1,1-Dimethylethyl)carbonyl]amino]-α-methyl-4-methoxybenzeneacetic acid (preparation described in step A of Example 101) was condensed with 4-chloroaniline following the procedure described in step A of Example 99. Pure (S)-N-(4-chlorophenyl)-α-[N-|(1,1-dimethylethyl)carbonyl|]-amino]-α-methyl-4-methoxybenzeneacetamide, obtained after chromatography on silica gel using 20% EtOAc/hexane as eluant, was converted to the title compound following the procedure described in step A of Example 98.

B. (R), (S)-N-(4-Chlorophenyl)-α-[|2-Hydroxy-2-[4-hydroxy-3-[(methyl-sulfonyl)amino|phenyl]ethyl]amino]-α-methyl-4-methoxybenzeneacetamide Following the procedure described in steps D, E, and F of Example 19, (S)-N-(4-chlorophenyl)[-α-amino]-α-methyl-4-methoxybenzeneacetamide was converted to the title compound with the following modifications. 1) In step D, the coupling reaction was heated at 100° for 7 days which was chromatographed twice on silica gel using 20% and 15% EtOAc/hexane respectively. 2) In step E, after desilylation, (R), (S)-N-(4-chlorophenyl)-α-|[2-hydroxy-2-[4-phenyl-methoxy-3-|(methylsulfonyl)amino|phenyl]ethyl]amino]-α-methyl-4-methoxybenzeneacetamide was purified by preparative HPLC using 57% solvent B. 3) In step F, the title compound was purified by preparative HPLC using 52% solvent B, after hydrogenolysis as the free base under 1 atom. $H_2$.

$^1$H NMR (270 MHz, CD$_3$OD): δ 7.41 (m, 5H) 7.26 (dd, 2H) 7.06 (dd, 1H) 6.87 (m, 3H) 4.67 (dd, 1H) 3.77 (s, 3H) 2.89 (s, 3H) 2.78 (dd, 1H) 2.55 (dd, 1H) 1.71 (s, 3H).

$^{13}$C NMR (68 MHz, CD$_3$OD): δ 176.05, 160.47, 150.91, 138.13, 136.14, 135.99, 130.12, 129.66, 128.57, 125.71, 125.63, 124.71, 122.75, 116.36, 114.77, 73.97, 65.67, 55.68, 52.40, 39.58, 22.51.

Mass (M+H) 534

$[α]_D^{22}$=−64.7° (c=0.20, MeOH)

HPLC: >99% pure, retention time 20.5 minutes, protocol described in Example 96

EXAMPLE 114

(R),(R)-4-|1-|[2-Hydroxy-2-[4-hydroxy-3-|(methylsulfonyl)amino]phenyl|ethyl|amino|-2-phenylethyl|-N-methylbenzeneacetamide, trifluoroacetate salt

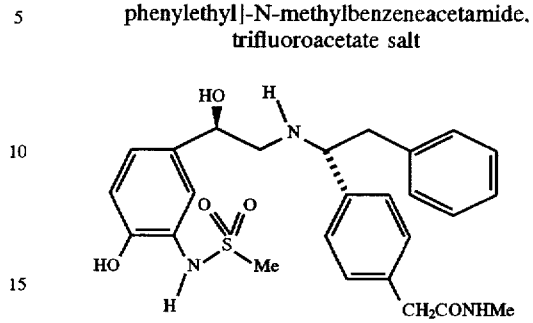

(R),(R)-4-|1-|[2-Hydroxy-2-|4-hydroxy-3-|(methylsulfonyl)amino]phenyl]ethyl]amino]-2-phenylethyl] benzeneacetic acid, trifluoroacetate salt (preparation described in Example 91) was converted to the title compound following the procedure described in Example 86.

$^1$H NMR (270 MHz, CD$_3$OD): δ 2.70 (s, 3H), 2.83–2.89 (m, 1H), 2.90 (s, 3H), 3.02–3.25 (m, 2H), 3.48 (s, 2H), 3.55 (dd, 1H), 4.50 (dd, 1H), 4.71 (dd, 1H), 6.85 (d, 1H), 6.99–7.04 (m, 3H), 7.14–7.17 (m, 3H), 7.30 (s, 5H).

$^{13}$C NMR (68 MHz, CD$_3$OD): δ 26.5, 39.6, 40.1, 43.2, 53.7, 65.6, 70.0, 116.6, 124.4, 125.5, 126.1, 128.1, 129.6, 129.9, 130.4, 131.0, 133.5, 133.7, 136.7, 138.8, 151.7, 174.0.

Mass (M+H) 497

$[α]_D^{22}$=−33.4° (c=0.5, MeOH)

Calculated for 1.68 H$_2$O and 1.10 mol TFA:

|   | Calc. | Found |
|---|-------|-------|
| C | 51.85 | 51.85 |
| H | 5.47  | 5.27  |
| N | 6.43  | 6.45  |
| S | 4.91  | 4.94  |
| F | 9.60  | 9.71  |

HPLC: >99% pure, retention time 14.9 minutes, protocol described in Example 1.

EXAMPLE 115

(R),(R)-4-[1-[[2-Hydroxy-2-|4-hydroxy-3-|(methylsulfonyl)amino]phenyl|ethyl|amino|-2-phenylethyl]-N,N-dimethylbenzeneacetamide, trifluoroacetate salt

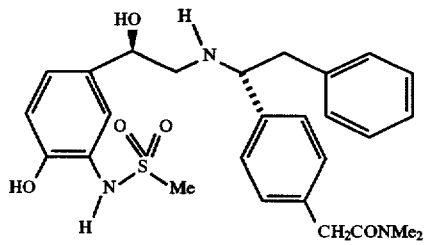

(R),(R)-4-[1-|[2-Hydroxy-2-|4-hydroxy-3-|(methylsulfonyl)amino]phenyl]ethyl]amino]-2-phenylethyl] benzeneacetic acid, trifluoroacetate salt (preparation described in Example 91) was converted to the title compound following the procedure described in Example 86, except that the preparative HPLC utilized 38% solvent B.

¹H NMR (270 MHz, CD₃OD): δ 2.85–2.95 (m, 1H), 2.90 (s, 3H), 2.93 (s, 3H), 3.03 (s, 3H), 3.0–3.3 (m, 2H), 3.58 (dd, 1H), 3.75 (s, 2H), 4.50 (dd, 1H), 4.71 (dd, 1H), 6.86 (d, 1H), 7.02 (d, 3H), 7.13–7.16 (m, 3H), 7.23–7.33 (m, 5H).

¹³C NMR (68 MHz, CD₃OD): δ 36.0, 38.2, 39.6, 40.1, 40.8, 53.7, 65.6, 70.0, 116.6, 124.4, 125.5, 126.0, 128.1, 129.6, 130.0, 130.4, 131.0, 133.5, 133.6, 136.7, 138.4, 151.6, 173.3.

Mass (M+H) 512

[α]$_D^{22}$=−34.4° (c=0.5, MeOH)

Calculated for 1.28 H₂O and 1.20 mol TFA:

|   | Calc. | Found |
|---|---|---|
| C | 52.59 | 52.59 |
| H | 5.52 | 5.37 |
| N | 6.26 | 6.24 |
| S | 4.77 | 4.76 |
| F | 10.18 | 10.13 |

HPLC: >97% pure, retention time 16.2 minutes, protocol described in Example 1.

EXAMPLE 116

(R),(R)-4-[1-[[2-Hydroxy-2-[4-hydroxy-3-[(methylsulfonyl)amino]phenyl]ethyl]amino]-2-phenylethyl]benzeneacetamide, trifluoroacetate salt

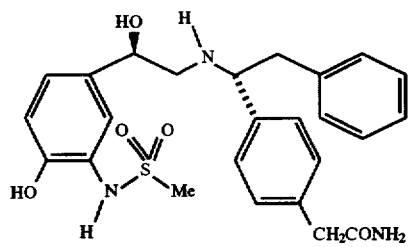

(R),(R)-4-[1-[[2-Hydroxy-2-[4-hydroxy-3-[(methylsulfonyl)amino]phenyl]ethyl]amino]-2-phenylethyl] benzeneacetic acid, trifluoroacetate salt (preparation described in Example 91) was converted to the title compound following the procedure described in Example 86, except that: 1) conc. NH₄OH was added last during formation of the amide moiety; and 2) 31% solvent B was employed for preparative HPLC.

¹H NMR (270 MHz, CD₃OD): δ 2.83–2.86 (m, 1H), 2.90 (s, 3H), 3.03–3.25 (m, 2H), 3.51 (s, 2H), 3.56 (dd, 1H), 4.50 (dd, 1H), 4.72 (dd, 1H), 6.85 (d, 1H), 7.00–7.08 (m, 3H), 7.10–7.20 (m, 3H), 7.31 (s, 5H).

¹³C NMR (68 MHz, CD₃OD): δ 39.6, 40.1, 42.8, 53.7, 65.6, 70.0, 116.6, 124.4, 125.5, 126.1, 128.1, 129.6, 129.9, 130.4, 131.1, 133.5, 133.7, 136.7, 138.8, 151.7, 176.3.

Mass (M+H) 484

[α]$_D^{22}$=−33.4° (c=0.5, MeOH)

Calculated for 2.15 H₂O and 1.25 mol TFA:

|   | Calc. | Found |
|---|---|---|
| C | 49.68 | 49.69 |
| H | 5.24 | 4.95 |
| N | 6.32 | 6.27 |
| S | 4.82 | 4.97 |
| F | 10.72 | 10.60 |

HPLC: 98% pure, retention time 14.2 minutes, protocol described in Example 1.

EXAMPLE 117

(R),(R)-4-[1-[[2-Hydroxy-2-[4-hydroxy-3-[(methylsulfonyl)amino]phenyl]ethyl]amino]-2-phenylethyl]benzamide, trifluoroacetate salt

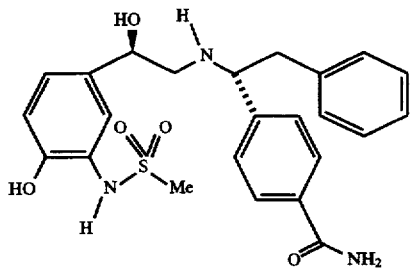

(R),(R)-4-[1-[[2-Hydroxy-2-[4-hydroxy-3-[(methylsulfonyl)amino]phenyl]ethyl]amino]-2-phenylethyl] benzoic acid, trifluoroacetate salt (preparation described in Example 84) was converted to the title compound following the procedure described in Example 86, except that: 1) conc. NH₄OH was added last during formation of the amide moiety; and 2) 31% solvent B was employed for preparative HPLC.

¹H NMR (270 MHz, CD₃OD): δ 2.90 (s, 3H), 2.91 (dd, 1H), 3.1–3.3 (m, 2H), 3.61 (dd, 1H), 4.61 (dd, 1H), 4.76 (dd, 1H), 6.85 (d, 1H), 7.0–7.1 (m, 3H), 7.1–7.2 (m, 3H), 7.32 (d, 1H), 7.44 (d, 2H), 7.86 (d, 2H).

¹³C NMR (68 MHz, CD₃OD): δ 39.6, 40.1, 53.9, 65.5, 70.0, 116.6, 124.5, 125.5, 126.1, 128.2, 129.5, 129.7, 129.9, 130.4, 133.5, 136.3, 136.4, 139.0, 151.7, 171.4

Mass (M+H) 470 and (M−H) 468.

[α]$_D$=−42.4° (c=0.5, MeOH)

Calculated for 1.4 mol H₂O and 1.1 mol TFA:

|   | Calc. | Found |
|---|---|---|
| C | 50.74 | 50.75 |
| H | 5.02 | 4.89 |
| N | 6.78 | 6.69 |
| S | 5.17 | 5.30 |
| F | 10.11 | 10.34 |

HPLC: >97% pure, retention time 13.6 minutes, protocol described in Example 1.

EXAMPLE 118

(R),(R)-4-[1-[[2-Hydroxy-2-[4-hydroxy-3-[(methylsulfonyl)amino]phenyl]ethyl]amino]-2-phenylethyl]-N,N-dimethylbenzamide, trifluoroacetate salt

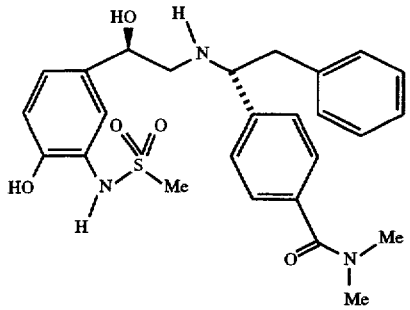

(R),(R)-4-[1-[[2-Hydroxy-2-[4-hydroxy-3-[(methylsulfonyl)amino]phenyl]ethyl]amino]-2-phenylethyl] benzoic acid, trifluoroacetate salt (preparation described in Example 84) was converted to the title compound following the procedure described in Example 86, except that 38% solvent B was employed for preparative HPLC.

$^1$H NMR (270 MHz, CD$_3$OD): δ 2.90 (s, 3H), 2.91 (dd, 1H), 2.92 (s, 3H), 3.08 (s, 3H), 3.1–3.3 (m, 2H), 3.60 (dd, 1H), 4.59 (dd, 1H), 4.75 (dd, 1H), 6.86 (d, 1H), 7.0–7.1 (m, 3H), 7.1–7.2 (m, 3H), 7.30 (d, 1H), 7.43 (s, 4H).

$^{13}$C NMR (68 MHz, CD$_3$OD): δ 35.6, 39.6, 39.9, 40.1, 53.8, 65.5, 69.9, 116.6, 124.3, 125.4, 126.1, 128.1, 128.8, 129.6, 130.1, 130.4, 133.5, 136.5, 137.0, 138.5, 151.6, 172.8.

Mass (M+H) 498

$[α]_D = -40.4°$ (c=0.5, MeOH)

Calculated for 1.0 mol H$_2$O and 1.1 mol TFA:

|   | Calc. | Found |
|---|-------|-------|
| C | 52.84 | 52.89 |
| H | 5.36  | 5.25  |
| N | 6.55  | 6.45  |
| S | 5.00  | 5.06  |
| F | 9.78  | 9.87  |

HPLC: 100% pure, retention time 15.5 minutes, protocol described in Example 1.

EXAMPLE 119

(R),(R)-N-[5-[1-(Hydroxy-2-[[1-(1-naphthalenyl)-2-phenylethyl]amino]ethyl]-2-(hydroxy)phenyl] methanesulfonamide, trifluoroacetate salt

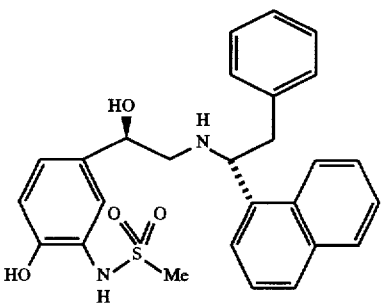

A. α-(1-Naphthalenyl)-1-benzeneethanamine

Following the general procedure described by D. Hart et. al., *J. Org. Chem.*, 48, 289 (1983), 1-naphthaldehyde (3.12 g, 20 mmol) was added to 0.65M lithium hexamethyldisilazide in THF (40 mL) at 4° C. under N$_2$. The solution was stirred two hours at 20° C., cooled to 4° C., and 12 mL of 2M benzylmagnesium chloride/THF was added. After 1.5 hours, the reaction was quenched with sat. aq. NH$_4$Cl, diluted with H$_2$O and extracted with EtOAc (3×). The organic layers were washed with H$_2$O, then with brine, dried over Na$_2$SO$_4$ and concentrated. Chromatography on silica gel using 5% MeOH/CH$_2$Cl$_2$ yielded the title compound.

B. (R),(R)-N-[5-[1-(Hydroxy-2-[[1-(1-naphthalenyl)-2-phenylethyl]amino]ethyl]-2-(hydroxy)phenyl] methanesulfonamide α-(1-Naphthalenyl)-1-benzeneethanamine was converted to (R)-N[5-[1-(triethylsilyl)oxy-2-[[1-(1-naphthalenyl)-2-phenylethyl]amino]ethyl]-2-(phenylmethoxy)phenyl] methanesulfonamide following the procedure outlined in step D of Example 19, except for the following modification: flash chromatography on silica gel eluting first with 3.3% EtOAc/toluene followed by 5% EtOAc/toluene eluted first the R,R diastereomer followed by the R,S diastereomer.

(R),(R)-N-[5-[1-(Triethylsilyl)oxy-2-[[1-(1-naphthalenyl)-2-phenylethyl]amino]ethyl]-2-(phenylmethoxy)phenyl]methanesulfonamide, was converted to the title compound following the procedures described in steps E and F of Example 19, except that 54% solvent B was utilized for the final preparative HPLC.

$^1$H NMR (270 MHz, CD$_3$OD): δ 2.80–2.94 (m, 1H), 2.86 (s, 3H), 3.15 (dd, 1H), 3.23–3.42 (m, 1H), 3.73 (dd, 1H), 4.73 (dd, 1H), 5.45–5.62 (m, 1H), 6.80 (d, 1H), 6.93 (dd, 1H), 6.95–7.25 (m, 6H), 7.26 (d, 1H), 7.38–7.50 (m, 2H), 7.64 (t, 1H), 7.81–8.00 (m, 4H).

$^{13}$C NMR (68 MHz, CD$_3$OD): δ 40.6, 41.9, 54.8, 70.9, 117.7, 124.1, 125.1, 126.4, 127.1, 127.5, 128.3, 129.0, 129.2, 130.4, 131.0, 131.4, 132.2, 133.0, 134.4, 134.5, 136.1, 137.4, 152.6.

Mass (M+H) 477

$[α]_D^{22} = -14.4°$ (c=0.25, MeOH)

Calculated for 0.45 H$_2$O and 1.16 mol TFA:

|   | Calc. | Found |
|---|-------|-------|
| C | 57.08 | 57.32 |
| H | 4.91  | 4.90  |
| N | 4.54  | 4.23  |

-continued

| | Calc. | Found |
|---|---|---|
| S | 5.20 | 4.85 |
| F | 10.72 | 10.86 |

HPLC: 99% pure, retention time 21.2 minutes, protocol described in Example 1.

EXAMPLE 120

(R),(S)-N-[5-[1-(Hydroxy-2-[[1-(1-naphthalenyl)-2-phenylethyl]amino]ethyl]-2-hydroxyphenyl] methanesulfonamide, trifluoroacetate salt

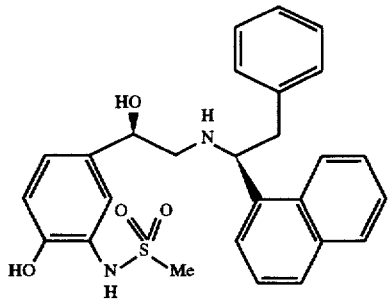

The title compound was prepared from (R),(S)-N-[5-[1-(triethylsilyl)oxy-2-[[1-(1-naphthalenyl)-2-phenylethyl] amino]ethyl]-2-(phenylmethoxy)phenyl] methanesulfonamide, preparation described in step B of Example 119, following the procedure described in step B of Example 119.

$^1$H NMR (270 MHz, CD$_3$OD): δ 2.78–2.88 (m, 1H), 2.84 (s, 3H), 3.06 (dd, 1H), 3.20–3.48 (m, 1H), 3.68 (dd, 1H), 4.80–5.00 (m, 1H), 5.55–5.70 (m, 1H), 6.77 (d, 1H), 6.86 (dd, 1H), 6.89–7.10 (m, 6H), 7.20 (d, 1H), 7.35–7.45 (m, 2H), 7.65 (t, 1H), 7.80–8.00 (m, 4H).

$^{13}$C NMR (68 MHz, CD$_3$OD): δ 39.6, 41.3, 53.5, 69.6, 116.6, 122.9, 124.0, 125.2, 126.0, 126.5, 127.2, 128.0, 128.1, 129.4, 130.1, 130.3, 131.2, 133.3, 133.4, 135.1, 136.3, 151.5.

Mass (M+H) 477

$[α]_D^{22}$=−5.5° (c=0.25, MeOH)

| | Calc. | Found |
|---|---|---|
| C | 55.62 | 55.59 |
| H | 4.87 | 4.43 |
| N | 4.38 | 4.17 |
| S | 5.02 | 4.79 |
| F | 11.59 | 11.56 |

HPLC: 99% pure, retention time 20.8 minutes, protocol described in Example 1.

EXAMPLE 121

(R),(R)-N-[5-[1-(Hydroxy-2-[[1-(4-methoxy-1-naphthalenyl)-2-phenylethyl]-amino]ethyl]-2-hydroxyphenyl]methanesulfonamide, trifluoroacetate salt

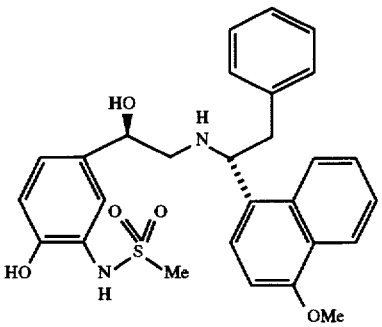

The title compound was prepared from 4-methoxy-1-naphthaldehyde following the procedure described in Example 119, except that 60% solvent B was utilized for the final HPLC purification.

$^1$H NMR (270 MHz, CD$_3$OD): δ 2.81–2.94 (m, 1H), 2.86 (s, 3H), 3.11 (t, 1H), 3.41 (t, 1H), 3.70 (dd, 1H), 4.03 (s, 3H), 4.72 (dd, 1H), 5.38–5.55 (m, 1H), 6.81 (d, 1H), 6.92 (dd, 1H), 7.00–7.20 (m, 6H), 7.26 (d, 1H), 7.36–7.45 (m, 2H), 7.80–7.95 (m, 2H), 8.20–8.26 (m, 1H).

$^{13}$C NMR (68 MHz, CD$_3$OD): δ 39.4, 40.5, 53.4, 56.0, 69.7, 104.4, 116.4, 122.6, 123.4, 123.8, 125.1, 125.8, 126.2, 126.6, 127.7, 128.3, 129.2, 130.1, 133.2, 136.4, 151.3, 157.5.

Mass (M+Na) 529

$[α]_D^{22}$=−18.4° (c=0.76, MeOH)

Calculated for 1.1 mol TFA:

| | Calc. | Found |
|---|---|---|
| C | 57.39 | 57.74 |
| H | 4.96 | 5.30 |
| N | 4.43 | 4.26 |
| S | 5.07 | 4.66 |
| F | 9.92 | 9.79 |

HPLC: 99% pure, retention time 22.6 minutes, protocol described in Example 1.

EXAMPLE 122

(R),(S)-N-[5-[1-(Hydroxy-2-[[1-(4-methoxy-1-naphthalenyl)-2-phenylethyl]amino]ethyl]-2-hydroxyphenyl]methanesulfonamide, trifluoroacetate salt

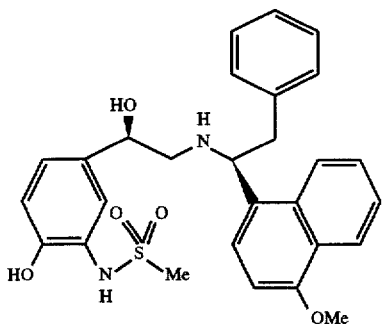

The title compound was prepared from 4-methoxy-1-naphthaldehyde following the procedure described in Example 119, except that 60% solvent B was utilized for the final HPLC purification.

$^1$H NMR (270 MHz, CD$_3$OD): δ 2.76–2.90 (m, 1H), 2.84 (s, 3H), 3.03 (dd, 1H), 3.36–3.50 (m, 1H), 3.63 (dd, 1H), 4.04 (s, 3H), 4.80–5.00 (m, 1H), 5.41–5.58 (m, 1H), 6.77 (d, 1H), 6.85 (dd, 1H), 6.95–7.08 (m, 6H), 7.19 (d, 1H), 7.35–7.45 (m, 2H), 7.66–7.90 (m, 2H), 8.20–8.28 (m, 1H).

$^{13}$C NMR (68 MHz, CD$_3$OD): δ 39.6, 41.1, 53.2, 56.2, 69.6, 104.7, 116.6, 122.7, 123.7, 124.2, 125.1, 126.0, 126.5, 128.0, 128.6, 129.5, 130.4, 133.5, 136.6, 151.6, 157.8.

Mass (M+H) 507

$[α]_D^{22} = -3.8°$ (c=0.6, MeOH)

Calculated for 0.79 H$_2$O and 1.95 mol TFA:

|   | Calc. | Found |
|---|-------|-------|
| C | 51.55 | 51.55 |
| H | 4.55  | 4.46  |
| N | 3.77  | 3.61  |
| S | 4.31  | 4.18  |
| F | 14.95 | 14.91 |

HPLC: 99% pure, retention time 22.5 minutes, protocol described in Example 1.

EXAMPLE 123

N-[5-[(R)-1-(Hydroxy-2-[[1-(benzo[b]thiophen-5-yl)-2-phenylethyl]amino]ethyl]-2-hydroxyphenyl]methanesulfonamide, trifluoroacetate salt

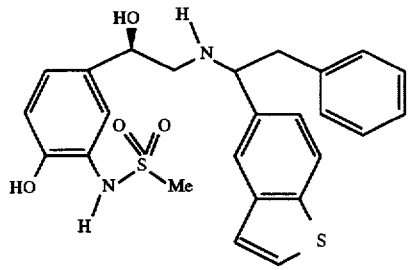

A. 5-Benzo[b]thiophenylcarboxaldehyde

A mixture of 5-methylbenzo[b]thiophene (3.8 g, 25.6 mmol), NBS (4.7 g, 27 mmol), and benzoyl peroxide (310 mg, 1.3 mmol) were refluxed one hour in CCl4 (100 mL) while being irradiated with a sunlamp. Upon completion, the reaction was cooled, diluted with Et$_2$O, filtered and concentrated to yield 5.8 g of 5-bromomethylbenzo[b]thiophene. The crude 5-bromomethylbenzo[b]thiophene was refluxed for 36 hours in 1:1 dioxane/2N aq. NaOH (128 mL). After cooling, extraction with EtOAc and concentration of the extracts, the residue was chromatographed on silica gel eluting 2.6 g of 5-hydroxymethylbenzo[b]thiophene with 35% EtOAc/hexane. The title compound (1.96 g) was obtained after filtration and concentration of the reaction product produced by refluxing 5-hydroxymethylbenzo[b]thiophene (2.08 g, 12.7 mmol) and 50% MnO$_2$/C (17.6 g, 101 mmol) for five hours in toluene while H$_2$O was continually removed using a Dean-Stark trap.

B. N-[5-[(R)-1-(Hydroxy-2-[[1-(Benzo[b]thiophen-5-yl)-2-phenylethyl]amino]ethyl]-2-hydroxyphenyl]methanesulfonamide 5-Benzo[b]thiophenylcarboxaldehyde was converted to α-(benzo[b]thiophen-5-yl)-1-benzeneethanamine following the procedures described in steps A–C of Example 1, except that the chromatographic purification of step B was omitted. The title compound was prepared from α-(benzo[b]thiophen-5-yl)-1-benzeneethanamine following the procedures described in steps D–F of Example 19, except that 52% solvent B was utilized for the final HPLC purification.

$^1$H NMR (270 MHz, CD$_3$OD): δ 2.76–2.96 (m, 1H), 2.86 and 2.88 (s, 3H), 3.02–3.20 (m, 1H), 3.22–3.42 (m, 1H), 3.50–3.68 (m, 1H), 4.58–4.95 (m, 2H), 6.79–6.85 (m,1H), 6.92–7.20 (m, 6H), 7.23–7.40 (m, 3H), 7.62–7.66 (m, 1H), 7.76–7.80 (m, 1H), 7.90–7.99 (m, 1H).

$^{13}$C NMR (68 MHz, CD$_3$OD): δ 39.7, 40.5, 40.8, 53.7, 53.8, 65.7, 66.3, 69.6, 70.0, 116.7, 124.2, 124.3, 124.5, 124.7, 124.8, 124.9, 125.3, 125.5, 126.1, 126.2, 128.1, 129.4, 129.6, 130.4, 131.0, 131.3, 133.6, 136.8, 141.6, 142.3, 151.6.

Mass (M+H) 483

Calculated for 0.65 H$_2$O and 1.42 mol TFA and 0.32 CH$_2$Cl$_2$:

|    | Calc. | Found |
|----|-------|-------|
| C  | 49.49 | 49.49 |
| H  | 4.33  | 3.94  |
| N  | 4.10  | 3.99  |
| S  | 9.38  | 9.46  |
| F  | 11.84 | 11.87 |
| Cl | 3.32  | 3.35  |

HPLC: 96% pure, retention time 23.0 minutes, protocol described in Example 1.

EXAMPLE 124

(R),(R)-N-[5-[1-(Hydroxy-2-[[1-(4-methoxy-3-pyridinyl)-2-phenylethyl]amino]ethyl]-2-hydroxyphenyl]methanesulfonamide

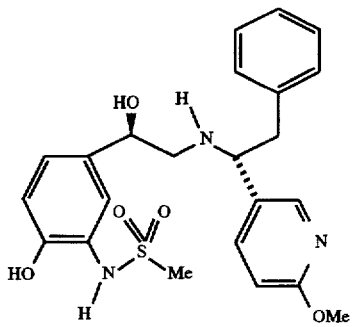

A. Methyl 6-methoxynicotinate

A mixture of 6-hydroxynicotinic acid (24.36 g, 175 mmol), $Ag_2CO_3$ (96.6 g, 350 mmol), and methyl iodide (32.7 mL, 525 mmol) in anhydrous toluene (400 mL) was refluxed for 20 hours. After cooling, filtering through celite and washing the residual solid with EtOAc, the combined organic layers were concentrated to obtain a pale yellowish solid which after passing through a pad of silica gel using 25% EtOAc/hexanes yielded 16.3 g of the title compound.

B. α-(4-Methoxy-3-pyridinyl)-1-benzeneethanamine

To a 0° C. THF (70 mL) solution of methyl 6-methoxynicotinate (6.0 g, 36 mmol) was added 36 mL of 1M LAH/THF. The reaction, after stirring at 20° C. for two hours, was quenched with aq. $NH_4Cl$, diluted with aq. HCl until all salts dissolved, and extracted with EtOAc (3×) after adjusting the pH to 5. The crude 4-hydroxymethyl-2-methoxypyridine (1.75 g), obtained after drying and concentration of the EtOAc layers, was converted to 4-methoxy-3-pyridinylcarboxaldehyde following the procedure described in step A of Example 123. The title compound was prepared from 4-methoxy-3-pyridinylcarboxaldehyde following the procedure described in step A of Example 119.

C. (R),(R)-N-[5-[1-(Hydroxy-2-[[1-(4-methoxy-3-pyridinyl)-2-phenylethyl]amino]ethyl]-2-hydroxyphenyl] methane sulfonamide α-(4-Methoxy-3-pyridinyl)-1-benzeneethanamine was converted to (R)-N-[5-[1-(triethylsilyl)oxy-2-[[1-(4-methoxy-3-pyridinyl)-2-phenylethyl]amino]ethyl]-2-(phenylmethoxy)phenyl]methanesulfonamide following the procedure outlined in step D of Example 19, except for the following modification: flash chromatography on silica gel eluting first with 5% EtOAc/toluene followed by 7% EtOAc/toluene eluted first the R,R diastereomer followed by the R,S diastereomer.

(R),(R)-N-[5-[1-(Triethylsilyl)oxy-2-[[1-(4-methoxy-3-pyridinyl))2-phenylethyl]-amino]ethyl]-2-(phenylmethoxy) phenyl]methanesulfonamide, was converted to the title compound following the procedures described in steps E and F of Example 19, except that in step F the title compound was purified by silica gel chromatography eluting with 8% $MeOH/CH_2Cl_2$.

$^1H$ NMR (270 MHz, $CD_3OD$): δ 2.53–2.61 (m, 2H), 2.92–2.98 (m, 3H), 2.93 (s, 3H), 3.87 (t, 1H), 3.90 (s, 3H), 4.36–4.44 (m, 2H), 6.73 (d, 1H), 6.85 (dd, 1H), 7.06–7.23 (m, 8H), 7.55 (dd, 1H), 7.91 (d, 1H).

$^{13}C$ NMR (68 MHz, $CD_3OD$): δ 39.0, 43.9, 53.7, 54.7, 62.1, 71.8, 110.8, 116.3, 121.5, 124.4, 126.7, 128.4, 128.5, 129.2, 130.4, 134.4, 137.5, 138.1, 145.8, 148.9, 163.7.

Mass (M+H) 458
$[α]_D^{22}$=−26.7° (c=0.12, MeOH)
Calculated for 1.00 $H_2O$:

|   | Calc. | Found |
|---|-------|-------|
| C | 57.02 | 57.04 |
| H | 6.18  | 6.05  |
| N | 8.31  | 8.21  |
| S | 6.34  | 6.30  |

HPLC: 99% pure, retention time 17.0 minutes, protocol described in Example 1.

EXAMPLE 125

(R),(R)-N-[5-[1-(Hydroxy-2-[[1-(2,4-dimethoxy-3-pyridinyl)-2-phenylethyl]amino]ethyl]-2-hydroxyphenyl]methanesulfonamide

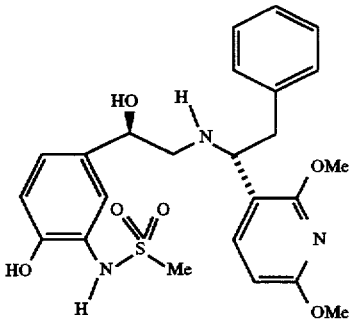

A. α-(2,4-Dimethoxy-3-pyridinyl)-1-benzeneethanamine

Following the procedure described in Example 86, condensation of commercial 2,4-dimethoxynicotinic acid and O-methylhydroxylamine to form N-methoxy-N-methyl-2,4-dimethoxynicotinamide was promoted by 1-(3-dimethylaminopropyl)-3-ethylcarbodiimide HCl and hydroxybenztriazol. To a 0° C. THF (80 mL) solution of N-methoxy-N-methyl-2,4-dimethoxynicotinamide (4.39 g, 19 mmol) was added 21 mL of 1M LAH/THF. The reaction, after stirring at 0° C. for one hour, was quenched with aq. $NH_4Cl$, diluted with aq. HCl, and extracted with EtOAc (3×). After isolation, the 2,4-dimethoxy-3-pyridinylcarboxaldehyde was converted to the title compound following the procedure described in step A of Example 119.

B. (R),(R)-N-[5-[1-(Hydroxy-2-[[1-(2,4-dimethoxy-3-pyridinyl)-2-phenylethyl]amino]ethyl]-2-hydroxyphenyl] methanesulfonamide α-(2,4-Dimethoxy-3-pyridinyl)-1-benzeneethanamine was converted to (R)-N-[5-[1-(triethylsilyl)oxy-2-[[1-(2,4-dimethoxy-3-pyridinyl)-2-phenylethyl]amino]ethyl]-2-(phenylmethoxy)phenyl]methanesulfonamide following the procedure outlined in step D of Example 19, except for the following modification: flash chromatography on silica gel eluting first with 7% EtOAc/toluene followed by 9% EtOAc/toluene eluted first the R,R diastereomer followed by the R,S diastereomer.

(R),(R)-N-[5-[1-(Triethylsilyl)oxy-2-[[1-(2,4-dimethoxy-3-pyridinyl))-2-phenylethyl]amino]ethyl]-2-(phenylmethoxy)phenyl]methanesulfonamide, was converted to the title compound following the procedures described in steps E and F of Example 19, except that in step F the title compound was purified by silica gel chromatography eluting with 10% $MeOH/CH_2Cl_2$.

¹H NMR (270 MHz, CD₃OD): δ 2.38–2.49 (m, 1H), 2.69–2.75 (m, 1H), 2.91 (s, 3H), 2.95–3.00 (m,2H), 3.05–3.22 (m, 2H), 3.89 (s, 3H), 3.93 (s, 3H), 3.95–4.00 (m, 1H), 4.40–4.47 (m,1H), 6.21 (d, 1H), 6.77 (d, 1H), 6.90–6.96 (m, 1H), 7.06–7.17 (m, 3H), 7.19–7.26 (m, 4H).

¹³C NMR (68 MHz, CDCl₃): δ 38.8, 41.5, 53.4, 53.6, 55.0, 59.8, 71.4, 100.7, 117.1, 122.2, 126.0, 128.3, 129.3, 133.6, 135.0, 138.1, 140.0, 148.5, 160.4, 162.9.

Mass (M+H) 488

$[\alpha]_D^{22} = -42.5°$ (c=0.24, MeOH)

Calculated for 1.00 H₂O:

|   | Calc. | Found |
|---|-------|-------|
| C | 57.02 | 57.04 |
| H | 6.18  | 6.05  |
| N | 8.31  | 8.21  |
| S | 6.34  | 6.30  |

HPLC: 99% pure, retention time 19.9 minutes, protocol described in Example 1.

Using the procedures described herein or by modification of the procedures described herein as known by the skilled artisan, the following additional compounds may also be prepared:

| Example # | R¹ | R² | R³ | R⁴ | R⁵ | R⁶ | R⁷ | R⁸ | R⁹ | A |
|-----------|----|----|----|----|----|----|----|----|----|----|
| 126 | Me | HO | Me | CONHR⁹ | 4-OMe | H | | | 2-H₂NCO-Ph | bond |
| 127 | Me | HO | Me | CONHR⁹ | 4-OMe | H | | | 3-H₂NCO-Ph | bond |
| 128 | Me | HO | Me | CONHR⁹ | 4-OMe | H | | | 4-H₂NCO-Ph | bond |
| 129 | Me | HO | Me | CONHR⁹ | 4-OMe | H | | | 2-HO₂C-Ph | bond |
| 130 | Me | HO | Me | CONHR⁹ | 4-OMe | H | | | 3-HO₂C-Ph | bond |
| 131 | Me | HO | Me | CONHR⁹ | 4-OMe | H | | | 2-t-Bu-Ph | bond |
| 132 | Me | HO | Me | CONHR⁹ | 4-OMe | H | | | 2-CF₃-Ph | bond |
| 133 | Me | HO | Me | CONHR⁹ | 4-OMe | H | | | 2-Cl-Ph | bond |
| 134 | Me | HO | Me | CONHR⁹ | 4-OMe | H | | | 2-MeO-Ph | bond |
| 135 | Me | HO | Me | CONHR⁹ | 4-OMe | H | | | 3-CF₃-Ph | bond |
| 136 | Me | HO | Me | CONHR⁹ | 4-OMe | H | | | 3-Cl-Ph | bond |
| 137 | Me | HO | Me | CONHR⁹ | 4-OMe | H | | | 3-MeO-Ph | bond |
| 138 | Me | HO | Me | CONHR⁹ | 4-OMe | H | | | 3-CF₃O-Ph | bond |
| 139 | Me | HO | Me | CONHR⁹ | 4-OMe | H | | | 4-Me-Ph | bond |
| 140 | Me | HO | Me | CONHR⁹ | 4-OMe | H | | | 4-t-Bu-Ph | bond |
| 141 | Me | HO | Me | CONHR⁹ | 4-OMe | H | | | 4-CF₃-Ph | bond |
| 142 | Me | HO | Me | CONHR⁹ | 4-OMe | H | | | 4-HO₂C-Ph | bond |
| 143 | Me | HO | Me | CONHR⁹ | 4-OMe | H | | | 4-CF₃O-Ph | bond |
| 144 | Me | HO | Me | CONHR⁹ | 4-OMe | H | | | 4-Ph-Ph | bond |
| 145 | Me | HO | Me | CONHR⁹ | 4-OMe | H | | | 3,5-Cl₂-4-NH₂-Ph | bond |
| 146 | Me | HO | Me | CONHR⁹ | 4-OMe | H | | | 2-Ph-Ph | bond |
| 147 | Me | HO | Me | CONHR⁹ | 4-OMe | H | | | 2-Bn-Ph | bond |
| 148 | Me | HO | Me | CONHR⁹ | 4-OMe | H | | | 2-PhO-Ph | bond |
| 149 | Me | HO | Me | CONHR⁹ | 4-OMe | H | | | 3-PhO-Ph | bond |
| 150 | Me | HO | Me | CONHR⁹ | 4-OMe | H | | | 4-PhO-Ph | bond |
| 151 | Me | HO | Me | CONHR⁹ | 4-OMe | H | | | 5-indane | bond |
| 152 | Me | HO | Me | CONHR⁹ | 4-OMe | H | | | 1-Naphthalene | bond |
| 153 | Me | HO | Me | CONHR⁹ | 4-OMe | H | | | 4-Cl-1-Naphthalene | bond |
| 154 | Me | HO | Me | CONHR⁹ | 4-OMe | H | | | 1-indane | bond |
| 155 | Me | HO | Me | CONHR⁹ | 4-OMe | H | | | 2-indane | bond |
| 156 | Me | HO | Me | CONHR⁹ | 4-OMe | H | | | 1-isoquinoline | bond |
| 157 | Me | HO | Me | CONHR⁹ | 4-OMe | H | | | 5-isoquinoline | bond |
| 158 | Me | HO | Me | CONHR⁹ | 4-OMe | H | | | 6-nicotinamide | bond |
| 159 | Me | HO | Me | CONHR⁹ | 4-OMe | H | | | 2-pyridine | bond |
| 160 | Me | HO | Me | CONHR⁹ | 4-OMe | H | | | 3-pyridine | bond |
| 161 | Me | HO | Me | CONHR⁹ | 4-OMe | H | | | 4-quinaldine | bond |
| 162 | Me | HO | Me | CONHR⁹ | 4-OMe | H | | | 5-quinoline | bond |
| 163 | Me | HO | Me | CONHR⁹ | 4-OMe | H | | | 3-pyrazole | bond |
| 164 | Me | HO | Me | CONHR⁹ | 4-OMe | H | | | 2-imidazole | bond |
| 165 | Me | HO | Me | CONHR⁹ | 4-OMe | H | | | 5-tetrazole | bond |
| 166 | Me | HO | Me | CONHR⁹ | 4-OMe | H | | | 3-methyl-5-isoxazole | bond |
| 167 | Me | HO | Me | CONHR⁹ | 4-OMe | H | | | 5-methyl-3-isoxazole | bond |
| 168 | Me | HO | Me | CONHR⁹ | 4-OMe | H | | | 3-methyl-5-isothiazole | bond |
| 169 | Me | HO | Me | CONHR⁹ | 4-OMe | H | | | 2-thiazole | bond |
| 170 | Me | HO | Me | CONHR⁹ | 4-OCHF₂ | H | | | 4-Cl-Ph | bond |
| 171 | Me | HO | Me | CONHR⁹ | 4-OCHF₂ | H | | | 2-t-Bu-Ph | bond |
| 172 | Me | HO | Me | CONHR⁹ | 4-OCHF₂ | H | | | 2-CF₃-Ph | bond |
| 173 | Me | HO | Me | CONHR⁹ | 4-OCHF₂ | H | | | 2-Cl-Ph | bond |
| 174 | Me | HO | Me | CONHR⁹ | 4-OCHF₂ | H | | | 2-MeO-Ph | bond |
| 175 | Me | HO | Me | CONHR⁹ | 4-OCHF₂ | H | | | 3-CF₃-Ph | bond |
| 176 | Me | HO | Me | CONHR⁹ | 4-OCHF₂ | H | | | 3-Cl-Ph | bond |
| 177 | Me | HO | Me | CONHR⁹ | 4-OCHF₂ | H | | | 3-MeO-Ph | bond |
| 178 | Me | HO | Me | CONHR⁹ | 4-OCHF₂ | H | | | 3-CF₃O-Ph | bond |
| 179 | Me | HO | Me | CONHR⁹ | 4-OCHF₂ | H | | | 4-Me-Ph | bond |
| 180 | Me | HO | Me | CONHR⁹ | 4-OCHF₂ | H | | | 4-t-Bu-Ph | bond |
| 181 | Me | HO | Me | CONHR⁹ | 4-OCHF₂ | H | | | 4-CF₃-Ph | bond |
| 182 | Me | HO | Me | CONHR⁹ | 4-OCHF₂ | H | | | 4-HO₂C-Ph | bond |

-continued

| Example # | R¹ | R² | R³ | R⁴ | R⁵ | R⁶ | R⁷ | R⁸ | R⁹ | A |
|---|---|---|---|---|---|---|---|---|---|---|
| 183 | Me | HO | Me | CONHR⁹ | 4-OCHF₂ | H | | | 4-CF₃O-Ph | bond |
| 184 | Me | HO | Me | CONHR⁹ | 4-OCHF₂ | H | | | 4-Ph-Ph | bond |
| 185 | Me | HO | Me | CONHR⁹ | 4-OCHF₂ | H | | | 3,5-Cl₂-4-NH₂-Ph | bond |
| 186 | Me | HO | Me | CONHR⁹ | 4-OCHF₂ | H | | | 2-Ph-Ph | bond |
| 187 | Me | HO | Me | CONHR⁹ | 4-OCHF₂ | H | | | 2-Bn-Ph | bond |
| 188 | Me | HO | Me | CONHR⁹ | 4-OCHF₂ | H | | | 2-PhO-Ph | bond |
| 189 | Me | HO | Me | CONHR⁹ | 4-OCHF₂ | H | | | 3-PhO-Ph | bond |
| 190 | Me | HO | Me | CONHR⁹ | 4-OCHF₂ | H | | | 4-PhO-Ph | bond |
| 191 | Me | HO | Me | CONHR⁹ | 4-OCHF₂ | H | | | 5-indane | bond |
| 192 | Me | HO | Me | CONHR⁹ | 4-OCHF₂ | H | | | 1-Naphthalene | bond |
| 193 | Me | HO | Me | CONHR⁹ | 4-OCHF₂ | H | | | 4-Cl-1-Naphthalene | bond |
| 194 | Me | HO | Me | CONHR⁹ | 4-OCHF₂ | H | | | 1-indane | bond |
| 195 | Me | HO | Me | CONHR⁹ | 4-OCHF₂ | H | | | 2-indane | bond |
| 196 | Me | HO | Me | CONHR⁹ | 4-OCHF₂ | H | | | 1-isoquinoline | bond |
| 197 | Me | HO | Me | CONHR⁹ | 4-OCHF₂ | H | | | 5-isoquinoline | bond |
| 198 | Me | HO | Me | CONHR⁹ | 4-OCHF₂ | H | | | 6-nicotinamide | bond |
| 199 | Me | HO | Me | CONHR⁹ | 4-OCHF₂ | H | | | 2-pyridine | bond |
| 200 | Me | HO | Me | CONHR⁹ | 4-OCHF₂ | H | | | 3-pyridine | bond |
| 201 | Me | HO | Me | CONHR⁹ | 4-OCHF₂ | H | | | 4-quinaldine | bond |
| 202 | Me | HO | Me | CONHR⁹ | 4-OCHF₂ | H | | | 5-quinoline | bond |
| 203 | Me | HO | Me | CONHR⁹ | 4-OCHF₂ | H | | | 3-pyrazole | bond |
| 204 | Me | HO | Me | CONHR⁹ | 4-OCHF₂ | H | | | 2-imidazole | bond |
| 205 | Me | HO | Me | CONHR⁹ | 4-OCHF₂ | H | | | 5-tetrazole | bond |
| 206 | Me | HO | Me | CONHR⁹ | 4-OCHF₂ | H | | | 3-methyl-5-isoxazole | bond |
| 207 | Me | HO | Me | CONHR⁹ | 4-OCHF₂ | H | | | 5-methyl-3-isoxazole | bond |
| 208 | Me | HO | Me | CONHR⁹ | 4-OCHF₂ | H | | | 3-methyl-5-isothiazole | bond |
| 209 | Me | HO | Me | CONHR⁹ | 4-OCHF₂ | H | | | 2-thiazole | bond |
| 210 | Me | HO | Me | CONHR⁹ | 4-OCHF₂ | H | | | Ph | bond |
| 211 | Me | HO | Me | CONHR⁹ | 4-OCHF₂ | H | | | 4-veratrole | bond |
| 212 | Me | HO | Me | CONHR⁹ | 4-OCHF₂ | H | | | 2-H₂NCO-Ph | bond |
| 213 | Me | HO | Me | CONHR⁹ | 4-OCHF₂ | H | | | 3-H₂NCO-Ph | bond |
| 214 | Me | HO | Me | CONHR⁹ | 4-OCHF₂ | H | | | 4-H₂NCO-Ph | bond |
| 215 | Me | HO | Me | CONHR⁹ | 4-OCHF₂ | H | | | 2-HO₂C-Ph | bond |
| 216 | Me | HO | Me | CONHR⁹ | 4-OCHF₂ | H | | | 3-HO₂C-Ph | bond |
| 217 | Me | HO | Me | CONHR⁹ | 4-CONH₂ | H | | | 4-Cl-Ph | bond |
| 218 | Me | HO | Me | CONHR⁹ | 4-CONH₂ | H | | | 2-t-Bu-Ph | bond |
| 219 | Me | HO | Me | CONHR⁹ | 4-CONH₂ | H | | | 2-CF₃-Ph | bond |
| 220 | Me | HO | Me | CONHR⁹ | 4-CONH₂ | H | | | 2-Cl-Ph | bond |
| 221 | Me | HO | Me | CONHR⁹ | 4-CONH₂ | H | | | 2-MeO-Ph | bond |
| 222 | Me | HO | Me | CONHR⁹ | 4-CONH₂ | H | | | 3-CF₃-Ph | bond |
| 223 | Me | HO | Me | CONHR⁹ | 4-CONH₂ | H | | | 3-Cl-Ph | bond |
| 224 | Me | HO | Me | CONHR⁹ | 4-CONH₂ | H | | | 3-MeO-Ph | bond |
| 225 | Me | HO | Me | CONHR⁹ | 4-CONH₂ | H | | | 3-CF₃O-Ph | bond |
| 226 | Me | HO | Me | CONHR⁹ | 4-CONH₂ | H | | | 4-Me-Ph | bond |
| 227 | Me | HO | Me | CONHR⁹ | 4-CONH₂ | H | | | 4-t-Bu-Ph | bond |
| 228 | Me | HO | Me | CONHR⁹ | 4-CONH₂ | H | | | 4-CF₃-Ph | bond |
| 229 | Me | HO | Me | CONHR⁹ | 4-CONH₂ | H | | | 4-HO₂C-Ph | bond |
| 230 | Me | HO | Me | CONHR⁹ | 4-CONH₂ | H | | | 4-CF₃O-Ph | bond |
| 231 | Me | HO | Me | CONHR⁹ | 4-CONH₂ | H | | | 4-Ph-Ph | bond |
| 232 | Me | HO | Me | CONHR⁹ | 4-CONH₂ | H | | | 3,5-Cl₂-4-NH₂-Ph | bond |
| 233 | Me | HO | Me | CONHR⁹ | 4-CONH₂ | H | | | 2-Ph-Ph | bond |
| 234 | Me | HO | Me | CONHR⁹ | 4-CONH₂ | H | | | 2-Bn-Ph | bond |
| 235 | Me | HO | Me | CONHR⁹ | 4-CONH₂ | H | | | 2-PhO-Ph | bond |
| 236 | Me | HO | Me | CONHR⁹ | 4-CONH₂ | H | | | 3-PhO-Ph | bond |
| 237 | Me | HO | Me | CONHR⁹ | 4-CONH₂ | H | | | 4-PhO-Ph | bond |
| 238 | Me | HO | Me | CONHR⁹ | 4-CONH₂ | H | | | 5-indane | bond |
| 239 | Me | HO | Me | CONHR⁹ | 4-CONH₂ | H | | | 1-Naphthalene | bond |
| 240 | Me | HO | Me | CONHR⁹ | 4-CONH₂ | H | | | 4-Cl-1-Naphthalene | bond |
| 241 | Me | HO | Me | CONHR⁹ | 4-CONH₂ | H | | | 1-indane | bond |
| 242 | Me | HO | Me | CONHR⁹ | 4-CONH₂ | H | | | 2-indane | bond |
| 243 | Me | HO | Me | CONHR⁹ | 4-CONH₂ | H | | | 1-isoquinoline | bond |
| 244 | Me | HO | Me | CONHR⁹ | 4-CONH₂ | H | | | 5-isoquinoline | bond |
| 245 | Me | HO | Me | CONHR⁹ | 4-CONH₂ | H | | | 6-nicotinamide | bond |
| 246 | Me | HO | Me | CONHR⁹ | 4-CONH₂ | H | | | 2-pyridine | bond |
| 247 | Me | HO | Me | CONHR⁹ | 4-CONH₂ | H | | | 3-pyridine | bond |
| 248 | Me | HO | Me | CONHR⁹ | 4-CONH₂ | H | | | 4-quinaldine | bond |
| 249 | Me | HO | Me | CONHR⁹ | 4-CONH₂ | H | | | 5-quinoline | bond |
| 250 | Me | HO | Me | CONHR⁹ | 4-CONH₂ | H | | | 3-pyrazole | bond |
| 251 | Me | HO | Me | CONHR⁹ | 4-CONH₂ | H | | | 2-imidazole | bond |
| 252 | Me | HO | Me | CONHR⁹ | 4-CONH₂ | H | | | 5-tetrazole | bond |
| 253 | Me | HO | Me | CONHR⁹ | 4-CONH₂ | H | | | 3-methyl-5-isoxazole | bond |
| 254 | Me | HO | Me | CONHR⁹ | 4-CONH₂ | H | | | 5-methyl-3-isoxazole | bond |
| 255 | Me | HO | Me | CONHR⁹ | 4-CONH₂ | H | | | 3-methyl-5-isothiazole | bond |
| 256 | Me | HO | Me | CONHR⁹ | 4-CONH₂ | H | | | 2-thiazole | bond |
| 257 | Me | HO | Me | CONHR⁹ | 4-CONH₂ | H | | | Ph | bond |
| 258 | Me | HO | Me | CONHR⁹ | 4-CONH₂ | H | | | 4-veratrole | bond |
| 259 | Me | HO | Me | CONHR⁹ | 4-CONH₂ | H | | | 2-H₂NCO-Ph | bond |
| 260 | Me | HO | Me | CONHR⁹ | 4-CONH₂ | H | | | 3-H₂NCO-Ph | bond |

-continued

| Example # | R¹ | R² | R³ | R⁴ | R⁵ | R⁶ | R⁷ | R⁸ | R⁹ | A |
|---|---|---|---|---|---|---|---|---|---|---|
| 261 | Me | HO | Me | CONHR⁹ | 4-CONH₂ | H | | | 4-H₂NCO-Ph | bond |
| 262 | Me | HO | Me | CONHR⁹ | 4-CONH₂ | H | | | 2-HO₂C-Ph | bond |
| 263 | Me | HO | Me | CONHR⁹ | 4-CONH₂ | H | | | 3-HO₂C-Ph | bond |
| 264 | Me | HO | Me | CONHR⁹ | 4-CONHOH | H | | | 4-Cl-Ph | bond |
| 265 | Me | HO | Me | CONHR⁹ | 4-CONHOH | H | | | 2-t-Bu-Ph | bond |
| 266 | Me | HO | Me | CONHR⁹ | 4-CONHOH | H | | | 2-CF₃-Ph | bond |
| 267 | Me | HO | Me | CONHR⁹ | 4-CONHOH | H | | | 2-Cl-Ph | bond |
| 268 | Me | HO | Me | CONHR⁹ | 4-CONHOH | H | | | 2-MeO-Ph | bond |
| 269 | Me | HO | Me | CONHR⁹ | 4-CONHOH | H | | | 3-CF₃-Ph | bond |
| 270 | Me | HO | Me | CONHR⁹ | 4-CONHOH | H | | | 3-Cl-Ph | bond |
| 271 | Me | HO | Me | CONHR⁹ | 4-CONHOH | H | | | 3-MeO-Ph | bond |
| 272 | Me | HO | Me | CONHR⁹ | 4-CONHOH | H | | | 3-CF₃O-Ph | bond |
| 273 | Me | HO | Me | CONHR⁹ | 4-CONHOH | H | | | 4-Me-Ph | bond |
| 274 | Me | HO | Me | CONHR⁹ | 4-CONHOH | H | | | 4-t-Bu-Ph | bond |
| 275 | Me | HO | Me | CONHR⁹ | 4-CONHOH | H | | | 4-CF₃-Ph | bond |
| 276 | Me | HO | Me | CONHR⁹ | 4-CONHOH | H | | | 4-HO₃C-Ph | bond |
| 277 | Me | HO | Me | CONHR⁹ | 4-CONHOH | H | | | 4-CF₃O-Ph | bond |
| 278 | Me | HO | Me | CONHR⁹ | 4-CONHOH | H | | | 4-Ph-Ph | bond |
| 279 | Me | HO | Me | CONHR⁹ | 4-CONHOH | H | | | 3,5-Cl₂-4-NH₂-Ph | bond |
| 280 | Me | HO | Me | CONHR⁹ | 4-CONHOH | H | | | 2-Ph-Ph | bond |
| 281 | Me | HO | Me | CONHR⁹ | 4-CONHOH | H | | | 2-Bn-Ph | bond |
| 282 | Me | HO | Me | CONHR⁹ | 4-CONHOH | H | | | 2-PhO-Ph | bond |
| 283 | Me | HO | Me | CONHR⁹ | 4-CONHOH | H | | | 3-PhO-Ph | bond |
| 284 | Me | HO | Me | CONHR⁹ | 4-CONHOH | H | | | 4-PhO-Ph | bond |
| 285 | Me | HO | Me | CONHR⁹ | 4-CONHOH | H | | | 5-indane | bond |
| 286 | Me | HO | Me | CONHR⁹ | 4-CONHOH | H | | | 1-Naphthalene | bond |
| 287 | Me | HO | Me | CONHR⁹ | 4-CONHOH | H | | | 4-Cl-1-Naphthalene | bond |
| 288 | Me | HO | Me | CONHR⁹ | 4-CONHOH | H | | | 1-indane | bond |
| 289 | Me | HO | Me | CONHR⁹ | 4-CONHOH | H | | | 2-indane | bond |
| 290 | Me | HO | Me | CONHR⁹ | 4-CONHOH | H | | | 1-isoquinoline | bond |
| 291 | Me | HO | Me | CONHR⁹ | 4-CONHOH | H | | | 5-isoquinoline | bond |
| 292 | Me | HO | Me | CONHR⁹ | 4-CONHOH | H | | | 6-nicotinamide | bond |
| 293 | Me | HO | Me | CONHR⁹ | 4-CONHOH | H | | | 2-pyridine | bond |
| 294 | Me | HO | Me | CONHR⁹ | 4-CONHOH | H | | | 3-pyridine | bond |
| 295 | Me | HO | Me | CONHR⁹ | 4-CONHOH | H | | | 4-quinaldine | bond |
| 296 | Me | HO | Me | CONHR⁹ | 4-CONHOH | H | | | 5-quinoline | bond |
| 297 | Me | HO | Me | CONHR⁹ | 4-CONHOH | H | | | 3-pyrazole | bond |
| 298 | Me | HO | Me | CONHR⁹ | 4-CONHOH | H | | | 2-imidazole | bond |
| 299 | Me | HO | Me | CONHR⁹ | 4-CONHOH | H | | | 5-tetrazole | bond |
| 300 | Me | HO | Me | CONHR⁹ | 4-CONHOW | H | | | 3-methyl-5-isoxazole | bond |
| 301 | Me | HO | Me | CONHR⁹ | 4-CONHOH | H | | | 5-methyl-3-isoxazole | bond |
| 302 | Me | HO | Me | CONHR⁹ | 4-CONHOH | H | | | 3-methyl-5-isothiazole | bond |
| 303 | Me | HO | Me | CONHR⁹ | 4-CONHOH | H | | | 2-thiazole | bond |
| 304 | Me | HO | Me | CONHR⁹ | 4-CONHOH | H | | | Ph | bond |
| 305 | Me | HO | Me | CONHR⁹ | 4-CONHOH | H | | | 4-veratrole | bond |
| 306 | Me | HO | Me | CONHR⁹ | 4-CONHOH | H | | | 2-H₂NCO-Ph | bond |
| 307 | Me | HO | Me | CONHR⁹ | 4-CONHOH | H | | | 3-H₂NCO-Ph | bond |
| 308 | Me | HO | Me | CONHR⁹ | 4-CONHOH | H | | | 4-H₂NCO-Ph | bond |
| 309 | Me | HO | Me | CONHR⁹ | 4-CONHOH | H | | | 2-HO₂C-Ph | bond |
| 310 | Me | HO | Me | CONHR⁹ | 4-CONHOH | H | | | 3-HO₂C-Ph | bond |
| 311 | Me | HO | Ph | Me | H | H | | 4-OCHF₂ | | CH₂ |
| 312 | Me | HO | Ph | Me | H | H | | 4-CONH₂ | | CH₂ |
| 313 | Me | HO | Ph | Me | H | H | | 4-CONHOH | | CH₂ |
| 314 | Me | HO | Ph | Me | H | H | | 4-OMe | | CH₂ |
| 315 | Me | HO | Ph | Me | H | H | | 4-CN | | CH₂ |
| 316 | Me | HO | 5-veratrole | Me | H | H | | | | CH₂ |
| 317 | Me | HO | Ph | Me | 4-F | H | | 4-OCHF₂ | | CH₂ |
| 318 | Me | HO | Ph | Me | 4-F | H | | 4-CONH₂ | | CH₂ |
| 319 | Me | HO | Ph | Me | 4-F | H | | 4-CONHOH | | CH₂ |
| 320 | Me | HO | Ph | Me | 4-F | H | | 4-OMe | | CH₂ |
| 321 | Me | HO | Ph | Me | 4-F | H | | 4-CN | | CH₂ |
| 322 | Me | HO | 5-veratrole | Me | 4-F | H | | | | CH₂ |
| 323 | Me | HO | Ph | Me | 4-Cl | H | | 4-OCHF₂ | | CH₂ |
| 324 | Me | HO | Ph | Me | 4-Cl | H | | 4-CONH₂ | | CH₂ |
| 325 | Me | HO | Ph | Me | 4-Cl | H | | 4-CONHOH | | CH₂ |
| 326 | Me | HO | Ph | Me | 4-Cl | H | | 4-OMe | | CH₂ |
| 327 | Me | HO | Ph | Me | 4-Cl | H | | 4-CN | | CH₂ |
| 328 | Me | HO | 5-veratrole | Me | 4-Cl | H | | | | CH₂ |
| 329 | Me | HO | Ph | Me | 3-CF₃ | H | | 4-OCHF₂ | | CH₂ |
| 330 | Me | HO | Ph | Me | 3-CF₃ | H | | 4-CONH₂ | | CH₂ |
| 331 | Me | HO | Ph | Me | 3-CF₃ | H | | 4-CONHOH | | CH₂ |
| 332 | Me | HO | Ph | Me | 3-CF₃ | H | | 4-OMe | | CH₂ |
| 333 | Me | HO | Ph | Me | 3-CF₃ | H | | 4-CN | | CH₂ |
| 334 | Me | HO | 5-veratrole | Me | 3-CF₃ | H | | | | CH₂ |
| 335 | Me | HO | Ph | CH₂OH | H | H | | 4-OCHF₂ | | CH₂ |
| 336 | Me | HO | Ph | CH₂OH | H | H | | 4-CONH₂ | | CH₂ |
| 337 | Me | HO | Ph | CH₂OH | H | H | | 4-CONHOH | | CH₂ |
| 338 | Me | HO | Ph | CH₂OH | H | H | | 4-OMe | | CH₂ |

-continued

| Example # | R¹ | R² | R³ | R⁴ | R⁵ | R⁶ | R⁷ | R⁸ | R⁹ | A |
|---|---|---|---|---|---|---|---|---|---|---|
| 339 | Me | HO | Ph | CH₂OH | H | H | | 4-CN | | CH₂ |
| 340 | Me | HO | 5-veratrole | CH₂OH | H | H | | | | CH₂ |
| 341 | Me | HO | Ph | CH₂OH | 4-F | H | | 4-OCHF₂ | | CH₂ |
| 342 | Me | HO | Ph | CH₂OH | 4-F | H | | 4-CONH₂ | | CH₂ |
| 343 | Me | HO | Ph | CH₂OH | 4-F | H | | 4-CONHOH | | CH₂ |
| 344 | Me | HO | Ph | CH₂OH | 4-F | H | | 4-OMe | | CH₂ |
| 345 | Me | HO | Ph | CH₂OH | 4-F | H | | 4-CN | | CH₂ |
| 346 | Me | HO | 5-veratrole | CH₂OH | 4-F | H | | | | CH₂ |
| 347 | Me | HO | Ph | CH₂OH | 4-Cl | H | | 4-OCHF₂ | | CH₂ |
| 348 | Me | HO | Ph | CH₂OH | 4-Cl | H | | 4-CONH₂ | | CH₂ |
| 349 | Me | HO | Ph | CH₂OH | 4-Cl | H | | 4-CONHOH | | CH₂ |
| 350 | Me | HO | Ph | CH₂OH | 4-Cl | H | | 4-OMe | | CH₂ |
| 351 | Me | HO | Ph | CH₂OH | 4-Cl | H | | 4-CN | | CH₂ |
| 352 | Me | HO | 5-veratrole | CH₂OH | 4-Cl | H | | | | CH₂ |
| 353 | Me | HO | Ph | CH₂OH | 3-CF₃ | H | | 4-OCHF₂ | | CH₂ |
| 354 | Me | HO | Ph | CH₂OH | 3-CF₃ | H | | 4-CONH₂ | | CH₂ |
| 355 | Me | HO | Ph | CH₂OH | 3-CF₃ | H | | 4-CONHOH | | CH₂ |
| 356 | Me | HO | Ph | CH₂OH | 3-CF₃ | H | | 4-OMe | | CH₂ |
| 357 | Me | HO | Ph | CH₂OH | 3-CF₃ | H | | 4-CN | | CH₂ |
| 358 | Me | HO | 5-veratrole | CH₂OH | 3-CF₃ | H | | | | CH₂ |
| 359 | Me | HO | Ph | CONH₂ | H | H | | 4-OCHF₂ | | CH₂ |
| 360 | Me | HO | Ph | CONH₂ | H | H | | 4-CONH₂ | | CH₂ |
| 361 | Me | HO | Ph | CONH₂ | H | H | | 4-CONHOH | | CH₂ |
| 362 | Me | HO | Ph | CONH₂ | H | H | | 4-OMe | | CH₂ |
| 363 | Me | HO | Ph | CONH₂ | H | H | | 4-CN | | CH₂ |
| 364 | Me | HO | 5-veratrole | CONH₂ | H | H | | | | CH₂ |
| 365 | Me | HO | Ph | CONH₂ | 4-F | H | | 4-OCHF₂ | | CH₂ |
| 366 | Me | HO | Ph | CONH₂ | 4-F | H | | 4-CONH₂ | | CH₂ |
| 367 | Me | HO | Ph | CONH₂ | 4-F | H | | 4-CONHOH | | CH₂ |
| 368 | Me | HO | Ph | CONH₂ | 4-F | H | | 4-OMe | | CH₂ |
| 369 | Me | HO | Ph | CONH₂ | 4-F | H | | 4-CN | | CH₂ |
| 370 | Me | HO | 5-veratrole | CONH₂ | 4-F | H | | | | CH₂ |
| 371 | Me | HO | Ph | CONH₂ | 4-Cl | H | | 4-OCHF₂ | | CH₂ |
| 372 | Me | HO | Ph | CONH₂ | 4-Cl | H | | 4-CONH₂ | | CH₂ |
| 373 | Me | HO | Ph | CONH₂ | 4-Cl | H | | 4-CONHOH | | CH₂ |
| 374 | Me | HO | Ph | CONH₂ | 4-Cl | H | | 4-OMe | | CH₂ |
| 375 | Me | HO | Ph | CONH₂ | 4-Cl | H | | 4-CN | | CH₂ |
| 376 | Me | HO | 5-veratrole | CONH₂ | 4-Cl | H | | | | CH₂ |
| 377 | Me | HO | Ph | CONH₂ | 3-CF₃ | H | | 4-OCHF₂ | | CH₂ |
| 378 | Me | HO | Ph | CONH₂ | 3-CF₃ | H | | 4-CONH₂ | | CH₂ |
| 379 | Me | HO | Ph | CONH₂ | 3-CF₃ | H | | 4-CONHOH | | CH₂ |
| 380 | Me | HO | Ph | CONH₂ | 3-CF₃ | H | | 4-OMe | | CH₂ |
| 381 | Me | HO | Ph | CONH₂ | 3-CF₃ | H | | 4-CN | | CH₂ |
| 382 | Me | HO | 5-veratrole | CONH₂ | 3-CF₃ | H | | | | CH₂ |
| 383 | Me | CH₂OH | Ph | H | H | H | | 4-OCHF₂ | | CH₂ |
| 384 | Me | CH₂OH | Ph | H | H | H | | 4-CONH₂ | | CH₂ |
| 385 | Me | CH₂OH | Ph | H | H | H | | 4-CONHOH | | CH₂ |
| 386 | Me | CH₂OH | Ph | H | H | H | | 4-OMe | | CH₂ |
| 387 | Me | CH₂OH | Ph | H | H | H | | 4-CN | | CH₂ |
| 388 | Me | CH₂OH | 5-veratrole | H | H | H | | | | CH₂ |
| 389 | Me | CH₂OH | Ph | H | 4-F | H | | 4-OCHF₂ | | CH₂ |
| 390 | Me | CH₂OH | Ph | H | 4-F | H | | 4-CONH₂ | | CH₂ |
| 391 | Me | CH₂OH | Ph | H | 4-F | H | | 4-CONHOH | | CH₂ |
| 392 | Me | CH₂OH | Ph | H | 4-F | H | | 4-OMe | | CH₂ |
| 393 | Me | CH₂OH | Ph | H | 4-F | H | | 4-CN | | CH₂ |
| 394 | Me | CH₂OH | 5-veratrole | H | 4-F | H | | | | CH₂ |
| 395 | Me | CH₂OH | Ph | H | 4-Cl | H | | 4-OCHF₂ | | CH₂ |
| 396 | Me | CH₂OH | Ph | H | 4-Cl | H | | 4-CONH₂ | | CH₂ |
| 397 | Me | CH₂OH | Ph | H | 4-Cl | H | | 4-CONHOH | | CH₂ |
| 398 | Me | CH₂OH | Ph | H | 4-Cl | H | | 4-OMe | | CH₂ |
| 399 | Me | CH₂OH | Ph | H | 4-Cl | H | | 4-CN | | CH₂ |
| 400 | Me | CH₂OH | 5-veratrole | H | 4-Cl | H | | | | CH₂ |
| 401 | Me | CH₂OH | Ph | H | 3-CF₃ | H | | 4-OCHF₂ | | CH₂ |
| 402 | Me | CH₂OH | Ph | H | 3-CF₃ | H | | 4-CONH₂ | | CH₂ |
| 403 | Me | CH₂OH | Ph | H | 3-CF₃ | H | | 4-CONHOH | | CH₂ |
| 404 | Me | CH₂OH | Ph | H | 3-CF₃ | H | | 4-OMe | | CH₂ |
| 405 | Me | CH₂OH | Ph | H | 3-CF₃ | H | | 4-CN | | CH₂ |
| 406 | Me | CH₂OH | 5-veratrole | H | 3-CF₃ | H | | | | CH₂ |
| 407 | Me | F | Ph | H | H | H | | 4-OCHF₂ | | CH₂ |
| 408 | Me | F | Ph | H | H | H | | 4-CONH₂ | | CH₂ |
| 409 | Me | F | Ph | H | H | H | | 4-CONHOH | | CH₂ |
| 410 | Me | F | Ph | H | H | H | | 4-OMe | | CH₂ |
| 411 | Me | F | Ph | H | H | H | | 4-CN | | CH₂ |
| 412 | Me | F | H | CONHR⁹ | 4-OMe | H | | | 4-Cl-Ph | bond |
| 413 | Me | Cl | Ph | H | H | H | | 4-OCHF₂ | | CH₂ |
| 414 | Me | Cl | Ph | H | H | H | | 4-CONH₂ | | CH₂ |
| 415 | Me | Cl | Ph | H | H | H | | 4-CONHOH | | CH₂ |
| 416 | Me | Cl | Ph | H | H | H | | 4-OMe | | CH₂ |

| Example # | R¹ | R² | R³ | R⁴ | R⁵ | R⁶ | R⁷ | R⁸ | R⁹ | A |
|---|---|---|---|---|---|---|---|---|---|---|
| 417 | Me | Cl | Ph | H | H | H | | | 4-CN | $CH_2$ |
| 418 | Me | Cl | H | $CONHR^9$ | 4-OMe | H | | | 4-Cl-Ph | bond |
| 419 | Me | HO | Ph | $CH_2OH$ | $4-OCHF_2$ | H | | | $4-OCHF_2$ | bond |
| 420 | Me | HO | Ph | $CH_2OH$ | $4-CONH_2$ | H | | | $4-CONH_2$ | bond |
| 421 | Me | HO | Ph | $CH_2OH$ | 4-CONHOH | H | | | 4-CONHOH | bond |
| 422 | Me | HO | Ph | $CH_2OH$ | 4-CN | H | | | 4-CN | bond |
| 423 | Me | HO | Ph | Me | $4-OCHF_2$ | H | | | $4-OCHF_2$ | bond |
| 424 | Me | HO | Ph | Me | $4-CONH_2$ | H | | | $4-CONH_2$ | bond |
| 425 | Me | HO | Ph | Me | 4-CONHOH | H | | | 4-CONHOH | bond |
| 426 | Me | HO | Ph | Me | 4-CN | H | | | 4-CN | bond |
| 427 | Me | $CH_2OH$ | Me | $CONHR^9$ | $4-CONH_2$ | H | | | 4-Cl-Ph | bond |
| 428 | Me | $CH_2OH$ | Me | $CONHR^9$ | 4-OMe | H | | | 4-Cl-Ph | bond |
| 429 | Me | $CH_2OH$ | Me | $CONHR^9$ | 4-CONHOH | H | | | 4-Cl-Ph | bond |
| 430 | Me | $CH_2OH$ | Me | $CONHR^9$ | $4-OCHF_2$ | H | | | 4-Cl-Ph | bond |

What is claimed is:

1. A compound of the formula

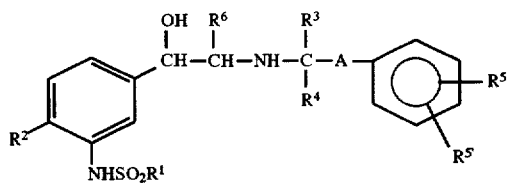

or pharmaceutically acceptable salts thereof wherein:

A is a bond, $-(CH_2)_n-$ or $-CH(B)-$, where n is an integer of 1 to 3 and B is $-CN$, $-CON(R^9)R^{9'}$ or $-CO_2R^7$;

$R^1$ is lower alkyl, aryl or arylalkyl;

$R^2$ is hydrogen, hydroxy, alkoxy, $-CH_2OH$, cyano, $-C(O)OR^7$, $-CO_2H$, $-CONH_2$, tetrazole, $-CH_2NH_2$ or halogen;

$R^3$ is

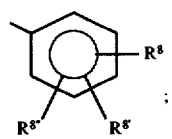

$R^4$ is hydrogen, alkyl or B;

$R^5$, $R^{5'}$, $R^8$, $R^{8'}$ or $R^{8''}$ are independently hydrogen, alkoxy, lower alkyl, halogen, $-OH$, $-CN$, $-(CH_2)_nNR^6COR^7$, $-CON(R^6)R^{6'}$, $-CON(R^6)OR^{6'}$, $-CO_2R^6$, $-SR^7$, $-SOR^7$, $-SO_2R^7$, $-N(R^6)SO_2R^1$, $-N(R^6)R^{6'}$, $-NR^6COR^7$, $-OCH_2CON(R^6)R^{6'}$, $-OCH_2CO_2R^7$ or aryl; or $R^5$ and $R^{5'}$ or $R^8$ and $R^{8'}$ may together with the carbon atoms to which they are attached form an aryl or heterocycle;

$R^6$ and $R^{6'}$ are independently hydrogen or lower alkyl; and $R^7$ is lower alkyl;

$R^9$ is hydrogen, lower alkyl, alkyl, cycloalkyl, arylalkyl, aryl, heteroaryl; or $R^9$ and $R^{9'}$ may together with the nitrogen atom to which they are attached form a heterocycle.

2. The compounds as recited in claim 1 wherein

A is a bond, $-(CH_2)_n-$, where n is 1 or $-CH(B)$;

$R^5$ and $R^{5'}$ are independently hydrogen, halogen, lower alkyl, alkoxy, $-CON(R^6)R^{6'}$, or $-CON(R^6)OR^{6'}$; and the benzylic hydroxyl stereocenter has the (R) configuration.

3. The compounds as recited in claim 1 wherein

A is a bond;

$R^1$ is a lower alkyl;

$R^4$ is hydrogen or alkyl;

$R^5$ and $R^8$ are both $-CN$, $-CON(R^6)R^{6'}$, $-CON(R^6)OR^{6'}$, hydroxy, alkoxy or $-CH_2Y$ where Y is $-CN$, alkoxy, $-CON(R^6)R^{6'}$, $-CO_2R^7$ or $-N(R^6)SO_2R^1$; or $R^5$, $R^{5'}$, $R^8$ and $R^{8'}$ together with the carbon atoms to which they are attached form an aryl or heterocycle; and the benzylic hydroxyl stereocenter has the (R) configuration.

4. The compound as recited in claim 1 wherein

A is $-CH_2$;

$R^1$ is a lower alkyl;

$R^4$ is hydrogen, alkyl, $-CN$, or $-CON(R^9)R^{9'}$;

$R^5$ is hydrogen, halogen or $CF_3$;

$R^8$ is $-CN$, $-CON(R^6)R^{6'}$, $-CON(R^6)OR^{6'}$, hydroxy, lower alkyl or alkoxy; or $R^8$ and $R^{8'}$ together with the carbon atoms to which they are attached form an aryl or heterocycle; and the configuration of the stereocenter bearing the $R^3$ and $R^4$ substituents is (R) when $R^4$ is hydrogen and the benzylic hydroxyl stereocenter has the (R) configuration.

5. The compound as recited in claim 1, which is

N-|5-[2-[[1-(3,4-dimethoxyphenyl)-2-phenylethyl| amino|-1-hydroxyethyl]-2-hydroxyphenyl| methanesulfonamide;

N-[5-[2-[(1,2-diphenylethyl)amino]-1-hydroxyethyl]-2-hydroxyphenyl|methanesulfonamide;

N-|5-[2-|[1-(1,3-benzodioxol-5-yl)-2-phenylethyl| amino|-1-hydroxyethyl]-2-hydroxyphenyl| methanesulfonamide;

N-|5-[1-hydroxy-2-|[1-(4-methoxyphenyl)-2-phenylethyl]amino|ethyl]-2-hydroxyphenyl] methanesulfonamide;

N-[5-[2-[[1-(3-methoxyphenyl)-2-phenylethyl|amino]-1-hydroxyethyl]-2-hydroxyphenyl]methanesulfonamide;

N-|5-[2-[[1-(2,4-dimethoxyphenyl)-2-phenylethyl| amino|-1-hydroxyethyl]-2-hydroxyphenyl| methanesulfonamide;

N-[5-[2-[[1-(3,4-dichlorophenyl)-2-phenylethyl|amino]-1-hydroxyethyl]-2-hydroxyphenyl| methanesulfonamide;

N-[5-[2-[[1-(4-methylsulfonylphenyl)-2-phenylethyl| amino|-1-hydroxyethyl]-2-hydroxyphenyl| methanesulfonamide;

N-[5-[2-[[1-(3,4-dimethylphenyl)-2-phenylethyl]amino]-1-hydroxyethyl]-2-hydroxyphenyl]methanesulfonamide;

N-[5-[2-[[1-(3,4-diethylphenyl)-2-phenylethyl]amino]-1-hydroxyethyl]-2-hydroxyphenyl]methanesulfonamide;

N-[5-[2-[[1-phenyl-2-(3,4-dimethoxyphenyl)ethyl]amino]-1-hydroxyethyl]-2-hydroxyphenyl]methanesulfonamide;

N-[5-[2-[[1-phenyl-2-(4-methoxyphenyl)ethyl]amino]-1-hydroxyethyl]-2-hydroxyphenyl]methanesulfonamide;

N-[5-[2-[[1-(4-methoxyphenyl)-2-(4-methoxyphenyl)ethyl]amino]-1-hydroxyethyl]-2-hydroxyphenyl]methanesulfonamide;

N-[5-[2-[[bis(4-Methoxyphenyl)methyl]amino]-1-hydroxyethyl]-2-hydroxyphenyl]methanesulfonamide;

N-[5-[1-hydroxy-2-[[(4-methoxyphenyl)phenylmethyl]amino]ethyl]-2-hydroxyphenyl]methanesulfonamide;

[α-[[[2-hydroxy-2-[4-hydroxy-3-[(methylsulfonyl)amino]phenyl]-ethyl]amino]methyl]benzeneacetic acid, ethyl ester;]

[α-[[[2-hydroxy-2-[4-hydroxy-3-[(methylsulfonyl)amino]phenyl]ethyl]amino]methyl]-3,4-dimethoxybenzeneacetic acid, methyl ester;]

[α-[[[2-hydroxy-2-[4-hydroxy-3-[(methylsulfonyl)amino]phenyl]ethyl]amino]methyl]-N,N-dimethylbenzeneacetamide;]

(R),(R)-N-[5-[1-(hydroxy-2-[[1-(3,4-dimethoxyphenyl)-2-phenylethyl]amino]ethyl]-2-(hydroxy)phenyl]methanesulfonamide;

(R)-N-[5-[2-[[bis(4-methoxyphenyl)methyl]amino]-1-hydroxy-ethyl]-2-hydroxyphenyl]methanesulfonamide;

(R)-N-[5-[2-[[bis(4-fluorophenyl)methyl]amino]-1-hydroxy-ethyl]-2-hydroxyphenyl]methanesulfonamide;

(R),(S)-N-[5-[1-(hydroxy-2-[[1-(3,4-dimethoxyphenyl)-2-phenylethyl]-amino]ethyl]-2-(hydroxy)phenyl]methanesulfonamide;

(threo)-β-[[(R)-2-hydroxy-2-[4-hydroxy-3-[(methylsulfonyl)-amino]phenyl]ethyl]amino]-4-methoxy-α-phenylbenzenepropanoic acid, methyl ester, diastereomer A;

(threo)-β-[[(R)-2-hydroxy-2-[4-hydroxy-3-[(methylsulfonyl)-amino]phenyl]ethyl]amino]-4-methoxy-α-phenylbenzenepropanoic acid, methyl ester, diastereomer B;

(erythro)-β-[[(R)-2-hydroxy-2-[4-hydroxy-3-[(methylsulfonyl)-amino]phenyl]ethyl]amino]-4-methoxy-α-phenylbenzenepropanoic acid, methyl ester, diastereomer A;

(erythro)-β-[[(R)-2-hydroxy-2-[4-hydroxy-3-[(methylsulfonyl)-amino]phenyl]ethyl]amino]-4-methoxy-α-phenylbenzenepropanoic acid, methyl ester, diastereomer B;

N-[3-[2-[[1-(3,4-dimethoxyphenyl)-2-phenylethyl]amino]-1-hydroxyethyl]phenyl]methanesulfonamide;

(R)-N-[3-[2-[[bis(4-methoxyphenyl)methyl]amino]-1-hydroxy-ethyl]phenyl]methanesulfonamide;

(R,R)-N-[3-[2-[[1-(3,4-dimethoxyphenyl)-2-phenylethyl]amino]-1-hydroxyethyl]phenyl]methanesulfonamide;

[ε-[[2-hydroxy-2-[4-hydroxy-3-[(methylsulfonyl)amino]phenyl]ethyl]amino]benzeneheptanoic acid, methyl ester;]

[ε-[[2-hydroxy-2-[4-hydroxy-3-[(methylsulfonyl)amino]phenyl]ethyl]amino]benzeneheptanoic acid;]

[N-[5-[1-hydroxy-2-[[6-hydroxy-1-(phenylmethyl)hexyl]amino]ethyl]-2-hydroxyphenyl]methanesulfonamide;]

[ε-[[2-hydroxy-2-[4-hydroxy-3-[(methylsulfonyl)amino]phenyl]ethyl]amino]-N,N-dimethylbenzeneheptanamide;]

[ε-[[2-hydroxy-2-[4-hydroxy-3-[(methylsulfonyl)amino]phenyl]-ethyl]amino]-N-methylbenzeneheptamide;]

[ε-[[2-hydroxy-2-[4-hydroxy-3-[(methylsulfonyl)amino]phenyl]-ethyl]amino]-3,4-dimethoxybenzeneheptanoic acid, methyl ester;]

[N-[2-hydroxy-5-[(R)-1-hydroxy-2-[[2-phenyl-1-(4-pyridinyl)-ethyl]amino]ethyl]phenyl]methanesulfonamide;]

[α-[[(R)-2-hydroxy-2-[4-hydroxy-3-[(methylsulfonyl)amino]phenyl]ethyl]amino]-4-methoxybenzeneacetamide, isomer B;]

(R)-α-[[2-hydroxy-2-[4-hydroxy-3-[(methylsulfonyl)amino]phenyl]ethyl]amino]-α-(4-methoxyphenyl)-4-methoxybenzeneacetamide;

N-[5-[2-[[bis(4-methoxymethylphenyl)methyl]amino]-1-hydroxy-ethyl]-2-hydroxyphenyl]methanesulfonamide;

(R),(R)-N-[5-[2-[[1-(1,3-benzodioxol-5-yl)-2-phenylethyl]amino]-1-hydroxyethyl]-2-hydroxyphenyl]methanesulfonamide;

(R),(S)-N-[5-[2-[[1-(1,3-benzodioxol-5-yl)-2-phenylethyl]amino]-1-hydroxyethyl]-2-hydroxyphenyl]methanesulfonamide;

N-[5-[2-[[bis(4-methoxyphenyl)methyl]amino]-1-hydroxyethyl]-2-fluorophenyl]methanesulfonamide;

[N-[2-hydroxy-5-[(R)-1-hydroxy-2-[[2-phenyl-1-(3-thienyl)ethyl]-amino]ethyl]phenyl]methanesulfonamide;]

(R),(R)-N-[5-[1-(hydroxy-2-[[1-(4-methoxyphenyl)-2-(4-fluorophenyl)ethyl]amino]ethyl]-2-(hydroxy)phenyl]methanesulfonamide;

(R),(S)-N-[5-[1-(hydroxy-2-[[1-(4-methoxyphenyl)-2-(4-fluorophenyl)ethyl]amino]ethyl]-2-(hydroxy)phenyl]methanesulfonamide;

(R),(R)-N-[5-[1-(hydroxy-2-[[1-(4-hydroxyphenyl)-2-(4-fluorophenyl)ethyl]amino]ethyl]-2-(hydroxy)phenyl]methanesulfonamide;

(R),(S)-N-[5-[1-(hydroxy-2-[[1-(4-hydroxyphenyl)-2-(4-fluorophenyl)ethyl]amino]ethyl]-2-(hydroxy)phenyl]methanesulfonamide;

(R),(S)-N-[5-[1-(hydroxy-2-[[1-(4-phenylmethoxyphenyl)-2-(4-fluorophenyl)ethyl]amino]ethyl]-2-(hydroxy)phenyl]methanesulfonamide;

(R),(R)-N-[5-[1-(hydroxy-2-[[1-(4-methoxyphenyl)-2-(3-trifluoromethylphenyl)ethyl]amino]ethyl]-2-(hydroxy)phenyl]methanesulfonamide;

(R),(S)-N-[5-[1-(hydroxy-2-[[1-(4-methoxyphenyl)-2-(3-trifluoromethylphenyl)ethyl]amino]ethyl]-2-(hydroxy)phenyl]methanesulfonamide;

(R),(R)-N-[5-[1-(hydroxy-2-[[1-(4-difluoromethoxyphenyl)-2-(4-fluorophenyl)ethyl]amino]ethyl]-2-(hydroxy)phenyl]methanesulfonamide;

(R),(S)-N-[5-[1-(hydroxy-2-[[1-(4-difluoromethoxyphenyl)-2-(4-fluorophenyl)ethyl]amino]ethyl]-2-(hydroxy)phenyl]methanesulfonamide;

(R),(R)-N-[5-[1-(hydroxy-2-[[1-(4-difluoromethoxyphenyl)-2-(phenyl)ethyl]amino]ethyl]-2-(hydroxy)phenyl]methanesulfonamide;

(R),(S)-N-[5-[1-(hydroxy-2-[[1-(4-difluoromethoxyphenyl)-2-(phenyl)ethyl]amino]ethyl]-2-(hydroxy)phenyl]methanesulfonamide;

(R)-N-[5-[2-[[bis-(4-difluoromethoxyphenyl)methyl]amino]-1-hydroxyethyl]-2-hydroxyphenyl]methanesulfonamide;

(R),(R)-N-[3-[2-[[1-(1,3-benzodioxol-5-yl)-2-phenylethyl]amino]-1-hydroxyethyl]phenyl]methanesulfonamide;

(R),(R)-N-[3-[2-[[1-(4-difluoromethoxyphenyl)-2-(4-fluorophenyl)-ethyl]amino]-1-hydroxyethyl]phenyl]methanesulfonamide;

(R),(S)-N-[3-[2-[[1-(4-difluoromethoxyphenyl)ethyl]amino]-1-hydroxyethyl]phenyl]methanesulfonamide;

(R),(R)-N-[5-[2-[[1-(4-difluoromethoxyphenyl)-2-(4-fluoro-phenyl)-ethyl]amino]-1-hydroxyethyl]-2-fluorophenyl]methanesulfonamide;

(R),(S)-N-[5-[2-[[1-(4-difluoromethoxyphenyl)-2-(4-fluoro-phenyl)ethyl]amino]-1-hydroxyethyl]-2-fluorophenyl]methanesulfonamide;

N-[5-[2-[[1,2-diphenyl-1-(trifluoromethyl)ethyl]amino]-1-hydroxy-ethyl]-2-hydroxyphenyl]methanesulfonamide;

[α-[[[(R)-2-hydroxy-2-[4-hydroxy-3-[(methylsulfonyl)amino]phenyl]ethyl]amino]methyl]-3,4-dimethoxy-N,N-dimethylbenzeneacetamide, diastereomer A;]

[α-[[[(R)-2-hydroxy-2-[4-hydroxy-3-[(methylsulfonyl)amino]phenyl]ethyl]amino]methyl]-3,4-dimethoxy-N,N-dimethylbenzenacetamide, diastereomer B;]

N-[5-[2-[[(R)1-(3,4-dimethoxyphenyl)-2-phenylethyl]amino]-1-hydroxyethyl]-2-fluorophenyl]methanesulfonamide;

N-[5-[2-[[(R)1-(1-(1,3-benzodioxol-5-yl)-2-phenylethyl]amino]-1-hydroxyethyl]-2-chlorophenyl]methanesulfonamide;

N-[5-[2-[[(R)1-(1-(1,3-benzodioxol-5-yl)-2-phenylethyl]amino]-1-hydroxyethyl]-2-methoxyphenyl]methanesulfonamide;

(R),(R)-N-[5-[2-[[1-(1-(1,3-benzodioxol-5-yl)-2-phenylethyl]-amino]-1-hydroxyethyl]-2-fluorophenyl]methanesulfonamide;

(R),(R)-N-[5-[2-[[1-(1-(3,4-dimethoxyphenyl)-2-phenylethyl]amino]-1-hydroxyethyl]-2-fluorophenyl]methanesulfonamide;

(R)-N-[5-[2-[[bis-(4-difluoromethoxyphenyl)methyl]amino]-1-hydroxyethyl]-2-fluorophenyl]methanesulfonamide;

(R),(R)-N-[5-[1-(hydroxy-2-[[1-(3,4-dimethylphenyl)-2-phenylethyl]-amino]ethyl]-2-(hydroxy)phenyl]methanesulfonamide;

[(R)-N-[5-[1-(hydroxy-2-[[1-(4-hydroxyphenyl)-2-(2-thienyl)ethyl]-amino]ethyl]-2-(hydroxy)phenyl]methanesulfonamide;]

(R)-N-[5-[2-[[bis[4-(2-methoxy-2-oxoethoxy)phenylmethyl]amino]-1-hydroxyethyl]-2-hydroxyphenyl]methanesulfonamide;

(R),(R)-N-[5-[2-[[1-(1-(1,3-benzodioxol-5-yl)-2-phenylethyl]-amino]-1-hydroxyethyl]-2-chlorophenyl]methanesulfonamide;

(R),(R)-4-[1-[[2-hydroxy-2-[4-hydroxy-3-[(methylsulfonyl)amino]-phenyl]ethyl]amino]-2-phenylethyl]benzoic acid, methyl ester;

(R),(S)-4-[1-[[2-hydroxy-2-[4-hydroxy-3-[(methylsulfonyl)amino]phenyl]ethyl]amino]-2-phenylethyl]benzoic acid, methyl ester;

(R),(R)-4-[1-[[2-hydroxy-2-[4-hydroxy-3-[(methylsulfonyl)amino]phenyl]ethyl]amino]-2-phenylethyl]benzoic acid;

(R),(S)-4-[1-[[2-hydroxy-2-[4-hydroxy-3-[(methylsulfonyl)amino]phenyl]ethyl]amino]-2-phenylethyl]benzoic acid;

(R),(R)-4-[1-[[2-hydroxy-2-[4-hydroxy-3-[(methylsulfonyl)amino]phenyl]ethyl]amino]-2-phenylethyl]-N-methylbenzamide;

(R),(R)-N-[5-[1-(hydroxy-2-[[1-(2-naphthalenyl)-2-(phenyl)ethyl]-amino]ethyl]-2-(hydroxy)phenyl]methanesulfonamide;

(R),(S)-N-[5-[1-(hydroxy-2-[[1-(2-naphthalenyl)-2-(phenyl)ethyl]-amino]ethyl]-2-(hydroxy)phenyl]methanesulfonamide;

(R),(S)-4-[1-[[2-hydroxy-2-[4-hydroxy-3-[(methylsulfonyl)amino]phenyl]ethyl]amino]-2-phenylethyl]benzeneacetic acid, methyl ester;

(R),(R)-4-[1-[[2-hydroxy-2-[4-hydroxy-3-[(methylsulfonyl)amino]phenyl]ethyl]amino]-2-phenylethyl]benzeneacetic acid, methyl ester;

(R),(R)-4-[1-[[2-hydroxy-2-[4-hydroxy-3-[(methylsulfonyl)amino]phenyl]ethyl]amino]-2-phenylethyl]benzeneacetic acid;

(R),(S)-4-[1-[[2-hydroxy-2-[4-hydroxy-3-[(methylsulfonyl)amino]phenyl]ethyl]amino]-2-phenylethyl]benzeneacetic acid;

(R, R)-4-[1-[[2-hydroxy-2-[4-hydroxy-3-[(methylsulfonyl)amino]phenyl]ethyl]amino]-2-phenylethyl]-N-phenylmethylbenzamide;

(R, R)-N-(2-hydroxyethyl)-4-[1-[[2-hydroxy-2-[4-hydroxy-3-[(methylsulfonyl)amino]-phenyl]ethyl]amino]-2-phenylethyl]benzamide;

(R),(R)-N-[3-[2-[[1-(1,3-benzodioxol-5-yl)-2-(4-fluorophenyl)-ethyl]amino]-1-hydroxyethyl]-2-hydroxyphenyl]methanesulfonamide;

[(R),(S)-N-(1,1-dimethylethyl)-α-[[2-hydroxy-3-[(methylsulfonyl)amino]phenyl]ethyl]amino]-4-methoxybenzeneacetamide;]

(R),(S)-α-[[2-hydroxy-2-[4-hydroxy-3-[(methylsulfonyl)amino]phenyl]ethyl]amino]-4-methoxy-N-phenylbenzeneacetamide;

(R),(S)-α-[[2-hydroxy-2-[4-hydroxy-3-[(methylsulfonyl)amino]phenyl]ethyl]amino]-4-methoxy-N-methyl-N-phenylbenzeneacetamide;

(R),(S)-N-(1,3-benzodioxol-5-yl)-α-[[2-hydroxy-2-[4-hydroxy-3-[(methylsulfonyl)amino]phenyl]ethyl]amino]-4-methoxybenzeneacetamide;

(R),(S)-N-(4-chlorophenyl)-α-[[2-hydroxy-2-[4-hydroxy-3-[(methylsulfonyl)amino]phenyl]ethyl]amino]-4-methoxybenzeneacetamide;

(R),(S)-α-[[2-hydroxy-2-[4-hydroxy-3-[(methylsulfonyl)amino]phenyl]ethyl]amino]-4-methoxy-α-methyl-N-phenylbenzeneacetamide;

(R),(R)-α-[[2-hydroxy-2-[4-hydroxy-3-[(methylsulfonyl)amino]phenyl]ethyl]amino]-4-methoxy-N-phenylbenzeneacetamide;

(R),(S)-α-[[2-hydroxy-2-[4-hydroxy-3-[(methylsulfonyl)amino]phenyl]ethyl]amino]-N-phenylbenzeneacetamide;

(R),(S)-α-[[2-hydroxy-2-[4-hydroxy-3-[(methylsulfonyl)amino]phenyl]ethyl]amino]-4-methoxy-N-(phenylmethyl)benzeneacetamide;

[(R),(S)-N-(cyclohexyl)-α-[[2-Hydroxy-2-[4-hydroxy-3-[(methylsulfonyl)amino]phenyl]ethyl]amino]-4-methoxybenzeneacetamide;]

(R, R)-N-hydroxy-4-[1-[[2-hydroxy-2-[4-hydroxy-3-[(methylsulfonyl)amino]-phenyl]ethyl]amino]-2-phenylethyl]benzamide;

[(R),(S)]-N-[5-[1-hydroxy-2-[[1-(4-methoxyphenyl)-2-oxo-2-(1-piperidinyl)ethyl]amino]ethyl]-2-hydroxyphenyl]methanesulfonamide;]

(R),(R)-4-[1-[[2-hydroxy-2-[4-hydroxy-3-[(methylsulfonyl)amino]phenyl]ethyl]amino]-2-phenylethyl]-N-methylbenzeneacetamide;

(R),(R)-4-[1-[[2-hydroxy-2-[4-hydroxy-3-[(methylsulfonyl)amino]phenyl]ethyl]amino]-2-phenylethyl]-N,N-dimethylbenzeneacetamide;

(R),(R)-4-[1-[[2-hydroxy-2-[4-hydroxy-3-[(methylsulfonyl)amino]phenyl]ethyl]amino]-2-phenylethyl]benzeneacetamide;

(R),(R)-4-[1-[[2-hydroxy-2-[4-hydroxy-3-[(methylsulfonyl)amino]phenyl]ethyl]amino]-2-phenylethyl]benzamide;

(R),(R)-4-[1-[[2-hydroxy-2-[4-hydroxy-3-[(methylsulfonyl)amino]phenyl]ethyl]amino]-2-phenylethyl]-N,N-dimethylbenzamide;

(R),(R)-N-[5-[1-(hydroxy-2-[[1-(1-naphthalenyl)-2-phenylethyl]-amino]ethyl]-2-(hydroxy)phenyl]methanesulfonamide;

(R),(S)-N-[5-[1-(hydroxy-2-[[1-(1-naphthalenyl)-2-phenylethyl]-amino]ethyl]-2-hydroxyphenyl]methanesulfonamide;

(R),(R)-N-[5-[1-(hydroxy-2-[[1-(4-methoxy-1-naphthalenyl)-2-phenylethyl]-amino]ethyl]-2-hydroxyphenyl]methanesulfonamide;

(R),(S)-N-[5-[1-(hydroxy-2-[[1-(4-methoxy-1-naphthalenyl)-2-phenylethyl]amino]ethyl]-2-hydroxyphenyl]methanesulfonamide;

N-[5-[(R)-1-(hydroxy-2-[[1-(benzo[b]thiophen-5-yl)-2-phenylethyl]-amino]ethyl]-2-hydroxyphenyl]methanesulfonamide;

(R),(S)-N-(1,3-benzodioxol-5-yl)-α-[[2-hydroxy-2-[4-hydroxy-3-[(methylsulfonyl)amino]phenyl]ethyl]amino]-4-methoxy-α-methylbenzeneacetamide;

(R),(R),(R)-N-[5-[2-[[1-(1,3-benzodioxol-5-yl)-2-phenylethyl]amino]-1-hydroxypropyl]-2-hydroxyphenyl]methanesulfonamide;

(R),(S),(R)-N-[5-[2-[[1-(1,3-benzodioxol-5-yl)-2-phenylethyl]-amino]-1-hydroxypropyl]-2-hydroxyphenyl]methanesulfonamide;

(R),(S)-N-(4-chlorophenyl)-α-[[2-hydroxy-2-[4-hydroxy-3-[(methylsulfonyl)-amino]phenyl]ethyl]amino]-α-methyl-4-methoxybenzeneacetamide; or a pharmaceutically acceptable salt thereof.

6. A pharmaceutical composition comprising a compound of claim 1 and a pharmaceutically acceptable carrier.

7. A method for treating diabetes comprising administering to a mammalian specie in need thereof a therapeutically effective amount of a composition of claim 6.

8. A method for treating obesity comprising administering to a mammalian specie in need thereof a therapeutically effective amount of a composition of claim 6.

9. A method for treating intestinal hypermotility comprising administering to a mammalian specie in need thereof a therapeutically effective amount of a composition of claim 6.

10. A pharmaceutical composition comprising a compound of claim 1 in combination with a beta$_1$ or beta$_2$ adrenergic blocker or stimulant and a pharmaceutically acceptable carrier.

11. A method for treating diabetes comprising administering to a mammalian specie in need thereof a therapeutically effective amount of a composition of claim 10.

12. A method for treating obesity comprising administering to a mammalian specie in need thereof a therapeutically effective amount of a composition of claim 10.

13. A method for treating gastrointestinal diseases comprising administering to a mammalian specie in need thereof a therapeutically effective amount of a composition of claim 10.

14. A compound of the formula

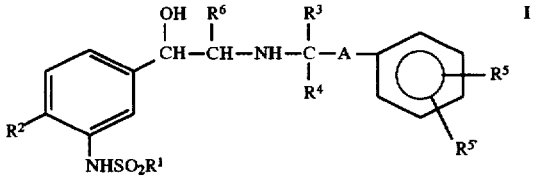

or pharmaceutically acceptable salts thereof wherein:

A is a bond, —(CH$_2$)$_n$— or —CH(B)—, where n is an integer of 1 to 3 and B is —CN, —CON(R$^6$)R$^{6'}$ or —CO$_2$R$^7$;

R$^1$ is lower alkyl, aryl or arylalkyl;

R$^2$ is hydrogen, hydroxy, alkoxy or halogen;

R$^3$ is

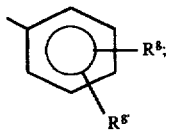

R$^4$ is hydrogen, alkyl or B;

R$^5$, R$^{5'}$, R$^8$ and R$^{8'}$ are independently hydrogen, alkoxy, lower alkyl, halogen, —OH, —CN, —(CH$_2$)$_n$NR$^6$COR$^7$, —CON(R$^6$)R$^{6'}$, —CO$_2$R$^7$, —SR$^7$, —SOR$^7$, —SO$_2$R$^7$, —N(R$^6$)SO$_2$R$^1$, —N(R$^6$)R$^{6'}$, —NR$^6$COR$^7$, —OCH$_2$CON(R$^6$)R$^{6'}$ or —OCH$_2$CO$_2$R$^7$; or R$^5$ and R$^{5'}$ or R$^8$ and R$^{8'}$ may together form a heterocycle;

R$^6$ and R$^{6'}$ are independently hydrogen or lower alkyl; and R$^7$ is lower alkyl.

* * * * *